United States Patent
Hewitt et al.

(10) Patent No.: US 10,858,632 B2
(45) Date of Patent: Dec. 8, 2020

(54) RESTRICTIVE INVERTED TERMINAL REPEATS FOR VIRAL VECTORS

(71) Applicant: The University of North Carolina at Chapel Hill, Chapel Hill, NC (US)

(72) Inventors: Curtis Hewitt, Austin, TX (US); Richard Jude Samulski, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/271,163

(22) Filed: Feb. 8, 2019

(65) Prior Publication Data
US 2019/0185823 A1 Jun. 20, 2019

Related U.S. Application Data

(62) Division of application No. 14/922,935, filed on Oct. 26, 2015, now Pat. No. 10,233,428, which is a division of application No. 13/521,448, filed as application No. PCT/US2011/020939 on Jan. 12, 2011, now Pat. No. 9,169,494.

(60) Provisional application No. 61/294,181, filed on Jan. 12, 2010.

(51) Int. Cl.
| | |
|---|---|
| *C12N 7/00* | (2006.01) |
| *C07K 14/01* | (2006.01) |
| *C12N 15/86* | (2006.01) |
| *C07K 14/015* | (2006.01) |
| *C07K 14/005* | (2006.01) |
| *C12N 15/864* | (2006.01) |

(52) U.S. Cl.
CPC .............. *C12N 7/00* (2013.01); *C07K 14/005* (2013.01); *C12N 15/86* (2013.01); *C12N 15/8645* (2013.01); *C12N 2750/14122* (2013.01); *C12N 2750/14143* (2013.01); *C12N 2750/14162* (2013.01); *C12N 2750/14322* (2013.01); *C12N 2750/14352* (2013.01); *C12N 2820/60* (2013.01)

(58) Field of Classification Search
None
See application file for complete search history.

(56) References Cited

U.S. PATENT DOCUMENTS

| | | | |
|---|---|---|---|
| 6,984,517 B1 | 1/2006 | Chiorini et al. | |
| 2003/0129203 A1 | 7/2003 | Vega et al. | |
| 2004/0197895 A1 | 10/2004 | Kotin et al. | |
| 2005/0002908 A1 | 1/2005 | Horer et al. | |

OTHER PUBLICATIONS

Goncalves et al. Transfer of the full-length dystrophin-coding sequence into muscle cells by a dual high-capacity hybrid viral vector with site-specific integration ability. J Virol. Mar. 2005;79(5):3146-62.*

Grimm et al. In Vitro and In Vivo Gene Therapy Vector Evolution via Multispecies Interbreeding and Retargeting of Adeno-Associated Viruses. J. Virol. 2008, 82: 5887-5911.*

Brister, J.R. et al., "Mechanism of Rep-Mediated Adeno-Associated Virus Origin Nicking", Journal of Virology, Sep. 2000, vol. 74, No. 17, p. 7762-7771.

Cathomen, T. et al., "A Chimeric Protein Containing the N Terminus of the Adeno-Associated Virus Rep Protein Recognizes its Target Site in an In Vivo Assay", Journal of Virology, Mar. 2000, vol. 74, No. 5, p. 2372-2382.

Chiorini et al. Adeno-associated virus (AAV) type 5 Rep protein cleaves a unique terminal resolution site compared with other AAV serotypes: J Virol. May 1999;73(5) :4293-8.

European Application No. 11733293.2; Summons to Attend Oral Proceedings issued Mar. 3, 2017.

Extended European Search Report for EP Applicaton No. 11733293. 2; dated Jan. 9, 2014; 10 Pages.

Farkas, S.L., et al., "A parvovirus isolated from royal python (*Python regius*) is a member of the genus Dependovirus", Journal of General Virology (2004), vol. 85, p. 555-561.

Hewitt "Toward a recombinant adeno-associated virus origin of replication", (2009) https://cdr.lib.unc.edu/indexablecontent/uuid Retrieved Mar. 3, 2016 (152 pages).

Hewitt et al. Creating a Novel Origin of Replication through Modulating DNA-Protein Interfaces. PLoS ONE 5(1 ): e8850.

Hewitt, F.C. et al., "Reducing the Risk of Adeno-Associated Virus (AAV) Vector Mobilization with AAV Type 5 Vectors", Journal of Virology, Apr. 2009, vol. 83, No. 8, p. 3919-3929, Published Feb. 11, 2009.

Hewitt, F.C. et al., "Replication Specificity of Adeno-Associated Virus Genomes", 2008 DNA Replication and Genome Integrity Meeting, Salk Institute, Jul. 20, 2008, 1 page.

International Preliminary Report on Patentability Corresponding to International Application No. PCT/US2011/020939; dated Jul. 26, 2012; 8 Pages.

International Preliminary Report on Patentability Corresponding to International Application No. PCT/US2011/036215; dated Nov. 29, 2012; 7 Pages.

Office Action corresponding to European Application No. 11733293.2 dated Apr. 1, 2016.

(Continued)

*Primary Examiner* — Nianxiang Zou
(74) *Attorney, Agent, or Firm* — Myers Bigel, P.A.

(57) ABSTRACT

This invention relates to modified parvovirus inverted terminal repeats (ITRs) that do not functionally interact with wild-type large Rep proteins, synthetic Rep proteins that functionally interact with the modified ITRs, and methods of using the same for delivery of nucleic acids to a cell or a subject. The modifications provide a novel Rep-ITR interaction that limits vector mobilization, increasing the safety of viral vectors.

23 Claims, 65 Drawing Sheets

Specification includes a Sequence Listing.

(56) References Cited

OTHER PUBLICATIONS

Rabinowitz, J.E. et al., "Cross-Packaging of a Single Adeno-Associated Virus (AAV) Type 2 Vector Genome into Multiple AAV Serotypes Enables Transduction with Broad Specificity", Journal of Virology, Jan. 2002, vol. 76, No. 2, p. 791-801.
Walker et al. Mutational analysis of the adeno-associated virus Rep68 protein: identification of critical residues necessary for site-specific endonuclease activity. J Virol. Apr. 1997;71 (4):2722-30.
Yoon et al., "Amino-terminal domain exchange redirects origin-specific interactions of adeno-associated virus Rep78 in vitro," J. Virol. 75:3230-3239 (2001).

* cited by examiner

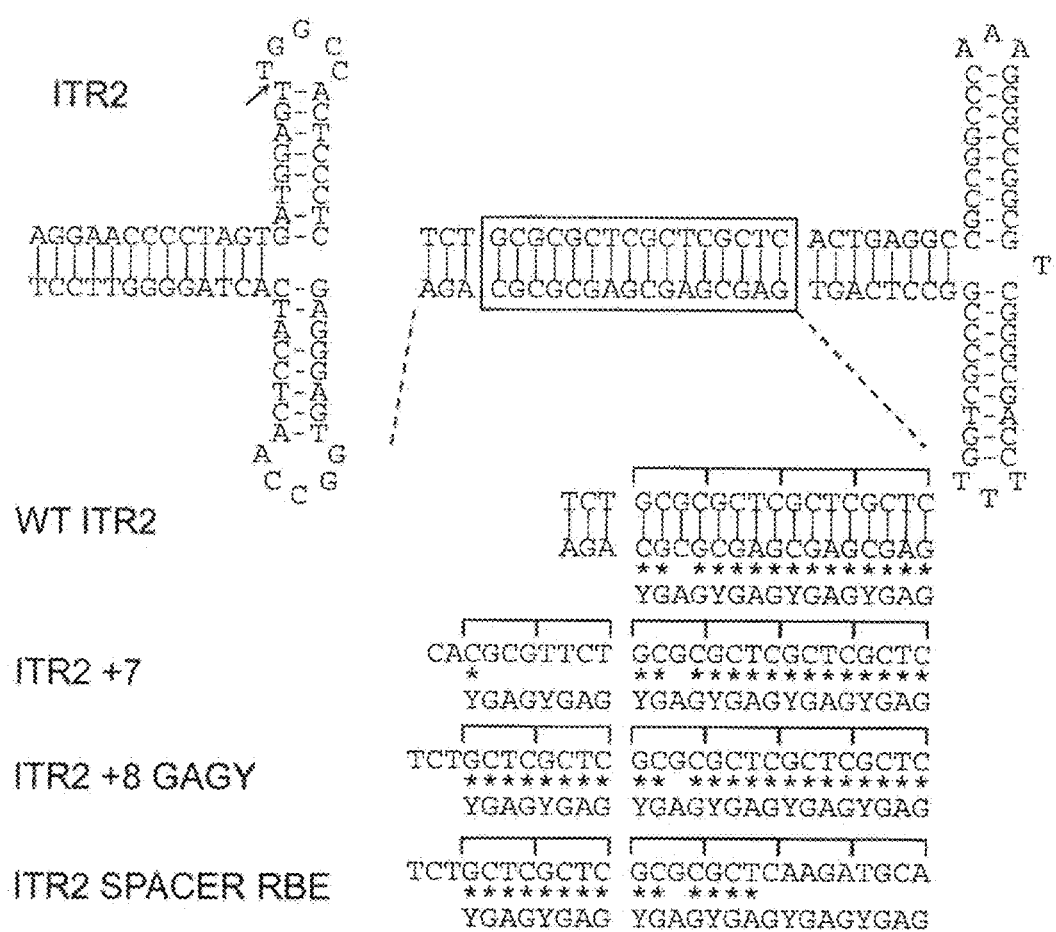
FIG. 4C
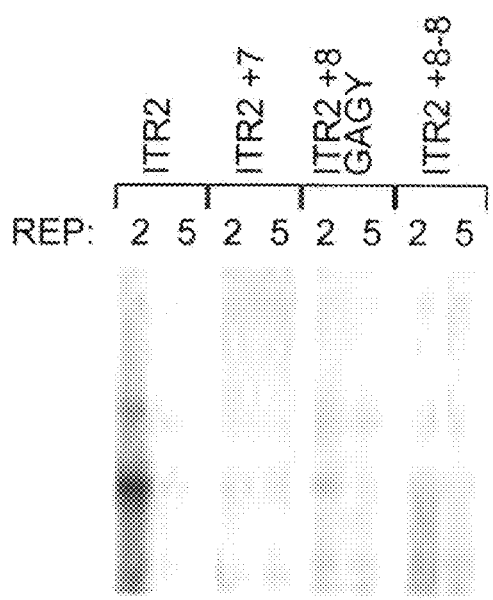
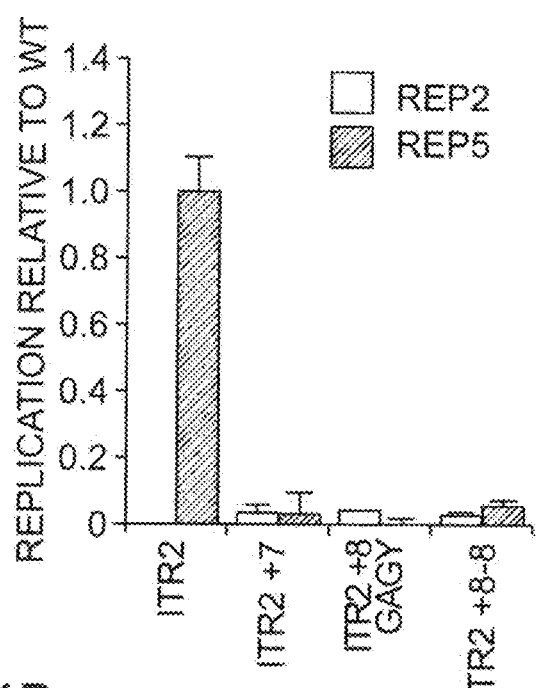
FIG. 4D

```
REP5 MATFYEVIVRVPFDVEEHLPGISDSFVDWVIGQIWELPPESDLNLTLVEQ    50
REP2 MPGFYEIVIKVPSDLDGHLPGISDSFVNWVAEKEWELPPDSDMDLNLIEQ    50
     *, ***:;:;** *;; *********;**; ; *****;**;;*,*;**

REP5 PQLTVADRIRRVFLYEWNKFSKQ-ESKFFVQFEKGSEYFHLHTLVETSGI    99
REP2 APLTVAEKLQRDFLTEWRRVSKAPEALFFVQFEKGESYFHMHVLVETTGV   100
     ****;:;;* ** **,;.**  *; ******* ***;*.****;*;

REP5 SSMVLGRYVSQIRAQLVKVVFQGIEPQINDWVAITKVKK--GGANKVVDS   147
REP2 KSMVLGRFLSQIREKLIQRIYRGIEPTLPNWFAVTKTRNGAGGGNKVVDE   159
     ;******;;**** ;*;;  ;;;****  ; ;*,*;**,;;  **,*****,

REP5 GYIPAYLLPKVQPELQWAWTNLDEYKLAALNLEERKRLVAQFLAESSQRS   197
REP2 CYIPNYLLPKTQPELQWAWTNMEQYLSACLNLTERKRLVAQHLTHVSQIQ   200
     *** *****,**********;;;*  *,*** ********.*;, **

REP5 -QEAASQREFSADPVIKSKTSQKYM   222
REP2 EQNKENQNPNSDAPVIRSKTSARYM   225
     *;   ,*, * ***;**** ;**
```

| | ITR2 | ITR5 | | ITR2 | ITR5 |
|---|---|---|---|---|---|
| | + | - | ▨ | - | + |
| ▨ 84 | + | - | 77 ▨ | - | + |
| ▨ 110 | + | - | 97 ▨ | - | + |
| ▨ 126 | - | - | 116 ▨ | - | + |
| ▨ 138 | - | - | 125 ▨ | - | + |
| ▨ 146 | + | + | 141 ▨ | + | + |
| ▨ 160 | - | + | 149 ▨ | + | - |
| ▨ 175 | - | + | 166 ▨ | + | - |
| ▨ 207 | - | + | 216 ▨ | + | - |

☐ REP2
▨ REP5

*FIG. 5B*

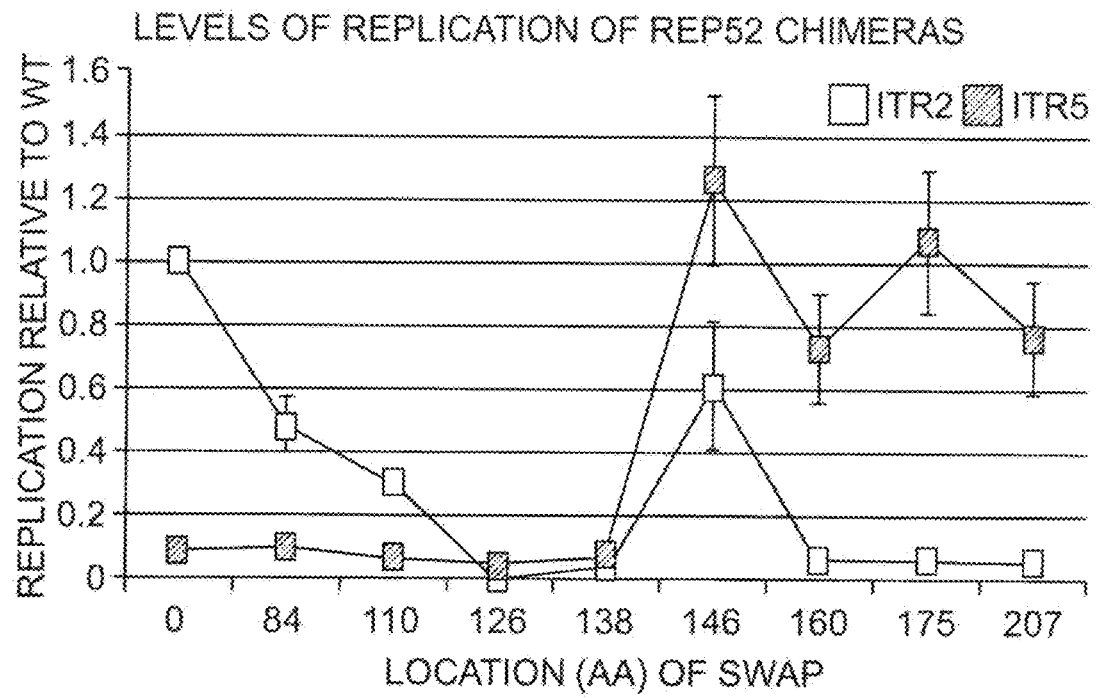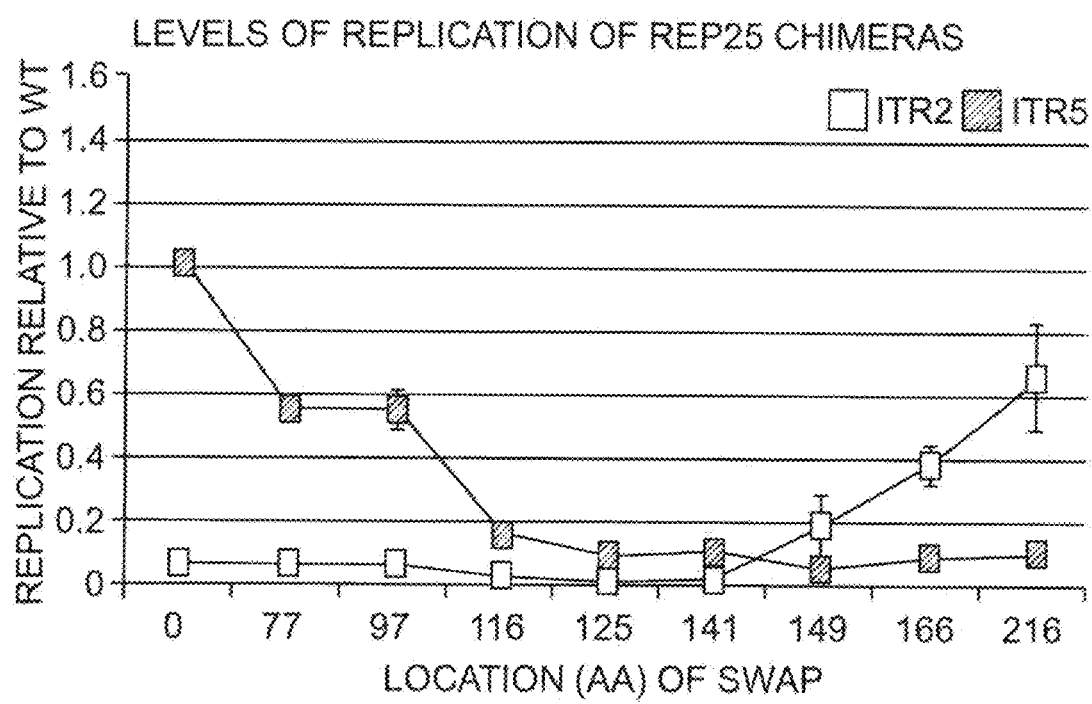
FIG. 5E

FIG. 8

AAV-2, COMPLETE SEQUENCE, GENBANK ACCESSION NO. NC_001401 AND
CHIORINI ET AL. (1999) J. VIROL. 73:1309

```
AAV-3B, COMPLETE SEQUENCE, GENBANK ACCESSION NO. NC_001863
TGGCCACTCCCTCTATGCGCACTCGCTCGCTCGGTGGGGCCTGGCGACCAAAGGTCGCCAGACGGACGT
GCTTTGCACGTCCGGCCCCACCGAGCGAGCGAGTGCGCATAGAGGGAGTGGCCAACTCCATCACTAGAG
GTATGGCAGTGACCTAACGCGAAGCGCGCGAAGCGAGACCACGCCTACCAGCTGCGTCAGCAGTCAGGT
GACCCTTTTGCGACAGTTTGCGACACCACGTGGCCGCTGAGGGTATATATTCTCGAGTGAGCGAACCAG
GAGCTCCATTTTGACCGCGGAAATTTGAACGAGCAGCAGCCATGCCGGGGTTCTACGAGATTGTCCTGAA
GGTCCCGAGTGACCTGGACGGAGCACCTGCCGGGCCATTTCTAACTCGTTTGTTAACTGGGTGGCCGAGAA
GGAATGGGAGCTGCCGCCCGGATTCTGACATGGATCCGAATCTGATTGAGCAGGCACCCCTGACCGTGGC
CGAAAAGCTTCAGCGCGAGTTCCTGGTGGAGTGGCGCCCGCGTGAGTAAGGCCCCGGAGGCCCTCTTTTT
TGTCCAGTTCGAAAAGGGGGAGACCTACTTCCACCTGCACGTGCTGATTGAGACCATCGGGGTCAAATC
CATGGTGGTCGGCCGCTACGTGAGCCAGATTAAAGAGAAGCTGGTGACCCGCATCTACCGCGGGGTCGA
GCCGCAGCTTCCGAAACTGGTTCGCGGTGACCAAAACGCGAAATGGCGCCGGGGCGGGAACAAGGTGGT
GGACGACTGCTACATCCCCAACTACCTGCTCCCCAAGACCCAGCCCGAGCTCCAGTGGGCGTGGACTAA
CATGGACCAGTATTTAAGCGCCTGTTTGAATCTCGCGGAGCGTAAACGTCTGGTGGCGCAGCATCTGAC
GCACGTGTCGCAGACGCAGGAGCAGAACAAAGAGAATCAGAACCCCAATTCTGACGCGCCGGTCATCAG
GTCAAAAACCTCAGCCAGGTACATGGAGCTGGTCCGGGTGGCTGGTGGACCGCGGGATCACGTCAGAAAA
GCAATGGATTCAGGAGGACCAGGCCTCGTACATCTCCTTCAACGCCGCCTCCAACTCGCGGTCCCAGAT
CAAGGCCGCGCTGGACAATGCCTCCAAGATCATGAGCCTGACAAAGACGGCTCCGGACTACCTGGTGGG
CAGCAACCCGCCGGAGGACATTACCAAAAATCGGATCTACCAAATCCTGGAGCTGAACGGGTACGATCC
GCAGTACGCGGCCTCCGTCTTCCTGGGCTGGGCGCAAAAGAAGTTCGGGAAGAGGAACACCATCTGGCT
CTTTGGGCCGGCCACGACGGGTAAAACCAACATCGCGGAAGCCATCGCCCACGCCGTGCCCTTCTACGG
CTGCGTAAACTGGACCAATGAGAACTTTCCCTTCAACGATTGCGTCGACAAGATGGTGATCTGGTGGGA
GGAGGGCAAGATGACCGGCCAAGGTCGTGGAGAGCGCCAAGGCCATTCTGGGCGGAAGCAAGGTGCGCGT
GGACCAAAAGTCAAGTCATCGGCCCAGATGAACCCCACTCCCGTGATCGTCACCTCCAACACCAACAT
GTGCGCCGTGATTGACGGGAACAGCACCACCTTCGAACATCAGCAGCCGCTGCAGGACCGGATGTTTAA
ATTTGAACTTACCCGCCGTTTGGACCATGACTTTGGGAAGGTCACCCAAACAGGAAGTAAAGGACTTTTT
CCCGTGGGCTTCCGATCACGTGACTGACGTGGCTCATGAGTTCTACGTCAGAAAGGGTGGAGCTAAGAA
ACGCCCCGCCTCCAATGACGCGGATGTAAGCGAGCCAAAACGGCAGTGCACGTCACTTGCGCAGCCGAC
AACGTCAGACGCGGAAGCACCGGCGGACTACGCGGACAGGTACCAAAACAAATGTTCTCGTCACGTGGG
CATGAATCTCGATGCTTTTCCCTTGTAAAACATGCGAGAGAATGAATCAAATTTCCAATGTCTGTTTTAC
GCATGGTCAAAGAGACTGTGGGGAATGCTTCCCGGAATATGCAGAATCTCAACCCGTTCTGTCGTCAA
AAAGAAGACTTATCAGAAACTGTGTCCAATTCATCATATCCTGGGAAGGGCACCCGAGATTGCCTGTTC
GGCCTGCGATTTGGCCAATGTGGACTTGGATGACTGTGTTTCTGAGCAATAAATGACTTAAACCAGGTA
TGGCTGCTGACGGTTATCTTCCAGATTGGCTCGAGGACAACCTTTCTGAAGGCATTCGTGAGTGGTGGG
CTCTGAAACCTGGAGTCCCTCAACCCAAAGCGAACCAACAACACCAGGACAAACCGTCGGGGTCTTGTGC
TTCCGGGTTACAAATACCTCCGAAAGCCGTTAACGGACTCGACAAAGGGAGAGCCGGTCAACGAGGCGGACG
CGGCAGCCCTCGAACACGACAAAGCCTTACGACCAGCAGCTCAAGGCCGGTGACAACCCGTACCTCAAGT
ACAACCACGCCGACGCCGAGTTTCAGGAGCGTCTTCAAGAAGATACGTCTTTTGGGGGCAACCTTGGCA
GAGCAGTCTTCCAGGCCAAAAAGAGGATCCTTGAGCCTCTTGGTCTGGTTGAGGAAGCAGCTAAAACGG
CTCCTGGAAAGAAGAGGCCTGTAGATCAGTCTCCTCAGGAACCGGACTCATCATCTGGTGTTGGCAAAT
CGGGCAAACAGCCTGCCAGAAAAAGACTAAATTTCGGTCAGACTGGCGACTCAGAGTCAGTCCCAGACC
CTCAACCTCTCGGAGAACCACCAGCAGCCCCCACAAGTTGGGATCTAATACAATGGCTTCAGGCGGTG
GCGCACCAATGCAGACAACAATAACGAGGGTGCCGATGGAGTGGGTAATTCCTTCAGGAAATTGGCATTGCG
ATTCCCAATGGCTGGGCGACAGAGTCATCACCACCAGCACCAGAACCTGGGCCCTGCCCACTTACAACA
ACCATCTCTACAAGCAAATCTCCAGCCAATCAGGAGCTTCAAACGACAACAACTACTTTGGCTACAGCA
CCCCTTGGGGGTATTTTGACTTTAACAGATTCCACTGCCACTTCTCACCACGTGACTGGCAGCGACTCA
TTAACAACAACTGGGGATTCCGGCCCAAGAAACTCAGCTTCAAGCTCTTCAACATCCAAGTTAAAGAGG
TCACGCAGAACGATGGCACGACGACTATTGCCAATAACCTTACCAGCACGGTTCAAGTGTTTACGGACT
CGGAGTATCAGCTCCGTACGTGCTCGGGTGCCGGCCACCAAGGCTGTCTCCCGCCGGTTTCCAGCCGACG
TCTTCATGGTCCCTCAGTATGGATACCTCACCCTGAACAACGGAAGTCAAGCGGTGGACGCTCATCCT
TTTACTGCCTGGAGTACTTCCCCTTCGCAGATGCTAAGGACTGGAAATAACTTCCAATTCAGCTATACCT
TCGAGGATGTACCTTTTCACAGCAGCTACGCTCACAGCCAGAGTTTGGATCGCTTGATGAATCCTCTTA
TTGATCAGTATCTGTACTACCTTGAACAGAACGCAAGGAACAACCTCTGGAACAACCAACCAATCACGGC
TGCTTTTTAGCCAGGCTGGGCCTCAGTCTATGTCTTGCAGGCCAGAAATTGGCTACCTGGGCCCTGCT
ACCGGCAACAGAGACTTTCAAAGACTGCTAACGACAACAACAGTAACTTTCCTTGGACAGCGGCCA
GCAAATATCATCTCAATGGCCGCGACTCGCTGGTGAATCCAGGACCAGCTATGGCCAGTCACAAGGACG
ATGAAGAAAATTTTTCCCTATGCACGGCAATCTAATATTTTGGCAAAGAAGGGACAACGGCAAGTAACG
CAGAATTAGATAATGTAATGATTACGGATGAAGAAGAGATTCGTACCACCAATCCTGTGGCAACAGAGC
AGTATGGAACTGTGGCAAATAACTTGCAGAGCTCAAATACAGCTCCCACGACTAGAACTGTCAATGATC
AGGGGGCCCTTACCTGGCATGGTGTGGCAAGATCGTGACGTGTACCTTCAAGGACCTATCTGGCAAAGA
TTCCTCACACGGATGGACACTTTCATCCTTCTCCTCTGATGGGAGGCTTTGGACTGAAACATCCGCCTC
CTCAAATCATGATCAAAAATACTCCGGTACCGGCCAAATCCTCGACGACTTTCAGCCCGGCCAAGTTTG
CTTCATTTATCACTCAGTACTCCACTGGACAGGTCAGCGTGGAAATTGAGTGGAGCTACAGAAAGAAA
ACAGCAAACGTTGGAATCCAGAGATTCAGTACACTTCCAACTACAACAAGTCTGTTAATGTGGACTTTA
CTGTAGACACTAATGGTGTTTATAGTGAACCTCGCCCTATTGGAACCCGGTATCTCACACGAAACTTGT
AATCCTGGTTAATCAATAAACCGTTTAATTCGTTTCAGTTGAACTTTGGCTCTTGTGCACTTCTTATCT
TATCCTTGTTTCCATGGCTACTGCGTAGATAAGCAGCGGCTGCGGGCCTTGCGCTTCGCGGTTTACAAC
TGCTGGTTAATATTTAACTCTCGCCATACCTCTAGTGATGGAGTTTGGCCACTCCCTCTATGCGCACTCG
CTCGCTCGGTGGGGCCGGACGTGCAAAGCACGTCCGTCTGGCGACCTTTGGTCGCCAGACGCCACCGAG
CGAGCGAGTGCGCATAGAGGGAGTGGCCAA
```

FIG. 11

AAV-4, COMPLETE SEQUENCE, GENBANK ACCESSION NO. NC_001829 AND
CHIORINI AT AL. (1997) J. VIROL. 71:6823

AAV-7, COMPLETE SEQUENCE, GENBANK ACCESSION NO. AF513851 AND GAO ET AL. (2002) PNAS 99:11854
```
TTGGCCACTCCCTCTATGCGCGCTCGCTCGGTGGGGCCTGCGGACCAAAGGTCCGCAGACGGCAG
AGCTCTGCTCTGCCGGCCCCACCGAGCGAGCGAGCGCGCATAGAGGGAGTGGCCAACTCCATCACTAGG
GGTACCGCGAAGCHCCTCCCACGCTGCCGCGTCAGCGCTGACGTAAATCACGTCATAGGGGAGTGGTCC
TGTATTAGCTGTCACGTGAGTGCTTTTGCGACATTTTGGACACCACGTGGCCATTTGAGGTATATATG
GCCGAGTGAGCGAGCAGGATCTCCATTTTGACCGGGAAATTTGAACGAGCAGCAGCCATGCCGGGTTTC
TACGAGATCGTGATCAAGGTGCCGAGCGACCTGGACGAGCACCTGCCGGGCATTTCTGACTCGTTTGTG
AACTGGGTGGCCGAGAAGGAATGGGAGCTGCCCCCGGATTCTGACATGGATCTGAATCTGATCGAGCAG
GCACCCCTGACCGTGGCCGAGAAGCTGCAGCGCGACTTCCTGGTCCAATGGCGCCGCGTGAGTAAGGCC
CCGGAGGCCCTGTTCTTTGTTCAGTTCGAGAAGGGCGAGAGCTACTTCCACCTTCACGTTCTGGTGGAG
ACCACGGGGGTCAAGTCCATGGTGCTAGGCCGCTTCCTGAGTCAGATTCGGGAGAAGCTGGTCCAGACC
ATCTACCGCGGGGTCGAGCCCACGCTGCCCAACTGGTTCGCGGTGACCAAGACGCGTAATCGCCGCGGC
GGGGGGAACAAGGTGGTGGACGAGTGCTACATCCCCAACTACCTCCTGCCCAAGACCCAGCCCGAGCTG
CAGTGGGCGTGGACTAACATGGAGGAGTATATAAGCGCGTGTTTGAACCTGGCCGAACGCAAACGGCTC
GTGGCGCAGCACCTGACCCACGTCAGCCAGACGCAGGAGCAGAACAAGGAGAATCTGAACCCCAATTCT
GACGCGCCCGTGATCAGGTCAAAAAACCTCCGCGCGCTACATGGAGCTGGTCGGGTGGCTGGTGGACCGG
GGCATCACCTCCGAGAAGCAGTGGATCCAGGAGGACCAGGCCTCGTACATCTCCTTCAACGCCGCCTCC
AACTCGCGGTCCCAGATCAAGGCCGCTGGACAAATCCCGCAAGATCATGCGCGCTGACCAAATCCGCG
CCCGACTACCTGGTGGGGCCCTCGCTGCCCGCGGACATTAAAAACCAACCGCATCTACCGCATCCTGGAG
CTGAACGGGTACGATCCTGCCTACGCCGGCTCCGTCTTTCTCGGCTGGGCCCAGAAAAAGTTCGGGAAG
CGCAACACCATCTGGCTGTTTGGGCCCGCCACCACCGGCAAGACCAACATTGCGGAAGCCATCGCCCAC
GCCGTGCCCTTCTACGGCTGCGTCAACTGGACCAATGAGAACTTTCCCTTCAACGATTGCGTCGACAAG
ATGGTGATCTGGTGGGAGGAGGGCAAGATGACGGCCAAGGTGGTGGAGTCCGCCAAGGCCATTCTCGGC
GGCAGCAAGGTGCGCGTGGACCAAAAGTGCAAGTCGTCCGCCCAGATCGACCCGACCCCCGTGATCGTC
ACCTCCAACACCAACATGTGCGCCGTGATTGACGGGAACAGCACCACCTTCGAGCACCAGCAGCCGTTG
CAGGACCGGATGTTCAAATTTGAACTCACCCGCCGTCTGGAGCACGACTTTGGCAAGGTGACGAAGCAG
GAAGTCAAAGAGTTCTTCCGCTGGGCCAGTGATCACGTGACCGAGGTGGCGCATGAGTTCTACGTCAGA
AAGGGCGGAGCCAGCAAAAGACCCGCCCCCGATGACGCGGATATAAGCGAGCCCAAGCGGGCCTGCCCC
TCAGTCGCGGATCCATCGACGTCAGACGCGGAAGCTCCGGTGACTTTGCCGACAGGTACCAAAAAC
AAATGTTCTCGTCACGCGGGCATGATTCAGATGCTGTTTCCCTGCAAAAACGTCGAGAGAATGAATCAG
AATTTCAACATTTGCTTCACACACGGGGTCAGAGACTGTTTAGAGTGTTTCCCGGCGTGTCAGAATCT
CAACTGGTCGTCAGAAAAAGACGTATCGGAAACTCTGCGCGATTCATCATCTGCTGGGGCGGGCGCCC
GAGATTGCTTGCTCGGCCTGCGACCTGGTCAACGTGGACCTGGACGACTGCGTTTCTGAGCAATAAATG
ACTTAAACCAGGTATGGCTGCCGATGGTTATCTTCCAGATTGGCTCGAGGACAACCTCTCTGAGGGCAT
TGGCGAGTGGTGGCACCTGAAACCTGAGCCCCGAAACCCAAAGCCAACCAGCAAAAGCAGGACAACGG
CCGGGGTCTGGTGCTTCCTGGCTACAAGTACCTCGGGACCCTTCAACGGACTCGACAAGGGGGAGCCCGT
CAACGCGGCGGACGCAGCGGGCCCTCGAGCACGACAAGGCCTACGACCAGCAGCTCAAAGCGGGTGACAA
TCCGTACCTGCGGTATAACCACGCCGACGCCGAGTTTCAGGAGCGTCTGCAAGAAGATACGTCATTTGG
GGGCAACCTCGGGCGAGCAGTCTTCCAGGCCAAGAAGCGGGTTCTCGAACCTCTCGGTCTGGTTGAGGA
AGGCGCTAAGACGGCTCCTGCAAAGAAGAGACCGGTAGAGCCGTCACCTCAGCGTTCCCCCCGACTCCTC
CACGGCATCCGCCAAGAAAGGCCAGCAGCCCGGCCAGAAAGACTCAATTTCGGTCAGACTGGCGACTC
AGAGTCAGTCCCCGACCCTCAACCTCTCGGAGAACCTCCAGCAGCGGCCCTCTAGTGTGGGATCTGGTAC
AGTGGCTGCAGGCCGGTGGCGCACCAATGGCAGACAATAACGAAGGTGCCGACGGAGTGGGTAATGCCTC
AGGAAATTGGCATTGCGATTCCACATGGCTGGGCGACAGAGTCATTACCACCAGCACCCGAACCTGGGC
CCTGCCCACCTACAACAACCACCTCTACAAGCAAATCTCCAGTGAAACTGCAGGTAGTACCAACGACAA
CACCTACTTCGGCTACAGCACCCCCTGGGGGTATTTTGACTTTAACAGATTCCACTGCCACTTCTCACC
ACGTGACTGGCAGCGACTCATCAACAACAACTGGGGATTCCGGCCCAAGAAGCTGCGGTTCAAGCTCTT
CAACATCCAGGTCAAGGAGGTCACGACGAATGACGGCGTTACGACCATCGCTAATAACCTTACCAGCAC
GATTCAGGTATTCTCGGACTCGGAATACCAGCTGCCGTACGTCCTCGGCTCTGCGCACCAGGGCTGCCT
GCCTCCGTTCCCGGCGGACGTCTTCATGATTCCTCAGTACGGCTACCTGACTCTCAACAATGGCAGTCA
GTCTGTGGGACGTTCCTCCTTCTACTGCCTGGAGTACTTCCCCTCTCAGATGCTGAGAACGGGCAACAA
CTTTGAGTTCAGCTACAGCTTCGAGGACGTGCCTTTCCACAGCAGCTACGCACACAGCCAGAGCCTGGA
CCGGCTGATGAATCCCCTCATCGACCAGTACTTGTACTACCTGTCCAGAACACAGAGTAACCCAGGAGG
CACAGCTGGCAATCGGGAACTGCAGTTTTTACCAGGGCGGGCCTTCAACTATGGCGAACAAGCCAAGAA
TTGGTTACCTGGACCTTGCTTCCGGCAACAAAGAGTCTCCAAAACGCTGGATCAAAAACAACAACAGCAA
CTTTGCTTGGACTGGTGCCACCAAATATCACCTGAACGGCAGAAACTCGTTGGTTAATCCCGGCGTCGC
CATGGCAACTCACAAGGACGACGAGGACCGCTTTTTCCCATCCAGCGGAGTCCTGATTTTTGGAAAAAC
TGGAGCAACTAACAAAACTACATTGGAAAATGTGTTAATGACAAATGAAGAAGAAATTCGTCCTACTAA
TCCTGTAGCCACGGAAGAATACGGGATAGTTCAGCAGCAACTTACAAGCGGCTAATCTGCAGCCCAGAC
ACAAGTTGTCAACAACTCAGCGAGCCTTACCTGGCATGGTCTGGCAGAACCGGGACGTGTACCTGCAGGG
TCCCATCTGGGCCAAGATTCCTCACACGGATGGCAACTTTCACCCGTCTCCTTTGATGGGCGGCTTTCGG
ACTTAAACATCCGCCTCCTCAGATCCTGATCAAGAACACTCCCGTTCCCGCTAATCCTCCGGAGGTGTT
TACTCCTGCCAAGTTTGCTTCGTTCATCACACAGTACAGCACCGGACAAGTCAGCGTGGAAATCGAGTG
GGGCTGCGAGAAGGAAAAACAGCAAGCGCTGGAACCCGGAGATTCAGTACACCTCCAACTTTGAAAAGCA
GACTGGTGTGGACTTTGCCGTTGACAGCCAGGGTGTTTACTCTGAGCCTCGCCCTATTGGCACTCGTTA
CCTCACCCGTAATCTGTAATTGCATGTTAATCAATAAACCGGTTGATTCGTTTCAGTTGAACTTTGGTC
TCCTGTGCCTTCTTATCTTATCGGTTTCCATAGCAACTGGTTACACATTAACTGCTTGGGTGCCGCTTCAC
GATAAGAACACTGACGTCACCGCGGTACCCCTAGTGATGGAGTTGGCCACTCCCTCTATGCGCGCTCGC
TCGCTCGGTGGGCCTGCGGACCAAAGGTCCGCAGACGGCAGAGCTCTGCTCTGCCGGCCCCACCGAGC
GAGCGAGCGCGCATAGAGGGAGTGGCCAA
```

FIG. 15

AAV-8, COMPLETE SEQUENCE, GENBANK ACCESSION NO. AF513852 AND GAO ET
AL. (2002) PNAS 99:11854
CAGAGAGGGAGTGGCCAACTCCATCACTAGGGGTAGCGCGAAGCGCCTCCCACGCTGCCGCGTCAGC
GCTGACGTAAATTACGTCATAGGGGAGTGGTCCTGTATTAGCTGTCACGTGAGTGCTTTTGCGGCAT
TTTGCGACACCACGTGGCCATTTGAGGTATATATGGCCGAGTGAGCGAGCAGGATCTCCATTTTGAC
CGCGAAATTTGAACGAGCAGCAGCCATGCCGGGCTTCTACGAGATCGTGATCAAGGTGCCGAGCGAC
CTGGACGAGCACCTGCCGGGCATTTCTGACTCGTTTGTGAACTGGGTGGCCGAGAAGGAATGGGAGC
TGCCCCCGGATTCTGACATGGATCGGAATCTGATCGAGCAGGCACCCCTGACCGTGGCCGAGAAGCT
GCAGCGCGACTTCCTGGTCCAATGGCGCCGCGTGAGTAAGGCCCCGGAGGCCCTCTTCTTTGTTCAG
TTCGAGAAGGGCGAGAGCTACTTTCACCTGCACGTTCTGGTCGAGACCACGGGGGTCAAGTCCATGG
TGCTAGGCCGCTTCCTGAGTCAGATTCGGGAAAAGCTTGGTCCAGACCATCTACCCCGCGGGGTCGAG
CCCCACCTTGCCCAACTGGTTCGCGGTGACCAAAAGACGCGGTAATGGCGCCGGCGGGGGGAACAAG
GTGGTGGACGAGTGCTACATCCCCAACTACCTCCTGCCCAAGACTCAGCCCGAGCTGCAGTGGGCGT
GGACTAACATGGAGGAGTATATAAGCGCGCGTGCTTGAACCTGGCCGAGCGCAAACGGCTCGTGGCGCA
GCACCTGACCCACGTCAGCCAGACGCAGGAGCAGAACAAGGAGAATCTGAACCCCAATTCTGACGCG
CCCGTGATCAGGTCAAAAACCTCCGCGCGCTATATGGAGCTGGTCGGGTGGCTGGTGGACCGGGGCA
TCACCTCCGAGAAGCAGTGGATCCAGGAGGACCAGGCCTCGTACATCTCCTTCAACGCCGCCTCCAA
CTCGCGGGTCCCAGATCAAGGCCGCGCTGGACAATGCCGGCAAGATCATGGCGCTGACCAAATCCGCG
CCCGACTACCTGGTGGGGCCCTCGCTCGCCGCGGACATTACCCAGAACCGCATCTACCGCATCCTCG
CTCTCAACGGCTACGACCCTGCCTACGCCGGCTCCGTCTTTCTCGGCTGGGCTCAGAAAAAGTTCGG
GAAACGCAACACCATCTGGCTGTTTGGACCCGCCACCACCGGCAAGACCAACATTGCGGAAGCCATC
GCCCACGCCGTGCCCTTCTACGGCTGCGTCAACTGGACCAATGAGAACTTTCCCTTCAATGATTGCG
TCGACAAGATGGTGATCTGGTGGGAGGAGGGCAAGATGACGGCCAAGGTCGTGGAGTCCGCCAAGGC
CATTCTCGGCGGCAGCAAGGTGCGCGTGGACCAAAAGTGCAAGTCGTCCGCCCAGATCGACCCCACC
CCCGTGATCGTCACCTCCAACACCAACATGTGCGCGGTGATTGACGGGAACAGCACCACCTTCGAGC
ACCAGCAGCCTCTCCAGGACCGGATGTTTAAGTTCGAACTCACCCGCCGTCTGGACCACGACTTTGG
CAAGGTGACAAAGCAGGAAGTCAAAGAGTTCTTCCGCTGGGCCAGTGATCACGTGACCGAGGTGGCG
CATGAGTTTTACGTCAGAAAGGGCGGAGCCAGCAAAAGACCCGCCCCCGATGACGCGGATAAAAGCG
AGCCCAAGCGGGCCTGCCCCTCAGTCGCGGATCCATCGACGTCAGACGCGGAAGGAGCTCCGGTGGA
CTTTGCCGACAGGTACCAAAACAAATGTTCTCGTCGACGGGCATGCTTCAGATGCTGTTTCCCTGC
AAAACGTGCGAGAGAATGAATCAGAATTTCAACATTTGCTTCACACACGGGTCAGAGACTGCTCAG
AGTGTTTCCCCGGCGTGTCAGAATCTCAACCGGTCGTCAGAAAGAGGACGTATCGGAAACTCTGTGC
GATTCATCATCTGCTGGGGCGGGCTCCCGAGATTGCTTGCTCGGCCTGCGATCTGGTCAACGTGGAC
CTGGATGACTGTGTTTCTGAGCAATAAATGACTTAAACCAGGTATGGCTGCCGATGGTTATCTTCCA
GATTGGCTCGAGGACAACCTCTCTGAGGGCATTCGCGAGTGGTGGGCGCTGAAACCTGGAGCCCCGA
AGCCCAAAGCCAACCAGCAAAAGCAGGACGACGGCCGGGGTCTGGTGGCTTCCTGGCTACAAGTACCT
CGGACCCTTCAACGGACTCAAGGGGAGCCGTCAACGCGGCGGACGCGGGCCCTCGAGCAC
GACAAGGCCTACGACCAGCAGCTGCAGGCGGGTGACAATCCGTACCTGCGGTATAACCACGCCGACG
CCGAGTTTCAGGAGCGTCTGCAAGAAGATACGTCTTTTGGGGGCAACCTCGGGCGAGCAGTCTTCCA
GGCCAAGAAGCGGGTTCTCGAACCTCTCGGTCTGGTTGAGGAAGGCGCTAAGACGGCTCCTGGAAAG
AAGAGACCGGTAGAGCCATCACCCCAGCGTTCTCCAGACTCCTCTACGGGCATCGGCAAGAAAGGCC
AACAGCCGCCAGAAAAGACTCAAATTTGGTCAGACTGGCGACTCAGAGTCAGTTCCAGACCCTCA
ACCTCTCGGAGAACCTCCAGCGCGCCCTCTGGTGTGGGACCTAATACAATGGCTGCAGCGGTGGC
GCACCAATGGCAGACAATAACGAAGGCCGCCGACGGAGTGGGTAGTTCCTCGGGAAATTGGCATTGCG
ATTCCACATGGCTGGGCGACAGAGTCATCACCACCAGCACCCGAACCTGGGCCCTGCCCACCTACAA
CAACCACCTCTACAAGCAAATCTCCAACGGGACATCGGGAGGAGCCACCAACGACAACACCTACTTC
GGCTACAGCACCCCCTGGGGGTATTTTGACTTTAACAGATTCCACTGCCACTTTTCACCACGTGACT
GGCAGGACTCATCAACAACAACTGGGGATTCCGGCCCAAGAGACTCAAGCTCTTCAACAT
CCAGGTCAAGGAGGTCACGCAGAATGAAGGCACCAAGACCATCGCCAATAACCTCACCAGCACCATC
CAGGTGTTTACGGACTCGGAGTACCAGCTGCCGTACGTTCTCGGCTCTGCCCACCAGGGCTGCCTGC
CTCCGTTCCCGGCGGACGTGTTCATGATTCCCCAGTACGGCTACCTAACACTCAACAACGGTAGTCA
GGCCGTGGGACGCTCCTCCTTCTACTGCCTGGAATACTTTCCTTCGCAGATGCTGAGAACCGGCAAC
AACTTCCAGTTTACTTACACCTTCGAGGACGTGCCTTTCCACAGCAGCTACGCCCACAGCCAGAGCT
TGGACCGGCTGATGAATCCTCTGATTGACCGTATTCGTGCCAGATAACTTGCAGCAGCA
AGGCACGCGCAAATACGACATCCTGGGCTTCAGCCAAGGTGGGCCTAATACAATGGCCAATCAGGCA
AAGAACTGGCTGCCAGGACCCTGTTACCGCCAACAACGCGTCTCAACGACAACCGGGCAAAACAACA
ATAGCAACTTTGCCTGGACTGCTGGGACCAAATACCATCTGAATGGAAGAAATTCATTGGCTAATCC
TGGCATCGCTATGGCAACACAAAGACGACGAGGAGCGTTTTTTCCCAGTAACGGGATCCTGATT
TTTGGCAAACAAAATGCTGCCAGAGACAATGCGGATTACAGCGATGTCATGCTCACCAGCGAGGAAG
AAATCAAAACCACTAACCCTGTGGCTACAGAGGAATACGGTATCGTGCCAGATAACTTGCAGCAGCA
AAACACGGCTCCTCAAATTGGAACTGTCAACAGCCAGGGGGCCTTACCCGGTATGGTCTGGCAGAAC
CGGGACGTGTACCTGCAGGGTCCCATCTGGGCCAAGATTCCTCACACGGACGGCAACTTCCACCCGT
CTCCGCTGATGGGCGGCTTTGGCCTGAAACATCCTCCGCCTCAGATCCTGATCAAGAACACGCCTGT
ACCTGCGGATCCTCCGACCACCTTCAACCAGTCAAAGCTGAACTCTTTCATCACGCAATACAGCACC
GGACAGGTCAGCGTGGAAATTGAATGGGAGCTGCAGAAGGAAAACAGCAAGCGCTGGAACCCCGAGA
TCCAGTACACCCTCCCAACTACTACAAATCTACAAGTGTGGACTTTGCTGTTAATACAGAAGGCGTGTA
CTCTGAACCTCGCCCCATTGGCACCCGGTTACCTCACCCGGTAATCTGTAATTGCCTGTTAATCAATAA
ACCGGTTGATTCGTTTCAGTTGAACTTTGGTCTCTGCG

*FIG. 16*

AAV-9, GENBANK ACCESSION NO. AX753250 AND GAO ET AL. (MAY 14, 2003)
EP1310571
CAGAGAGGGAGTGGCCAACTCCATCACTAGGGGTAATCGCGAAGCGCCTCCCACGCTGCCGCGTC
AGCGCTGACGTAGATTACGTCATAGGGGAGTGGTCCTGTATTAGCTGTCACGTGAGTGCTTTTGC
GACATTTTGCGACACCACATGGCCATTTGAGGTATATATGGCCGAGTGAGCGAGCAGGATCTCCA
TTTTGACCGCGAAATTTGAACGAGCAGCAGCCATGCCGGGCTTCTACGAGATTGTGATCAAGGTG
CCGAGCGACCTGGACGAGCACCTGCCGGGCACTCTCTTTGTGAACTGGGTGGCCGAGAA
GGAATGGGAGCTGCCCCCGGATTCTGACATGGATCGGAATCTGATCGAGCAGGCACCCCTGACCG
TGGCCGAGAAGCTGCAGCGCGACTTCCTGGTCCAATGGCGCCGCGTGAGTAAGGCCCCGGAGGCC
CTCTTCTTTGTTCAGTTCGAGAAGGGCGAGAGCTACTTTCACCTGCACGTTCTGGTCGAGACCAC
GGGGGTCAAGTCCATGGTGCTAGGCCGCTTCCTGAGTCAGATTCGGGAGAAGCTGGTCCAGACCA
TCTACCGCGGATCGAGCCGACCCTGCCCAACTGGTTCGCGGTGACCAAGACGCGTAATGGCGCC
GGCGGGGGAACAAGGTGGTGGACGAGTGCTACATCCCCAACTACCTCCTGCCCAAGACTCAGCC
CGAGCTGCAGTGGGCGTGGACTAACATGGAGGAGTATATAAGCGCGTGCTTGAACCTGGCCGAGC
GCAAACGGCTCGTGGCGCAGCACCTGACCCACGTCAGCCAGACGCAGGAGCAGAACAAGGAGAAT
CTGAACCCCAATTCTGACGCGCCCGTGATCAGGTCAAAAACCTCCGCGCGCTACATGGAGCTGGT
CGGGTGGCTGGTGGACCGGGGCATCACCTCCGAGAAGCAGTGGATCCAGGAGGACCAGGCCTCGT
ACATCTCCTTCAACGCCGCCCTCCAACTCGCGGTCCCAGATCAAGGCCGCGCTGGACAATGCCGGC
AAGATCATGGCGCTGACCAAATCCGCGCCCGACTACCTGGTAGGCCCCTTCACTTCCGGTGGACAT
TACGCAGAACCGGCATCTACCGCATCCTGCAGCTCAACGGCTACGACCCTGCCTACGCCGGCTCCG
TCTTTCTCGGCTGGGCACAAAAGAAGTTCGGGAAACGCAACACCATCTGGCTGTTTGGGCCGGCC
ACCACGGGAAAGACCAACATCGCAGAAGCCATTGCCCACGCCGTGCCCTTCTACGGCTGCGTCAA
CTGGACCAATGAGAACTTTCCCTTCAACGATTGCGTCGACAAGATGGTGATCTGGTGGGAGGAGG
GCAAGATGACGGCCAAGGTCGTGGAGTCCGCCAAGGCCATTCTCGGCGGCAGCAAGGTGCGCGTG
GACCAAAAGTGCAAGTCGTCCGCCCAGATCGACCCCACTCCCGTGATCGTCACCTCCAACACCAA
CATGTGCGCCGTGATTGACGGGAACAGCACCACCTTCGAGCACCAGCAGCCTCTCCAGGACCGGA
TGTTTAAGTTCGAACTCACCCGCCGTCTGGAGCACGACTTTGGCAAGGTGACAAAGCAGGAAGTC
AAAGAGTTCTTCCGCTGGGCCAGTGATCACGTGACCGAGGTGGCGCATGAGTTTTACGTCAGAAA
GGGCGGAGCCAGCAAAAGACCCGCCCCCGATGACGCGGATAAAAGCGAGCCCAAGCGGGCCTGCC
CCTCAGTCGCCGGATCCATCGACGTCAGACGCGGAAGGAGCTCCGGTGACTTTGCCGACAGGTAC
CAAAACAAATGTTCTCGTCACGCGGGCATGCTTCAGATGCTGCTTCCCTGCAAAACGTGCGAGAG
AATGAATCAGAATTTTCAACATTTGCTTCACACACGGGGTCAGAGACTGCTCAGAGTGTTTCCCCG
GCGTGTCAGAATCTCAACCGGTCGTCAGAAAGAGGACGTATCGGAAACTCTGTGCGATTCATCAT
CTGCTGGGGCGGGCTCCCGAGATTGCTTGCTCGGCCTGCGATCTGGTCAACGTGGACCTGGATGA
CTGTGTTTCTGAGCAATAAATGACTTAAACCAGGTATGGCTGCCGATGGTTATCTTCCAGATTGG
CTCGAGGACAACCTCTCTGAGGGCATTCGCGAGTGGTGGGCGCTGAAACCTGGAGCCCCGAAGCC
CAAAGCCAACCAGCAAAAGCAGGACGACGGCCGGGGTCTGGTCGCTTCCTGGCCTACAAGTACCTCG
GACCCTTCAACGGACTCGACAAGGGGGAGCCCGTCAACGCGGCGGACGCAGCGGCCCTCGAGCAC
GGCAAGGCCTACGACCAGCAGCTGCAGGCGGGTGACAATCCGTACCTGCGGTATAACCACGCCGA
CGCCGAGTTTCAGGAGCGTCTGCAAGAAGATACGTCTTTTGGGGGCAACCTCGGGCGAGCAGTCT
TCCAGGCCAAGAAGCGGGTTCTCGAACCTCTCGGTCTGGTTGAGGAAGGCGCTAAGACGGCTCCT
GGAAAGAAGAGACCCGTAGAGCCATCACCCCCAGCGTTCTCCAGACTCCTCTACGGGCATCGGCAA
GAAAGGCCAACAGCCCGCCAGAAAAAGACCTCAATTTTGGTCAGACTGGCGACTCAGAGTCAGTTC
CAGACCCTCAACCTCTCGGAGAACCTCCAGCAGCGCCCTCTGGTGTGGGACCTAATACAATGGCT
GCAGGCGGTGGCGCACCAATGGCAGACAATAACGAAGGCGCCGACGGAGTGGGTAATTCCTCGGG
AAATTGGCATTGCGATTCCACATGGCTGGGGGACAGAGTCATCACCACCAGCACCCGAACCTGGG
CATTGCCCACCTACAACAACCACCTCTACAAGCAAATCTCCAATGGAACATCGGGAGGAAGCACC
AACGACAACACCTACTTTGGCTACAGCACCCCCTGGGGGTATTTTGACTTCAACAGATTCCACTG
CCACTTCTCACCACGTGACTGGCAGCGACCTCATCAACAACAACTGGGGATTCCGGCCAAAGAGAC
TCAACTTCAAGCTGTTCAACATCCAGGTCAAGGAGGTTACGACGAACGAAGGCACCAAGACCATC
GCCAATAACCTTACCAGCACCGTCCAGGTCTTTACGGACTCGGAGTACCAGCTACCGTACGTCCT
AGGCTCTGCCCACCAAGGATGCCTGCCACCGTTTCCTGCAGACGTCTTCATGGTTCCTCAGTACG
GCTACCTGACGCTCAACAATGGAAGTCAAGCGTTAGGACGTTCTTCTTTCTACTGTCTGGAATAC
TTCCCTTCTCAGATGCTGAGAACCGGCAACAACTTTCAGTTCAGCTACACTTCGAGGACGTGCC
TTTCCACAGCAGCTACGCACACACCAGAGTCTAGATCGACTGATGAACCCCCTCATCGACCAGT
ACCTATACTACCTGGTCAGAACACAGACAACTGGAACTGGGGGAACTCAAACTTTGGCATTCAGC
CAAGCAGGCCCTAGCTCAATGGCCAATCAGGCTAGAAACTGGGTACCCGGGCCTTGCTACCGTCA
GCAGCGCGTCTCCACAACCACCAACCAAAATAACAACAGCAACTTTGCGTGGACGGGAGCTGCTA
AATTCAAGCTGAACGGGAGAGACTCGCTAATGAATCCTGGCGTGGCTATGGCATCGCACAAAGAC
GACGAGGACGCCGCTTCTTTCCATCAAGTGACGTTCTCATATATTTGGCAAGCAAGGAGCGGGAACGA
TGGAGTCGACTACAGCAGGTGCTGATTACAGATGAGGAAGAAATTAAAGCCACCAACCCTGTAG
CCACAGAGGAATACGGAGCAGTGGCCATCAACAACCAGGCCGCTAACACGCAGGCGCAAACTGGA
CTTGTGCATAACCAGGGAGTTATTCCTGGTATGGTCTGGCAGAACCGGGACGTGTACCTGCAGGG
CCCTATTTGGGCTAAAATACCTCACACAGATGGCAACTTTCACCCGTCTCCTCTGATGGGTGGAT
TTGGACTGAAACACCCACCTCCACAGATTCTAATTAAAAATACACCAGTGCCGGCAGATCCTCCT
CTTACCTTCAATCAAGCCAAGCTGAACTCTTTCATCACGCAGTACAGCACCGGGCAAGTCAGCGT
GGAAATCGAGTGGGAGCTGCAGAAAGAAAACAGCAAGCGCTGGAACCCAGAGATCCAGTATACTT
CAAACTACTACAAATCTACAAATGTGGACTTTGCTGTCAATACCAAAGGTGTTTACTCTGAGCCT
CGCCCCATTGGTACTCGTTACCTCACCCGTAATTTGTAATTGCCTGTTAATCAATAAACCGGTTA
ATTCGTTTCAGTTGAACTTTGGTCTCTGCG

FIG. 17

AAV-11, NONSTRUCTURAL PROTEIN AND CAPSID PROTEIN GENES, COMPLETE CDS,
GENBANK ACCESSION NO. AY631966 AND MORI ET AL. (2004) VIROL. 330:375
ATGCCGGGCTTCTACGAGATCGTGATCAAGGTGCCGAGCGACCTGGACGAGCACCTGCCGGGC
ATTTCTGACTCGTTTGTGAACTGGGTGGCCGAGAAGGAATGGGAGCTGCCCCCGGATTCTGAC
ATGGATCGGAATCTGATCGAGCAGGCACCCCTGACCGTGGCCGAGAAGCTGCAGCGCGACTTC
CTGGTCCACTGGCGCCGCGTGAGTAAGGCCCGCGGAGGCCCTCTTCTTTGTTCAGTTCGAGAAG
GGCGAGTCCTACTTCCACCTCCACGTTCTCGTCGAGACCACGGGGGTCAAGTCCATGGTCCTG
GGCCGCTTCCTGAGTCAGATCAGAGACAGGCTGGTGCAGACCATCTACCGGGGTCGAGCCC
ACGCTGCCCAACTGGTTCGCGGTGACCAAGACGCGAAATGGCGCCGGCGGGGGGAACAAGGTG
GTGGACGAGTGCTACATCCCCAACTACCTCCTGCCCAAGACCCAGCCCGAGCTGCAGTGGGCG
TGGACTAACATGGAGGAGTATATAAGCGCGTGTCTAAACCTCGCGGAGCGTAAACGGCTCGTG
GCGCAGCACCTGACCCACGTCAGCCAGCACGACGGAGCGAACAAGGAGAATCTGAACCCGAAT
TCTGACGCGCCCGTGATCAGGTCAAAAACCTCCGCGCGCTACATGGAGCTGGTCGGGTGGCTG
GTGGACCGGGGCATCACCTCCGAGAAGCAGTGGATCCAGGAGGACCAGGCCTCGTACATCTCC
TTCAACGCCGCCTCCAACTCGCGGTCCCAGATCAAGGCCGCGCTGGACAATGCCGGAAAGATC
ATGGCGCTGACCAAATCCGCGCCCGACTACCTGGTAGGCCCGTCCTTACCCGCGGACATTAAG
GCCAACCGCATCTACCGCATCCTGGAGCTCAACGGCTACGACCCCGCCTACGCCGGCTCCGTC
TTCCTGGGCTGGCGCAGAAAAAGTTCGGTAAACGCAACACCATCTGCTGTGTTTGGGCCCGCC
ACCACCGGCAAGCAACATCGCGGAAGCCATAGCCCACGCCGTGCCCTTCTACGGCTGCGTG
AACTGGACCAATGAGAACTTTCCCTTCAACGATTGCGTCGACAAGATGGTGATCTGGTGGGAG
GAGGGCAAGATGACCGCCAAGGTCGTGGAGTCCGCCAAGGCCATTCTGGGCGGAAGCAAGGTG
CGCGTGGACCAAAAGTGCAAGTCCTCGGCCCAGATCGACCCCACGCCCGTGATCGTCACCTCC
AACACCAACATGTGCGCCGTGATCGACGGGAACAGCACCACCTTCGAGCACCAGCAGCCGCTG
CAGGACCGCATGTTCAAGTTCGAGCTCACCCGCCGTCTGGAGCACGACTTTGGCAAGGTGACC
AAGCAGGAAGTCAAAGAGTTCTTCCGCTGGGCTCAGGATCACGTGACTGAGGTGGCGCATGAG
TTCTACGTCAGAAAGGGCGGAGCCACCAAAAGACCCGCCCCCAGTGACGCGGATATAAGCGAG
CCCAAGCGGGCCTGCCCCTCAGTTCCGGAGCCATCGACGTCAGACGCGGAAGCACCGGTGGAC
TTTGCGGACAGGTACCAAAACAAATGTTCTCGTCACGCGGGCATGCTTCAGATGCTGTTTCCC
TGCAAGACATGCGAGAGAATGAATCAGAATTTCAACGTCTGCTTCACGCACGGGGTCAGAGAC
TGCTCAGAGTGCTTCCCCGGCGCGTCAGAATCTCAACCCGTCGTCAGAAAAAGACGTATCAG
AAACTGTGCGCGATTCATCATCTGCTGGGGCGGGCACCCGAGATTGCGTGTTCGGCCTGCGAT
CTCGTCAACGTGGACTTGGATGACTGTGTTTCTGAGCAATAAATGACTTAAACCAGGTATGGC
TGCTGACGGTTATCTTCCAGATTGGCTCGAGGACAACCTCTCTGAGGGCATTCGCGAGTGGTG
GGACCTGAAACCTGGAGCCCCGAAGCCCAAGGCCAACCAGCAGAAGCAGGACGACGGCCGGGG
TCTGGTGCTTCCTGGCTACAAGTACCTCGGACCCTTCAACGGACTCGACAAGGGGGAGCCCGT
CAACGCGACGACGCAGCGCCCTCGAGCACGACAAGGCCTACGACCCAGCAGCTCAAAGCGGG
TGACAATCCGTACCTGCGGTATAACACGCCGACGCCGAGTTTCAGGAGCGTCTGCAAGAAGA
TACGTCTTTTGGGGGCAACCTCGGGCGAGCAGTCTTCCAGGCCAAGAAGAGGGTACTCGAACC
TCTGGGCCTGGTTGAAGAAGGTGCTAAAACGGCTCCTGGAAAGAAGAGACCGTTAGAGTCACC
ACAAGAGCCCGACTCCTCCTCGGGCATCGGCAAAAAAGGCAAACAACCAGCCAGAAAGAGGCT
CAACTTTGAAGAGGACACTGGAGCCGGACACGGACCCCCTGAAGGATCAGATACCAGCGCCAT
GTCTTCAGACATTGAAATGCGTGCAGCACCGGGCGGAAATGCTGTCGATGCGGGACAAGGTTC
CGATGGAGTGGGTAATGCCTCGGGTGATTGGCATTGCGATTCCACCTGGTCTGAGGGCAAGGT
CACAACAACCTCGACCAGAACCTGGGTCTTGCCCACCTACAACAACCACTTGTACCTGCGTCT
CGGAACAACATCAAGCAGCAACACCTACAACGGATTCTCCACCCCCTGGGGATATTTTGACTT
CAACAGATTCCACTGTCACTTCTCACCACGTGACTGGCAAAGACTCATCAACAACAACTGGGG
ACTACGACCAAAAGCCATGCGCGTTAAAATCTTCAATATCCTAAGTTAAGGAGGTCACAACGTC
GAACGGCGAGACTACGGTCGCTAATAACCTTACCGACCACCGGTTCAGATATTTGCGGACTCGTC
GTATGAGCTCCCGTACGTGATGGACGCTGGACAAGAGGGGGAGCCTGCCTCCTTTCCCCAATGA
CGTGTTCATGGTGCCTCAATATGGCTACTGTGGCATCGTGACTGGCGAGAATCAGAACCAAAC
GGACAGAAACGCTTTCTACTGCCTGGAGTATTTCCTTCGCAAATGTTGAGAACTGGCAACAA
CTTTGAAATGGCTTACAACTTTGAGAAGGTGCCGTTCCACTCAATGTATGCTCACAGCCAGAG
CCTGGACAGACTGATGAATCCCCTCCTGGACCAGTACCTGTGGCACTTACAGTCGACTACCTC
TGGAGAGACTCTGAATCAAGCAATGCCAACCACATTTGGAAAAATCAGGAGTGGAGACTT
TGCCTTTTACAGAAAGAACTGGCTGCCTGGGCCTTGTGTTAAACAGCAGAGATTCTCAAAAAC
TGCCAGTCAAAATTACAAGATTCCTGCCAGCGGGGGCAACGCTCTGTTAAAGTATGACACCCA
CTATACCTTAAACAACCGCTGGAGCAACATCGCGCCCGGACCTCCAATGGCCACAGCCGGACC
TTCGGATGGGGACTTCAGTAACGCCCAGCTTATATTCCCTGGACCATCTGTTACCGGAAATAC
AACAACTTCAGCCAACAATCTGTTGTTTACATCAGAAGAAATTGCTGCCACCAACCCAAG
AGACACGGACATGTTTGGCCAGATTGCTGACAATAATCAGAATGCTACAACTGCTCCCATAAC
CGGCAACGTGACTGCTATGGGAGTGCTGCCTGGCATGGTGTGCAAAACAGAGACATTTACTA
CCAAGGGCCAATTTGGGCCAAGATCCCACACGCGGACGGACATTTTCATCCTTCACCGCTGAT
TGGTGGGTTTGGACTGAAACACCCGCCTCCCCAGATATTCATCAAGAACACTCCCGTACCTGC
CAATCCTGCGACAACCTTCACTGCAGCCAGAGTGGACTCTTTCATCACACAATACAGCACCGG
CCAGGTCGCTGTTCAGATTGAATGGGAAATTGAAAAGGAACGCTCCAAACGCTGGAATCCTGA
AGTGCAGTTTACTTCAAACTATGGGAACCAGTCTTTCTATGTTGTGGGCTCCTGATACAACTGG
GAAGTATACAGAGCCGCGGGTTATTGGCTCTCGTTATTTGACTAATCATTTGTAA

FIG. 18

AAV-13, NONSTRUCTURAL PROTEIN AND CAPSID PROTEIN GENES, COMPLETE CDS.
GENBANK ACCESSION NO. EU285562 AND SCHMIDT ET AL. (2008) J. VIROL.
82:8911

```
CCGCGAGTGAGCGAACCAGGAGCTCCATTTTGCCCGCGAATTTTGAACGAGCAGCAGCCATGC
CGGGATTCTACGAGATTGTCCTGAAGGTGCCCAGCGACCTGGACGAGCACCTGCCTGGCATTT
CTGACTCTTTTGTAAACTGGTGGCGGAGAAGGAATGGGAGCTGCCGCCGGATTCTGACATGG
ATCTGAATCTGATTGAGCAGGCACCCCTAACCGTGCCGAAAAGCTGCAACGCGAATTCCTGG
TCGAGTGGCGCCGCGTGAGTAAGGCCCCGGAGGCCCTCTTCTTTGTTCAGTTCGAGAAGGGGG
ACAGCTACTTCCACCTACACATTCTGGTGGAGACCGTGGGCGTGAAATCCATGGTGGTGGGCC
GCTACGTGAGCCAGATTAAAGAGAAGCTGGTGACCCGCATCTACCGCGGGGTCGAGCCGCAGC
TTCCGAACTGGTTCGCGGTGACCAAGACGCGTAATGGCGCCGGAGGCGGGAACAAGGTGGTGG
ACGACTGCTACATCCCCAACTACCTGCTCCCCAAGACCCAGCCCGAGCTCCAGTGGGCGTGGA
CTAATATGGACCAGTATTTAAGCGCCTGTTTGAATCTCCGGGAGCGTAAACGGCTGGTGGCGC
AGCATCTGACGCACGTGTCGCAGACGCAGGAGCAGAACAAAGAGAACCAGAATCCCAATTCTG
ACGCGCCGGTGATCAGATCAAAAACCTCCGCGAGGTACATGGAGCTGGTCGGGTGGCTGGTGG
ACCGCGGGATCACGTCAGAAAAGCAATGGATCCAGGAGGACCAGGCCTCTTACATCTCCTTCA
ACGCCGCCTCCAACTCGCGGTCACAAATCAAGGCCGCACTGGACAATGCCTCCAAATTTATGA
GCCTGACAAAAACGCCTCCGGACTACCTGGTGGGAAACAACCCGCCGGAGGACATTACCAGCA
ACCGGATCTACAAAATCCTCGAGATGAACGGGTACGATCCGCAGTACGCCGCCTCCGTCTTCC
TGGGCTGGGCGCAAAAGAAGTTCGGGAAGAGGAACACCATCTGGCTCTTTGGGCCGGCCACGA
CGGGTAAAACCAACATCGCTGAAGCTATCGCCCACGCCGTGCCCTTTTACGGCTGCGTGAACT
GGACCAATGAGAACTTTCCGTTCAACGATTGCGTCGACAAGATGGTGATCTGGTGGGAGGAGG
GCAAGATGACGGCCAAGGTCGTGGAGTCCGCCAAGGCCATTCTGGGCGGAAGCAAGGTGCGCG
TGGACCAAAAGTGCAAGTCATCCGCCATCGATCGACCCAACTCCCGTCATCGTCACCTCCAACA
CCAACATGTGCGCGGTCATCGACGGAAATTCCACCACCTTCGAGCACCAACAACCACTCCAAG
ACCGGATGTTCAAGTTCGAGCTCACCAAGCGCCTGGAGCACGACTTTGGCAAGGTCACCAAGC
AGGAAGTCAAGGACTTTTTCCGGTGGGCGTCAGATCACGTGACTGAGGTGTCTCACGAGTTTT
ACGTCAGAAAGGGTGGAGCTAGAAAGAGGCCCGCCCCAATGACGCAGATATAAGTGAGCCCA
AGCGGGCCTGTCCGTCAGTTGCGCAGCCATCGACGTCAGACGCGGAAGCTCCGGTGGACTACG
CGGACAGGTACCAAAACAAAATGTTCTCGTCACGTGGGCATGAATCTGATGCTTTTTCCCTGCC
GGCAATGCGAGAATGAATCAGAATGTGGACATTTGCTTCACGCACGGGTCATGGACTGTG
CCGAGTGCTTCCCCGTGTCAGAATCTCAACCCGTGTCTGTCGTCAGAAAGCGGACATATCAGA
AACTGTGTCCGATTCATCACATCATGGGGAGGGCGCCCGAGGTGGCTTGTTCGGCCTGCGATC
TGGCCAATGTGGACTTGGATGACTGTGACATGGAGCAATAAATGACTCAAACCAGATATGACT
GACGGTTACCTTCCAGATTGGCTAGAGGACAACCTCTCTGAAGGCGTTCGAGAGTGGTGGGCG
CTGCAACCTGAGCCCCTAAACCCAAGGCAAATCAACAACATCAGGACAACGCTCGGGGTCTT
GTGCTTCCGGGTTCAAATACCTCGGACCCGGCAACGGACTTGACAAGGGGGAACCCGTCAAC
GCAGCGGACGCGGCAGCCCTCGAACACGACAAGGCCTACGACCAGCAGCTCAAGGCCGGTGAC
AACCCCTACCTCAAGTACAACCACGCCGACGCCGAGTTTCAGGAGCGTCTTCAAGAAGATACG
TCTTTTGGGGGCAACCTCGGACGAGCAGTCTTCCAGGCCAAAAAGAGGATCCTTGAGCCTCTG
GGTCTGGTTGAGGAAGCGGCTAAGACGGCTCCTGGAAAAAAGAGACCTGTAGAGCAATCTCCA
GCAGAACCGGGACTCCTCTTCGGGCATCGGCAAATGACGGCCAGCGACCCGCTAGAAAAAGACTG
AATTTTGGTCAGACTGGCCACAGAGTCAGTCCCAGACCCTCAACCACTCGGACAACCTCCC
GCAGCCCCCTCTGGTGTGGGATCTACTACAATGGCTTCAGGCGGTGGCGCACCAATGGCAGAC
AATAACGAGGGTGCCGATGGAGTGGGTAATTCCTCAGGAAATTGGCATTGCGATTCCCAATGG
CTGGGCGACAGAGTCATCACCACCAGCACCCGCACCTGGGCCCTGCCCACCTACAACAATCAC
CTCTACAAGCAAATCTCCAGCCAATCAGGAGCCGCACCAACGACAACCACTACTTTGGCTACAGC
ACCCCCTGGGGGTATTTTGACTTCAACAGATTCCACTGCCACTTTTCACCACGTGACTGGCAA
AGACTCATCAACAACAACTGGGGATTCCGACCCAAGGAGACTCAACTTCAAGCTCTTTAACATT
CAAGTCAAAGAGGTCACGCAGAATGACGGTACGACGACGATTGCCAATAACCTTACCAGCACG
GTTCAGGTGTTTACTGACTCCGAGTACCAGCTCCCGTACGTCCTCGGCTCGGCGCATCAGGGA
TGCCTCCCGCCGTTCCCAGCAGACGTCTTCATGGTCCCACAGTATGGATACCTCACCCTGAAC
AACGGGAGTCAGGCGGTAGGACGCTCTTCCTTTTACTGCCTGGAGTACTTTCCTTCTCAGATG
CTGCGTACTGGAAACAACTTTCAGTTTAGCTACACATTTTGAAGACGTGCCTTTCCACAGCAGC
TACGCTCACAGCCAAAGTCTGGACCGTCTCATGAATCCTCTGATCGTGACCAGTACCTGTACTAT
CTGAACAGGACACAAACAGCCAGTGGAACTCAGCAGTCTCGGCTACTGTTTAGCCAAGCTGGA
CCCACCAGTATGTCTCTTCAAGCTAAAAACTGGCTGCCTGGACCTTGCTACAGACAGCAGCGT
CTGTCAAAGCAGGCAAACGACAACAACAACAGCAACTTTCCCTGGACTGGTGCCACCAAATAT
CATCTGAATGGCCGGACTCATTGGTGAACCCGGGCCCTGCTATGCCAGTCACAAGGCATGAC
AAAGAAAAGTTTTTCCCCATGCATGGAACCCTGAAATTTGGTAAAGAAGGAACAAATGCCAAC
AACGCGGATTTGGAAAATGTCATGATTACAGATGAAGAAGAAATCCGCACCACCAATCCCGTG
GCTACGGAGCAGTACGGGACTGTGTCAAATAATTTGCAAAACTCAAACGCTGGTCCAACTACT
GGAACTGTCAATCACCAAGGAGCGTTACCTGGTATGGTGTGGCAGGATCGAGACGTGTACCTG
CAGGGACCCATTTGGGCCAAGATTCCTCACACCGATGGACACTTTCATCCTTCTCCACTGATG
GGAGGTTTTGGGCTCAAACACCCGCCTCCTCAGATCATGATCAAAAACACTCCCGTTCCAGCC
AATCCTCCCACAAATTTAGTGCGGCAAGTTTCCTTCATCACACAGTACTCCACGGGG
CAGGTCAGCGTGGAGATCGAGTGGGAGCTGCAGAAGGAGAACAGCAAACGCTGGAATCCCGAA
ATTCAGTACACTTCCAACTACAACAAATCTGTTAATGTGGACTTTACTGTGGACACTAATGGT
GTGTATTCAGAGCCTCGCCCCATTGGCACCAGATACCTGACTCGTAATCTGTAATTGCTTGTT
AATCAATAAACCGGTTAATTCG
```

MINUTE VIRUS FROM MOUSE (MVM), COMPLETE SEQUENCE, GENBANK ACCESSION
NO. NC 001510
ATTTTTAGAACTGACCAACCATGTTCACGTAAGTGACGTGATGACGCGCGCTGCGCGCGCGCCTTCGGACGTC
ACACGTCACTTACGTTTCACATGGTTGGTCAGTTCTAAAAATGATAAGCGGTTCAGGGAGTTTAAACCAAGGC
GCGAAAAGGAAGTGGGCGTGGTTTAAAGTATATAAGCAACTACTAGTGAAGTCAGTTACTTATCTTTTCTTTCATT
CTGTGAGTCGAGACGCACAGAAAGAGAGTAACCAACTAACCATGGCTGGAAATGCTTACTCTGATCAAGTTTT
GGGAGCAACCAACTGGTTAAAGGAAAAAGTAACCAGGCAAGTGTTCTCATTTGTTTTTAAAAATGAAAATGTT
CAACTGAATGGAAAAGATATCGGATGGAATAGTTACAAAAAAGAGCTGCAGGAGGACGAGCTGAAATCTTTAC
AACGGAGGAGCGGAAACTACTTGGGACCAAAGCGAGCGACATGGGAATGGGGAAACCACAGTGGATGAAATGACCAA
AAAGCAAGTATTCATTTTTGATTCTTTGGTTAAAAAATGTTTATTTGAAGTGCTTAACACAAAGAATATATTT
CCTGGTGATGTTAATTGGTTTGTGCAACATGAATGGGGAAAAGACCAAGGCTGGCACTGCCATGTACTAAGTG
GAGGAAAGGACTTTAGTCAAGCTCAAGGGGAAATGGTGGAGAAGGCAACTAAATGTTTACTGGAGCAGATGGTT
GGTAACAGCCTGTAATGTGCAACTAACACCCAGCTGAAAGAATTAAACTAAGAGAAATAGCAGAAGACAATGAG
TGGGTTACTCTACTTACTTATAAGCATAAGCAAACCAAAAAGACTATACCAAGTGTGTTCTTTTTGGAAACA
TGATTGCTTACTATTTTTAACTAAAAAGAAAATAAGCACTAGTCCACCAAGAGACGGACGGCTATTTTCTTAG
CAGTGACTCTGGCTGGAAAACTAACTTTTTAAAAGAAGCGCAGCGCCATCTAGTGAGCAAACTATACACTGAT
GACATGCGGCCAGAAACGGTTGAAACCACAGTAACCACTGCGCAGGAAACTAAGCGCGCGCAGAATTCAAACTA
AAAAAGAAGTTTCTATTAAAACTACACTTAAAGAGCTGGTGCATAAAGAGTAACCTCACCAGAGGACTGGAT
GATGATGCAGCCAGACAGTTACATTGAAATGATGGCTCAACCAGGTGGAGAAAACCTGCTGAAAAATACGCTA
GAGATTTTGTACACTAACTCTAGCCAGAAGTAACACAGCATTTGACTTAATTTTAGAAAAAGCTGAAACCAGCA
AACTAACCAACTTTTCACTGCCTGACACAAGAACCTGCAGAATTTTTGCTTTTCATGGCTGGAACTATGTTAA
AGTTTGCCATGCTATTTGCTGTGTTTTAAACAGACAAGGCAGGCAAAAGAAATACTGTTTTATTTCATGGACCA
GCCAGGCACAGGCAAATCTATTATTGCACAAGCCATAGCACAAGCAGTTGGCAATGTTGGTTGCTATAATGCAG
CCAATGTAAACTTTCCATTTAATGACTGTACCAACAAGAACCTGATTTGGGTAGAAGAAGCTGGTAACTTTGG
ACAGCAAGTAAACCAGTTTAAAGCCATTTGCTCTCTGGTCAAACTATTCGCATTGATCAAAAAGGAAAAGGCAGC
AAACAGATTGAACCAACACCAGTCATCATGACCACAAATGAGAACATTACAGTGGTCACAATAGGCTGCGAAG
AAAGACCAGAACACACTCAACCAATCAGAGACAGAATGCTTAACATTCATCTAACACATACCTTGCCTGGTGA
CTTTGGTTTGGTTGACAAAAATGAATGGCCCATGATTGTTGTGCTTGGTTGGTAAGAATCGTTACCAATCTACC
ATGGCAAGCTACTGTGCTAAATGGGGCAAAGTTCCTGATTGGTCAGAAAACTGGGCGGAGCCAAAGGTGCCAA
CTCCTATAAATTTACTAGGTTCGGCACGCTCACCATTCACGACACCGAAAAGTACGCCTCTCAGCCAGAACTA
TGCACTAACTCCACTTGCATCGGATCTCGAGGACCTGGCTTTAGAGCCTTGGGAGCACACCAAATACTCCTGTT
GCGGGCACTGCAGAAACCCAGAACACTGGGGAAGCTGGTTCCAAAGCCTGCCAAGATGGTCAACTCAGCCCAA
CTTGGTCAGAGATCGAGGAGGATTTGAGAGCGTGCTTCGGTGCGGAACCGTTCAAGAAAGACTTCAGCGAGCC
GCTGAACTTGGACTAAGGTACGATGGCGCCTCCAGCTAAAAGAGCTAAAAGAGGTAAGGGTTTAAGGGATGGT
TGGTTGGTGGGGTATTAATTGTTTAATTACCTGTTTACAGGCCCTGAAATCACTTGGTTTTTAGGTTGGGTGCCT
CCTGGCTACAAGTACCTGGGACCAGGGAACAGCCTTTGACCAAGGAGACAACCAATCCATCTGACGCGCTG
CCAAAGAGCACGACGAGGCCTATGATCAATACATCAAATCTGGAAAAAATCCTTACCTGTACTTCTCTGCTGC
TGATCAACGCTTTATTGACCAAACCAAGGACGCCAAAGACTGGGGAGGCAAGGTTGGTCACTACTTTTTTAGA
ACCAAGCGCGCTTTTCCACCTAAGCCTTGCTACTGACTCTGAACCTGGAACTTCTGGTGTAAGCAGAGCTGGTA
AACGCACTAGACCACCTGCTTACATTTTTATTAACCAAGCCAGAGCTAAAAAAAACTTACTTCTTCTGCTGC
ACAGCAAAGCAGTCAAACCATGACTGATGGCACCAGCCAACCTGACAGCGGAAACGCTGTCCACTCAGCTGCA
AGAGTTGAACGAGCAGCTGACGGCCCTGGAGGCTCTGGGGGTGGGGCTCTGGCGGGGGTGGGGTTGGTGTTT
CTACGGGTCTTATGATAATCAAACGCATTATAGATTCTTGGGTGACGCGTGGGTAGAAATTACTGCACTAGC
AACTAGACTAGTACATTTAAACATGCCTAAATCAGAAAACTATTGCAGAATCAGAGTTCACAATACAACAGAC
ACATCAGTCAAAGGCAACATGGCAAAAGATGATGCTCATGAGCAAATTTGGACACCATGGAGCTTGGTGGATG
CTAATGCTTGGGGAGTTTGCTCCAGCCAAGTGACTGGCAATACATTTGCAACACCATGAGCCAGCTTAACTT
GGTATCACTTGATCAAGAAATATTCAATGTAGTGCTGAAAACCTGTTACAGCAAGACTTAGGAGGGTCAAGCT
ATAAAAATATACAACAATGACCTTACAGCTTGCATGATGGTTGCAGTAGACTCAAACAACATTTTGCCATACA
CACCTGCAGCAAACTCAATGGAAACACTTGGTTTCTACCCCTGGAAACCAACCATAGCATCACCATACAGGTA
CTATTTTTGCGTTTGACAGATCTTTCAGTGACCTACCGAAAATCAAGAAGGCACAGTTGAACATAATGTGATG
GGAACACCAAAAGGAATGAATTCTAACATTTCTTACCATTGGAACAACACACAAACAATTCATTGCTCAGAACAG
GGGACGAATTTGCCACAGGTACTTACTACTTTGACACAAATTCAGTTAAACTCACACACACGTGGCAAACCAA
CCGTCAACTTGGACAGCCTCCACTGCTGTCAACCTTTCCTGAAGCTGACACTGATGCAGGTACACTTACTGCT
CAAGGGACAGCATGGAACAACAAAAATGGGGGTTAACTGGGTGAGTGAAGCAATCAGAACCAGACCTGCTC
AAGTAGGGATTTTGTCAACCACACAATGACTTTGAAGCCAGCAGAGCTGGACCATTGTGCCCCCAAAAGTTCC
AGCAGATATTACTCAAGGGAGTAGACAAAGAAGGCCAATGGCAGTGTTAGATACAGTTATGGCAAACAGCATGGT
GAAAATTGGGCTTCACATGGACCAGCACCAGAGCGCTACACATGGGATGAAACAAGCTTTGGTTCAGGTAGAG
ACACCAAAGATGGTTTATTCAATCAGCACCACTAGTTGTTCCCACCACCACTAAATGGCATTCTTACAAATGC
AAACCCTATTGGGACTAAAAATGACATTCATTTTTCAAATGTTTTAACAGCTATGGTCCACTAACTGCATTT
TCACACCCAAGTCCTGTATACCCTCAAGGACAAATATGGGACAAAGAACTAGATCTTGAACACAAACCTAGAC
TTCACATAACTGCTCCATTTGTTTGTAAAAACAATGCACCTGGACAAATGTTGGTTAGATTAGGACCAAAACCT
AACTGACCAATATGATCCAGAACGCACACTTTCTACGAATGTTACCATATAGCGTACATTTTTCTGGAAAGGA
AAACTAACCATGAGAGCAAAACTTAGAGCTAACACCACTTGGAACCCAGTGTACCAAGTAAGTGCTGAAGACA
ATGGCAACTCATACATGAGTGTAACTAAATGGTTACCAACTGCTACTGGAAACATGCAGTCTGTGCCGCTTAT
AACAAGACCTGTTGCTAGAAATACTTACTAACTAACCATGCTTTTTCTTTCTGTACTTCATATATTATTAAGA
CTAATAAAGATACAACATAGAAATATAATATTACGTATAGATTTAAGAAATAGAATAATATGGTACTTAGTAA
CTGTTAAAAATAATAGAACCTTTGGAATAACAAGATAGTTAGTTGGTTAATGTTAGATAGAATAAGAAGATCA
TGTATAATGAATAAAAGGGTGGAAGGGTGGTTGGTAGGTTAATGTTAGATAGAATAAGAAGATCATGTATAAT
GAATAAAAGGGTGGAAGGGTGGTTGGTAGGTATTCCCTTAGACTTGATGTTAAGGACCAAAAAAATAATAAAA
CTTTTTTAAAACTCAACCAAGACTACTGTCATTCAGTGAACCATTAGTATTACTATGTTTTTA
GGGTGGGAGGGTGGAGATACATGTGTTCGCTATGAGCGAACTGGTACTGGTTGGTTGCTCTGCTCAACCAAC
CAGACCGGCAAAGCCGGTCTGGTTGGTTGAGCGCAACCAACCAGTACCAGTTCGCTCATAGCGAACACATGTA
TCTCCCACCCTCCCACCCTAAAAACATAGTAATACTAAT
```

SNAKE PARVOVIRUS 1, COMPLETE GENOME, GENBANK ACCESSION NO. NC_006148
AND FARKAS ET AL. (2004) J. GEN. VIROL. 85:555

```
CGCCCCACCCCTAGTGATCGCGCGCGCTCTCTCTTGGGGCCTGACGGCCGAAGGCCGTCAGCTGCCGAGC
TTCGCTCGGCAGGCCCCAAGAGAGAGCGCGCGGATCACTAGGGGTGGGGCGGAGTGCCCTGCTCAACGGG
TTTTTTGGTGGGCGGAGCAATGACGTCAGCGGACATGTCTGCACATGTCTTTGAGCAAGTCCATATAAGG
AGTTCCGCCGGATATGCAAATGAGCAATCGCGCAAAGCATTTTGGGTAGTCACCATGAATAAAAAGGACA
GCAAGAAAGATGACGCCCCATAATTTTAATAGGAATTTTAACCATGGCGTTTTACGAGGTTGTGTTTCGT
TTGCCAAGAGACAATAACAACTTGTTGGATGAAGATAGATATCAGCCAGAGTTGAAAGAAGAAGATGACT
GGCCTGAGGAATATTTAACCAGTGAAGATGCCAGCTTTATCGGACTAGCGTATGCTGTGCTAAGTGAAAT
TCGGAGATTCTTTGGAAAGGAACTACAATGGTTTGCCCAGGTTGAATGGTGTCCTACTGCTGGTTACCAC
ATGCATGTTTGTTGAACCATCCTAAGCTGAGTAACCAGACTTATGGAAGAAAGGTCAATGAACTGGCTT
GCCGTATAGTGCATACCCTTTGGCCTAATTAATCCAGAAGAAGTCATCAGTACCCATTATGTTAAAAGCAA
CTATGGACATAAAAAGGTGAGAGTCATTCACCTAGAGTGTTATTTGAAGAACTACTTTTTTCAGAAAGCACT
TTAGCTCCTCCCAATTATACCGAGGAAGGAGACTATAAAAGAGGAAGAAGTCGTGCTGTGGGCATTTA
CGAATATCGTCGCTTGGAAGCCATTCGTGCGGAATCTCATCAAGAGATCGGAGCTAGCGACTGTTCCTAA
GCAACCAGAGAATCCGGCGGGAGACGGACCGGCACCTCGAGTGACTGCAGGAACCCGCCATTTTATGGAA
ACCATCGACTGGTTGGTGAAACATGGAATTACTACAGAACGAGAATTCTGCCACGCCAACCGCCCTTTGT
ACCTGTCTATGCTGGCTTCTACTTCGGGTGCTGGGCAGATTAAAAGAGCGCTGGACCAGGCGAAACACAT
GATGACCAGCACCATGTCAGCAGAGGGATTACCTGACAACAGAAGAGGATGTGATCGAACCACCTACTGAA
AATAGAATCTACAAGATTATGAAACTGAATCGCTATGATCCAGAACTAGCAGCTGCTCTCTTCTACGGCT
GGACCTGCAAGAACTTTGGCAAGAGAAACACCATCTGGCTGTATGGTCCAGCTACTACCGGCAAAACCAT
CATCGCTCAAGCTATTGCACATGCTGTTAAACTGTTTGCTGGTGTTAATTGGACTAATGAAAACTTTCCC
TTCTGTAACTGTCCAGGGAAACTGCTTATCTGGTGGGAGGAGGGCAAGATGACAAACAAAATGGTGGAGA
CGGCTAAATGTATACTGGGGGGATCTGCTGTACCTGTAGACATCAAAGGCAAACCCGCTGAAATGTGTCC
TCAAACACCTGTATTATTACTAGCAATACTAACATGTCTCAAGTATATGATGGTAATAGTTCTAGCTTT
GAGCACCAGAGAACCCCTAGAGAACGCATGTTTATGTTCAGACTTAATACTAAACTGCCATCGACCTTTG
GCAAGATCACAGAAGAGGAAGTCAAACAGTTTATTACCTGGGGGAGGAGCTTAAAGGTTCAAGTTCCACA
TCAGTTCAGAGTGCCTACCACAGGAGAGTATAAAAGGCCAGCCCCCGAGGCGAAAGCTCATTCTTCGGAT
GAGCCGCCAAAAGAGAAGGTCGCGCGTATTGATGACTCTCTAACCAGGTATGTTAACAATATTGATGAGT
CAGCTACCAGTAGAGAAATGTTTCTAGAGATTGCTAATACTAATCAATGTATGTTGCATCATTGCTTTTC
TTGTACCGAATGTTATCCTGAATTGCTTGATGACATGGACAAGGAACAATAAACTTACTGATAACAGATA
TGGATTTTCTCGATGATTTCTTTGCAGATAAATATAAAGAGACTGTTAACGAACTCGGTAAACCGGTCAA
TCCTAAACCTGTAAAACACATTAGCGAAGCTCACTCGCAACCTGGCAGCAGGAGGGGCTTTGTGGTGCCT
GGGTATCGGTATCTTGGGCCTGGTAATAGCTTGGACCGTGGAAAGCCCGTTAACAAAGCAGACGAGGCTG
CTAAAAAGCACGATCAAGAATACGATCAACAGCTTAAAGCGGGAGACAATCCCTACATAAAATATAATCA
CGCGGACGAACAGTTCCAGAAAGCACCTACAAGGTGATACCAGTCTAGCCCGCAACGCGGCTAACGCTCTA
TTTCAAGGCAAAAAGACTCTACTAGCGCCCCTTGGCCTAGTAGAGACCCCTGTCGGCAAAACGTCTGAAA
AGCACAAATTAGACGAATACTATCCTAAAGCTAAAAAGGCCAAACAAGGCTTGCAGATACCAGCTCCACC
TAAAGGCGGAGAAGAAGAAGCTACATCGTCACAATCTGGAGGGAGCCCAGCAGGTTCCGATACTAGCGGC
ACATCTGTCATGGCTACAGGAGGAGGCGGTCCGATGGCAGACGATAACCAGGGCGCCGAGGGAGTGGGTA
ATTCCTCAGGTGATTGGCATTGCGATACCAAGTGGATGGGAGACCACGTCATTACAAAGTCAACCAGAAC
TTGGGTGCTCCCCACTTACGGGAATCATCTCTACGGGCCTATCAACTTTTGACGGCACCACAGGTTCGGGT
GCTAATGCAGCCTATGCAGGATACAAGACTCCCTGGGGGTACTTTGACTTCAATCGATTCCATTGCCACT
TCTCCCCCCGAGACTGGCAAAGACTCATCAACAACCACACAGGCATCAGGCCGAAAGGACTCAAAATCAA
AGTCTTTAACGTCCAAGTCAAAGAAGTTACAACACAAGATTCAACGAAAACAATTGCCAACAATCTCACC
AGCACCGTACAGATCTTTGCGGACGAGAACTACGACTTACCATATGTATTAGGCAGTGCTACACAAGGCA
CATTTCCTCCATTTCCCAATGATGTATTTATGTTACCACAATATGCTTATTGTACACTTCAAGGAAATTC
GGGGAAATTTGTAGATAGAAGTCGCCTTTATTGTTTAGAATATTTTCCTTCACAAATGCTGAGAACAGGA
AACAATTTTGAGTTCCAGTTTAAATTTGAAGAAGTTCCCTTTCATTCTGGATGGGCACAGAGTCAAAGCC
TAGACAGATTGATGAATCCGTTGCTTGATCAATATCTGATAGGAGACTATGGAACAGATGCATCAGGAAA
CCTTATTTATCACAGAGCTGGTCCAAATGATTTGAATGAATTCTACAAGAATTGGGCACCTGCACCCTAT
GAATGTATCCAGAATATTAACAGCAGTGATAATACCAAGAATGCTAATTCTATAAATGGTTCAAATTCTA
CCAACAAATGGGGACTACAAGGAAGACAAGCATGGATGCTCCAGGATTTGTTCAAGCTAGTACCTATGA
AGGTCAGCAGCAGGACAATCTCTTCTTAATGGCGTACTTCAGTAAAGGTTCAGCTACTACTTCA
TCTCCAGCTGCTACTGCAGTAAACAGAACAATTGAAGACGAAATACAGGGTACCAATAATTTTGGTAATG
CTAGAAATAACATTGTTGCTATCAATCAACAAACGAAAGGAACAAATCCAACAACAGGTAGTACATCTCA
ATTGAGACAATGCCAGGTATGGTGTGGTCTAATAGAGACATTTACTTACAGGGGCCTATTTGGGCTAAA
ATTCCAAATACAGATGGACATTTTCATCCTTCTCCCAGAATGGGTGGTTTTGATTAAACATCCTCCGC
CTATGATTCTGATCAAAAATACACCAGTTCCTGCTGATCCTCCAACTACCTTCAATCCAATGCCACAGAC
TAGTTTCATTACTGAATACAGTACAGAAGTAACTGTTGAAAATGTTGTGGGAGGTACAGAAAGAATCC
TCCAAAAGATGGAATCCAGAAGTACAGTTTACTTCCAATTTTGGAACTTCAGATCCAGCTGTTGATGGAA
TACCGTTTGGAATTAATAATTTGGGTACTTATGTTGAATCTAGACCTATTGGAACTCGTTATATTTCTAA
ACACTTGTAAATAATAAAATTGTCAAATTTGCACTAAGAATTGTTGTCACGTGGTTGTTTACATGCTTG
CTAAAACACGCCCACCAAAAAACCCGTTGAGCAGGGCACTCGCCCCACCCCTAGTGATCGCGCGCGCTCT
CTCTTGGGGCCTGCCGAGCGAAGCTCGGCAGCTGACGGCCTTCGGCCGTCAGGCCCAAGAGAGAGCGCG
CGCGATCACTAGGGGTGGGGCG
```

FIG. 23

CHIMERIC ITRS

```
ITR2
    1 AGGAACCCCT AGTGATGGAG TTGGCCACTC CCTCTCTGCG CGCTCGCTCG CTCACTGAGG CCGGGCGACC AAAGGTCGCC CGACGCCCGG CCTTTGGCGC
  101 GTCGCGCTCA GTGAGCGAGC GAGCGCGCAG AGAGGGAGTG GCCAACTCCA TCACTAGGGG TTCCT
ITR5
    1 TACAAAACCT CCTTGCTTGA GAGTGTGGCA CTTCTGCCCC GCTCCGCTCC TGCTGCGCGT CGCGCAGTG GGGCGGGCGA CCTCCCAAAG GCCGGTGTC
  101 TGCAGCTCT TTGAGTTGCC ACCGCCCA ACGAGCCAGC GAGCGACGAG GGGGAGAGTG CCAAGACTCT AAGCAAGAGAG GTTTTGTA
ITR5+3SNS
    1 AGGAACCCCT AGTGATGGAG TTGGCCACTC CTCTCTGCT CCGCTCGCT GTCGTGCTGA GGCGGGCGA CCTCACTGAG GGGCGGGGCG CCCGAGCCCG
  101 GCCTTTGGCG CCGGCCCCT CAGTGAGCGA GCGAGCGGCG AGGGACAC AGTGCGCAAC TCATCACTA GGGGTTCCT
ITR2+5SNS
    1 TACAAAACCT CCTTGCTTGA GAGTGTGGCA CTCCCCCCT AGCGAGCGCG TCACGCGACC TGCTCGACTG AGGCGGGCGA ACCAAAGGTC GCCCGACGCC
  101 CGGCCCTTGG GCCGGCCCCT TCAGTGAGCG CTCAAGCGAGC CGAACCGGAG GTCCACACT CTGAAGCCAG GAGGTTTTGT A
ITR2+2NS
    1 AGGAACCCCT AGTGATGGAG CCTTGCTTGA TTGGCCACTC CCTCTCTGCT CTGCTCGCT CGCTCACTGAG GCCGGGCGAC CTGAGCGCCG GCCGGTGTCT
  101 GCCAGCTCTT TGAGTGCCCA CCGCCCCAA CGAGCGAGCG AGCGAGCGAG TGCCACACT CTGCAACTCC ATCACTAGGG GCCCTTTGCG
ITR5+5NS
    1 TACAAAACCT CCTTGCTTGA GAGTGTGGCA TGGCCCCT GCGCTCGCTC GCTCACTGAG GCGGGCGAC GCTCACTGAG GCCGGGCGAC CAAAGTCGCC
  101 CCGGCGCCC CTAGTGAGC CTGAGTGAGC TGCCACACTC TGAAGCAAG AGGTTTTGTA
ITR2 - TA
    1 AGGAACCCCT AGTGATGGAG TTGGCCACTC TCTCTGCGCG CTCGCTCGCT CACTGAGGCC GGGCGACCAA AGGTCGCCCG ACGCCCGGGC
  101 CTTTGGGCCG GCCTCCTCAG TGAGCGAGCG AGCGCGCAGA GAGGGAGTGG CCAACTCCAT CACTAGGGGT TCCT
ITR5 + TA
    1 TACAAAACCT CCTTGCTTGA GAGTGTTGGA TGGCCCCCTC CGCGAGCGC GTCACGCGAC CTGCTCGACT GAGGCGGGCG AACCAAAGTC GCCCGACCGG
  201 TA
ITR2 -GC
    1 AGGAACCCCT AGTATGGAGT TGGCCACTCC ATTTCTGGCG GCTCGCTCGC CACTGAGGCC GGGCGACCAA AGGCCGTGGG TTTGGCGGGC
  101 GCCCCTCAGT GAGGGAGCGA GCGCGCAGAA TGGAGCGCAGAA AACTCCATAC TAGGGTTCC T
```

CHIMERIC REP PROTEINS

REP52AA73
  1 MATFYEVTVR VPFTVEEHLP GISDSFVDWV TQQIWHLPFE SDLNLITLVEQ PQLTVADRIR RVFLYEWNKF SKAPEALFFV QPFKGESYFH MAVLVETTGV
101 KSMVLGRFLS QIREKLIQRI YRGIEPTLPN WFAVTKTRNG LMDKGITSEK QWIQEDQASY ISFNAASNSR CYTPNYLLPK TQPELQWAWT NLTERRLVA QHLTHVSQTQ
201 EQNKENQNPN SDAPVIRSKT SARYMELVGM TKKFGKRNTI WLFGPATTGK TNIAEAIAHT VPFYGCVWNT SQIKAALDNA GKIMSLTKTA PDYLVGQQPV EDISSNRIYK
301 ILELNGYDPQ YAASVFLGWA TKKFGKRNTI NTMCAVIDG NSTTFEHQQP LQRMFKFEL TRRLLDHDFGK VTKQEVKDFF RMVTAKVVES AKAIILGGSKVR
401 VDQKCKSSAQ IDPTPVIVTS NTMCAVIDG EASINYADRY QNKCSRHVGM NLMLFPCRQC FTHQKDCLE RWAKDHVVEV EHEFVKRGG AKKRPAPSDA
501 DISEPKRVRE SVAQPSTSDA EASINYADRY Q* FPVSESQPV SVVKAYQRL CYIHHIMGKV
601 FDACTACDLV NVLIDCIFEQ Q*

REP52AA84
  1 MATFYEVIVR VPFDVEEHLP GISDSFVDWV TQQIWLFPE SDLNLITLVEQ PQLTVADRIR RVFLYEWNKF SKQESKFFVQ NMEQYLSACL MAVLVETTGV
101 KSMVLGRFLS QIREKLIQRI YRGIEPTLPN WFAVTKTRNG AGGENKVVDE CYLENYLLPK TQPELQWAWT NMEQYLSACL NLTERRLVA QHLTHVSQTO
201 EQNKENQNPN SDAPVIRSKT SARYMELVGM LMDKGITSEK QWIQEDQASY ISFNAASNSR PDYLVGQQPV EDISSNRIYK
301 ILELNGYDPQ YAASVFLGWA TRKFGKRNTI NTMCAVIDG NSTTFEHQQP LQRMFKFEL VTKQEVKDFF RMVTAKVVES AKAIILGGSKVR
401 VDQKCKSSAQ IDPTPVIVTS NTMCAVIDG EASINYADRY QNKCSRHVGM NLMLFPCRQC FTKQKDCLE RWAKDHVVEV EREFVKKGG AKKRPAPSDA
501 DISEPKRVRE SVAQPSTSDA EASINYADRY Q* FPVSESQPV SVVKAYQRL CYIHHIMGKV
601 FDACTACDLV NVLIDCIFEQ Q*

REP52AA110
  1 MATFYEVIVR VPFTVEEHLP GISDSFVDWV TQQIWHLPFE SDLNLITLVEQ PQLTVADRIR RVFLYEWNKF SKQESKFFVQ MEQYLSACLN HLTHVSQTOE
101 SMVLGRYVSQ IREKLIQRTY QGIHEPTLPNW KHEPTLPNW KCIHEPTLPNWF AVTKTRNGA GGGNKVVDEC YIPNYLLPKT QPELQMAWTN DISSNRIYKI
201 QNKENQNPNS DAPVIRSKIS ARYMELVGML VDKGITSEKQ WIQEDQASYI SFNAASNSRS DISSNRIYKI
301 LELNGYDPQY AASVFLGWAT KKFGKRNTIW LFGPATTIGKT NIAEATAHTV PFYGCVMWTN ENFPENDCV QTKAALDNA KRFGPATTIGKT AILGGSKVRV
401 DQKCKSSAQI DPTPVIVTSN TMCAVIDGEN STTTFEHQQPL QRMKFEFELT TKQEVKFFR ERLDHDFGKV TKQEVKFFR WAKDHVEVEH EFYVKRGGA KRPAPSDAD
501 ISEPKRVRES VAQPSTSDAE ASINYADRYQ NKCSRHVGMN LMLFPCRQCF THQKDCLEC FPVSESQPVS VVKAYQKL CYIHHIMGKVP
601 DACTACDLVN VLIDCIFEQ *

REP52AA126
  1 MATFYEVIVR VPFTVEEHLP GISDSFVDWV TQQIWHLPFE SDLNLITLVEQ PQLTVADRIR RVFLYEWNKF SKQESKFFVQ MEQYLSACLN HLTHVSQTOE
101 SMVLGRYVSQ IRAQLVKVF QGIHEPTLPNW FAVTKTRNGA GGGNKVVDEC YIPNYLLPKT QPELQWAWTN MEQYLSACLN LTERRINAQ HLTHVSQTQE
201 QNKENQNPNS DAPVIRSKIS ARYMELVGWL KHFGKRNTIW LFGPATTIGKT NIAEATAHTV PFYGCVMWTN ENFPENDCV DYLVGQQPVE DISSNRIYKI
301 LELNGYDPQY AASVFLGWAT KHFGKRNTIW LFGPATTIGKT NIAEATAHTV PFYGCVMWTN ENFPENDCV MTAKVVESAK AILGGSKVRV
401 DQKCKSSAQI DPTPVIVTSN TMCAVIDGEN STTTFEHQQPL QRMKFEFELT RRLDHDFGKV TKQSVKFDFF WAKDHVEVEH EFYVKRGGA KRPAPSDAD
501 ISEPKRVRES VAQPSTSDAE ASINYADRYQ NKCSRHVGMN LMLFPCRQCE THQKDCLEC FPVSESQPVS VVKAYQKL YIHHIMGKVP
601 DACTACDLVN VLIDCIFEQ *

FIG. 25

```
REP52AA138
   1 MATFYEVTVR VPFTVEEHLP GISDSFVDWV TGQIWELPPE SDINLITLVEQ PQLTVADRIR RVELYEMNKF SKQESKFFVQ HTLVETSGIS
 101 SMVLGRYVSQ IRAQLVKVVF QGIEPQINEW VAITKVKKGG GNKVDECYI PNYLLPKTQP ELQWAWINME KAALDNAGKI QYLSACLNLT THVSQTQEQN
 201 KENQNRSHA PVIRSKTSAR YMELVGMLND KGITSEKQWI QEDQASYISF NAASNSRSQI KAALDNAGKI MSIITKTAEDY LVGQQPVEDI SSNRIYKILE
 301 INGYDRQYAA SVFLGWATKK RGKRNTIWLF GPATTKCINI AEAIAHTVPF YGCVNMTNEN FPPNDCVDKM VTWWEEGKMT AKVESAKAI LGGSKVRVEQ
 401 KCKSSAQIIP TPVTVTSNIM MCAVIDGNST TFEHQQPLQD RMFKFELITRR LDHEGKVTLK QEVKDFFRWA KDHVEVEHE FVKKCGAKK RPAPSDADIS
 501 EPKKVRESVA QPSTSDAEAS INYADRYQNK CSRHVGMNLM LFPCRQCERM NQNSNICFTH GQKQLCIECTP VSESQPVSVV KKAYQKLCYI HHIMGKVPDA
 601 CTACDLVNVDL DCIFEQ*
REP52AA160
   1 MATFYEVTVR VPFTVEEHLP GISDSFVDWV TGQIWELPPE SDINLITLVEQ PQLTVADRIR RVFLYEMNKF SKQESKFFVQ HTLVETSGIS
 101 SMVLGRYVSQ IRAQLVKVVF QGIEPQINEW VAITKVKKGG ANKVVDSGYI PAYLLPKVQP ELQWAWINME KFKRLVAQHL THVSQTQEQN
 201 KENQNHNSIA PVIRSKITARY MELVGMLIMDK GITSEKQWIQ EDQASYISFN AASNSRSQIK SLIKTAPDYL VGQQPVEHIS SNRIYKILEL
 301 MGYDRQYAAS VFLGWATKKF PAITGKINIA EAIAHTVPFY GCVNWTNENF PPNDCVDRMV IWEEGKMIA KVESANAIL GGSKVRVDQK
 401 CKSSAQIDPT PVIVTSNIMM CAVIDGNSTT FEHQQPLQDR MFKFELITRRL DHDGKVTKQ EVKDFFRWAK DHVEVEHEF YVKKGGAKKR PAPSDADISE
 501 PKKVRESVAQ PSTSDAEAST MYADRYQNKC FPCRQCERMN QNSNICFTHG QKQKLCIECFPV KAYQKLCYIH HIMGKVPDAC
 601 TACDLVNVDL DCIFEQ*
REP52AA175
   1 NATFYEVTVR VPFTVEEHLP GISDSFVDWV TGQIWELPPE SDINLITLVEQ PQLTVADRIR RVFLYEMNKF SKQESKFFVQ HTLVETSGIS
 101 SMVLGRYVSQ IRAQLVKVVF QGIEPQINEW VAITKVKEHE ANKVVDSKYI PAYLLPKVQP ELQWAWINLD EFFRLVAQHL THVSQTQEQN
 201 KENQNPNDAP VIRSKTARYM ELVGMLVDKS ITSEKQWIQE DQASYISFNA ASNSRSQIKA ALDNAGKIMS LIKTADYLV GQQPVEDISS NRIYKILEIN
 301 GYDRQYAASV FLQWATKKFG KRNTTWLFGP ATTUKINIAE ATAHTVPFYG CVNMTNENFP ENLCVDRAVI WHEEGKMTAK VESAKAIIG GSKVRVDQKC
 401 KSSAQIDPTP VIVTSNIMWC AVIDENSTTF FKFELITRRLD PCRQCERM RVKDFFRWAKD HVEVEHEFY VKKGGAKKRP APSDADISEP
 501 KRVRESVAQP STSDAEASIN VADRYQNKCS RHVGMNLMLF PCRQCERMNQ NSNICFTHGQ KQCLCIECFFV KQCLCIECFPV AYQKLCYIHH IMGKVPDACT
 601 ACDLVNVDLD DCIFEQ*
REP52AA187
   1 MATFYEVTVR VPFTVEEHLP GISDSFVDWV TGQIWELPPE SDINLITLVEQ PQLTVADRIR RVFLYEMNKF SKQESKFFVQ HTLVETSGIS
 101 SMVLGRYVSQ IRAQLVKVVF QGIEPQINDW VAITKVKKGS ANKVVDSKYI PAYLLPKVQP ELQWAWTNLD EYKLAAINLE ERRKHRKVA QHIMVSQTQ
 201 EQNKENQNPEN SDAPVIRSKT SARYMELVGM LVDKGITSEK QWIQEDQASY ISFNRAASNSR SQIKAALIXNA GKIMSLIKTA HDYLMQQPV EDISSNRIYK
 301 ILELMGYDRQ YAASVFLGWA TKKRGKRNTI WLPGPATTGK TNLAEAIAHT VPFYGCVNWT NENTPPDCV DROMVIWHEEG KMTAKVVESA KAILGGSKVR
 401 VDQKCKSSAQ IDPTPVIVTS NIMMCAVIDG EASINVADRY LQDRMFKFEL TRRLJHDFGK VTKQEVKDFF RMAKDHVVEV EHEFVKKGG AKKRPAPSDA
 501 DISEPKRVRE SVAQPSTSDA EASINVADRY QNKCSRHVGM NLMLFPCRQC ERMQNSNIC PTHGQKQCLE CTPVSESQPV SVVKKAYQKL CYIHHIMGKV
 601 RDACHACDLV NVDLDCIFEQ*
```

FIG. 25 (cont.)

```
REP52AA207
  1 MATFYENTVR VPFHDVEEHLP GISDSFVDWV TQQIWLFPE SDINLITLVEQ PQLIVAIRIR KVTLYEWNKP SKQESKFFVQ FEKGSEYFHL HTLVETSGIS
101 SMVLGRYVSQ IRAQLVKVVF QGIEPQINEW VAITKVRKGS ANKVVDSGYI PAYLLPKVQP AASNSRSQIK ELQNAWINLD EYKLAAINLE ERKRLVAQFL AESSQRSEQA
201 KENQNENSDA PVTRSKSARY MKLVSWLNDK GITSEKQWIQ EDQASYISFN STGNSRSQIK SHKTAPDYL VGSQPVEDIS SNRIVKILEL
301 NGYDPQAAS VTLGWATKKF GKRNTWLPG PATIGKINIA EAIAHTVPFY GCVNWTNENF PFNDCVDKMV IWWEEGKMTA KVVESAKAIL GGSKVRVDQK
401 CKSSAQIDFT PVIVISNTNM CAVIDGNSTT FEHQPLQDR MFKFELTRPL DHDFGKVTKQ EVKDFFRWAK DHVEVEHEF YVFKGSAKER DAPSDADISE
501 PKRVESVAQ PSTSSPAEASI NVADRYQNKC SRHVVMNLML FPCRQCRMN QNSRICFTHG SESQPVSVVK KAVQKLCYTH HIMGKVRHAC
601 TACDLMNIL SDCIFEQ*

REP25AA73
  1 MRGFYEIVIK VPSSLDDEHLP GISDSFVNWV AEKEMELPED SDMQINLIEQ APLIVAERLQ HDFLITEWRRV SKQESKFFVQ FEKGSEYFHL HTLVETSGIS
101 SMVLGRYVSQ IRAQLVKVVF QGIEPQINEW VAITKVRKGS ANKVVDSGYI PAYLLPKVQP ELQNAWINLD EYKLAAINLE ERKRLVAQFL AESSQRSEQA
201 ASQREFSADP VLKSKTSQKY MALNNWLVEH GITSEKQWIQ ENQESYLSEN STGNSRSQIK SLITKSAVDVL VGSSVFEDIS KNRIWQIFEM
301 NGYDPAYAGS ILYGWCQRSF NKRNTVWLYG PATIGKINIA EAIAHTVPFY GCVNWTNENP PFNDCVDKML IWWEEGKMIN KVVESAKAIL QESKVRVDQK
401 CKSSVQIDST PVTVISNTNM CVVVDGNSTT FEHQPLHER MFKFELTKRL PFDFGKITNQ EVKDFFAWAK VNQVPVTHEP KVPERLAGTIK GAEKSLRPL
501 GDVTNTSYKS ERRARLGFV PETPRSSDVT VDPAPLRPLN WNSRYDCKCD YHAQFTNIS GKNGCICHNV THCQICHGI PWEKENLSDF
601 GDFDDANKEQ *

REP25AA77
  1 MRGFYEIVIK VPSSLDGHLP GISUSFVNWV AEKEMELPED SDMQINLIEQ APLIVAERLQ RDFLITEWRRV SKAPEALFFV QPEKGSEYFH LHTLVETSGI
101 SSMVLGRYVS QIRAQLVKVV FQGIEPQIND WVAITKVRKG GANKVVDSGY IPAYLLPKVQ PELQWAWINL EREKRLVAQF LAESSQRSQE
201 AASQREFSAD PVTKSITSQK YMALNWLVE HGITSEKQWI QENQESYLSF NSTGNSRSQI KAALDNATKI MSLITKSAVDY LVGSSVFEDI SKNRIWQIFE
301 MNGYDPAYAG SILYGWCQRS FNKRNTVWLY GPATTGKINI AEAIAHTVPF YGCVNWTNEN FFHNDCVDKM LPPDFGKITK QEVKDFFAWA KVNQVPVTHE LGGSKVRVDQ
401 KCKSSVQIDS TFVTVTSNTN MCVVDGNSTT TFEHQQPLED RMFKFELITKR LPEDFGKITK QEVKDFFAWA KVNQVPVTHE FKVPRELAGT KGAEKSLRP
501 LGDVTNTSYK SLEKRARLSF VPETPRSSIV TVDPAPLRPL MNSRYDCKC DYHAQFTNIS NKCDEKTLN RGRNCICHN VTHCQICHGI PWEKENLSD
601 FGDFDDANKE Q*

REP25AA97
  1 MRGFYEIVIK VPSSLDGHLP GISDSFVNWV AEKEMELPED SDMQINLIEQ APLIVAERLQ RDFLITEWRRV SKAPEALFFV QPEKGSEYFH MAVLVETSGI
101 SSMVLGRYVS QIRAQLVKVV FQGIEPQIND WVAITKVRKG GANKVVDSGY IPAYLLPKVQ PELQWAWINL EREKRLVAQF LAESSQRSQE
201 AASQREFSAD PVTKSITSQK YMALNWLVE HGITSEKQWI QENQESYLSF NSTGNSRSQI KAALDNATKI MSLITKSAVDY LVGSSVFEDI SKNRIWQIFE
301 MNGYDPAYAG SILYGWCQES HNKRNTVWLY GPATTGKINI AEAIAHTVPF YGCVNWTNEN LPEDFGKITK QEVKDFFAWA KVNQVPVTHE LGGSKVRVDQ
401 KCKSSVQIDS TFVTVTSNTN MCVVVDGNST TFEHQQPLED RMFKFELITK RFMFKFELITK QEVKDFFAWA KVNQVPVTHE FKVPRELAGT KGAEKSLRP
501 LGDVTNTSYK SLEKRARLSF VPETPRSSIV TVDPAPLRPL MNSRYDCKC DYHAQFTNIS NKCDEKTLN RGRNCICHN VTHCQICHGI PWEKENLSD
601 FGDFDDANKE Q*
```

FIG. 25 (cont.)

```
REF25AA116
  1 MPGFYEIVIK VPSILYEHLP GISDSFVNWV AEKEMELPED SDMDLNLIEQ APLTVAEKLQ RDFLIEWRRV SKAPEALFFV QFEKGESYFH MHVLVETTGV
101 KSMVLGRFLS QIREKLVKVV FQGHERQIND WAITKVKKG YMALNNMLVE HGITSEKQWI GFATTGKTNI AEAIAHTVFF YGCVNMTNEN FPFNDCVDKM LIWWEEGKMT NKVVESAKAI LGGSKVRVEDQ
201 AASQREFSAD PVIKSKTSQK SILNGWQRS FNKRNTWLY MCVVDGNST TFEHQQPLED RMFKFELTKR LPPDFGKIFK QEVKDFFAWA KVNQVPVTHE FKVPKHLAGT KGAEKSLKRP
301 MNGYDPAYAG KCKSSVQILS TPVIVTSNTN SLEKRARLSF VPETPRSSDV TVDPAPLRPL MNSRYDCKC DYHAQFTNIS NKCDECEYLN RGKNGCICHN VTHCQICHGI PWEKENLSD
401 KCKSSVQILS LGVINTISYK SLEKRARLSF VPETPRSSDV TVDPAPLRPL MNSRYDCKC
501 LGVINTISYK FQFDDANKE Q*
601 FQFDDANKE

REF25AA125
  1 MPGFYEIVIK VPSILDGHLP GISDSFVNWV AEKEWELPED SDMDLNLIEQ APLTVAEKLQ RDFLIEWRRV SKAPEALFFV QFEKGESYFH MHVLVETTGV
101 KSMVLGRFLS QIREKLIQRI YRGHEPQIND WAITKVKG YMALNNMLVE HGITSEKQWI QEMQESYLSF NSTGNSRSQI AEALAHTVFF YGCVNMTNEN FPFNDCVDKM LIWWEEGKMI MKVVESARAI LGSSKVRVDQ
201 AASQREFSAD PVIKSNTSQK SILNGWQRS FNKRNTWLY MCVVDGNST TFEHQQPLED RMFKFELITKR LPPDFGKITK QEVKDFFAWA KVNQVPVTHH FKVEHLAGT KGAEKSLKRP
301 MNGYDPAYAG KCNSSVQILS TPVTVTSNTN SLEKRARLSF VPETPRSSDV TVDPAPLRPL MNSRYDCKC DYHAQFTNIS REKNGCICHN VTHCQICHGI PWEKENLSD
401 KCNSSVQILS LGVTNTSYK SLEKRARLSF VPETPRSSDV TVDPAPLRPL MNSRYDCKC
501 LGVTNTSYK FQFDDANKE Q*
601 FQFDDANKE

REF25AA141
  1 MRGFYEIVIK VPSULDGHLP GISDSFVNWV AEKEMELPED SDMDLNLIEQ APLTVAEKLQ RDFLIEWRRV SKAPEALFFV QFEKGESYTH MAVLVETTGV
101 KSMVLGRFLS QIREKLIQRI YRGIEPTLPN WFAVTKTRNG AGGANKVUIS WIQENQESYL SFNSTGNSRS QIKAALINAT KIMSLITKSAV DYLVGSSVFE DISKNRIWQI
201 QEAASQREFS ADPVIKSKTS QKYMALVNML VEHGITSEKQ RSFNKRNTVM LYGPATTGKT NIAEAIAHTV PFYGCVNWTN ENFPFNDCVD KMLIWWEEGK MTNKVVESAK ALLGGSKVFV
301 FEMNGYDPAY AGSILYGWCQ RSFNKRNTVM LYGPATTGKT NIAEAIAHTV PFYGCVNWTN ENFPFNDCVD KMLIWWEEGK MTNKVVESAK ALLGGSKVFV
401 DQKCKSSVQI ISTFVIVTSN TNMCVVVDGN STTFEHQQPL EDRMFKFELT TKQEVKDFFA WAKVNQVFVT HEFKVPKHLA GTKGAEKSLK
501 RPLGDVTNTS YKSLEKRARL SFVPETPRSS DVTVDPAPLR FLMNSRYDC KDYHAQFTDN ISNKCDECSY LNRGKNGCIC HNVTHCQICH GIPWEKENL
601 SDFEDFDIAN KEQ*

REF25AA149
  1 MPGFYEIVIK VPSILDGHLP GISDSFVNWV AEKEMELPED SDMDLNLIEQ APLTVAEKLQ RDFLIEWRRV SKAPEALFFV QFEKGESYFH MAVLVETTGV
101 KSMVLGRFLS QIREKLIQRI YRGIEPTLFN WFAVTKTRNG AEKENKVDS WIQERNQESYL NIAEAIAHTV PFYGCVNWTN ENFPFNDCVD KMLIWWEEGK MTNKVVESAK ALLGGSKVRV
201 QEAASQREFS ADPVIKSKTS QKYMALVNML VEHGITSEHQ LYGPATTGKT NIAEAIAHTV PFYGCVNWTN ENFPFNDCVD KMLIWWEEGK MTNKVVESAK ALLGGSKVRV
301 FEMNGYDPAY AGSILYGWCQ RSFNKRNTVM LYGPATTGKT NIAEAIAHTV PFYGCVNWTN ENFPFNDCVD KMLIWWEEGK MTNKVVESAK ALLGGSKVRV
401 DQKCKSSVQI DSTFVIVTSN TNMCVVVDGN STTFEHQQPL EDRMFKFELT TKQESVKDFFA WAKVNQVPVT HEFKVPRELA GTKGAEKSIK
501 RPLGDVTNTS YKSLEKRARL SFVPETPRSS DVTVDPAPLR FLMNSRYDC KDYHAQFTN ISNKCDEKEY HNVTHCQICH GIPWEKENL
601 SDFEDFDIAN KEQ*
```

```
AAV1 REP40    MELVGWLVDRGITSEKQWIQEDQASYISFNAASNSRSQIKAALDNAGKIMALTKSAPDYLVGPAPPADIKTNRIY
AAV2 REP40    MELVGWLVDRGITSEKQWIQEDQASYISFNAASNSRSQIKAALDNAGKIMSLTKTAPDYLVGQQPVEDISSNRIY
AAV3A REP40   MELVGWLVDRGITSEKQWIQEDQASYISFNAASNSRSQIKAALDNAGKIMSLTKTAPDYLVGSNPPEDITKNRIY
AAV3B REP40   MELVGWLVDRGITSEKQWIQEDQASYISFNAASNSRSQIKAALDNASKIMSLTKTAPDYLVGSNPPEDITKNRIY
AAV4 REP40    MELVGWLVDRGITSEKQWIQEDQASYISFNAASNSRSQIKAALDNASKIMSLTKTAPDYLVGQNPPEDISSNRIY
AAV5 REP40    MALVNWLVEHGITSEKQWIQENQESYLSFNSTGNSRSQIKAALDNATKIMSLTKSAVDYLVGSSVPEDISKNRIW
AAV6 REP40    MELVGWLVDRGITSEKQWIQEDQASYISFNAASNSRSQIKAALDNAGKIMALTKSAPDYLVGPAPPADIKTNRIY
AAV7 REP40    MELVGWLVDRGITSEKQWIQEDQASYISFNAASNSRSQIKAALDNAGKIMALTKSAPDYLVGPSLPADIKTNRIY
AAV8 REP40    MELVGWLVDRGITSEKQWIQEDQASYISFNAASNSRSQIKAALDNAGKIMSLTKSAPDYLVGPSLPADITQNRIY
CONSENSUS     MELVGWLVDRGITSEKQWIQEDQASYISFNAASNSRSQIKAALDNAGKIMSLTKSAPDYLVG  SPPEDISTNRIY

AAV1 REP40    RILELNGYEPAYAGSVFLGWAQKRFGKRNTIWLFGPATTGKTNIAEAIAHAVPFYGCVNWTNENFPFNDCVDKM
AAV2 REP40    KILELNGYDPAYAGSVFLGWATKKFGKRNTIWLFGPATTGKTNIAEAIAHTVPFYGCVNWTNENFPFNDCVDKM
AAV3A REP40   QILELNGYDPQYAASVFLGWAQKKFGKRNTIWLFGPATTGKTNIAEAIAHAVPFYGCVNWTNENFPFNDCVDKM
AAV3B REP40   QILELNGYDPQYAASVFLGWAQKKFGKRNTIWLFGPATTGKTNIAEAIAHAVPFYGCVNWTNENFPFNDCVDKM
AAV4 REP40    RILEMNGYDPAYAGSILYGWCQRSFNKRNTVWLYGPATTGKTNIAEAIAHAVPFYGCVNWTNENFPFNDCVDKM
AAV5 REP40    QIFEMNGYDPAYAGSVFLGWAQKKFGKRNTIWLFGPATTGKTNIAEAIAHTVPFYGCVNWTNENFPFNDCVDKM
AAV6 REP40    RILELNGYEPAYAGSVFLGWAQKRFGKRNTIWLFGPATTGKTNIAEAIAHAVPFYGCVNWTNENFPFNDCVDKM
AAV7 REP40    RILALNGYDPAYAGSVFLGWAQKKFGKRNTIWLFGPATTGKTNIAEAIAHAVPFYGCVNWTNENFPFNDCVDKM
AAV8 REP40    RILELNGYDPAYAGSVFLGWAQKKFGKRNTIWLFGPATTGKTNIAEAIAHAVPFYGCVNWTNENFPFNDCVDKM
CONSENSUS     RILELNGYDPAYAGSVFLGWAQKKFGKRNTIWLFGPATTGKTNIAEAIAHAVPFYGCVNWTNENFPFNDCVDKM
```

FIG. 29

```
              150       160       170       180       190       200       210       220
AAV1 REP40    VIWWEEGKMTAKVVESAKAILGGSKVRVDQKCKSSAQIDPTPVIVTSNTNMCAVIDGNSTTFEHQQPLQDRMFKF
AAV2 REP40    VIWWEEGKMTAKVVESAKAILGGSKVRVDQKCKSSAQIDPTPVIVTSNTNMCAVIDGNSTTFEHQQPLQDRMFKF
AAV3A REP40   VIWWEEGKMTAKVVESAKAILGGSKVRVDQKCKSSAQIEPTPVIVTSNTNMCAVIDGNSTTFEHQQPLQDRMFEP
AAV3B REP40   VIWWEEGKMTAKVVESAKAILGGSKVRVDQKCKSSAQIEPTPVIVTSNTNMCAVIDGNSTTFEHQQPLQDRMFKF
AAV4 REP40    LIWWEEGKMTAKVVESAKAILGGSKVRVDQKCKSSVQIDSTPVIVTSNTNMCVVDGNSTTFEHQQPLQDRMFKF
AAV5 REP40    VIWWEEGKMTAKVVESAKAILGGSKVRVDQKCKSSAQIDPTPVIVTSNTNMCAVIDGNSTTFEHQQPLEDRMFKF
AAV6 REP40    VIWWEEGKMTAKVVESAKAILGGSKVRVDQKCKSSAQIDPTPVIVTSNTNMCAVIDGNSTTFEHQQPLQDRMFKF
AAV7 REP40    VIWWEEGKMTAKVVESAKAILGGSKVRVDQKCKSSAQIDPTPVIVTSNTNMCAVIDGNSTTFEHQQPLQDRMFKF
AAV8 REP40    VIWWEEGKMTAKVVESAKAILGGSKVRVDQKCKSSAQIDPTPVIVTSNTNMCAVIDGNSTTFEHQQPLQDRMFKF
CONSENSUS 230       240       250       260       270       280       290
AAV1 REP40    ELTRRLEHDFGKVTKQEVKEFFRWAQDHVTEVAHEFYVR------KGGAN--KRPAPDDADKSEP----KRACP
AAV2 REP40    ELTRRLDHDFGKVTKQEVKDFFRWAKDHVVEVEHEFYVK------KGGAK--KRPAPSDADISEP----KRVRE
AAV3A REP40   ELTRRLDHDFGKVTKQEVKDFFRWASDHVTDVAHEFYVR------KGGAK--KRPASNDADVSEP----KRECT
AAV3B REP40   ELTRRLDHDFGKVTKQEVKDFFRWASDHVTDVAHEFYVR------KGGAK--KRPASNDADVSEP----KRQCT
AAV4 REP40    ELTRRLEHDFGKVTKQEVKDFFRWASDHVTEVTHEFYVR------KGGAR--KRPAPNDADISEP----KRACP
AAV5 REP40    ELTKRLPPDFCKITKQEVKDFFAWAKVNQVPVTHEFKVPRELAGTKGAEKSLKRPLGDVTNTSYKSLEKRARLSP
AAV6 REP40    ELTRRLEHDFGKVTKQEVKDFFRWAQDHVTEVAHEFYVR------KGGAN--KRPAPDDADKSEP----KRACP
AAV7 REP40    ELTRRLEHDFGKVTKQEVKEFFRWASDHVTEVAHEFYVR------KGGAS--KRPAPDDADISEP----KRACP
AAV8 REP40    ELTRRLEHDFGKVTKQEVKEFFRWASDHVTEVAHEFYVR------KGGAS--KRPAPDDADISEP----KRACP
CONSENSUS
```

FIG. 29 (cont.)

```
              300              310                329
AAV1 REP40    SVADPSTSDAEGAPVDFADLARGQPL----    (SEQ ID NO:84)
AAV2 REP40    SVAQPSTSDAE-ASINYADLARGHSL----    (SEQ ID NO:85)
AAV3A REP40   SLAQPTTSDAE-APADYADLARGQPF----    (SEQ ID NO:86)
AAV3B REP40   SLAQPTTSDAE-APADYADLARGQPP----    (SEQ ID NO:87)
AAV4 REP40    SVAQPSTSDAE-APVDYADLARGQPL----    (SEQ ID NO:88)
AAV5 REP40    VPETPRSSDVTVDPAPLRPLNWNSLVGPSW    (SEQ ID NO:89)
AAV6 REP40    SVADPSTSDAEGAPVDFADLARGQPL----    (SEQ ID NO:90)
AAV7 REP40    SVADPSTSDAEGAPVDFADLARGQPL----    (SEQ ID NO:91)
AAV8 REP40    SVADPSTSDAEGAPVDFADLARGQPL----    (SEQ ID NO:92)
CONSENSUS     SVA PSTSDAE APVDFADLARGQPL        (SEQ ID NO:93)
```

FIG. 29 (cont.)

```
              1         10        20        30        40        50        60        70
AAV1 REP52    MELVGWLVDRGITSEKQWIQEDQASYISFNAASNSRSQIKAALDNAGKIMALTKSAPDYLVGPAPPADIKTNRI
AAV2 REP52    MELVGWLVDRGITSEKQWIQEDQASYISFNAASNSRSQIKAALDNAGKIMSLTKTAPDYLVGQQPVEDISSNRI
AAV3A REP52   MELVGWLVDRGITSEKQWIQEDQASYISFNAASNSRSQIKAALDNASKIMSLTKTAPDYLVGSNPPEDITKNRI
AAV3B REP52   MELVGWLVDRGITSEKQWIQEDQASYISFNAASNSRSQIKAALDNASKIMSLTKTAPDYLVGSNPPEDITKNRI
AAV4 REP52    MELVGWLVDRGITSEKQWIQEDQASYISFNAASNSRSQIKAALDNASKIMSLTKTAPDYLVGQNPPEDISSNRI
AAV5 REP52    MALVNWLVEHGITSEKQWIQENQEFVLSFNSTGNSRSQIKAALDNATKIMSLTKSAVDYLVGSSVPEDISKNRI
AAV6 REP52    MELVGWLVDRGITSEKQWIQEDQASYISFNAASNSRSQIKAALDNAGKIMALTKSAPDYLVGPAPPADIKTNRI
AAV7 REP52    MELVGWLVDRGITSEKQWIQEDQASYISFNAASNSRSQIKAALDNAGKIMALITKSAPDYLVGPSLPADIKTNRI
AAV8 REP52    MELVGWLVDRGITSEKQWIQEDQASYISFNAASNSRSQIKAALDNAGKIMALITKSAPDYLVGPSLPADITQNRI
CONSENSUS     MELVGWLVDRGITSEKQWIQEDQASYISFNAASNSRSQIKAALDNAGKIMSLTKSAPDYLVG SPPEDISTNRI
```

FIG. 30

```
AAV1 REP52   YRILELNGYEPAYAGSVFLGWAQKRFGKRNTIWLFGPATTGKTNIAEAIAHAVPFYGCVNWTNENFPFNDCVDKM
AAV2 REP52   YRIKELNGYDPQYAASVFLGWATKKFGKRNTIWLFGPATTGKTNIAEAIAHTVPFYGCVNWTNENFPFNDCVDKM
AAV3A REP52  YQILELNGYDPQYAASVFLGWAQKKFGKRNTIWLFGPATTGKTNIAEAIAHAVPFYGCVNWTNENFPFNDCVDKM
AAV3B REP52  YQILELNGYDPQYAASVFLGWAQKKFGKRNTIWLFGPATTGKTNIAEAIAHAVPFYGCVNWTNENFPFNDCVDKM
AAV4 REP52   YRILEMNGYDPQYAASVFLGWAQSILYGWCQRSFNKRNTVWLYGPATTGKTNIAEAIAHTVPFYGCVNWTNENFPFNDCVDKM
AAV5 REP52   WQIFEMNGYDPAYAGSILYGWCQRSFNKRNTVWLYGPATTGKTNIAEAIAHTVPFYGCVNWTNENFPFNDCVDKM
AAV6 REP52   YRILELNGYDPAYAGSVFLGWAQKRFGKRNTIWLFGPATTGKTNIAEAIAHAVPFYGCVNWTNENFPFNDCVDKM
AAV7 REP52   YRILELNGYDPAYAGSVFLGWAQKKFGKRNTIWLFGPATTGKTNIAERAIAHAVPFYGCVNWTNENFPFNDCVDKM
AAV8 REP52   YRILALNGYDPAYAGSVFLGWAQKKFGKRNTIWLFGPATTGKTNIAEAIAHAVPFYGCVNWTNENFPFNDCVDKM
CONSENSUS    YRILELNGYDPAYAGSVFLGWAQKKFGKRNTIWLFGPATTGKTNIAEAIAHAVPFYGCVNWTNENFPFNDCVDKM

AAV1 REP52   VIWWEEGKMTAKVVESAKAILGGSKVRVDQKCKSSAQIDPTPVIVTSNTNMCAVIDGNSTTFEHQQPLQDRMFKF
AAV2 REP52   VINWEEGKMTAKVVESAKAILGGSKVRVDQKCKSSAQIDPTPVIVTSNTNMCAVIDGNSTTFEHQQPLEDRMFKF
AAV3A REP52  VTWWEEGKMTAKVVESAKAILGGSKVRVDQKCKSSAQIEPTPVIVTSNTNMCAVIDGNSTTFEHQQPLQDRMFKF
AAV3B REP52  VIWWEEGKMTAKVVESAKAILGGSKVRVDQKCKSSAQIEPTPVIVTSNTNMCAVIDGNSTTFEHQQPLQDRMFKF
AAV4 REP52   VIWWEEGKMTAKVVESAKAILGGSKVRVDQKCKSSAQIDSTPVIVTSNTNMCVVDGNSTTFEHQQPLQDRMFKF
AAV5 REP52   LIWWEEGKMTNKVVESAKAILGGSKVRVDQKCKSSVQIDSTFVIVTSNTNMCAVIDGNSTTFEHQQPLEDRMFKF
AAV6 REP52   VIWWEEGKMTAKVVESAKAILGGSKVRVDQKCKSSAQIDPTPVIVTSNTNMCAVIDGNSTTFEHQQPLQDRMFKF
AAV7 REP52   VIWWEEGKMTAKVVESAKAILGGSKVRVDQKCKSSAQIDPTPVIVTSNTNMCAVIDGNSTTFEHQQPLQDRMFKF
AAV8 REP52   VIWWEEGKMTAKVVESAKAILGGSKVRVDQKCKSSAQIDPTPVIVTSNTNMCAVIDGNSTTFEHQQPLQDRMFKF
CONSENSUS    VIWWEEGKMTAKVVESAKAILGGSKVRVDQKCKSSAQIDPTPVIVTSNTNMCAVIDGNSTTFEHQQPLQDRMFKF
```

FIG. 30 (cont.)

```
AAV1  REP52    ELTRRLEHDFGKVTKQEVKEFFRWAQDHVTEVAHEFYVR----KGGAN--KRPAPDDADKSEP--KRA-
AAV2  REP52    ELTRRLDHDFGKVTKQEVKDFFRWAKDHVVEVEHEFYVK====KGGAK--KRPAPSDADISEP--KRV-
AAV3A REP52    ELTRRLDHDFGKVTKQEVKDFFRWASDHVTDVAHEFYVR----KGGAK--KRPASNDADVSEP--KRE-
AAV3B REP52    ELTRRLDHDFGKVTKQEVKDFFRWASDHVTDVAHEFYVR----KGGAK--KRPASNDADVSEP--KRQ-
AAV4  REP52    ELTRRLEHDFGKVTKQEVKDFFRWASDHVTEVTHEFYVR----KGGAR--KRPAPNDADISEP--KRA-
AAV5  REP52    ELTKRLPPDFGKITTKQEVKDFFAWAKVNQVPVTHEFKVPRELAGTKGAEKSLKRPLGDVTNTSYKSLEKRARLSF
AAV6  REP52    ELTRRLEHDFGKVTKQEVKEFFRWAQDHVTEVAHEFYVR----KGGAN--KRPAPDDADKSEP--KAR-
AAV7  REP52    ELTRRLEHDFGKVTKQEVKEFFRWASDHVTEVAHEFYVR----KGGAS--KRPAPDDADISEP--KRA-
AAV8  REP52    ELTRRLEHDFGKVTKQEVKEFFRWASDHVTEVAHEFYVR----KGGAS--KRPAPDDADKSEP--KRA-
CONSENSUS      ELTRRLEHDFGKVTKQEVKDFFRWASDHVTEVAHEFYVR     KGGAK   KRPAPDDADISEP   KRA

AAV1  REP52    ---CPSVADPSTSDAEGAPVDFADRYQNKCSRHAGMLQMLFPCKTCERMNQFNICFTHGTRDCSECFPG
AAV2  REP52    ---RESVAQPSTSDAE-ASINYADRYQNKCSRHVGMNLMLFPCRQCERMNQSNICFTHGQKDCLECFPV
AAV3A REP52    ---CTSLAQPTTSDAE-APADVADRYQNKCSRHVGMNLMLFPCKTCERMNQISNVCFTHGQRDCGECFPG
AAV3B REP52    ---CTSLAQPTTSDAE-APADYADRYQNKCSRHVGMNLMLFPCKTCERMNQISNVCFTHGQRDCGECFPG
AAV4  REP52    ---CPSVAQPSTSDAE-APVDYADRYQNKCSRHVGMNLMLFPCRQCERMNQNVDICFTHGVMDCAECFPV
AAV5  REP52    VPETPRSSDVTVDPAPLRPLNWNSKYDCKCDYHAQFDNISNKCDECEYLNRGKNGCICHNVTHCQICHGI
AAV6  REP52    ---CPSVADPSTSDAEGAPVDFADRYQNKCSFHAGMLQMLFPCKTCERMNQNFNICFTHGTRDCSECFPG
AAV7  REP52    ---CPSVADPSTSDAEGAPVDFADRYQNKCSRHAGMIQMLFPCKTCERMNQNFNICFTHGVRDCLECPPG
AAV8  REP52    ---CPSVADPSTSDAEGAPVDFADRYQNKCSRHAGMLQMLFPCKTCERMNQNFNICFTHGVRDCSECFPG
CONSENSUS      CPSVADPSTSDAE APVDFADRYQNKCSRHAGM QMLFPCKTCERMNQN NICFTHG RDC ECFPG
```

*FIG. 30 (cont.)*

```
                370        380        390        400        410        420
AAV1 REP52   VSESQ--PVVRKRTYRKLCAIHHLLGRAPEIACSACDLVNVDLDDCVSEQ-  (SEQ ID NO:94)
AAV2 REP52   S-ESQPVSVVKK-AVQKLCYIHHIMGKVPD-ACTACDLVNVDLDDCIPEQ-  (SEQ ID NO:96)
AAV3A REP52  MSESQPVSVVKKTYQKLCPIHHILGRAPEIACSACDLANVDLDDCVSEQ-  (SEQ ID NO:97)
AAV3B REP52  MSESQPVSVVKKTYQKLCPIHHILGRAPEIACSACDLANVDLDDCVSEQ-  (SEQ ID NO:98)
AAV4 REP52   S-ESQPVSVVRKRTYQKLCPIHHIMGRAPEVACSACELANVDLDDCDMEQ-  (SEQ ID NO:99)
AAV5 REP52   P------------PWEK--ENLS------DFG--DFDDANKEQ-  (SEQ ID NO:100)
AAV6 REP52   VSESQ--PVVRKRTYRKLCAIHHLLGRAPEIACSACDLVNVDLDDCVSEQ-  (SEQ ID NO:101)
AAV7 REP52   VSESQ--PVVRKRTYRKLCAIHHLLGRAPEIACSACDLVNVDLDDCVSEQ-  (SEQ ID D NO:95)
AAV8 REP52   VSESQ--PVVRKRTYRKLCAIHHLLGRAPEIACSACDLVNVDLDDCVSEQ-  (SEQ ID NO:102)
CONSENSUS    VSESQ    VVRKRTY KLC IHHIILGRAPEIACSACDLVNVDLDDCVSEQ  (SEQ ID NO:103)
```

*FIG. 30 (cont.)*

```
             1         10        20        30        40        50        60        70
AAV1 REP68   MPGFYEIVIKVPSDLDEHLPGISDSFVSWVAEKEWELPPDSDMDLNLIEQAPLTVAEKLQRDFLVQWRRVSKAP
AAV2 REP68   MPGFYEIVIKVPSDLDEHLPGISDSFVNWVAEKEWELPPDSDMDLNLIEQAPLTVAEKLQRDFLVEWRRVSKAP
AAV3A REP68  MPGFYEIVLKVPSDLDERLPGISNSFVNWVAEKEWDVPPDSDMDPNLIEQAPLTVAEKLQREFLVEWRRVSKAP
AAV3B REP68  MPGFYEIVLKVPSDLDEHLPGISNSFVNWVAEKEWELPPDSDMDPNLIEQAPLTVAEKLQREFLVEWRRVSKAP
AAV4 REP68   MATFYEVIRVPFDVEEHLPGISDSFVDWVTGQIWELPPESDLNLTIVEQPQLTVADRIRRVFLYEWNKFSKQ-
AAV5 REP68   MPGFYEIVIKVPSDLDEHLPGISDSFVSWVAEKEWELPPDSDMDLNLIEQAPLTVAEKLQRDFLVQWRRVSKAP
AAV6 REP68   MPGFYEIVIKVPSDLDEHLPGISDSFVNWVAEKEWELPPDSDMDLNLIEQAPLTVAEKLQRDFLVQWRRVSKAP
AAV7 REP68   MPGFYEIVIKVPSDLDEHLPGISDSFVNWVAEKEWELPPDSDMDRNLIEQAPLTVAEKLQRDFLVQWRRVSKAP
AAV8 REP68   MPGFYEIVIKVPSDLDEHLPGISDSFVNWVAEKEWELPPDSDMDRNLIEQAPLTVAEKLQRDFLVQWRRVSKQ-
```

*FIG. 31*

```
                80         90        100        110        120        130        140
AAV1  REP68  EALFFVQFEKGESYFHLHILVETTGVKSMVLGRFLSQIRDKLVQTIYRG-IEPTLPNWFAVTKTRNGAGGG-NKV
AAV2  REP68  EALFFVQFEKGESYFHMHVLVETTGVKSMVLGRFLSQIREKLIQRIYRG-IEPTLPNWFAVTKTRNGAGGG-NKV
AAV3A REP68  EALFFVQFEKGETYFHLHVLIETIGVKSMVGRYVSQIKEKLVTRIYRG-VEPQLPNWFAVTKTRNGAGGG-NKV
AAV3B REP68  EALFFVQFEKGETYFHLHVLIETIGVKSMVGRYVSQIKEKLVTRIYRG-VEPQLPNWFAVTKTRNGAGGG-NKV
AAV4  REP68  ESKFFVQFEKGSEYFHLHTLVETSGISSMVLGRYVSQIRAQLVKTIYRG-VEPQLPNWFAVTKTRNGAGGG-NKV
AAV5  REP68  EALFFVQFEKGESYFHLHILVETSGIVKVKVVFQG-IEPQINDWVAITKVK--GGANKV
AAV6  REP68  EALFFVQFEKGESYFHMHVLVETTGVKSMVLGRFLSQIRDKLVQTIYRG-IEPTLPNWFAVTKTRNGAGGG-NKV
AAV7  REP68  EALFFVQFEKGESYFHLHVLVETTGVKSMVLGRFLSQIREKLVQTIYRG-VEPTLPNWFAVTKTRNGAGGG-NKV
AAV8  REP68  EALFFVQFELGESYFHLHVLVETTGVKSMVLGRFLSQIREKLGPDHLPAGSSPTLPNWFAVTKDAVMAPAGGNKV 150       160       170       180       190       200       210       220
AAV1  REP68  VDECYIPNYLLPKTQPELQWAWTNMEEYISACLNLAERKRLVAQHLTHVSQTQEQNKENLNPNSDAPVIRSKTSA
AAV2  REP68  VDECYIPNYLLPKTQPELQWAWTNMEQYLSACLNLTERKRLVAERKRLVAQHLTHVSQTQEQNKENLNPNSDAPVIRSKTSA
AAV3A REP68  VDDCYIPNYLLPKTQPELQWAWTNMDQYLSACLNLAERKRLVAQHLTHVSQTQEQNKENQNPNSDAPVIRSKTSA
AAV3B REP68  VDDCYIPNYLLPKTQPELQWAWTNMDQYLSACLNLAERKRLVAQHLTHVSQTQEQNKENQNPNSDAPVIRSKTSA
AAV4  REP68  VDDCYIPNYLLPKTQPELQWAWTNMDQYISACLNLAERKRLVAQHLTHVSQTQEQNKENQNPNSDAPVIRSKTSA
AAV5  REP68  VDSGYIPAYLLPKTQPELQWAWTNLDEYKLAALNLEERKRLVAQFLAESSQRS-QEAASQREFSADPVIKSKTSQ
AAV6  REP68  VDECYIPNYLLPKTQPELQWAWTNMEEYISACLNLAERKRLVAHDLTHVSQTQEQNKENLNPNSDAPVIRSKTSA
AAV7  REP68  VDECYIPNYLLPKTQPELQWAWTNMEEYISACLNLAERKRLVAQHLTHVSQTQEQNKENLNPNSDAPVIRSKTSA
AAV8  REP68  VDECYIPNYLLPKTQPELQWAWTNMEEYISACLNLAERKRLVAQHLTHVSQTQEQNKENLNPNSDAPVIRSKTSA
```

FIG. 31 (cont.)

|  |  | 230 | 240 | 250 | 260 | 270 | 280 | 290 |
|---|---|---|---|---|---|---|---|---|
| AAV1 | REP68 | RYMELVGWLVDRGITSEKQWIQEDQASYISFNAASNSRSQIKAALDNAGKIMALTKSAPDYLVGPAPPADIKTNR |
| AAV2 | REP68 | RYMELVGWLVDRGITSEKQWIQEDQASYISFNAASNSRSQIKAALDNAGKIMSLTKTAPDYLVGQQPVEDISSNR |
| AAV3A | REP68 | RYMELVGWLVDRGITSEKQWIQEDQASYISFNAASNSRSQIKAALDNASKIMSLITKTAPDYLVGSNPPEDITKNR |
| AAV3B | REP68 | RYMELVGWLVDRGITSEKQWIQEDQASYISFNAASNSRSQIKAALDNASKIMSLITKTAPDYLVGSNPPEDITKNR |
| AAV4 | REP68 | RYMELVGWLVDRGITSEKQWIQEDQASYISFNAASNSRSQIKAALDNASKIMSLITKTAPDYLVGQNPPEDISSNR |
| AAV5 | REP68 | KYMALVNWLVEHGITSEKQWIQENQESYLSFNSTGNSRSQIKAALDNATKIMSLITKSAVDYLVGSSVPEDISKNR |
| AAV6 | REP68 | RYMELVGWLVDRGITSEKQWIQEDQASYISFNAASNSRSQIKAALDNAGKIMALTKSAPDYLVGPAPPADIKTNR |
| AAV7 | REP68 | RYM LVGWLVDRGITSEKQWIQEDQASYISFNAASNSRSQIKAALDNAGKIMALTKSAPDYLVGPSLPADIKTNR |
| AAV8 | REP68 | RYMELVGWLVDRGITSEKQWIQEDQASYISFNAASNSRSQIKAALDNAGKIMALTKSAPDYLVGPSLPADITQNR |

|  |  | 300 | 310 | 320 | 330 | 340 | 350 | 360 | 370 |
|---|---|---|---|---|---|---|---|---|---|
| AAV1 | REP68 | IYRILELNGYEPAYAGSVFLGWAQKRFGKRNTIWLFGPATTGKTNIAEAIAHAVPFYGCVNWTNENFPFNDCVDK |
| AAV2 | REP68 | IYKILELNGYDPQYAASVFLGWATKKFGKRNTIWLFGPATTGKTNIAEAIAHTVPFYGCVNWTNENFPFNDCVDK |
| AAV3A | REP68 | IYQILELNGYDPQYAASVFLGWAQKRFGKRNTIWLFGPATTGKTNIAEAIAHAVPFYGCVNWTNENFPFNDCVDK |
| AAV3B | REP68 | IYQILELNGYDPQYAASVFLGWAQKKFGKRNTIWLFGPATTGKTNIAEAIAHAVPFYGCVNWTNENFPFNDCVDK |
| AAV4 | REP68 | IYRILEMNGYDPQYAASVFLGWAQKKFGKRNTIWLFGPATTGKTNIAEAIAHAVPFYGCVNWTNENFPFNDCVDK |
| AAV5 | REP68 | IWQIFEMNGYDPAYAGSILYGWCQRSPNKRNTIWLYGPATTGKTNIAEAIAHTVPFYGCVNWTNENFPFNDCVDK |
| AAV6 | REP68 | IYRILELNGYDPQYAASVFLGWAQKRFGKRNTIWLFGPATTGKTNIABAIAHAVPFYGCVNWTNENFPFNDCVDK |
| AAV7 | REP68 | IYRILELNGYDPAVAGSVFLGWAQKKFGKRNTIWLFGPATTGKTNIAEAIAHAVPFYGCVNWTNENFPFNDCVDK |
| AAV8 | REP68 | IYRILALNGYDPAVAGSVFLGWAQKKFGKRNTIWLFGPATTGKTNIAEAIAHAVPFYGCVNWTNENFPFNDCVDK |

FIG. 31 (cont.)

```
AAV1 REP68   MVIWWEEGKMTAKVVESAKAILGGSKVRVDQKCKSSAQIDPTPVIVTSNTNMCAVIDGNSTTFEHQQPLQDRMFK
AAV2 REP68   MVIWWEEGKMTAKVVESAKAILGGSKVRVDQKCKSSAQIDPTPVIVTSNTNMCAVIDGNSTTFEHQQPLQDRMFK
AAV3A REP68  MVIWWEEGKMTAKVVESAKAILGGSKVRVDQKCKSSAQIDPTPVIVTSNTNMCAVIDGNSTTFEHQPLQDRMFE
AAV3B REP68  MVIWWEEGKMTAKVVESAKAILGGSKVRVDQKCKSSAQIEPTPVIVTSNTNMCAVIDGNSTTFEHQQPLQDRMFE
AAV4 REP68   MVIWWEEGKMTAKVVESAKAILGGSKVRVDQKCKSSAQIEPTPVIVTSNTNMCAVIDGNSTTFEHQQPLQDRMFK
AAV5 REP68   MLIWWEEGKMTNKVVESAKAILGGSKVRVDQKCKCKSSVQIDSTPVIVTSNTNMCVVDGNSTTFEHQQPLEDRMFK
AAV6 REP68   MVIWWEEGKMTAKVVESAKAILGGSKVRVDQKCKSSAQIDPTPVIVTSNTNMCAVIDGNSTTFEHQQPLQDRMFK
AAV7 REP68   MVIWWEEGKMTAKVVESAKAILGGSKVRVDQKCKSSAQIDPTPVIVTSNTNMCAVIDGNSTTFEHQQPLQDRMFK
AAV8 REP68   MVIWWEEGKMTAKVVESAKAILGGSKVRVDQKCKSSAQIDPTPVIVTSNTNMCAVIDGNSTTFEHQQPLQDRMFK

AAV1 REP68   FELTRRLEHDFGKVTKQEVKEFFRWAQDHVTEVAHEFYVR-----KGGAN--KRPAPDDADKSEP----
AAV2 REP68   FELTRRLDHDFGKVTKQEVKDFFRWAKDHVTEVAHEFYVR-----KGGAK--KRPAPSDADISEP----
AAV3A REP68  FELTRRLDHDFGKVTKQEVKDFFRWASDHVTDVAHEFYVR-----KGGAK--KRPASNDADVSEP----
AAV3B REP68  FELTRRLDHDFGKVTKQEVKDFFRWASDHVTDVAHEFYVR-----KGGAK--KRPASNDADVSEP----
AAV4 REP68   FELTRRLDHDFGKVTKQEVKDFFRWASDHVTEVTHEFYVR-----KGGAR--KRPAPNDADISEP----
AAV5 REP68   FELTKRLPPDFGKITKQEVKDFFAWAKVNQVPVTHEFKVPRELAGTKGAEKSLKRPLGDVTNTSYKSLEK
AAV6 REP68   FELTRRLEHDFGKVTKQEVKEFFRWAQDHVTEVAHEFYVR-----KGGAN--KRPAPDDADKSEP----
AAV7 REP68   FELTRRLEHDFGKVTKQEVKDFFRWASDHVTEVAHEFYVR-----KGGAS--KRPAPDDADISEP----
AAV8 REP68   FELTRRLEHDFGKVTKQEVKEFFRWASDHVTEVAHEFYVR-----KGGAS--KRPAPDDADKSEP----
```

*FIG. 31 (cont.)*

```
             520       530       540       555
AAV1 REP68   -KRACPSVADPSTSDAEGAPVDFADLARGQPL----    (SEQ ID NO:104)
AAV2 REP68   -KRVRESVAQPSTSDAE-ASINYADLARGHSL----    (SEQ ID NO:105)
AAV3A REP68  -KRECTSLAQPTTSDAE-APADYADLARGQPF----    (SEQ ID NO:106)
AAV3B REP68  -KRQCTSLAQPTTSDAE-APADYADLARGQPF----    (SEQ ID NO:107)
AAV4 REP68   -KRACPSVAQPSTSDAE-APVDYADLARGQPL----    (SEQ ID NO:108)
AAV5 REP68   RARLSFVPETPRSSDVTVDPAPLRPLNWNSLVGRSW    (SEQ ID NO:109)
AAV6 REP68   -KRACPSVADPSTSDAEGAPVDFADLARGQPL----    (SEQ ID NO:110)
AAV7 REP68   -KRACPSVADPSTSDAEGAPVDFADLARGQPL----    (SEQ ID NO:111)
AAV8 REP68   -KRACPSVADPSTSDAEGAPVDFADLARGQPL----    (SEQ ID NO:112)
```

FIG. 31 (cont.)

```
              1         10        20        30        40        50        60        70
AAV1 REP78    MPGFYEIVIKVPSDLDEHLPGISDSFVSWVAEKEWELPPDSDMDLNLIEQAPLTVAEKLQRDFLVQWRRVSKAP
AAV2 REP78    MPGFYEIVLKVPSDLDEHLPGISDSFVNWVAEKEWELPPDSDMDLNLIEQAPLTVAEKLQRDFLTEWRRVSKAP
AAV3A REP78   MPGFYEIVLKVPSDLDEHLPGISNSFVNWVAEKEWELPPDSDMDPNLIEQAPLTVAEKLQREFLVEWRRVSKAP
AAV3B REP78   MPGFYEIVLKVPSDLDEHLPGISNSFVNWVAEKEWELPPDSDMDPNLIEQAPLTVAEKLQREFLVEWRRVSKAP
AAV4 REP78    MPGFYEIVIKVPSDLDEHLPGISDSFVNWVAEKEWDVPPDSDMDLNLIEQAPLTVAEKLQREPLVEWRRVSKAP
AAV5 REP78    MATPYEIVIKVPSDLDEHLPGISDSFVDWVTGQIWELPPESDLNLTLVEQPQLTVADRIRRVFLYEWNKFSKQ-
AAV6 REP78    MPGFYEIVIKVPSDLDEHLPGISDSFVSWVAEKEWELPPDSDMDLNLIEQAPLTVAEKLQRDFLVQWRRVSKAP
AAV7 REP78    MPGFYEIVIKVPSDLDEHLPGISDSFVNWVAEKEWELPPDSDMDLNLIEQAPLTVAEKLQRDFLVQWRRVSKAP
AAV8 REP78    MPGFYEIVIKVPSDLDEHLPGISDSFVNWVAEKEWELPPDSDMDRNLIEQAPLTVAEKLQRDFLVQWRRVSKAP
CONSENSUS
```

FIG. 32

```
                80         90        100        110        120        130        140
AAV1 REP78   EALFFVQFEKGESYFHLHILVETTGVKSMVLGRFLSQIRDKLVQTIYRG-IEPTLPNWFAVTKTRNGAGGG-NKV
AAV2 REP78   EALFFVQFEKGESYFHMHVLVETTGVKSMVLGRFLSQIREKLIQRIYRG-IEPTLPNWFAVTKTRNGAGGG-NKV
AAV3A REP78  EALFFVQFEKGETYFHLHVLIETTGVKSMVLGRFLSQIREKLIQRIYRG-VEPQLPNWFAVTKTRNGAGGG-NKV
AAV3B REP78  EALFFVQFEKGETYFHLHVLIETTGVKSMVVGRYVSQIKEKLVTRIYRG-VEPQLPNWFAVTKTRNGAGGG-NKV
AAV4 REP78   EALFFVQFEKGDSYFHLHILVETTGVKSMVVGRYVSQIKENLVTRIYRG-VEPQLPNWFAVTKTRNGAGGG-NKV
AAV5 REP78   ESKFFVQFEKGESYFHLHILVETTSGISSMVLGRYVSQIRAQLVKVPQG-IEPQINDWVAITKVK--GGANKV
AAV6 REP78   EALFFVQFEKGESYFHLHILVETTGVKSMVLGRFLSQIRDKLVQTIYRG-IEPTLPNWFAVTKTRNGAGGG-NKV
AAV7 REP78   EALFFVQFEKGESYFHLHVLVETTGVKSMVLGRFLSQIREKLVQTIYRG-IEPTLPNWFAVTKTRNGAGGG-NKV
AAV8 REP78   EALFFVQFEKGESYFHLHVLVETTGVKSMVLGRFLSQIREKLVQTIYRG-VEPTLPNWFAVTKTRNGAGGG-NKV
             EALFFVQFEKGESYFHLHVLVETTGVKSMVLGRFLSQIREKLV       IYRG IEPTLPNWFAVTKTRNGAGGG NKV
CONSENSUS 150        160        170        180        190        200        210        220
AAV1 REP78   VDECYIPNYLLPKTQPELQWAWTNMEEYISACLNLAERKRLVAQHLTHVSQTQEQNKENLNPNSDAPVIRSKTSA
AAV2 REP78   VDECYIPNYLLPKTQPELQWAWTNMEQYISACLNLAERKRLVAQHLTHVSQTQEQNKENLNPNSDAPVIRSKTSA
AAV3A REP78  VDDCYIPNYLLPKTQPELQWAWTNMDQYISACLNLAERKRLVAQHLTHVSQTQEQNKENQNPNSDAPVIRSKTSA
AAV3B REP78  VDDCYIPNYLLPKTQPELQWAWTNMDQYISACLNLAERKRLVAQHLTHVSQTQEQNKENQNPNSDAPVIRSKTSA
AAV4 REP78   VDDCYIPNYLLPKTQPELQWAWTNLDEYKLAALNLEERKRLVAQHLTHVSQTQEQNKENQNPNSDAPVIRSKTSA
AAV5 REP78   VDSCYIPAYLLPKVQPELQWAWTNMEEYISACINLAERKRLVAQFLAESSQRS-QEAASQREFSADPVIRSKTSQ
AAV6 REP78   VDECYIPNYLLPKTQPELQWAWTNMEEYISACLNLAERKRLVAHDLTHVSQTQEQNKENLNPNSDAPVIRSKTSA
AAV7 REP78   VDECYIPNYLLPKTQPELQWAWTNMEEYISACLNLTERKRLVAQHLTHVSQTQEQNKENLNPNSDAPVIRSKTSA
AAV8 REP78   VDECYIPNYLLPKTQPELQWAWTNMEEYISACLNLAERKRLVAQHLTHVSQTQEQNKENLNPNSDAPVIRSKTSA
CONSENSUS
```

FIG. 32 (cont.)

```
              230       240       250       260       270       280       290
AAV1 REP78    RYMELVGWLVDRGITSEKQWIQEDQASYISFNAASNSRSQIKAALDNAGKIMALTKSAPDYLVGPAPPADIKTNR
AAV2 REP78    RVMELVGWLVDKGITSEKQWIQEDQASYISFNAASNSRSQIKAALDNAGKIMSLTKTAPDYLVGQQPVEDISSNR
AAV3A REP78   RVMELVGWLVDKGITSEKQWIQEDQASYISFNAASNSRSQIKAALDNAGKIMSLTKTAPDYLVGSNPPEDITKNF
AAV3B REP78   RVMELVGWLVDKGITSEKQWIQEDQASYISFNAASNSRSQIKAALDNASKIMSLTKTAPDYLVGSNPPEDITKNR
AAV4 REP78    RYMELVGWLVDRGITSEKQWIQEDQASYISFNAASNSRSQIKAALDNATKIMSLTKSAVDYLVGSNPPEDISSNR
AAV5 REP78    KYMALVNWLVEHGITSEKQWIQBNQESYLSFNSTGNSRSQIKAALDNATKIMSLTKSAVDYLVGSSVPEDISKNR
AAV6 REP78    RYMELVGWLVDRGITSEKQWIQEDQASYISFNAASNSRSQIKAALDNAGKIMALTKSAPDYLVGPAPPADIKTNR
AAV7 REP78    RVMELVGWLVDRGITSEKQWIQEDQASYISFNAASNSRSQIKAALDNAGKIMALTKSAPDYLVGPSLPADIKTNR
AAV8 REP78    RYMELVGWLVDRGITSEKQWIQEDQASYISFNAASNSRSQIKAALDNAGKIMALTKSAPDYLVGPSLPADITQNR
CONSENSUS                                                       SAPDYLVG SPPEDISTNR 300       310       320       330       340       350       360       370
AAV1 REP78    IYRILELNGYEPAYAGSVFLGWAQKRFGKRNTIWLFGPATTGKTNIAEAIAHAVPFYGCVNWTNENFPFNDCVDK
AAV2 REP78    IYKILELNGYDPQYAASVFLGWATKKFGKRNTIWLFGPATTGKTNIAEAIAHTVPFYGCVNWTNENFPFNDCVDK
AAV3A REP78   IYQILELNGYDPQYAASVFLGWAQKKFGKRNTIWLFGPATTGKTNIAEAIAHAVPFYGCVNWTNENFPFNDCVDK
AAV3B REP78   IYQILELNGYDPQYAASVFLGWAQKKFGKRNTIWLFGPATTGKTNIAEAIAHAVPFYGCVNWTNENFPFNDCVDK
AAV4 REP78    IYRILEMNGYDPAYAGSVFLGWAQKKFGKRNTIWLFGPATTGKTNIAEAIAHAVPFYGCVNWTNENFPFNDCVDK
AAV5 REP78    IWQIFEMNGYDPAYAGSILYGWCQRSFNKRNTVWLYGPATTGKTNIAEAIAHTVPFYGCVNWTNENFPFNDCVDK
AAV6 REP78    IYRILELNGYEPAYAGSVFLGWAQKRFGKRNTIWLFGPATTGKTNIAEAIAHAVPFYGCVNWTNENFPFNDCVDK
AAV7 REP78    IYRILELNGYDPAYAGSVFLGWAQKKFGKRNTIWLFGPATTGKTNIAEAIAHAVPFYGCVNWTNENFPFNDCVDK
AAV8 REP78    IYRILALNGYDPAYAGSVFLGWAQKKFGKRNTIWLFGPATTGKTNIAEAIAHAVPFYGCVNWTNENFPFNDCVDK
CONSENSUS     IYRILELNGYDPAYAGSVFLGWAQKKFGKRNTIWLFGPATTGKTNIAEAIAHAVPFYGCVNWTNENFPFNDCVDK
```

FIG. 32 (cont.)

```
                380       390       400       410       420       430       440
AAV1  REP78  MVIWWEEGKMTAKVVESAKAILGGSKVRVDQKCKSSAQIDPTPVIVTSNTNMCAVIDGNSTTFEHQQPLQDRMFK
AAV2  REP78  MVIWWEEGKMTAKVVESAKAILGGSKVRVDQKCKSSAQIDPTPVIVTSNTNMCAVIDGNSTTFEHQPLQDRMFK
AAV3A REP78  MVIWWEEGKMTAKVVESAKAILGGSKVRVDQKCKSSAQIDPTPVIVTSNTNMCAVIDGNSTTFEHQPLQDRMFK
AAV3B REP78  MVIWWEEGKMTAKVVESAKAILGGSKVRVDQKCKSSAQIEPTPVIVTSNTNMCAVIDGNSTTFEHQPLQDRMFE
AAV4  REP78  MVIWWEEGKMTAKVVESAKAILGGSKVRVDQKCKSSAQIEPTPVIVTSNTNMCAVIDGNSTTFEHQPLQDRMFK
AAV5  REP78  MVIWWEEGKMTAKVVESAKAILGGSKVRVDQKCKCKSSVQIDSTPVIVTSNTNMCVVVDGNSTTFEHQPLEDRMFK
AAV6  REP78  MLIWWEEGKMTNKVVESAKAILGGSKVRVDQKCKSSAQIDPTPVIVTSNTNMCAVIDGNSTTFEHQPLQDRMFK
AAV7  REP78  MVIWWEEGKMTAKVVESAKAILGGSKVRVDQKCKSSAQIDPTPVIVTSNTNMCAVIDGNSTTFEHQPLQDRMFK
AAV8  REP78  MVIWWEEGKMTAKVVESAKAILGGSKVRVDQKCKSSAQIDPTPVIVTSNTNMCAVIDGNSTTFEHQPLQDRMFK
CONSENSUS    MVIWWEEGKMTAKVVESAKAILGGSKVRVDQKCKSSAQIDPTPVIVTSNTNMCAVIDGNSTTFEHQPLQDRMFK 450       460       470       480       490       500       510       520
AAV1  REP78  FELTRRLEHDFGKVTKQEVKEFFRWAQDHVTEVAHEFYVR------KGGAN--KRPAPDDADKSEP----KRA---
AAV2  REP78  FELTRRLDHDFGKVTKQEVKEFFRWAKDHVVEVEHEFYVK------KGGAK--KRPAPSDADISEP----KRV---
AAV3A REP78  FELTRRLDHDFGKVTKQEVKDFFRWASDHVTDVAHEFYVR------KGGAK--KRPASNDADVSEP----KRE---
AAV3B REP78  FELTRRLDHDFGKVTKQEVKDFFRWASDHVTDVAHEFYVR------KGGAK--KRPASNDADVSEP----KRQ---
AAV4  REP78  FELTKRLPPDFGKITKQEVKDFFRWASDHVTDVAHEFYVR------KGGAR--KRPAPNDADISEP----KRA---
AAV5  REP78  FELTRRLEHDFGKVTKQEVKDFFPAWAKVNQVPTHEFKVPRELAGTKGAEKSLKRPLGDVTNTSYKSLEKRARLS
AAV6  REP78  FELTRRLEHDFGKVTKQEVKEFFRWAQDHVTEVAHEFYVR------KGGAN--KRPAPDDADKSEP----KRA---
AAV7  REP78  FELTRRLEHDFGKVTKQEVKEFFRWASDHVTEVAHEFYVR------KGGAS--KRPAPDDADISEP----KRA---
AAV8  REP78  FELTRRLEHDFGKVTKQEVKEFFRWASDHVTEVAHEFYVR------KGGAK--KRPAPDDADISEP----KRA---
CONSENSUS    FELTRRLEHDFGKVTKQEVKEFFRWASDHVTEVAHEFYVR      KGGAK  KRPAPDDADISEP    KRA
```

*FIG. 32 (cont.)*

```
                    530        540         550         560           570              580              590
AAV1 REP78   ----CPSVADPSTSDAEGAPVDFADRYQNKCSRHAGMLQMLFPCKTCERMNQNFNICFTHGTRDCSECFPGVSES-ES
AAV2 REP78   ----RESVAQPSTSDAE-ASINYADRYQNKCSRHVGMNLMLFPCRQCERMNQSNICFTHGQKDCLECFPVS-ES
AAV3A REP78  ----CTSLAQPTTSDAE-APADYADRYQNKCSRHVGMNLMLFPCRQCERMNQISNVCFTHGQRDCGECFPGMSES
AAV3B REP78  ----CTSLAQPTTSDAE-APADYADRYQNKCSRHVGMNLMLFPCRQCERMNQISNVCFTHGQRDCGECFPGMSES
AAV4 REP78   ----CPSVAQPSTSDAE-APVDYADRYQNKCSRHVGMNLMLFPCRQCERMNQVDICFTHGVMDCAECFFVS-ES
AAV5 REP78   FVPETPRSSDVTVDPAPLRPLNWNSRYDCKCDYHAQFDNISNKCDECEYLNRGKNGCICHNVTHCQICHGIPPWE
AAV6 REP78   ----CPSVADPSTSDAEGAPVDFADRYQNKCSRHAGMLQMLFPCKTCERMNQNFNICFTHGTRDCSECFPGVSES
AAV7 REP78   ----CPSVADPSTSDAEGAPVDFADRYQNKCSRHAGMLQMLFPCKTCERMNQNFNICFTHGVRDCLECFPGVSES
AAV8 REP78   ----CPSVADPSTSDAEGAPVDFADRYQNKCSRHAGMLQMLFPCKTCERMNQNFNICFTHGVRDCSECFPGVSES
CONSENSUS        CPSVADPSTSDAE APVDFADRYQNKCSRHAGM QMLFPCKTCERMNQN NICFTHG RDC ECFPGVSES 600        610         620         630      646
AAV1 REP78   Q--PVVRKRTYRKLCAIHHLLGRAPEIACSACDLVNVDLDDCVSEQ-       (SEQ ID NO:113)
AAV2 REP78   QPVSVVKK-AYQKLCYIHHIMGKVPD-ACTACDLVNVDLDDCIFEQ-       (SEQ ID NO:114)
AAV3A REP78  QPVSVVKKTYQKLCPIHHILGRAPEIACSACDLANVDLDDCVSEQ-        (SEQ ID NO:115)
AAV3B REP78  QPVSVVKKTYQKLCPIHHILGRAPEIACSACDLANVDLDDCVSEQ-        (SEQ ID NO:116)
AAV4 REP78   QPVSVVRKRTYQKLCPIHHIMGRAPEVACSACELANVDLDDCMEQ-        (SEQ ID NO:117)
AAV5 REP78   K------------E--NLSD---FGDFDDANKEQ-                   (SEQ ID NO:118)
AAV6 REP78   Q--PVVRKRTYRKLCAIHHLLGRAPEIACSACDLVNVDLDDCVSEQ-       (SEQ ID NO:119)
AAV7 REP78   Q--PVVRKRTYRKLCAIHHLLGRAPEIACSACDLVNVDLDDCVSEQ-       (SEQ ID NO:120)
AAV8 REP78   Q--PVVRKRTYRKLCAIHHLLGRAPEIACSACDLVNVDLDDCVSEQ-       (SEQ ID NO:121)
CONSENSUS    Q   VVRKRTY KLC IHHHLLGRAPEIACSACDLVNVDLDDCVSEQ       (SEQ ID NO:122)
```

FIG. 32 (cont.)

```
SNAKE ITR
 1 CGCCCACTC CTAGTGATCG CGGGCGCTCT CTCTTGGGGC CTGACGGCCG AAGGCCGTCA GCTGCCGAGC TTGCTCGGC AGGCTTCAAG
91 AGAGAGCGCG CGCGATCACT AGGGGTGGG CG
```

FIG. 33

SNAKE ITR EGFP VECTOR PLASMID (pSnITR-eGFP)

FIG. 34

SNAKE REPCAP2 PLASMID (PSNREPCAP2)
TCGCGCGTTTCGGTGATGACGGTGAAAACCTCTGACACATGCAGCTCCCGGAGACGGTCACAGCTTGTCTGTAAGCG
GATGCCGGGAGCAGACAAGCCCGTCAGGGCGCGTCAGCGGGTGTTGGCGGGTGTCGGGGCTGGCTTAACTATGCGGC
ATCAGAGCAGATTGTACTGAGAGTGCACCATATGCGGTGTGAAATACCGCACAGATGCGTAAGGAGAAAATACCGCA
TCACGGAAATTGTAAACGTTAATATTTTGTTAAAATTCGCGTTAAATTTTTGTTAAATCAGCTCATTTTTTAACCAAT
AGGCCGAAATCGGCAAAATCCCTTATAAATCAAAAGAATAGACCGAGATAGGGTTGAGTGTTGTTCCAGTTTGGAAC
AAGAGTCCACTATTAAAGAACGTGGACTCCAACGTCAAAGGGCGAAAAACCGTCTATCAGGGCGATGGCCCACTACG
TGAACCATCACCCTAATCAAGTTTTTTGGGGTCGAGGTGCCGTAAAGCACTAAATCGGAACCCTAAAGGGAGCCCCC
GATTTAGAGCTTGACGGGGAAAGCCGGCGAACGTGGCGAGAAGGAAGGGAAGAAAGCGAAAGGAGCGGGCGCTAGG
GCGCTGGCAAGTGTAGCGGTCACGCTGCGCGTAACCACCACACCCGCCGCGCTTAATGCGCCGCTACAGGGCGCGTC
GCGCCATTCGCCATTCAGGCTGCGCAACTGTTGGGAAGGGCGATCGGTGCGGGCCTCTTCGCTATTACGCCAGCTGG
CGAAAGGGGGATGTGCTGCAAGGCGATTAAGTTGGGTAACGCCAGGGTTTTCCCAGTCACGACGTTGTAAAACGACG
GCCAGTGAATTGTAATACGACTCACTATAGGGCGAATTCGAGCTCGGTAGCCAAGCTTGGCTGCAGGTCGACGGATCCGCGGCCGCTAGG
AGTCCATATAAGGAGTTCCCGGGATATGCAAATGAGCAATCGCCAAAGCATTTGGGTAGTCACCATGAATAAAAA
AGGACAGCAAGAAAGATGACGCCCCATAATTTTAATAGGAATTTTAACCATGGCGTTTACGAGGTTGTGTTTCGTT
TGCCAAGAGACAATAACAACTGTTGGATGAAGATAGATATCAGCCAGAGTTGAAAGAAGAAGATGACTGGCCTGAG
GAATATTTAACCAGTGAAGATGCCAGCTTTATCGGACTAGCGTATGCTGTGCTAAGTGAAATTCGGAGATTCTTTGG
AAAGGAACTACAATGGTTTGCCCAGGTTGAATGTGTCCTACTGCTGGTTACCACATGCATGTTTGTTGAACCATC
CTAAGCTGAGTAACCAGACTTATGGAAGAAAGGTCAATGAACTGGCTTGCCGTATAGTCGATACCTTTGCCTAATT
AATCCAGAAGAAGTCATCAGTACCCATTATGTTAAAAGCAACTATGGACATAAAAAGGTGAGAGTCATTCACCTAGA
GTCTTATTGAAGAACTACTTTTTCAGAAAGACTTTAGCTCCTCCCAATTATACCGAGGAACGGAGACTATAAAAGAG
AGGAAGAAGTCGTGCTGTGGGCATTTACGAATATCGTCGCTTGGAAGCCATTCGTGCCGAATCTCATCAAGAGATCG
GAGCTAGCGACTGTTCCTAAGCAACCAGAGAATCCGGCGGGAGACGGACCGGCACCTCGAGTGACTGCAGGAACCCG
CCATTTTATGGAAACCATCGACTGGTTGGTGAAACATGGAATTACTACAGAACGAGAATTCTGCCACGCCAACCGCC
CTTTGTACCTGTCTATGCTGGCTTCTACTTCGGGTGCTGGGCAGATTAAAAGAGCGGCTGGACCAGGCGAAACACATG
ATGACGCAACCATGCTCAGCGAGGATTACCTGACAACAGAACGGATGTCGATCGAACCACCTACTGAAAATAGAAT
CTACAAGATTATGAAACTGAATCGCTATGATCCAGAACTAGCAGCTGCTCTTTCTACGCCTGAGAACCTGCAAGAACT
TTGGCAAGAGAAACACCATCTGGCTGTATGGTCCAGCTACTACCGCAAAACCATCGATGGCTCAAGCTATGCACAT
GCTGTTAAACTGTTGCTGGTGTTAATTGGACTAATGAAAACTTTCCCTTCTGTAACTGTCCAGGGAAACGCTTAT
CTGGTGGGACGAGGGCAAGATGACAAACAAAATGGTGGAGACGGCTAAATGTATACTGGGGGATCTGCTGTACCTG
TAGACATCAAAGGCAAACCCGCTGAAATGTGTCCTCAAACACCCTGTATTATTACTAGCAATACTAACATGTGTCAA
GTATATGATGGTAATAGTTCTAGCTTTGAGCACCAAGAACCCCTAGACGAACGCATGTTTATGTTCAGACTTAATAC
TAAACTGCCATCGACCTTTGGCAAGATCACAGAACGAGGAAGTCAAACAGTTTATTACCTGGGGACGAGCTTAAAGG
TTCAAGTTCCACATCAGTTCAGAGTGCCTACCACAGGAGAGTATAAAAGGCCAGCCCCCGAGGCGAAAGCTCATTCT
TCGGATGAGCCGCCAAAAGAGAAGGTCGCGCGTATTGATGACTCTCTACCAGGTATGTTAACAATATTGATGAGTC
AGCTACCAGTAGAGAAATGTTTCTAGAGATGCTAATACTAATCAATGTATGTTGCATCAGTGCTTTCTTGTACCG
AATGTATCCTGAATTGCTTGATGACATGGACAAGGAACAATAAACTTACTGATAACAGATATGGCTGCCGATGGTT
ATCTTCCAGGATTGGCTCGAGGACACTCTCTCTGAAGGAATAAGACAGTGGTGAAGCTCAAACCTGGCCCACCACCA
CCAAAGCCCAGAGCCGGCGGCATTAGGGACGACGCAGCGGGTCTTGTGCTTCCTGGGTACAAGTACCTCGGACCCTTCAA
CGGACTCGACAAGGGGGAGGTCAACGAGGCAGACGCGGCCCCTCGACAGCACATCGAGCACAAGCTACGACCGGCAGC
TCGACAGCGGAGACAACCCGTACCTCAAGTACAACCACGCCGACGCGGAGTTTCAGGAGCGCCTTAAAGAAGATACG
TCTTTTGGGGGCAACCTCGGACGAGCAGTCTTCCAGGCGAAAAAGAGGGTTCTTGAACCTCTGGGCCTGGTTGAGGA
ACCTGTTAAGACGGCTCCGGGAAAAAAGAGGCCGGTAGAGCACTCTCCTGTGGAGCCAGACTGCCTCCTGGGAACCG
GAAAGGCGGGCCAGCAGCCTGCAAGAAAAGATTGAATTTTGGTCAGACTGGAGACGCAGACTCAGTACCTGACCCC
CAGCCTCTCGGACAGCCACCAGCAGCCCCCTCTGGTCTGGAACTAATACGATGGCTACAGGCAGTGGCGCACCAAT
GGCAGACAATAACGAGGGCGCCGACGGAGTGGGTAATTCCTCGGCGAAATTGGCATTGCCGATTCCACATGGATGGCG
ACAGAGTCATCACCACCAGCACCCCGAACCTGGGCCCCTGCCCACCTACAACAACCACCTCTACAAACAAATTCCAGC
CAATCAGGAGCCTGGAACGACAATCACTACTTTGGCTACAGCACCCCTTGGGGGTATTTTGACTTCAACAGATTCCA
CTGCCACTTTTCACCACGTGACTGGCAAAGACTCATCAACAACAACTGGGGATTCCGACCCAAGAGACTCAACTTCA
AGCTCTTTAACATTCAAGTCAAAGAGGTCACGCAGAATGACGGTACGACGACGATTGCAATAACCTTACCAGCACG
GTTCAGGTGTTTACTGACTCGGAGTACCAGCTCCCGTACGTCCTCGGCTCGGCGCATCAAGGATGCCTCCCGGCCGTT
CCCAGCCAGACGTCTTCATGGTGCCACAGTATGGATACCTCACCCTGAACAACGGGAGTCAGGCAGTAGGACGCTCTT
CATTTTTACTGCCTGGGATACTTTCCTTCTCAGATGCTGGCGTAACCGGAAAACAACTTTACCGACGCTACACTTTTGAG
GACGTTCCTTTCCACAGCAGCTACGCTCACAGCCCAGCTCTGGACCGTCTCATGAATCCTCTCATCGACCAGTACCT
GTATTACTTGAGCAGACAAACACTCCAAGTGGAACCACCACGCAGTCAAGGCTTCAGTTTTCTCAGCCGGAGCGA
GTGACATTCGGGACCAGTCTAGGAACTGGCTTCCTGGACCCTGTTACCGCCAGCAGCGAGTATCAAAGACATCTGCG
GATAACAACAACAGTGAATACTCGTGGACTGGAGCTACCAAGTACCACCTCAATGGCAGAGACTCTCTGGTGAATCC
CGGCCCGGCCATGGCAAGCCACAAGGACGATGAAGAAAAGTTTTTTCCTCAGAGCGGGGTTCTCATCTTTGGGAAGC
AAGGCTCAGAGAAAACAAATGTGGACATTGAAAAGGTCATGATTACAGACGAAGAGGAAATCAGGACAACCAATCCC
GTGGCTACGGAGCAGTATGGTTCTGTATCTACCAACCTCCAGAGAGGCAACAGACAAGCAGCTACCGCAGATGTCAA
CACACAAGGCGTTCTTCCAGGCATGGTCTGGCAGGACAGAGATGTGTACCTTCAGGGGCCCATCTGGGCAAAGATTC
CACACACGGACGGACATTTTCACCCCTCTCCCCTCATGGGTGGATTCGGACTTAAACACCCTCCTCCACAGATTCTC

FIG. 35 (cont.)

RESTRICTIVE INVERTED TERMINAL REPEATS FOR VIRAL VECTORS

RELATED APPLICATIONS

This application is a divisional of and claims priority to U.S. patent application Ser. No. 14/922,935, filed Oct. 26, 2015, which is a divisional application of and claims priority to U.S. patent application Ser. No. 13/521,448, filed Jul. 11, 2012, now U.S. Pat. No. 9,169,494, which claims priority to and is a 35 U.S.C. § 371 national phase application of PCT Application PCT/US2011/020939, filed Jan. 12, 2011 which claims the benefit of U.S. Provisional Application No. 61/294,181, filed Jan. 12, 2010. The entire content of each of these applications is incorporated herein by reference.

STATEMENT OF FEDERAL SUPPORT

This invention was made with government support under GM059299, HL066973, HL051818, AI072176 awarded by the National Institutes of Health and AI007419 awarded by the National Institute of Allergy and Infection Diseases. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-547TSDV2 ST25.txt, 454,220 bytes in size, generated on Feb. 7, 2019 and filed via EFS-Web, is provided in lieu of a paper copy. This Sequence Listing is hereby incorporated by reference into the specification for its disclosures.

FIELD OF THE INVENTION

This invention relates to modified parvovirus inverted terminal repeats (ITRs) that do not functionally interact with wild-type large Rep proteins, synthetic Rep proteins that functionally interact with the modified ITRs, and methods of using the same for delivery of nucleic acids to a cell or a subject. The modifications provide a novel Rep-ITR interaction that may limit vector mobilization, increasing the safety of viral vectors.

BACKGROUND OF THE INVENTION

The adeno-associated viruses (AAV) are members of the family Parvoviridae and the genera *Dependoviruses*. Serotypes 1 through 4 were originally identified as contaminates of adenovirus preparations (Carter and Laughlin (1984) in, The Parvoviruses p. 67-152 New York, N.Y.) whereas type 5 was isolated from a patient wart that was HPV positive. To date, twelve molecular clones have been generated representing the serotypes of human/primate AAV (Bantel-Schaal et al. (1999) *J. Virol.* 73: 939; Chiorini at al. (1997) *J. Virol.* 71:6823; Chiorini et al. (1999) *J. Virol.* 73:1309; Gao et al. (2002) *Proc. Nat. Acad. Sci. USA* 99:11854; Mori et al. (2004) *Virol.* 330:375; Muramatsu et al. (1996) *Virol.* 221: 208; Ruffing et al. (1994) *J. Gen. Virol.* 75:3385; Rutledge et al. (1998) *J. Virol.* 72:309; Schmidt et al. (2008) *J. Virol.* 82:8911; Srivastava et al. (1983) *J. Virol.* 45:555; Xiao et al. (1999) *J. Virol.* 73:3994). These clones have provided valuable reagents for studying the molecular biology of serotype specific infection. Transduction of these viruses naturally results in latent infections, with completion of the life cycle generally requiring helper functions not associated with AAV viral gene products. As a result, all of these serotypes are classified as non-pathogenic and are believed to share a safety profile similar to the more extensively studied AAV type 2 (Carter and Laughlin (1984) in, The Parvoviruses p. 67-152 New York, N.Y.).

General understanding of the mechanisms required for function at origins of replication has grown immensely since the first prokaryotic origins were characterized. While the DNA-protein interactions necessary for replication in prokaryotes, lower eukaryotes, and bacteriophages are generally well understood, mechanisms employed in the majority of higher eukaryotes and vertebrate viruses, such as AAV, are still being determined. The inverted terminal repeats (ITRs) of AAV and other Parvoviruses act as the origin of replication. These elements flank the short, single stranded genome and typically possess a T-shaped secondary structure. The replication strategies of the genus *Dependovirus*, including those of AAV, have been well characterized. The viral non-structural or Replication proteins (Rep) are the only factors required to interact with the ITR in order to catalyze replication (Im and Muzyczka (1990) *Cell* 61:447). The majority of AAV serotypes possess highly conserved origins of replication with interchangeable DNA-protein interactions. However, the Rep proteins of several serotypes interact exclusively with their cognate ITR. Discovering the mechanisms which drive Rep-ITR specificity promises to advance our understanding of DNA-protein interactions at viral origins of replication. These findings also promise to shed light on how eukaryotic and prokaryotic proteins achieve selectivity to DNA substrates.

The AAV rep gene encodes four multifunctional proteins (Hermonat et al. (1984) *J. Virol.* 51:329; Tratschin et al. (1984) *J. Virol.* 51:611; Mendelson et al. (1986) *J. Virol.* 60:823; Trempe et al. (1987) *Virol.* 161:18) that are expressed from two promoters at map units 5 (p5) and 19 (p19). The larger Rep proteins transcribed from the p5 promoter (Rep78 and Rep68), are essentially identical except for unique carboxy termini generated from unspliced (Rep78) and spliced (Rep68) transcripts, respectively (Srivastava et al, (1983) *J. Virol.* 45:555). The two smaller Rep proteins, Rep52 and Rep40, are transcribed from the p19 promoter and represent amino terminal truncations of Rep78 and Rep68, respectively.

Several biochemical activities of Rep78 and Rep68 have been characterized as involved in AAV replication. These include specific binding to the AAV ITR (Ashktorab et al. (1989) *J. Virol.* 63:3034; Im et al. (1989) *J. Virol.* 63:3095; Snyder et al. (1993) *J. Virol.* 67:6096) and site-specific endonuclease cleavage at the terminal resolution site (trs) (Im et al. (1990) *J. Virol.* 63:447; Im et al. (1992) *J. Virol.* 66:1119; Snyder et al., (1990) *Cell* 60:105; Snyder et al. (1990) *J. Virol.* 64:6204). Rep78/68 also possess ATP dependent DNA-DNA helicase (Im et al., (1990) *J. Virol.* 63:447; Im et al. (1992) *J. Virol.* 66:1119) and DNA-RNA helicase as well as ATPase activities (Wonderling et al. (1995) *J. Virol.* 69:3542). In addition to these activities involved in replication, Rep78/68 also regulate transcription from the viral promoters (Beaton et al. (1989) *J. Virol.* 63:4450; Labow et al. (1986) *J. Virol.* 60:251; Tratschin et al. (1986) *Mol. Cell. Biol.* 6:2884; Kyostio et al. (1994) *J. Virol.* 68:2947; Pereira et al. (1997) *J. Virol.* 71:1079), and have been shown to mediate viral targeted integration (Xiao, W., (1996), "Characterization of cis and trans elements essential for the targeted integration of recombinant adeno-associated virus plasmid vectors", Ph.D. Dissertation, University of North Carolina-Chapel Hill; Balague et al. (1997) *J. Virol.* 71:3299; LaMartina et al. (1998) *J. Virol.* 72:7653; Pieroni et al. (1998) *Virol.* 249:249).

Like Rep proteins, the AAV ITRs are involved in nearly every aspect of the viral life-cycle. The secondary structure of the ITR is necessary to prime synthesis of the second strand to allow transcription of the viral genes (Hauswirth and Berns (1977) *J. Virol.* 78:488). The full length Rep proteins contain a unique N-terminal DNA binding region which specifically recognizes the ITR at the 16 nt Rep-binding element (RBE) and at the tip of one of the hairpin stems known as the RBE' (FIG. 1A) (Ryan et al. (1996) *J. Virol.* 70:1542; Brister and Muzyczka (2000) *J. Virol.* 74:7762). Rep molecules multimerize on the ITR allowing the C-terminus of Rep, acting as an ATP-dependent SF3 helicase, to unwind the ITR and form a putative internal hairpin (Im and Muzyczka (1990) *Cell* 61:447; Hermonat and Batchu (1997) *FEBS Lett.* 20:180). This hairpin, (here, termed 'nicking stem') contains the terminal resolution site (trs) where Rep nicks the ITR in a site-specific manner (Brister and Muzyczka (1999) *J. Virol.* 73:9325). This DNA cleavage is important for replication of the closed ITR and to initiate subsequent rounds of genomic replication. Replicated genomes can undergo replication again or be encapsidated in the presence of the smaller Rep proteins (King et al. (2001) *EMBO J.* 20:3282).

The ITR sequences of twelve human/primate AAV serotypes have been published. These sequences typically display 80% or greater nucleotide conservation and segregate into two groups (Hewitt et al. (2009) *J. Virol.* 83:3919). The AAV2 Rep proteins (Rep2) are able to function on the ITR of every known AAV serotype except those of AAV5 (ITR5; Hewitt et al. (2009) *J. Virol.* 83:3919; Grimm et al. (2006) *J. Virol.* 80:426). Consistently, the AAV5 Rep proteins (Rep5) are unable to catalyze replication of the ITR of AAV2 (ITR2). Replicative specificity between these serotypes does not exist at the level of binding, as Rep2 and Rep5 can bind interchangeably to ITR2 or ITR5 (Chiorini et al. (1999) *J. Virol.* 73:4293). Instead, specificity is created by the inability of Rep to cleave the ITR of the opposite serotype. This occurs despite high conservation between the ITR2 and ITR5 sequence, secondary structure, and location of elements required for Rep interaction (RBE, RBE', trs, nicking stem).

All current AAV vectors in clinical trials utilize ITR2s. However, using ITR2s for therapeutic purposes creates a safety risk due to the ubiquity of AAV2 in the human population as well as other AAVs whose Rep proteins can replicate ITR2s. In this manner, rAAV vectors have the potential to be "mobilized" out of the target tissue into different tissues of the body or into other individuals in the population (Hewitt et al. (2009) *J. Virol.* 83:3919).

The present invention provides a solution to vector mobilization through the creation of a novel Rep-ITR interaction. A vector utilizing this novel interaction cannot be mobilized by one or more of the wild-type AAV serotypes which infect humans, nor the non-human serotypes which can potentially infect human hosts.

SUMMARY OF THE INVENTION

The present invention relates to the discovery of unique mechanisms at the DNA and protein level to achieve Rep-ITR specificity and utilizes these factors to create novel AAV origins of replication. Thus, one aspect of the invention relates to a polynucleotide comprising at least one parvovirus inverted terminal repeat (ITR), wherein said ITR comprises: (a) a first structural element that functionally interacts with a large Rep protein from a first AAV but does not functionally interact with a large Rep protein from a second AAV; and (b) a second structural element that that functionally interacts with the large Rep protein from the second AAV but does not functionally interact with the large Rep protein from the first AAV; wherein the ITR functionally interacts with a synthetic AAV large Rep protein. The invention further relates to a viral vector and a recombinant parvovirus particle comprising the polynucleotide of the invention. Further provided are pharmaceutical formulations comprising a virus particle of the invention in a pharmaceutically acceptable carrier.

Another aspect of the invention relates to a synthetic large Rep protein comprising a first portion that functionally interacts with a first structural element of a parvovirus ITR and a second portion that functionally interacts with a second structural element of a parvovirus ITR, wherein said first structural element functionally interacts with a large Rep protein from a first AAV and said second structural element functionally interacts with a large Rep protein from a second AAV that is different from the first AAV. The invention further relates to polynucleotides encoding the synthetic large Rep protein and vectors and cells comprising the polynucleotide.

An additional aspect of the invention relates to a method of producing a recombinant parvovirus particle, comprising providing to a cell permissive for parvovirus replication: (a) a recombinant parvovirus template comprising (i) a heterologous nucleotide sequence, and (ii) the parvovirus terminal repeat sequence of the invention; (b) a polynucleotide encoding a Rep protein of the invention; under conditions sufficient for the replication and packaging of the recombinant parvovirus template; whereby recombinant parvovirus particles comprising the parvovirus capsid encoded by the cap coding sequences and packaging the recombinant parvovirus template are produced in the cell.

A further aspect of the invention relates to a method of delivering a nucleic acid to a cell, comprising introducing into a cell the recombinant parvovirus particle of the invention.

Another aspect of the invention relates to a method of administering a nucleic acid to a mammalian subject comprising administering to the mammalian subject a cell that has been contacted with the recombinant parvovirus particle of the invention under conditions sufficient for the parvovirus particle vector genome to enter the cell.

A further aspect of the invention relates to a method of administering a nucleic acid to a mammalian subject comprising administering to the mammalian subject the recombinant parvovirus particle of the invention.

An additional aspect of the invention relates to a parvovirus template comprising (i) a heterologous nucleotide sequence, and (ii) at least one snake AAV ITR sequence and a parvovirus particle comprising the parvovirus template.

A further aspect of the invention relates to a method of producing a parvovirus particle, comprising providing to a cell permissive for parvovirus replication: (a) a recombinant parvovirus template comprising (i) a heterologous nucleotide sequence, and (ii) at least one snake AAV ITR sequence; (b) a polynucleotide encoding snake AAV Rep protein and mammalian AAV Cap protein; (c) a polynucleotide encoding mammalian Rep52 and/or Rep40 proteins; under conditions sufficient for the replication and packaging of the recombinant parvovirus template; whereby recombinant parvovirus particles comprising a parvovirus capsid encoded by the cap coding sequences and packaging the recombinant parvovirus template are produced in the cell.

Another aspect of the invention relates to use of the recombinant parvovirus particle of the invention for delivering a nucleic acid to a cell.

An additional aspect of the invention relates to use of a cell that has been contacted with the recombinant parvovirus particle of the invention for delivering a nucleic acid to a mammalian subject.

A further aspect of the invention relates to use of the recombinant parvovirus particle of the invention for delivering a nucleic acid to a mammalian subject.

Another aspect of the invention relates to use of the recombinant parvovirus particle of the invention for the manufacture of a medicament for delivering a nucleic acid to a cell.

An additional aspect of the invention relates to use of a cell that has been contacted with the recombinant parvovirus particle of the invention for the manufacture of a medicament for delivering a nucleic acid to a mammalian subject.

A further aspect of the invention relates to use of the recombinant parvovirus particle of the invention for the manufacture of a medicament for delivering a nucleic acid to a mammalian subject.

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

These and other aspects of the invention are set forth in more detail in the description of the invention below.

BRIEF DESCRIPTION OF THE DRAWINGS

(FIG. 1A) Sequence and structure of ITR2 (SEQ ID NO:17) (black) and ITR5 (SEQ ID NO:18) (italic) shown with incorporation of SfiI sites for cloning (bold). Length in nt of ITR elements indicated above brackets. RBE is boxed. RBE' is indicated by a hatched circle. Nicking stem is extruded with arrow indicating the nicking site and hatched box indicating the trs. The four initial chimeric ITRs generated (SEQ ID NOS:19-22) are shown (right). (FIG. 1B) Replication assay and quantitation of chimeric Reps. Replication products from the indicated ITR and either Rep2 or Rep5 were analyzed by Southern blot. Monomeric (m) and dimeric (d) replicating species are indicated. The level of replication of each sample was measured by densitometric analysis and compared to wt replication.

(FIG. 2A) Sequence of nicking stem in an otherwise ITR2 context (SEQ ID NOS: 17, 18, 23, 25, 30, 32, 28). Arrow indicates trs site. Brackets indicate height of putative stems in nt from the base of the stem to the putative nicking site. Predicted ΔG values for the hairpins are below. Southern blot analysis of the ITRs replicated by Rep2 or Rep5 are shown below. (FIG. 2B) Quantitation of the Southern blots relative to wt replication from FIG. 2A. (FIG. 2C) Same as FIG. 2A, except nicking stems indicated were used in an ITR5 context (SEQ ID NOS:17, 18, 24, 26, 35). (FIG. 2D) Quantitation of the Southern blots relative to wt replication from FIG. 2C.

(FIG. 3A) ITR2 mutants were synthesized with the indicated spacing between the RBE and nicking stem (SEQ ID NOS:17, 31, 33). (FIG. 3B) Southern blot analysis of the ITRs depicted in FIG. 3A replicated by either Rep2 or Rep5 (Left). Quantitation of Southern blots relative to wt replication (Right). (FIG. 3C) ITR5 mutants synthesized as in FIG. 3A (SEQ ID NOS:34, 18, 37, 38). (FIG. 3D) Southern blot analysis and quantitation of FIG. 3C.

FIGS. 4A-4D demonstrate that the ITR5 spacer acts as a RBE for Rep5. (FIG. 4A) ITR5 mutants were synthesized with the indicated RBE and spacer sequence (SEQ ID NOS:18, 40, 39, 42). Brackets indicate individual tetranucleotide repeats bound by Rep monomers. Both strands of the wt ITR5 sequence are shown to illustrate conservation with the GAGY motif (indicated by *). Only one strand shown on others. (FIG. 4B) Southern blot analysis of the ITRs depicted in FIG. 4A replicated by either Rep2 or Rep5 (Left). Quantitation of Southern blots relative to wt replication (Right). (FIG. 4C) ITR2 mutants were generated with the RBE and spacer sequences indicated (SEQ ID NOS:17, 29, 41, 43). (FIG. 4D) Southern blot analysis and quantitation for FIG. 4C.

FIGS. 5A-5E show the cloning and characterization of chimeric Reps. (FIG. 5A) An alignment of the N-termini of Rep2 (SEQ ID NO:114) and Rep5 (SEQ ID NO:118). (*) represents conserved amino acids. (:) and (.) indicate conservative substitutions. (^) indicates residues implicated in RBE binding interactions. (') indicates residues which participate in the endonucleolytic active site. (+) indicates residues implicated in RBE' binding. (FIG. 5B) Chimeric Reps created and their ability to replicate ITR2 or ITR5 flanked vectors. Numbers indicate the amino acid (aa) position of the switch from one Rep to the other. (+) indicates the presence of replication, (−) indicates the absence. (FIG. 5C) Western blot for expression of the chimeric Reps. (FIG. 5D) Southern blot demonstrating replication of an ITR2 or an ITR5 vector by the chimeric Reps. Note that the ITR5 vector is 500 bp larger than the ITR2 vector. (FIG. 5E) Level of replication of the chimeric Reps relative to wt Rep2 or Rep5.

(FIG. 6A) Chimeric Reps and their ability to replicate ITR2 or ITR5 flanked vectors. Numbers indicate the aa position of the switch from one Rep to the other. (+) indicates the presence of replication, (−) indicates the absence. Region 1 and 2 involved in Rep-ITR specificity are indicated. (FIG. 6B) Western blot for expression of chimeric Reps. (FIG. 6C) Southern blot demonstrating replication of an ITR2 or ITR5 vector by the chimeric Reps. Note that the ITR5 vector is 500 bp larger than the ITR2 vector. (FIG. 6D) Structural model illustrating the two Rep regions. The nucleophilic tyrosine is indicated. Black hatched circle indicates the predicted structural difference of region 1 in the major groove of the ITR. (FIG. 6E) Structural model as in FIG. 6D. The nucleophilic tyrosine is indicated. (FIG. 6F) Detailed structural view of region 1. The sidechains of non-conserved residues from Rep5 and Rep2 are shown. Three Rep5 residues implicated in RBE' binding are indicated. (FIG. 6G) Detailed structural view of region 2. Side chains of active site residues are shown in black. Side chains of non-conserved residues in this region are shown for Rep2 and Rep5. The nucleophilic tyrosine is indicated, as is the adjacent Rep2 Asn-155.

(FIG. 7A) Southern blot of Hirt DNA demonstrating replication of the indicated ITR vector by the indicated Rep. (FIG. 7B) Table indicating the presence (+) or absence (−) of replication of the gel from FIG. 7A. (FIG. 7C) Model of a novel AAV origin of replication. The chimeric ITR can be replicated only by a chimeric Rep protein. Rep5 sequence in region 1 is required for the extended RBE of ITR5. Rep2 sequence in region 2 is required to function on an ITR2 nicking stem.

FIG. 8 shows an illustrative genomic DNA sequence for AAV-1; GenBank Accession No. NC 002077; SEQ ID NO:1.

FIG. 9 shows an illustrative genomic DNA sequence for AAV-2; GenBank Accession No. NC 001401; SEQ ID NO:2.

FIG. 10 shows an illustrative genomic DNA sequence for AAV-3A; GenBank Accession No. NC 001729; SEQ ID NO:3.

FIG. 11 shows an illustrative genomic DNA sequence for AAV-3B; GenBank Accession No. NC 001863; SEQ ID NO:4.

FIG. 12 shows an illustrative genomic DNA sequence for AAV-4; GenBank Accession No. NC 001829; SEQ ID NO:5.

FIG. 13 shows an illustrative genomic DNA sequence for AAV-5; GenBank Accession No. NC 006152; SEQ ID NO:6.

FIG. 14 shows an illustrative genomic DNA sequence for AAV-6; GenBank Accession No. NC 001862; SEQ ID NO:7.

FIG. 15 shows an illustrative genomic DNA sequence for AAV-7; GenBank Accession No. AF513851; SEQ ID NO:8.

FIG. 16 shows an illustrative genomic DNA sequence for AAV-8; GenBank Accession No. AF513852; SEQ ID NO:9.

FIG. 17 shows an illustrative genomic DNA sequence for AAV-9; GenBank Accession No. AX753250; SEQ ID NO:10.

FIG. 18 shows an illustrative genomic DNA sequence for AAV-11; GenBank Accession No. AY631966; SEQ ID NO:11.

FIG. 19 shows an illustrative genomic DNA sequence for AAV-13; GenBank Accession No. EU285562; SEQ ID NO:12.

FIG. 20 shows an illustrative genomic DNA sequence for B19 parvovirus; GenBank Accession No. NC 000883; SEQ ID NO:13.

FIG. 21 shows an illustrative genomic DNA sequence for Minute Virus from Mouse (MVM); GenBank Accession No. NC 001510; SEQ ID NO:14.

FIG. 22 shows an illustrative genomic DNA sequence for goose parvovirus; GenBank Accession No. NC 001701; SEQ ID NO:15.

FIG. 23 shows an illustrative genomic DNA sequence for snake parvovirus 1; GenBank Accession No. NC 006148; SEQ ID NO:16.

FIG. 24 provides an exemplary listing of the chimeric ITRs that were synthesized as part of the Examples described below: ITR2 (SEQ ID NO:17), ITR5 (SEQ ID NO:18), ITR5+2SNS (SEQ ID NO:19), ITR2+5SNS (SEQ ID NO:20), ITR5+2NS (SEQ ID NO:21), ITR2+5NS (SEQ ID NO:22), ITR2−TA (SEQ ID NO:23), ITR5+TA (SEQ ID NO:24), ITR2−GC (SEQ ID NO:25), ITR5+GC (SEQ ID NO:26), ITR2-2 nt (SEQ ID NO:27), ITR2 5 nt (SEQ ID NO:28), ITR2+7 (SEQ ID NO:29), ITR2 9 nt (SEQ ID NO:30), ITR2 10 nt (SEQ ID NO:31), ITR2 11 nt (SEQ ID NO:32), ITR2 15 nt (SEQ ID NO:33), ITR5 3 nt (SEQ ID NO:34), ITR5 6 nt (SEQ ID NO:35), ITR5 9 bp NS (SEQ ID NO:36), ITR5 21 nt (SEQ ID NO:37), ITR5 30 nt (SEQ ID NO:38), ITR5 GAGY (SEQ ID NO:39), ITR5 no GAGY (SEQ ID NO:40), ITR2+8 nt GAGY (SEQ ID NO:41), ITR5 Spacer RBE (SEQ ID NO:42), ITR2+8–8 Spacer RBE (SEQ ID NO:43), ITR5 with ITR2 hairpins (SEQ ID NO:44), ITR2 no hairpins (SEQ ID NO:45), ITR2 T1 (SEQ ID NO:46), ITR2 T2 (SEQ ID NO:47), ITR2 T2 #2 (SEQ ID NO:48), ITR2 T3 (SEQ ID NO:49), ITR2 T4 (SEQ ID NO:50), ITR5+3 nt Spacer & ITR5 NS (SEQ ID NO:51), and ITR2 pHpa8 (SEQ ID NO:52).

FIG. 25 provides an exemplary listing of the chimeric Rep proteins that were synthesized as part of the Examples described below: Rep52aa73 (SEQ ID NO:53), Rep52aa84 (SEQ ID NO:54), Rep52aa110 (SEQ ID NO:55), Rep52aa126 (SEQ ID NO:56), Rep52aa138 (SEQ ID NO:57), Rep52aa160 (SEQ ID NO:58), Rep52aa175 (SEQ ID NO:59), Rep52aa187 (SEQ ID NO:60), Rep52aa207 (SEQ ID NO:61), Rep25aa73 (SEQ ID NO:62), Rep25aa77 (SEQ ID NO:63), Rep25aa97 (SEQ ID NO:64), Rep25aa116 (SEQ ID NO:65), Rep25aa125 (SEQ ID NO:66), Rep25aa141 (SEQ ID NO:67), Rep25aa149 (SEQ ID NO:68), Rep25aa166 (SEQ ID NO:69), Rep25aa187 (SEQ ID NO:70), Rep25aa216 (SEQ ID NO:71), Rep525aa110-148 (SEQ ID NO:72), Rep525aa146-187 (SEQ ID NO:73), Rep525aa110-187 (SEQ ID NO:74), Rep252aa97-146 (SEQ ID NO:75), Rep252aa149-187 (SEQ ID NO:76), and Rep252aa97-187 (SEQ ID NO:77).

FIG. 26 shows both the nucleotide and amino acid sequences of a chimeric Rep protein of the invention: Rep52aa146 (SEQ ID NO:78 and SEQ ID NO:79, respectively).

FIG. 27 shows both the nucleotide and amino acid sequences of a chimeric Rep protein of the invention: Rep52aa147 (SEQ ID NO:80 and SEQ ID NO:81, respectively).

FIG. 28 shows both the nucleotide and amino acid sequences of a chimeric Rep protein of the invention: Rep52aa151 (SEQ ID NO:82 and SEQ ID NO:83, respectively).

FIG. 29 shows an alignment of the amino acid sequences of exemplary Rep40 proteins from AAV1 (SEQ ID NO:84), AAV2 (SEQ ID NO:85), AAV3A (SEQ ID NO:86), AAV3B (SEQ ID NO:87), AAV4 (SEQ ID NO:88), AAV5 (SEQ ID NO:89), AAV6 (SEQ ID NO:90), AAV7 (SEQ ID NO:91) and AAV8 (SEQ ID NO:92), as well as a consensus sequence (SEQ ID NO:93). Dashes indicate gaps in the sequence and shading indicates positions of sequence homology.

FIG. 30 shows an alignment of the amino acid sequences of exemplary Rep52 proteins from AAV1 (SEQ ID NO:94), AAV2 (SEQ ID NO:95), AAV3A (SEQ ID NO:96), AAV3B (SEQ ID NO:97), AAV4 (SEQ ID NO:98), AAV5 (SEQ ID NO:99), AAV6 (SEQ ID NO:100), AAV7 (SEQ ID NO:101) and AAV8 (SEQ ID NO:102), as well as a consensus sequence (SEQ ID NO:103). Dashes indicate gaps in the sequence and shading indicates positions of sequence homology.

FIG. 31 shows an alignment of the amino acid sequences of exemplary Rep68 proteins from AAV1 (SEQ ID NO:104), AAV2 (SEQ ID NO:105), AAV3A (SEQ ID NO:106), AAV3B (SEQ ID NO:107), AAV4 (SEQ ID NO:108), AAV5 (SEQ ID NO:109), AAV6 (SEQ ID NO:110), AAV7 (SEQ ID NO:111) and AAV8 (SEQ ID NO:112). Dashes indicate gaps in the sequence and shading indicates positions of sequence homology.

FIG. 32 shows an alignment of the amino acid sequences of exemplary Rep78 proteins from AAV1 (SEQ ID NO:113), AAV2 (SEQ ID NO:114), AAV3A (SEQ ID NO:115), AAV3B (SEQ ID NO:116), AAV4 (SEQ ID NO:117), AAV5 (SEQ ID NO:118), AAV6 (SEQ ID NO:119), AAV7 (SEQ ID NO:120) and AAV8 (SEQ ID NO:121), as well as a consensus sequence (SEQ ID NO:122). Dashes indicate gaps in the sequence and shading indicates positions of sequence homology.

FIG. 33 shows the nucleotide sequence of the snake ITR utilized in Example 9 (SEQ ID NO:123).

FIG. 34 shows the nucleotide sequence of the snake ITR eGFP vector plasmid (SEQ ID NO:124) used to synthesize the snake vector described in Example 9.

FIG. 35 shows the nucleotide sequence of the pSnRep-Cap2 plasmid (SEQ ID NO:125) used to synthesize the snake vector described in Example 9.

(FIG. 36A) The ITR was synthesized in two pieces ——— and — — —) overlapping across one hairpin stem holding the SfiI site (········) (FIG. 36B) Each half was amplified via PCR prior to digestion and cloning. (FIG. 36C) Proper triple-ligation with pUC18-CMV GFP produced an ITR in DD format.

DETAILED DESCRIPTION OF THE INVENTION

Figure 1A:
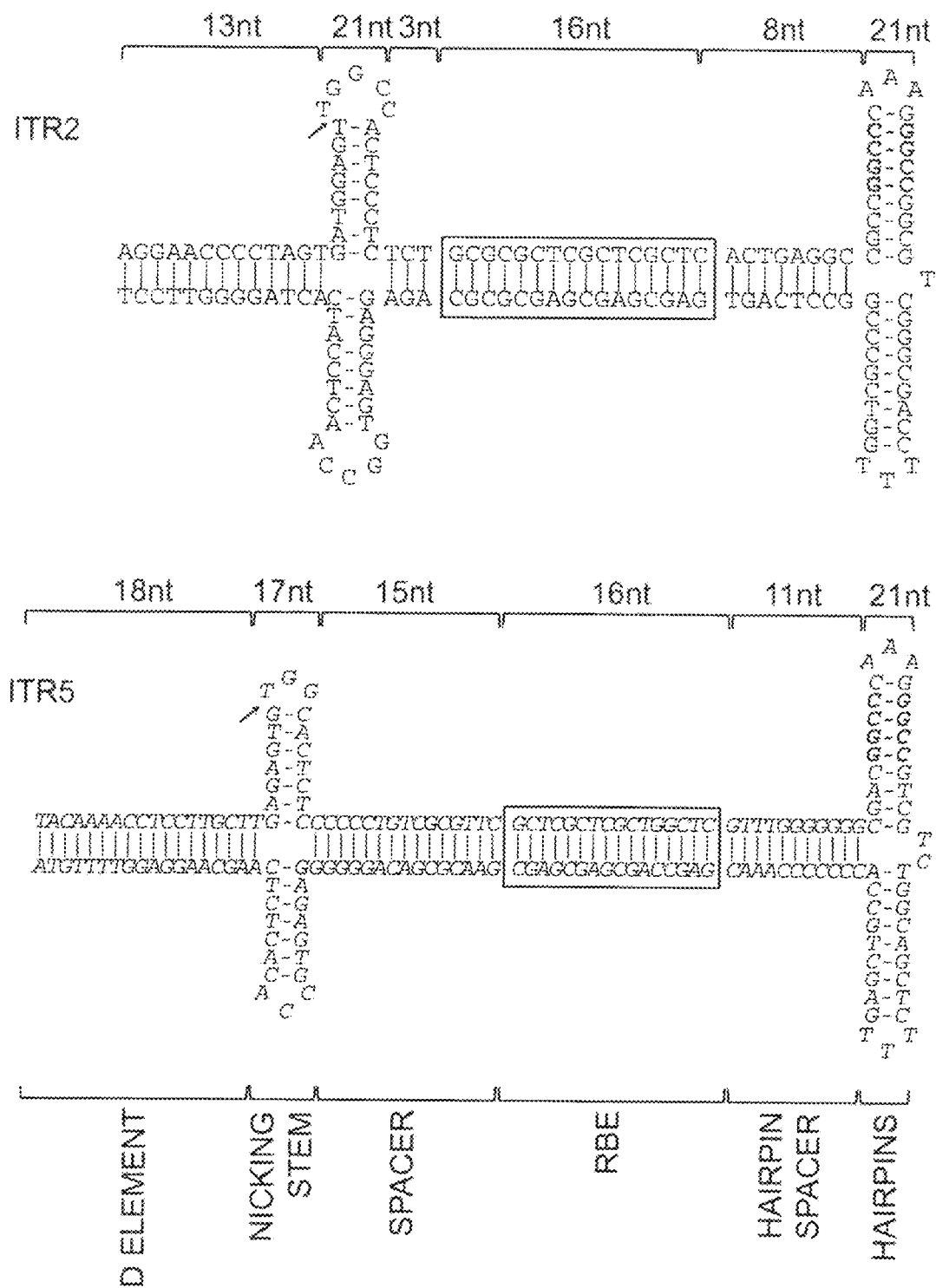
FIGS. 1A-1B show the cloning and characterization of chimeric ITRs.
Figure 1A:
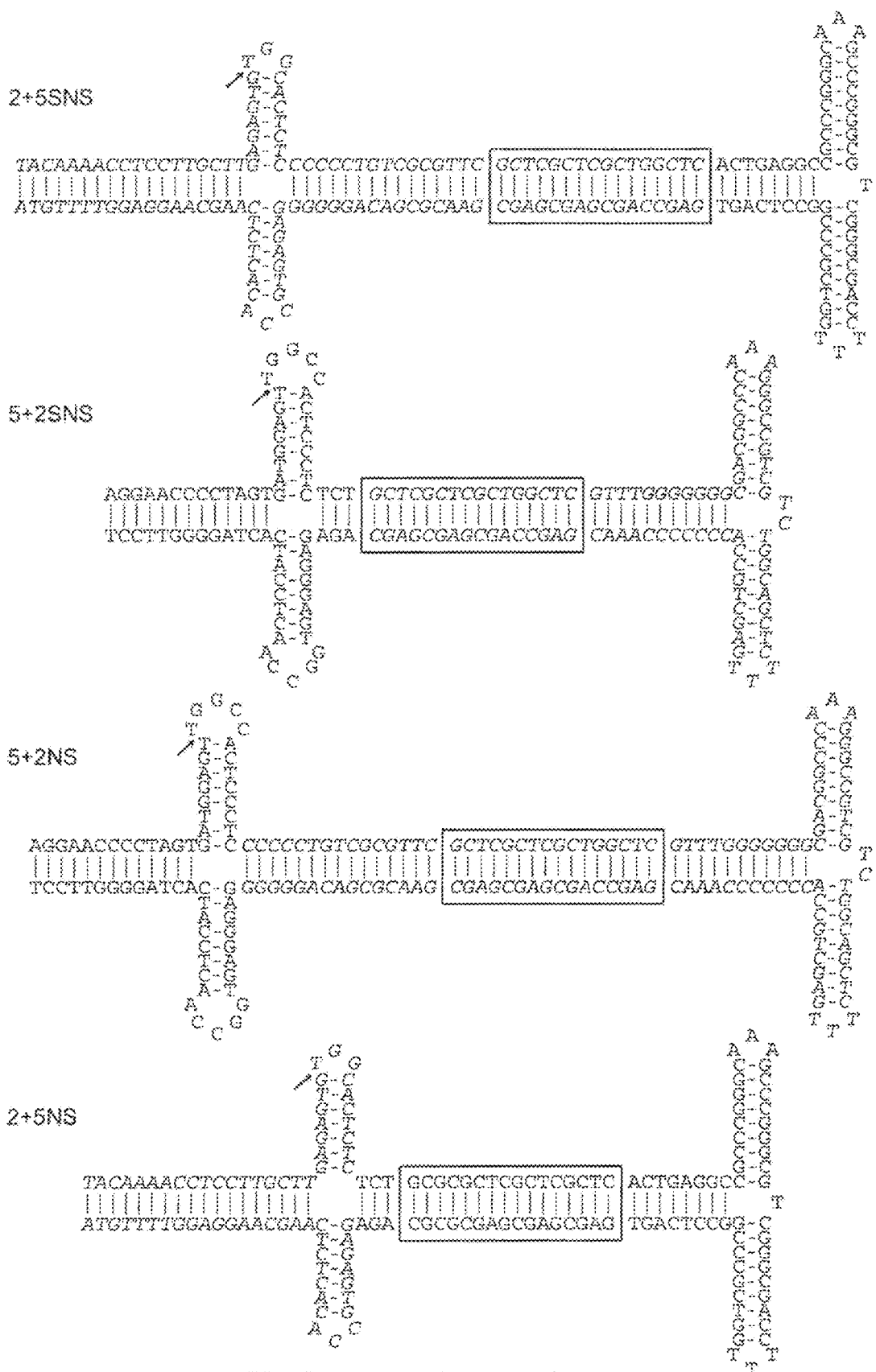

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR § 1.822 and established usage. See, e.g., *PatentIn User Manual*, 99-102 (November 1990) (U.S. Patent and Trademark Office).

Except as otherwise indicated, standard methods known to those skilled in the art may be used for the construction of recombinant parvovirus and rAAV constructs, packaging vectors expressing the parvovirus Rep and/or Cap sequences, and transiently and stably transfected packaging cells. Such techniques are known to those skilled in the art. See, e.g., SAMBROOK et al. MOLECULAR CLONING: A LABORATORY MANUAL 2nd Ed. (Cold Spring Harbor, N.Y., 1989); AUSUBEL et al. CURRENT PROTOCOLS IN MOLECULAR BIOLOGY (Green Publishing Associates, Inc. and John Wiley & Sons, Inc., New York).

Definitions

The following terms are used in the description herein and the appended claims:

The singular forms "a" and "an" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of 20%, 10%, 5%, 1%, 0.5%, or even 0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" is to be interpreted as encompassing the recited materials or steps "and those that do not materially affect the basic and novel characteristic(s)" of the claimed invention (e.g., rAAV replication). See, *In re Herz*, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "parvovirus" as used herein encompasses the family Parvoviridae, including autonomously-replicating parvoviruses and dependoviruses. The autonomous parvoviruses include members of the genera *Parvovirus, Erythrovirus, Densovirus, Iteravirus*, and *Contravirus*. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus (See, e.g., FIGS. 20-23). Other autonomous parvoviruses are known to those skilled in the art. See, e.g., FIELDS et al. VIROLOGY, volume 2, chapter 69 (4th ed., Lippincott-Raven Publishers).

The genus *Dependovirus* contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIGS. 8-19; FIELDS et al. VIROLOGY, volume 2, chapter 69 (4th ed., Lippincott-Raven Publishers); and Table 1.

TABLE 1

| | GenBank Accession Number |
|---|---|
| Complete Genomes | |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |

TABLE 1-continued

| | GenBank Accession Number |
|---|---|
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV3 | NC_001729 |
| AAV3B | NC_001863 |
| AAV4 | NC_001829 |
| Rh34 | AY243001 |
| Rh33 | AY243002 |
| Rh32 | AY243003 |

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any other AAV now known or later discovered. See, e.g., FIELDS et al. VIROLOGY, volume 2, chapter 69 (4th ed., Lippincott-Raven Publishers). A number of relatively new AAV serotypes and clades have been identified (See, e.g., Gao et al. (2004) *J. Virol.* 78:6381; Moris et al. (2004) *Virol.* 33-:375; and Table 1).

The parvovirus particles and genomes of the present invention can be from, but are not limited to, AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., FIGS. 8-23; GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al. (1999) *J. Virol.* 73: 939; Chiorini et al. (1997) *J. Virol.* 71:6823; Chiorini et al. (1999) *J. Virol.* 73:1309; Gao et al. (2002) *Proc. Nat. Acad. Sci. USA* 99:11854; Moris et al. (2004) *Virol.* 33-:375-383; Mori et al. (2004) *Virol.* 330:375; Muramatsu et al. (1996) *Virol.* 221: 208; Ruffing et al. (1994) *J. Gen. Virol.* 75:3385; Rutledge et al. (1998) *J. Virol.* 72:309; Schmidt et al. (2008) *J. Virol.* 82:8911; Shade et al., (1986) *J. Virol.* 58:921; Srivastava et al. (1983) *J. Virol.* 45:555; Xiao et al. (1999) *J. Virol.* 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, Pa. (incorporated herein it its entirety).

The term "tropism" as used herein refers to entry of the virus into the cell, optionally and preferably followed by expression (e.g., transcription and, optionally, translation) of sequences carried by the viral genome in the cell, e.g., for a recombinant virus, expression of the heterologous nucleotide sequences(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of AAV, gene expression from the viral genome may be from a stably integrated provirus, from a non-integrated episome, as well as any other form in which the virus may take within the cell.

As used herein, "transduction" or "infection" of a cell by a parvovirus or AAV means that the parvovirus/AAV enters the cell to establish an active (i.e., lytic) infection. As used herein, "transduction" of a cell by AAV means that the AAV enters the cell to establish a latent infection. See, e.g., FIELDS et al. VIROLOGY, volume 2, chapter 69 (3d ed., Lippincott-Raven Publishers).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), and can be either single or double stranded DNA sequences.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.*, 266:460 (1996); blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity with respect to the coding sequence of the polypeptides disclosed herein is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components or other polypeptides or nucleic acids commonly found associated with the polynucleotide.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

A "therapeutic polypeptide" is a polypeptide that may alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify" (or grammatical equivalents) a virus vector, it is meant that the virus vector is at least partially separated from at least some of the other components in the starting material.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid" are used interchangeably herein and refer to a sequence that is not naturally occurring in the virus. Generally, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the invention.

A "rAAV vector genome" or "rAAV genome" is an AAV genome (i.e., vDNA) that comprises one or more heterologous nucleic acid sequences. rAAV vectors generally require only the 145 base ITR in cis to generate virus. All other viral sequences are dispensable and may be supplied in trans (Muzyczka (1992) Curr. Topics Microbiol. Immunol. 158:97). Typically, the rAAV vector genome will only retain the one or more ITR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one ITR sequence (e.g., AAV ITR sequence), optionally two ITRs (e.g., two AAV ITRs), which typically will be at the 5' and 3' ends of the vector genome and flank the heterologous nucleic acid, but need not be contiguous thereto. The ITRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The ITR can be an AAV ITR or a non-AAV ITR. For example, a non-AAV ITR sequence such as those of other parvoviruses (e.g., canine parvovirus, bovine parvovirus, mouse parvovirus, porcine parvovirus, human parvovirus B-19) or the SV40 hairpin that serves as the origin of SV40 replication can be used as an ITR, which can further be modified by truncation, substitution, deletion, insertion and/or addition. Further, the ITR can be partially or completely synthetic, such as the "double-D sequence" as described in U.S. Pat. No. 5,478,745 to Samulski et al. FIG. 24 provides examples of synthetic ITRs contemplated by the present invention.

Parvovirus genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al. VIROLOGY, volume 2, chapters 69 & 70 (4th ed., Lippincott-Raven Publishers).

An "AAV inverted terminal repeat" or "AAV ITR" may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered (see, e.g., Table 1). An AAV ITR need not have the native terminal repeat sequence (e.g., a native AAV ITR sequence may be altered by insertion, deletion, truncation and/or missense mutations), as long as the terminal repeat mediates the desired functions, e.g., replication, virus packaging, integration, and/or provirus rescue, and the like.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) *Mol. Therapy* 2:619.

Further, the viral capsid or genomic elements can contain other modifications, including insertions, deletions and/or substitutions.

As used herein, the term "amino acid" encompasses any naturally occurring amino acids, modified forms thereof, and synthetic amino acids.

Naturally occurring, levorotatory (L-) amino acids are shown in Table 2.

TABLE 2

| Amino Acid Residue | Abbreviation | |
|---|---|---|
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 3) or can be an amino acid that is modified by post-translation modification (e.g., acetylation, amidation, formylation, hydroxylation, methylation, phosphorylation or sulfatation).

TABLE 3

| Modified Amino Acid Residue | Abbreviation |
|---|---|
| Amino Acid Residue Derivatives | |
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

Further, the non-naturally occurring amino acid can be an "unnatural" amino acid as described by Wang et al. (2006) *Annu. Rev. Biophys. Biomol. Struct.* 35:225-49. These unnatural amino acids can advantageously be used to chemically link molecules of interest to the AAV capsid protein.

The term "template" or "substrate" is used herein to refer to a polynucleotide sequence that may be replicated to produce the parvovirus viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., FIELDS et al. VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) *Human Gene Therapy* 13:1935).

As used herein, the term "synthetic large Rep protein" refers to a large Rep protein having an amino acid sequence that differs from a wild-type large Rep protein sequence. The sequence of the synthetic large Rep protein may differ from a wild-type sequence due to one or more deletions, additions, substitutions, or any combination thereof. The difference between the synthetic and wild-type sequences may be as little as a single amino acid change, e.g., a change in 1, 2, 3, 4, 5,6, 7, 8, 9, 10, 15, 20, 25, 30, 35, 40, 45, 60, 60, 70, 80, 90, 100, 125, 150, 175, 200, 225, 250, 275, 300, 325, 350, 375, 400. 425, 450, 475, 500, 525, 550, 575, or 600 or more amino acids or any range therein. In certain embodiments, the synthetic large Rep protein is a chimeric Rep protein comprising portions of the wild-type sequence of two or more different large Rep proteins. In other embodiments, the synthetic large Rep protein is a chimeric Rep protein comprising portions of the wild-type sequence of two or more different large Rep proteins, one or more portions of which have been modified from the wild-type sequence.

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

As used herein, the term "structural element," when used with respect to a parvovirus ITR, refers to a portion of the ITR that, based on nucleotide sequence, secondary structure, or both, plays a role in the functional interaction of a large Rep protein with the ITR, e.g., a portion that, when removed from the ITR, prevents functional interaction with a large Rep protein. In some embodiments, the structural element physically interacts with the large Rep protein.

As used herein, the term "functionally interacts" refers to an interaction between an ITR and a large Rep protein (e.g., binding) that ultimately results in nicking of the ITR and replication of a polynucleotide in which the ITR is present.

As used herein, the term "nicking stem" refers to a hairpin loop structure present in a parvovirus ITR that is nicked by a large Rep protein during replication of a polynucleotide in which the ITR is present.

As used herein, the term "extended RBE" refers to the nucleotide sequence of a parvovirus ITR between the nicking stem and the RBE (the spacer sequence as shown in FIG. 1A) which, in certain parvoviruses (e.g., AAV5), functions as an extension of the RBE (i.e., is recognized and bound by a large Rep protein). The term "extended RBE" is only applicable to the spacer sequence when the sequence functions as an extension of the RBE.

Modified Parvovirus ITRs

The present invention provides modified parvovirus ITRs and synthetic Rep proteins that functionally interact with the modified ITRs. The modified ITRs are unique in that they do not functionally interact with wild-type Rep proteins and may reduce or avoid vector mobilization.

One aspect of the invention relates to a polynucleotide comprising at least one parvovirus ITR, wherein the ITR comprises: (a) a first structural element that functionally interacts with a large Rep protein from a AAV but does not functionally interact with a large Rep protein from a second AAV; and (b) a second structural element that functionally interacts with the large Rep protein from the second AAV but does not functionally interact with the large Rep protein from the first AAV; wherein the ITR functionally interacts with a synthetic AAV large Rep protein. In one embodiment, the ITR does not functionally interact with any wild-type large Rep protein, e.g., AAV2 Rep, AAV5 Rep, or any other known Rep protein. In particular embodiments, the synthetic large Rep protein comprises an amino acid sequence selected from the group consisting of SEQ ID NOS:79, 81, and 83 or an amino acid sequence having at least 80% identity to one of SEQ ID NOS: 79, 81, and 83, e.g., at least 85%, 90%, 95%, 96%, 97%, 98%, or 99% identity. In one embodiment, the ITR further comprises a third structural element that functionally interacts with a large Rep protein from an AAV that is the same as or different from the first and/or second AAV.

In one embodiment of the invention, the parvovirus ITR is from an autonomous parvovirus. In another embodiment, the parvovirus ITR is from an AAV, e.g., an AAV selected from the group consisting of AAV1, AAV2, AAV3, AAV4, AAV5, AAV6, AAV7, AAV8, AAV9, AAV10, AAV11, AAV12, and AAV13. In a further embodiment, the parvovirus ITR is from a non-human AAV such as snake AAV, avian AAV, bovine AAV, canine AAV, equine AAV, ovine AAV, goat AAV, or shrimp AAV.

The structural element of the ITR can be any structural element that is involved in the functional interaction of the ITR with a large Rep protein. In certain embodiments, the structural element provides selectivity to the interaction of an ITR with a large Rep protein, i.e., determines at least in part which Rep protein functionally interacts with the ITR. In other embodiments, the structural element physically interacts with a large Rep protein when the Rep protein is bound to the ITR. Each structural element can be, e.g., a secondary structure of the ITR, a nucleotide sequence of the ITR, a spacing between two or more elements, or a combination of any of the above. In one embodiment, the structural elements are selected from the group consisting of a nicking stem, a spacer, a RBE, an extended RBE, and any combination thereof. In a particular embodiment, the first structural element is a nicking stem. In another embodiment, the second structural element is a RBE. In a further embodiment, the second structural element is an extended RBE. In an additional embodiment, the second structural element is a spacer.

The ability of a structural element to functionally interact with a particular large Rep protein can be altered by modifying the structural element. For example, the nucleotide sequence of the structural element can be modified as compared to the wild-type sequence of the ITR. In one embodiment, the structural element (e.g., the nicking stem, spacer, RBE, and/or extended RBE) of an ITR can be removed and replaced with a wild-type structural element from a different parvovirus. For example, the replacement structure can be from AAV1, AAV2, AAV3, AAV4, AAV5, AAV6, AAV7, AAV8, AAV9, AAV10, AAV11, AAV12, AAV13, snake parvovirus (e.g., royal python parvovirus), bovine parvovirus, goat parvovirus, avian parvovirus, canine parvovirus, equine parvovirus, shrimp parvovirus, porcine parvovirus, or insect AAV. For example, the ITR can be an AAV2 ITR and the nicking stem or RBE can be replaced with a structural element from AAV5. In another example, the ITR can be an AAV5 ITR and the nicking stem, RBE, or extended RBE can be replaced with a structural element from AAV2. In one example, the ITR can be an AAV2 ITR with the nicking stem replaced with the AAV5 ITR nicking stem, e.g., the ITR of SEQ ID NO:22 or a modified sequence thereof. In another example, the AAV ITR can be an AAV5 ITR with the nicking stem replaced with the AAV2 ITR nicking stem, e.g., the ITR of SEQ ID NO:21 or a modified sequence thereof.

In one embodiment, the nucleotide sequence of the structural element can be modified (e.g., by modifying 1, 2, 3, 4, 5, 6, 7, 8, 9, 10, 11, 12, 13, 14, 15, 16, 17, 18, 19, or 20 or more nucleotides or any range therein) to produce a synthetic structural element. In certain embodiments, the specific ITRs exemplified herein (SEQ ID NOS:17-52) can be modified (e.g., by modifying 1, 2, 3, 4, 5, 6, 7, 8, 9, 10, 11, 12, 13, 14, 15, 16, 17, 18, 19, or 20 or more nucleotides or any range therein). In other embodiments, the ITR can have at least 80% identity with one of the ITRs of SEQ ID NOS:17-52, e.g., at least 85%, 90%, 95%, 96%, 97%, 98%, or 99% identity. In one embodiment, the structural element is a nicking stem and the modified sequence is a modified terminal resolution site (trs) sequence. For example, a nicking stem can be modified to comprise the ITR2 trs (GGT/TGG) or the ITR5 trs (AGTG/TGG). In another embodiment, the structural element is a RBE or an extended RBE and the sequence is a modified at the nucleotides responsible for binding specificity. For example, the sequence of a RBE or an extended RBE can be modified to make the sequence closer to or further from the consensus GAGY binding sites recognized by Rep. In one example, the spacer or extended RBE can be modified to comprise one or more exact GAGY repeats (e.g., the ITR of SEQ ID NO:39 or a modified sequence thereof), e.g., 1, 2, 3, or 4 or more exact GAGY repeats.

In a different embodiment, the structure of the structural element can be modified. For example, the structural element can be a nicking stem and the modification can be a change in the height of the stem and/or the number of nucleotides in the loop. For example, the height of the stem can be about 2, 3, 4, 5, 6, 7, 8, or 9 nucleotides or more or any range therein. In one embodiment, the nicking stem height can be about 5 nucleotides to about 9 nucleotides and functionally interacts with Rep2. In another embodiment, the nicking stem height can be about 7 nucleotides and functionally interacts with Rep5. In another example, the loop can have 3, 4, 5, 6, 7, 8, 9, or 10 nucleotides or more or any range therein. In another example, the structural element can be a RBE or an extended RBE and the number of GAGY binding sites or GAGY-related binding sites within the RBE or extended RBE can be increased or decreased. In one example, the RBE or extended RBE can comprise 1, 2, 3, 4, 5, or 6 or more GAGY binding sites or any range therein. Each GAGY binding site can independently be an exact GAGY sequence or a sequence similar to GAGY as long as the sequence is sufficient to bind a Rep protein.

In another embodiment, the spacing between two elements (such as the nicking stem and the RBE or the RBE and a hairpin) can be altered (e.g., increased or decreased) to alter functional interaction with a large Rep protein. For example, the spacing can be about 1, 2, 3, 4, 5, 6, 7, 8, 9, 10, 11, 12, 13, 14, 15, 16, 17, 18, 19, 20, or 21 nucleotides or more or any range therein. In one embodiment, the spacer between the nicking stem and the RBE is about 3 nucleotides in length and functionally interacts with Rep2. In another embodiment, the spacer between the nicking stem and the RBE is about 3 nucleotides (e.g., the ITR of SEQ ID NO:34 or a modified sequence thereof) to about 21 nucleotides in length (e.g., the ITR of SEQ ID NO:37 or a modified sequence thereof) and functionally interacts with Rep5. In one embodiment, the spacer is the 15 nucleotide spacer of the AAV5 ITR or a sequence having at least 80% identity thereto, e.g., at least 85%, 90%, 95%, 96%, 97%, 98%, or 99% identity.

In a representative embodiment, the polynucleotide comprises at least one parvovirus ITR, wherein said ITR comprises: (a) a first structural element that functionally interacts with a large Rep protein from one or more of AAV1, AAV2, AAV3, AAV4, AAV6, AAV7, AAV8, AAV9, AAV10, AAV11, AAV12, and AAV13 but does not functionally interact with a large Rep protein from AAV5; and (b) a second structural element that functionally interacts with the large Rep protein from AAV5 but does not functionally interact with the large Rep protein from one or more of AAV1, AAV2, AAV3, AAV4, AAV6, AAV7, AAV8, AAV9, AAV10, AAV11, AAV12, and AAV13; wherein the ITR functionally interacts with a synthetic AAV large Rep protein comprising an amino acid sequence selected from SEQ ID NOS: 79, 81, and 83.

In one aspect of the invention the polynucleotide comprising the modified ITR of the invention further comprises a second ITR which may be the same as or different from the first ITR. In one embodiment, the polynucleotide further comprises a heterologous nucleic acid, e.g., a sequence encoding a protein or a functional RNA. In some embodiments, the second ITR cannot be resolved by the Rep protein, i.e., resulting in a double stranded viral DNA.

The invention also provides a viral vector comprising the polynucleotide comprising the modified ITR of the invention. The viral vector can be a parvovirus vector, e.g., an AAV vector. The invention further provides a recombinant parvovirus particle (e.g., a recombinant AAV particle) comprising the modified ITR of the invention. Viral vectors and viral particles are discussed further below.

Synthetic Rep Proteins

One aspect of the invention relates to synthetic large Rep proteins that functionally interact with the modified ITRs of the invention. Thus, in one aspect, the invention relates to a synthetic large Rep protein comprising a first portion that functionally interacts with a first structural element of a parvovirus ITR and a second portion that functionally interacts with a second structural element of a parvovirus ITR, wherein said first structural element functionally interacts with a large Rep protein from a first AAV but does not functionally interact with a large Rep protein from a second AAV and said second structural element functionally interacts with a large Rep protein from a second AAV but does not functionally interact with a large Rep protein from the first AAV. In one embodiment, the protein comprises a third portion that functionally interacts with a third structural element that functionally interacts with a large Rep protein from an AAV that is the same as or different from the first and/or second AAV. In one embodiment, the first structural element is a nicking stem and the first portion of the synthetic large Rep protein functional interacts with the nicking stem. In another embodiment, the second structural element is a spacer, RBE, or extended RBE and the second portion of the synthetic large Rep protein functional interacts with the spacer, RBE, or extended RBE.

In one embodiment, one or more portions of the synthetic large Rep protein comprise a wild-type amino acid sequence from a parvovirus Rep protein. In another embodiment, one or more portions of the synthetic large Rep protein comprise an amino acid sequence that is modified as compared to the wild-type sequence of a parvovirus Rep protein. The modification can be an addition, deletion, substitution, or any combination thereof. The synthetic large Rep protein can comprise one or more modified amino acids, e.g., about 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 150, 175, 200, 225, 250, 275, 300, 325, 350, 375, 400, 425, 450, 475, 500, 525, 550, 575, or 600 or more amino acids or any range therein.

In one embodiment of the invention, the first and second portions (and/or the third portion) are directly linked to each other. In another embodiment, the portions are connected by a linker, e.g., 1, 2, 3, 4, 5, or 6 or more amino acids. The synthetic large Rep protein can comprise further portions (e.g., from Rep or another protein or synthetic sequences) that are not involved in the functional interaction with an ITR. Examples of other sequences can include, without limitation, localization signals, tags for improved isolation, etc.

In one embodiment, the first portion of the synthetic large Rep protein comprises, consists essentially of, or consists of an amino acid sequence from about residue 97 to about residues 146-151 of a wild-type AAV5 Rep sequence, e.g., SEQ ID NO:118. For example the first portion can comprise, consist essentially of, or consist of an amino acid sequence from about residue 1, 5, 10, 15, 20, 25, 30, 35, 40, 45, 50, 55, 60, 65, 70, 75, 80, 85, 90, or 95 to about residue 146, 147, 148, 149, 151, or 151 of a wild-type AAV5 Rep sequence or any range therein. In certain embodiments, the first portion comprises, consists essentially of, or consists of an amino acid sequence having at least 80% identity to a sequence from about residue 97 to about residues 146-151 of a wild-type AAV5 Rep sequence, e.g., at least 85%, 90%, 95%, 96%, 97%, 98%, or 99% identity.

In one embodiment, the second portion of the synthetic large Rep protein comprises, consists essentially of, or consists of an amino acid sequence from about residue 149 to about residue 187 of a wild-type AAV2 Rep sequence, e.g., SEQ ID NO:114. For example, the second portion can comprise, consist essentially of, or consist of an amino acid sequence from about residue 149 to about residue 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, or 620 of a wild-type AAV2 Rep sequence or any range therein. In certain embodiments, the second portion comprises, consists essentially of, or consists of an amino acid sequence having at least 80% identity to a sequence from about residue 149 to about residue 187 of a wild-type AAV5 Rep sequence, e.g., at least 85%, 90%, 95%, 96%, 97%, 98%, or 99% identity.

In a representative embodiment of the synthetic large Rep protein, the first portion comprises, consists essentially of, or consists of an amino acid sequence from about residue 97 to about residues 146-151 of a wild-type AAV5 Rep sequence and the second portion comprises, consists essentially of, or consists of an amino acid sequence from about residue 149 to about residue 187 of a wild-type AAV2 Rep sequence. In another representative embodiment, the first portion comprises, consists essentially of, or consists of an amino acid sequence from about residue 1 to about residues 146-151 of a wild-type AAV5 Rep sequence and the second portion comprises, consists essentially of, or consists of an amino acid sequence from about residue 149 to about residue 621 of a wild-type AAV2 Rep sequence. In certain embodiments, the synthetic large Rep protein comprises, consists essentially of, or consists of an amino acid sequence of SEQ ID NOS: 79, 81, and 83. In other embodiments, the synthetic large Rep protein comprises, consists essentially of, or consists of an amino acid sequence having at least 80% identity to an amino acid sequence of SEQ ID NOS: 79, 81, and 83, e.g., at least 85%, 90%, 95%, 96%, 97%, 98%, or 99% identity.

In certain embodiments, the portion of the synthetic large Rep protein from a wild-type AAV2 Rep sequence as described above can be replaced with the corresponding portion from another human AAV serotype Rep protein other than AAV5, e.g., AAV1, AAV3, AAV4, AAV6, AAV7, AAV8, AAV9, AAV10, AAV11, AAV12, or AAV13. The structural and functional similarity between the Rep proteins of AAV2 and other human serotypes (with the exception of AAV5) may allow substitution of Rep sequences between the serotypes (see FIGS. 31 and 32).

In certain embodiments, one or more of the portions the synthetic Rep proteins can be modified to differ from the wild-type sequence (e.g., by modifying 1, 2, 3, 4, 5, 6, 7, 8, 9, 10, 11, 12, 13, 14, 15, 16, 17, 18, 19, 20 or more aa or any range therein). In other embodiments, the synthetic Rep proteins exemplified herein can be modified (e.g., by modifying 1, 2, 3, 4, 5, 6, 7, 8, 9, 10, 11, 12, 13, 14, 15, 16, 17, 18, 19, or 20 or more aa or any range therein). In some embodiments, the modified synthetic Rep proteins retain amino acid Y156 (numbering according to Rep2). In other embodiments, modified synthetic Rep proteins retain amino acids C151, N155, and/or T161 (numbering according to Rep2). In other embodiments, modified synthetic Rep proteins retain amino acids G148, A152, and/or V158 (numbering according to Rep5). These specific amino acids may be important for activity and/or specificity.

The invention also provides polynucleotides (optionally, isolated polynucleotides) encoding the synthetic Rep proteins of the invention. In some embodiments, the polynucleotides further encode one or more parvovirus Cap proteins. Further provided are vectors comprising the polynucleotides, and cells (in vivo or in culture) comprising the polynucleotides and/or vectors of the invention. Suitable vectors include, without limitation, viral vectors (e.g., adenovirus, AAV, herpesvirus, vaccinia, poxviruses, baculoviruses, Epstein-Barr virus, and the like), plasmids, phage, YACs, BACs, and the like. In some embodiments, the polynucleotide is stably integrated into the genome of a cell. Such polynucleotides, vectors and cells can be used, for example, as reagents (e.g., helper packaging constructs or packaging cells) for the production of virus vectors as described herein.

Snake AAV ITRs

One aspect of the invention relates to the discovery that a snake AAV ITR sequence can function as a part of a parvovirus vector yet is not recognized by the Rep proteins of mammalian (e.g., human or primate) parvoviruses. Vector mobilization may therefore be reduced or avoided. Thus, one aspect of the invention relates to a parvovirus template comprising (i) a heterologous nucleotide sequence, and (ii) at least one snake AAV ITR sequence. The snake AAV ITR sequence can be from a royal python AAV. In one embodiment, the snake AAV ITR sequence comprises the nucleotide sequence of SEQ ID NO:123. In a further embodiment, the snake AAV ITR sequence comprises the nucleotide sequence of SEQ ID NO:123 that has been modified (e.g., by modifying 1, 2, 3, 4, 5, 6, 7, 8, 9, 10, 11, 12, 13, 14, 15, 16, 17, 18, 19, or 20 or more nucleotides or any range therein). In other embodiments, the parvovirus template comprises at least a portion of a snake AAV ITR, e.g., at least 10, 15, 20, 25, 30, 35, 40, 45, 50, 55, 60, 65, 70, 75, 80, 85, 90, 95, 100, 105, 110, 115, 120, 125, 130, 135, 140, 145, or 150 or more contiguous nucleotides of a snake AAV ITR or any range therein. In certain embodiments, the parvovirus template comprises two snake AAV ITR sequences.

The invention further relates to a parvovirus particle comprising the snake parvovirus template of the invention. In certain embodiments, the parvovirus particle comprises a mammalian capsid, e.g., a human or primate capsid.

In one aspect, the invention relates to the discovery of methods for producing parvovirus particles comprising a snake AAV ITR, including the requirement for a mammalian small Rep protein. Thus, one aspect of the invention relates to a method of producing a parvovirus particle, comprising providing to a cell (e.g., a mammalian cell such as a human or primate cell) permissive for parvovirus replication: (a) a recombinant parvovirus template comprising (i) a heterologous nucleotide sequence, and (ii) at least one snake AAV ITR sequence; (b) a polynucleotide encoding one or more snake AAV Rep proteins and mammalian AAV Cap protein(s); and (c) a polynucleotide encoding mammalian Rep52 and/or Rep40 proteins; under conditions sufficient for the replication and packaging of the recombinant parvovirus template; whereby recombinant parvovirus particles packaging the recombinant parvovirus template are produced in the cell. In one embodiment, the mammalian AAV Cap protein is a human or primate AAV Cap protein. In another embodiment, the mammalian AAV Rep 52 and/or Rep 40 proteins are human or primate Rep52 and/or Rep40 proteins (including modified forms thereof), e.g., from AAV2. In some embodiments, the polynucleotide encoding snake AAV Rep protein and mammalian AAV Cap protein also encodes the mammalian Rep52 and/or Rep40 proteins. In other embodiments, the polynucleotide encoding snake AAV Rep protein and mammalian AAV Cap protein is separate from the polynucleotide encoding the mammalian Rep52 and/or Rep40 proteins. In some embodiments, the polynucleotide encoding snake AAV Rep protein and mammalian AAV Cap protein is the plasmid pSnRepCap2 (SEQ ID NO:125).

In other embodiments, other non-human AAV ITR sequences not recognized by the Rep proteins of human or primate parvoviruses may be used. Examples include, without limitation, sequences from shrimp, insect, goat, bovine, equine, canine, and equine AAVs.

Methods of Producing Virus Vectors

The present invention further provides methods of producing virus vectors. In one particular embodiment, the present invention provides a method of producing a recombinant parvovirus particle, comprising providing to a cell permissive for parvovirus replication: (a) a recombinant parvovirus template comprising (i) a heterologous nucleotide sequence, and (ii) the modified parvovirus ITR of the invention; (b) a polynucleotide encoding a synthetic large Rep protein of the invention; under conditions sufficient for the replication and packaging of the recombinant parvovirus template; whereby recombinant parvovirus particles are produced in the cell. Conditions sufficient for the replication and packaging of the recombinant parvovirus template can be, e.g., the presence of AAV sequences sufficient for replication of the parvovirus template and encapsidation into parvovirus capsids (e.g., parvovirus rep sequences and parvovirus cap sequences) and helper sequences from adenovirus and/or herpesvirus. In particular embodiments, the parvovirus template comprises two parvovirus ITR sequences, which are located 5' and 3' to the heterologous nucleic acid sequence, although they need not be directly contiguous thereto.

In some embodiments, the recombinant parvovirus template comprises an ITR that is not resolved by Rep to make duplexed AAV vectors as described in international patent publication WO 01/92551

The parvovirus template and parvovirus rep and cap sequences are provided under conditions such that virus vector comprising the parvovirus template packaged within the parvovirus capsid is produced in the cell. The method can further comprise the step of collecting the virus vector from the cell. The virus vector can be collected from the medium and/or by lysing the cells.

The cell can be a cell that is permissive for parvovirus viral replication. Any suitable cell known in the art may be employed. In particular embodiments, the cell is a mammalian cell (e.g., a primate or human cell). As another option, the cell can be a trans-complementing packaging cell line that provide functions deleted from a replication-defective helper virus, e.g., 293 cells or other E1a trans-complementing cells.

The parvovirus replication and capsid sequences may be provided by any method known in the art. Current protocols typically express the parvovirus rep/cap genes on a single plasmid. The parvovirus replication and packaging sequences need not be provided together, although it may be convenient to do so. The parvovirus rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the parvovirus cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) Curr. Top. Microbiol. Immun. 158:67).

As a further alternative, the rep/cap sequences may be stably incorporated into a cell.

Typically the parvovirus rep cap sequences will not be flanked by the TRs, to prevent rescue and/or packaging of these sequences.

The parvovirus template can be provided to the cell using any method known in the art. For example, the template can be supplied by a non-viral (e.g., plasmid) or viral vector. In particular embodiments, the parvovirus template is supplied by a herpesvirus or adenovirus vector (e.g., inserted into the E1a or E3 regions of a deleted adenovirus). As another illustration, Palombo et al., (1998) 1 Virology 72:5025, describes a baculovirus vector carrying a reporter gene flanked by the AAV TRs. EBV vectors may also be employed to deliver the template, as described above with respect to the rep/cap genes.

In another representative embodiment, the parvovirus template is provided by a replicating rAAV virus. In still other embodiments, an AAV provirus comprising the parvovirus template is stably integrated into the chromosome of the cell.

To enhance virus titers, helper virus functions (e.g., adenovirus or herpesvirus) that promote a productive parvovirus infection can be provided to the cell. Helper virus sequences necessary for parvovirus replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient parvovirus production as described by Ferrari et al., (1997) Nature Med. 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into parvovirus virions, e.g., are not flanked by TRs.

Those skilled in the art will appreciate that it may be advantageous to provide the parvovirus replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the parvovirus rep/cap genes.

In one particular embodiment, the parvovirus rep/cap sequences and the adenovirus helper sequences are supplied by a single adenovirus helper vector. This vector can further comprise the parvovirus template. The parvovirus rep/cap sequences and/or the parvovirus template can be inserted into a deleted region (e.g., the E1a or E3 regions) of the adenovirus.

In a further embodiment, the parvovirus rep/cap sequences and the adenovirus helper sequences are supplied by a single adenovirus helper vector. According to this embodiment, the parvovirus template can be provided as a plasmid template.

In another illustrative embodiment, the parvovirus rep/cap sequences and adenovirus helper sequences are provided by a single adenovirus helper vector, and the parvovirus template is integrated into the cell as a provirus. Alternatively, the parvovirus template is provided by an EBV vector that is maintained within the cell as an extrachromosomal element (e.g., as an EBV based nuclear episome).

In a further exemplary embodiment, the parvovirus rep/cap sequences and adenovirus helper sequences are provided by a single adenovirus helper. The parvovirus template can be provided as a separate replicating viral vector. For example, the parvovirus template can be provided by a parvovirus particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The parvovirus rep/cap sequences and, if present, the parvovirus template are embedded in the adenovirus backbone and are flanked by the 5' and 3' cis sequences, so that these sequences may be packaged into adenovirus capsids. As described above, the adenovirus helper sequences and the parvovirus rep/cap sequences are generally not flanked by TRs so that these sequences are not packaged into the parvovirus virions.

Zhang et al., ((2001) Gene Ther. 18:704-12) describe a chimeric helper comprising both adenovirus and the AAV rep and cap genes.

Herpesvirus may also be used as a helper virus in parvovirus packaging methods. Hybrid herpesviruses encoding the parvovirus Rep protein(s) may advantageously facilitate scalable parvovirus vector production schemes. A hybrid herpes simplex virus type I (HSV-1) vector expressing the AAV-2 rep and cap genes has been described (Conway et al., (1999) Gene Ther. 6:986 and WO 00/17377.

As a further alternative, the virus vectors of the invention can be produced in insect cells using baculovirus vectors to deliver the rep/cap genes and parvovirus template as described, for example, by Urabe et al., (2002) Human Gene Ther. 13:1935-43.

Parvovirus vector stocks free of contaminating helper virus may be obtained by any method known in the art. For example, parvovirus and helper virus may be readily differentiated based on size. Parvovirus may also be separated away from helper virus based on affinity for a heparin substrate (Zolotukhin et al. (1999)Gene Therapy 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of parvovirus. Adenovirus mutants defective for late gene expression are known in the art (e.g., ts100K and ts149 adenovirus mutants).

Recombinant Virus Vectors

The virus vectors of the present invention are useful for the delivery of nucleic acids to cells in vitro, ex vivo, and in vivo. In particular, the virus vectors can be advantageously employed to deliver or transfer nucleic acids to animal, including mammalian, cells.

Any heterologous nucleic acid sequence(s) of interest may be delivered in the virus vectors of the present invention. Nucleic acids of interest include nucleic acids encoding polypeptides, including therapeutic (e.g., for medical or veterinary uses), immunogenic (e.g., for vaccines), or diagnostic polypeptides.

Therapeutic polypeptides include, but are not limited to, cystic fibrosis transmembrane regulator protein (CFTR), dystrophin (including mini- and micro-dystrophins (see, e.g, Vincent et al., (1993) *Nature Genetics* 5:130; U.S. Patent Publication No. 2003/017131; International publication WO/2008/088895, Wang et al., *Proc. Natl. Acad. Sci. USA* 97:13714-13719 (2000); and Gregorevic et al., *Mol. Ther.* 16:657-64 (2008)), myostatin propeptide, follistatin, activin type II soluble receptor, IGF-1, anti-inflammatory polypeptides such as the Ikappa B dominant mutant, sarcospan, utrophin (Tinsley et al., (1996) *Nature* 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, $α_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor −3 and −4, brain-derived neurotrophic factor, bone morphogenic proteins [including RANKL and VEGF], glial derived growth factor, transforming growth factor −α and −β, and the like), lysosomal acid α-glucosidase, α-galactosidase A, receptors (e.g., the tumor necrosis growth factorα soluble receptor), S100A1, parvalbumin, adenylyl cyclase type 6, a molecule that effects G-protein coupled receptor kinase type 2 knockdown such as a truncated constitutively active bARKct, anti-inflammatory factors such as IRAP, anti-myostatin proteins, aspartoacylase, and monoclonal antibodies (including single chain monoclonal antibodies; an exemplary Mab is the Herceptin® Mab). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. Parvovirus vectors can also be used to deliver monoclonal antibodies and antibody fragments, for example, an antibody or antibody fragment directed against myostatin (see, e.g., Fang et al., *Nature Biotechnol.* 23:584-590 (2005)).

Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Alternatively, in particular embodiments of this invention, the heterologous nucleic acid may encode an antisense nucleic acid, a ribozyme (e.g., as described in U.S. Pat. No. 5,877,022), RNAs that effect spliceosome-mediated trans-splicing (see, Puttaraju et al., (1999) *Nature Biotech.* 17:246; U.S. Pat. Nos. 6,013,487; 6,083,702), interfering RNAs (RNAi) including siRNA, shRNA or miRNA that mediate gene silencing (see, Sharp et al., (2000) *Science* 287:2431), and other non-translated RNAs, such as "guide" RNAs (Gorman et al., (1998) *Proc. Nat. Acad. Sci. USA* 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al., *J. Gene Med.* 10:132-142 (2008) and Li et al., *Acta Pharmacol Sin.* 26:51-55 (2005)); phospholamban inhibitory or dominant-negative molecules such as phospholamban S16E (e.g., to treat cardiovascular disease, see, e.g., Hoshijima et al. *Nat. Med.* 8:864-871 (2002)), RNAi to adenosine kinase (e.g., for epilepsy), RNAi to a sarcoglycan [e.g., α, β, γ], RNAi against myostatin, myostatin propeptide, follistatin, or activin type II soluble receptor, RNAi against anti-inflammatory polypeptides such as the Ikappa B dominant mutant, and RNAi directed against pathogenic organisms and viruses (e.g., hepatitis B virus, human immunodeficiency virus, CMV, herpes simplex virus, human papilloma virus, etc.).

Alternatively, in particular embodiments of this invention, the heterologous nucleic acid may encode protein phosphatase inhibitor I (I-1), serca2a, zinc finger proteins that regulate the phospholamban gene, Barkct, β2-adrenergic receptor, β2-adrenergic receptor kinase (BARK), phosphoinositide-3 kinase (PI3 kinase), a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, enos, inos, or bone morphogenic proteins (including BNP 2, 7, etc., RANKL and/or VEGF).

The virus vector may also comprise a heterologous nucleic acid that shares homology with and recombines with a locus on a host chromosome. This approach can be utilized, for example, to correct a genetic defect in the host cell.

The present invention also provides virus vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccine vectors is known in the art (see, e.g., Miyamura et al., (1994) *Proc. Nat. Acad. Sci USA* 91:8507; U.S. Pat. No. 5,916,563 to Young et al., U.S. Pat. No. 5,905,040 to Mazzara et al., U.S. Pat. Nos. 5,882, 652, 5,863,541 to Samulski et al.). The antigen may be presented in the parvovirus capsid. Alternatively, the antigen may be expressed from a heterologous nucleic acid introduced into a recombinant vector genome. Any immunogen of interest as described herein and/or as is known in the art can be provided by the virus vector of the present invention.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a Filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens) a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S. A. Rosenberg (*Immunity* 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al., (1994) *Proc. Natl. Acad. Sci. USA* 91:3515; Kawakami et al., (1994) *J. Exp. Med.*, 180:347; Kawakami et al., (1994) *Cancer Res.* 54:3124), MART-1, gp100 MAGE-1, MAGE-2, MAGE-3, CEA, TRP-1, TRP-2, P-15, tyrosinase (Brichard et al., (1993) *J. Exp. Med.* 178: 489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) *Ann. Rev. Biochem.* 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg, (1996) *Ann. Rev. Med.* 47:481-91).

As a further alternative, the heterologous nucleic acid can encode any polypeptide that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present invention provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present invention can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders, Alzheimer's disease (GDF; neprilysin), multiple sclerosis (β-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic defects, congenital emphysema (α1-antitrypsin), Lesch-Nyhan Syndrome (hypoxanthine guanine phosphoribosyl transferase), Niemann-Pick disease (sphingomyelinase), Tays Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1), serca2a, zinc finger proteins that regulate the phospholamban gene, Barkct, β2-adrenergic receptor, β2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (a-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors according to the present invention permit the treatment and/or prevention of genetic diseases.

The virus vectors according to the present invention may also be employed to provide a functional RNA to a cell in vitro or in vivo. Expression of the functional RNA in the cell, for example, can diminish expression of a particular target protein by the cell. Accordingly, functional RNA can be administered to decrease expression of a particular protein in a subject in need thereof. Functional RNA can also be administered to cells in vitro to regulate gene expression and/or cell physiology, e.g., to optimize cell or tissue culture systems or in screening methods.

Virus vectors according to the instant invention find use in diagnostic and screening methods, whereby a nucleic acid of interest is transiently or stably expressed in a cell culture system, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors of the present invention may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In particular embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, the virus vector or cell comprising the heterologous nucleic acid can be administered in an immunogenically effective amount, as described below.

The virus vectors of the present invention can also be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein. Alternatively, the cancer antigen can be expressed as part of the virus capsid or be otherwise associated with the virus capsid as described above.

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the invention provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In particular embodiments, cells may be removed from a subject with cancer and contacted with a virus vector according to the instant invention. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., $\alpha$-interferon, $\beta$-interferon, $\gamma$-interferon, $\omega$-interferon, $\tau$-interferon, interleukin-1$\alpha$, interleukin-1$\beta$, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-$\alpha$, tumor necrosis factor-$\beta$, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration

Virus vectors and capsids according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles and adults.

In particular embodiments, the present invention provides a pharmaceutical composition comprising a virus vector and/or capsid of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, more preferably at least about $10^5$ infectious units are introduced to the cell.

The cell(s) into which the virus vector is introduced can be of any type, including but not limited to neural cells (including cells of the peripheral and central nervous systems, in particular, brain cells such as neurons and oligodendrocytes), lung cells, cells of the eye (including retinal cells, retinal pigment epithelium, and corneal cells), blood vessel cells (e.g., endothelial cells, intimal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, kidney cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo gene delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vector to subjects. Administration of the virus vectors and/or capsids according to the present invention to a human subject or an animal in need thereof can be by any means known in the art. Optionally, the virus vector and/or capsid is delivered in a treatment effective or prevention effective dose in a pharmaceutically acceptable carrier.

The virus vectors and/or capsids of the invention can further be administered to elicit an immunogenic response (e.g., as a vaccine). Typically, immunogenic compositions of the present invention comprise an immunogenically effective amount of virus vector and/or capsid in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$ transducing units, optionally about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, intraendothelial, in utero (or in ovo), parenteral (e.g., intravenous, subcutaneous, intradermal, intracranial, intramuscular [including administration to skeletal, diaphragm and/or cardiac muscle], intrapleural, intracerebral, and intraarticular), topical (e.g., to both skin and mucosal surfaces, including airway surfaces, and transdermal administration), intralymphatic, and the like, as well as direct tissue or organ injection (e.g., to liver, eye, skeletal muscle, cardiac muscle, diaphragm muscle or brain).

Administration can be to any site in a subject, including, without limitation, a site selected from the group consisting of the brain, a skeletal muscle, a smooth muscle, the heart, the diaphragm, the airway epithelium, the liver, the kidney, the spleen, the pancreas, the skin, and the eye.

Administration can also be to a tumor (e.g., in or near a tumor or a lymph node). The most suitable route in any given case will depend on the nature and severity of the condition being treated and/or prevented and on the nature of the particular vector that is being used.

Administration to skeletal muscle according to the present invention includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, articularis genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis brevis, extensor carpi radialis longus, extensor carpi ulnaris, extensor digiti minimi, extensor digitorum, extensor digitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficialis, flexor hallucis brevis, flexor hallucis longus, flexor pollicis brevis, flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus medialis, zygomaticus major, and zygomaticus minor, and any other suitable skeletal muscle as known in the art.

The virus vector can be delivered to skeletal muscle by intravenous administration, intra-arterial administration, intraperitoneal administration, limb perfusion, (optionally, isolated limb perfusion of a leg and/or arm; see, e.g. Arruda et al., (2005) *Blood* 105: 3458-3464), and/or direct intramuscular injection. In particular embodiments, the virus vector and/or capsid is administered to a limb (arm and/or leg) of a subject (e.g., a subject with muscular dystrophy such as DMD) by limb perfusion, optionally isolated limb perfusion (e.g., by intravenous or intra-articular administration. In embodiments of the invention, the virus vectors and/or capsids of the invention can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the vector to cross the endothelial cell barrier. In particular embodiments, the viral vectors and/or capsids of the invention can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome.

Administration to cardiac muscle includes administration to the left atrium, right atrium, left ventricle, right ventricle and/or septum. The virus vector and/or capsid can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Administration to smooth muscle can be by any suitable method including intravenous administration, intra-arterial administration, and/or intra-peritoneal administration. In one embodiment, administration can be to endothelial cells present in, near, and/or on smooth muscle.

Delivery to a target tissue can also be achieved by delivering a depot comprising the virus vector and/or capsid. In representative embodiments, a depot comprising the virus vector and/or capsid is implanted into skeletal, smooth, cardiac and/or diaphragm muscle tissue or the tissue can be contacted with a film or other matrix comprising the virus vector and/or capsid. Such implantable matrices or substrates are described in U.S. Pat. No. 7,201,898.

In particular embodiments, a virus vector according to the present invention is administered to skeletal muscle, diaphragm muscle and/or cardiac muscle (e.g., to treat and/or prevent muscular dystrophy or heart disease [for example, PAD or congestive heart failure]).

In representative embodiments, the invention is used to treat and/or prevent disorders of skeletal, cardiac and/or diaphragm muscle.

In a representative embodiment, the invention provides a method of treating and/or preventing muscular dystrophy in a subject in need thereof, the method comprising: administering a treatment or prevention effective amount of a virus vector of the invention to a mammalian subject, wherein the virus vector comprises a heterologous nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-α2, α-sarcoglycan, β-sarcoglycan, γ-sarcoglycan, δ-sarcoglycan, IGF-1, an antibody or antibody fragment against myostatin or myostatin propeptide, and/or RNAi against myostatin. In particular embodiments, the virus vector can be administered to skeletal, diaphragm and/or cardiac muscle as described elsewhere herein.

Alternatively, the invention can be practiced to deliver a nucleic acid to skeletal, cardiac or diaphragm muscle, which is used as a platform for production of a polypeptide (e.g., an enzyme) or functional RNA (e.g., RNAi, microRNA, antisense RNA) that normally circulates in the blood or for systemic delivery to other tissues to treat and/or prevent a disorder (e.g., a metabolic disorder, such as diabetes (e.g., insulin), hemophilia (e.g., Factor IX or Factor VIII), a mucopolysaccharide disorder (e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.) or a lysosomal storage disorder (such as Gaucher's disease [glucocerebrosidase], Pompe disease [lysosomal acid a-glucosidase] or Fabry disease [a-galactosidase A]) or a glycogen storage disorder (such as Pompe disease [lysosomal acid a glucosidase]). Other suitable proteins for treating and/or preventing metabolic disorders are described above. The use of muscle as a platform to express a nucleic acid of interest is described in U.S. Patent Publication No. 2002/0192189.

Thus, as one aspect, the invention further encompasses a method of treating and/or preventing a metabolic disorder in a subject in need thereof, the method comprising: administering a treatment or prevention effective amount of a virus vector of the invention to a subject (e.g., to skeletal muscle of a subject), wherein the virus vector comprises a heterologous nucleic acid encoding a polypeptide, wherein the metabolic disorder is a result of a deficiency and/or defect in the polypeptide. Illustrative metabolic disorders and heterologous nucleic acids encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art). Without being limited by any particular theory of the invention, according to this embodiment, administration to the skeletal muscle can result in secretion of the polypeptide into the systemic circulation and delivery to target tissue(s). Methods of delivering virus vectors to skeletal muscle are described in more detail herein.

The invention can also be practiced to produce antisense RNA, RNAi or other functional RNA (e.g., a ribozyme) for systemic delivery.

The invention also provides a method of treating and/or preventing congenital heart failure or PAD in a subject in need thereof, the method comprising administering a treatment or prevention effective amount of a virus vector of the invention to a mammalian subject, wherein the virus vector comprises a heterologous nucleic acid encoding, for example, a sarcoplasmic endoreticulum $Ca^{2+}$-ATPase (SERCA2a), an angiogenic factor, phosphatase inhibitor I (I-1), RNAi against phospholamban; a phospholamban inhibitory or dominant-negative molecule such as phospholamban S16E, a zinc finger protein that regulates the phospholamban gene, β2-adrenergic receptor, β2-adrenergic receptor kinase (BARK), PI3 kinase, calsarcan, a β-adrenergic receptor kinase inhibitor (βARKct), inhibitor 1 of protein phosphatase 1, S100A1, parvalbumin, adenylyl cyclase type 6, a molecule that effects G-protein coupled receptor kinase type 2 knockdown such as a truncated constitutively active bARKct, Pim-1, PGC-1α, SOD-1, SOD-2, EC-SOD, kallikrein, HIF, thymosin-β4, mir-1, mir-133, mir-206 and/or mir-208.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustained-release formulation. Further, the virus vector and/or virus capsid can be delivered adhered to a surgically implantable matrix (e.g., as described in U.S. Patent Publication No. 2004-0013645).

The virus vectors disclosed herein can be administered to the lungs of a subject by any suitable means, optionally by administering an aerosol suspension of respirable particles comprised of the virus vectors and/or virus capsids, which the subject inhales. The respirable particles can be liquid or solid. Aerosols of liquid particles comprising the virus vectors and/or virus capsids may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors and/or capsids may likewise be produced with any solid particulate medicament aerosol generator, by techniques known in the pharmaceutical art.

The virus vectors can be administered to tissues of the CNS (e.g., brain, eye) and may advantageously result in broader distribution of the virus vector or capsid than would be observed in the absence of the present invention.

In particular embodiments, the delivery vectors of the invention may be administered to treat diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present invention can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the invention.

Retinitis pigmentosa, by comparison, is characterized by retinal degeneration. In representative embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive delivery vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present invention may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the invention can also be used to treat epilepsy, which is marked by multiple seizures over time.

In one representative embodiment, somatostatin (or an active fragment thereof) is administered to the brain using a delivery vector of the invention to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins are as known in the art.

In particular embodiments, the vector can comprise a secretory signal as described in U.S. Pat. No. 7,071,172.

In representative embodiments of the invention, the virus vector and/or virus capsid is administered to the CNS (e.g., to the brain or to the eye). The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes. cortex, basal ganglia, hippocampus and portaamygdala), limbic system, neocortex, corpus striatum, cerebrum, and inferior colliculus. The virus vector and/or capsid may also be administered to different regions of the eye such as the retina, cornea and/or optic nerve.

The virus vector and/or capsid may be delivered into the cerebrospinal fluid (e.g., by lumbar puncture) for more disperse administration of the delivery vector. The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and peri-ocular (e.g., sub-Tenon's region) delivery as well as intramuscular delivery with retrograde delivery to motor neurons.

In particular embodiments, the virus vector and/or capsid is administered in a liquid formulation by direct injection (e.g., stereotactic injection) to the desired region or compartment in the CNS. In other embodiments, the virus vector and/or capsid may be provided by topical application to the desired region or by intra-nasal administration of an aerosol formulation. Administration to the eye, may be by topical application of liquid droplets. As a further alternative, the virus vector and/or capsid may be administered as a solid, slow-release formulation (see, e.g., U.S. Pat. No. 7,201, 898).

In yet additional embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

Having described the present invention, the same will be explained in greater detail in the following examples, which are included herein for illustration purposes only, and which are not intended to be limiting to the invention.

Example 1

Materials and Methods

Rep Cloning—pXR2 (Rep2Cap2) and pRep5Cap2 AAV helper plasmids served as templates for Rep cloning. The primer sequences used are indicated in Table 4. Two cloning strategies were used. Existing restriction sites were incorporated into primers for PCR (PCR-RD in Table 4) utilizing either pXR out fw or pXR out rev primers. PfuTurbo DNA Polymerase (Stratagene, La Jolla, Calif.) was used at the manufacturer's recommendations for all PCR reactions. PCR-RD products were digested with the enzymes indicated in Table 4 (NEB, Ipswich, Mass.) prior to ligation with T4 DNA Ligase (Invitrogen, Carlsbad, Calif.) according to the manufacturer's instructions. Alternately, an overlap-extension mediated PCR (OE-PCR) approach was used to produce Rep chimeras (Higuchi et al. (1988) *Nucleic Acids Res.* 16:7351). The Rep2 and Rep5 junction was incorporated into forward and reverse primers which were used in separate PCR reactions with the pXR out fw and rev primers (Table 4, only fw oligos indicated, rev oligos complimentary to fw). These overlapping PCR products were combined into a single PCR reaction and cycled as follows: 1 cycle at 94° C. for 30 seconds, 18 cycles of 30 seconds at 94° C., 30 seconds at 65° C., and 4 minutes at 72° C., 1 cycle of 10 minutes at 72° C. 1 µl of this reaction was used as template for a nested PCR with the pXR in fw and rev primers.

Chimeras with the N-terminus of Rep2 and C-terminus of Rep5 were cloned into the Rep25aa166 construct between the PpuMI and MfeI sites. Chimeras with the N-terminus of Rep5 and C-terminus of Rep2 were cloned into the 52aa160 construct between the PpuMI and BstBI sites. All constructs were verified by DNA sequencing at the UNC-CH Genome Analysis Facility.

TABLE 4

| Clone/Primer | Cloning Method | Orientation | Sequence | SEQ ID NO |
|---|---|---|---|---|
| pXR out fw | | Forward | 5' CGAAAAGTGCCACCTGACGTCTAAGAAACC | 126 |
| pXR in fw | | Forward | 5' TCGAATTCGACGGCCAGTGAATTGTAATACGACTC | 127 |
| pXR out rev | | Reverse | 5' CCATGATTACGCCAAGCTCGGAATTAACCGCATGCGA | 128 |
| pXR in rev | | Reverse | 5' CCATGGCCGGGCCCGGATTCACC | 129 |
| Rep52aa84 | PCR-RD AleI | Reverse | 5' TTCACCCCGGTGGTTTCCACGAGCACGTGCATGTGGAAGTAGCTCTCTCCCTTTTCAAACTGCACAAAG | 130 |
| Rep52aa110 | PCR-RD EagI | Forward | 5' CCTCGGCCGCTACGTGAGTCAGATTCGCGAAAAACTGATTCAGAG | 131 |
| Rep52aa126 | OE PCR | Forward | 5' GTGGTCTTCCAGGGAATTGAACCCACTTTGCCAAACTGGTTCGCGGTC | 132 |
| Rep52aa138 | OE PCR | Forward | 5' CTGGGTCGCCATCACCAAGGTAAAGAAGGGAGGCGGGAACAAGGTGGTGGATGAG | 133 |
| Rep52aa146 | OE PCR | Forward | 5' GCGGAGCCAATAAGGTGGTGGATGAGTGCTACATCCCCAATTACTTGCTC | 134 |
| Rep52aa160 | PCR-RD Bpu10I | Reverse | 5' ACTGGAGCTCAGGTTGGACCTTCGGCAGCAGGTAG | 135 |
| Rep52aa175 | OE PCR | Forward | 5' CGTGGACAAACCTGGACGAGTATAAATTGGCCTGTTTGAATCTCACGGAGCGTAAAC | 136 |
| Rep52aa187 | OE PCR | Forward | 5' CTGAATCTGGAGGAGCGCAAACGGTTGGTGGCGCAGCATCTGACGCAC | 137 |
| Rep52aa207 | PCR-RD SgrAI | Reverse | 5' GATCACCGGCGCATCCGAGAACTCACGCTGCGAAGC | 138 |
| Rep25aa77 | OE PCR | Forward | 5' TAAGGCCCCGGAGGCCCTTTTCTTTGTGCAGTTTGAAAAGGGATCTG | 139 |
| Rep25aa97 | OE PCR | Forward | 5' CCACATGCACGTGCTCGTGGAAACCTCCGGCATCTCTTCCATGGTCCTCG | 140 |
| Rep25aa116 | PCR-RD NruI | Forward | 5' TCAGATTCGCGAAAAACTGGTGAAAGTGGTCTTCCAGG | 141 |
| Rep25aa125 | OE PCR | Forward | 5' GAATTTACCGCGGGATCGAGCCGCAGATCAACGACTGGGTCGCCATC | 142 |
| Rep25aa141 | OE PCR | Forward | 5' GGTCACAAAGACCAGAAATGGCGCCGGCGGAGCCAATAAGGTGGTGGATTCTGG | 143 |
| Rep25aa149 | OE PCR | Forward | 5' GAGGCGGGAACAAGGTGGTGGATTCTGGGTATATTCCCGCCTACCTGC | 144 |
| Rep25aa166 | PCR-RD Bpu10I | Forward | 5' CCAGCCTGAGCTCCAGTGGGCGTGGACAAACCTG | 145 |
| Rep25aa187 | OE PCR | Forward | 5' GTTTGAATCTCACGGAGCGTAAACGGCTCGTCGCGCAGTTTCTGGCAG | 146 |
| Rep25aa216 | PCR-RD SgrAI | Forward | 5' ATGCGCCGGTGATCAAAAGCAAGACTTCCCAGAAATACATGG | 147 |
| ITR2 Half1 Kpn | | Forward | 5' ATTATAGGTACCAGGAACCCCTAGTGATG | 148 |
| ITR2 Half1 Sfi | | Reverse | 5' TAATAGGGCCCAAAGGGCCGGG | 149 |
| ITR2 Half2 Sfi | | Forward | 5' TTAATAGGCCCTTTGGGCCGGG | 150 |
| ITR2 Half2 Hind | | Reverse | 5' TATAATAAGCTTAGGAACCCCTAGTGATGGAG | 151 |
| ITR5 Half1 Kpn | | Forward | 5' ATTATAGGTACCTACAAAACCTCCTTGCTTGAG | 152 |
| ITR5 Half1 Sfi | | Reverse | 5' TTAATAGGCCCTTTGGGCCGTCGC | 153 |
| ITR5 Half2 Sfi | | Forward | 5' TTAATAGGCCCAAAGGGCCGTCGTC | 154 |
| ITR5 Half2 Hind | | Reverse | 5' TATAATAAGCTTTACAAAACCTCCTTGCTTGAGAG | 155 |

ITR Cloning—ITRs were cloned into a pUC-18 plasmid with a GFP cassette (CMV promoter, SV40 polyA) cloned between the KpnI and EcoRI restriction sites. The ITRs were synthesized in two halves as 4 nmol Ultramer DNA oligos (Integrated DNA Technologies, Coralville, Iowa). SfiI restriction sites were incorporated into one hairpin arm the ITR for cloning (FIG. 1A). Due to inconsistencies of the reported sequence at the tip of the ITR5 hairpins between Chiorini et al. (1999), the published GenBank sequence (accession number NC_006152), and restriction mapping, an ITR2 hairpin was utilized for the ITR5 construct (FIG. 1A). 200 pg of each oligo was amplified in a PCR reaction using the ITR primers listed in Table 4. 2.5 U of PfuTurbo DNA Polymerase (Stratagene, La Jolla, Calif.) was used to amplify each half of the ITR as follows: 1 cycle at 94° C. for 4 minutes, 35 cycles of 45 seconds at 94° C., 30 seconds at 50° C., and 30 seconds at 72° C., 1 cycle of 10 minutes at 72° C. PCR reactions were purified and subject to digestion by KpnI and SfiI or HindIII and SfiI (NEB, Ipswich, Mass.). A triple ligation with the pUC-18 GFP plasmid and each half of the ITR was performed with T4 DNA Ligase (Invitrogen, Carlsbad, Calif.) for 1.5 hours at room temperature. All constructs were verified by DNA sequencing at the UNC-CH Genome Analysis Facility after linearization of the plasmid and ablation of the ITR secondary structure by SfiI digestion.

Western Blot Analysis—Samples for Western blot analysis were harvested 48-72 hours after transfection of Ad-helper plasmid and the appropriate AAV helper construct. Cells were washed and resuspended in 100 μl PBS prior to addition of 100 μl 2× Laemmli Sample Buffer (100 mM Tris pH 6.8, 4% SDS, 200 mM DTT, 20% glycerol, 0.1% Bromophenol Blue). Samples were briefly sonicated and boiled for 10 minutes. Samples were run on NUPAGE 4-12% Bis-Tris gels (Invitrogen, Carlsbad, Calif.) at 160 volts for 90 minutes. Protein was transferred to a Nitrocellulose membrane (Invitrogen, Carlsbad, Calif.) via a wet transfer for 60 minutes at 30 volts. Gels were blocked overnight in 10% nonfat dry milk in 1×PBS/Tween (0.05%). Detection of both Rep2 and Rep5 proteins (all four sizes) was achieved with a monoclonal Anti-Adeno-Associated Virus Rep Protein antibody (clone 259.5, American Research Products, Belmont, Mass.) at a 1:20 dilution in PBS/Tween for 60 minutes at room temperature. After washing, a secondary HRP anti-mouse antibody was added at a 1:5,000 dilution in PBS/Tween for one hour at room temperature. After washing, SuperSignal West Femto Maximum Sensitivity Substrate (Pierce, Rockford, Ill.) was added and blots were exposed to X-ray film.

Cell Culture and rAAV Production—HEK 293 cells were obtained from ATCC and cultured in Dulbecco Modified Eagle Medium (DMEM) supplemented with 10% Fetal Bovine Serum (Sigma, St. Louis, Mo.) and 100 units/ml penicillin and 100 μg/ml streptomycin and grown at 37° C. with 5% $CO_2$ saturation. Transfections were performed in six-well cell culture plates. 0.75 μg each of Ad-helper plasmid, AAV helper plasmid (either Rep2Cap2, Rep5Cap2, or the Rep mutant described), and the GFP plasmid containing the ITR (mutant or wt ITR as specified in text) were triple-transfected with polyethyleneimine (PEI) (25,000 linear molecular weight) as described (Xiao et al. (1998) *J. Virol.* 72:2224). Cells were harvested 48-72 hours post-transfection.

Hirt DNA Purification and Southern Blot Analysis—

Hirt DNA purification was performed as described (Hirt (1967) *J. Mol. Biol.* 26:365). Cells were harvested 48-72 hours post-transfection, washed in PBS, and resuspended in 370 μl Hirt Solution (0.01M Tris-HCl pH 7.5 and 0.1M EDTA) prior to addition of 25 μl 10% SDS and 165 |||| 5M NaCl. Samples were incubated at 4° C. overnight prior to centrifugation. DNA was purified by phenol chloroform extraction and precipitated by an equal volume of isopropanol prior to resuspension in 50 μl sterile $ddH_2O$. 5 ul of each sample was digested with 4 U DpnI (NEB, Ipswich, Mass.) 2-4 hours at 37° C. prior to gel electrophoresis and Southern blot analysis to remove non-replicated transfected plasmid (Chomczynski (1992) *Anal. Biochem.* 201:134). The nylon membrane (Hybond-XL; GE Healthcare Life Sciences, Piscataway, N.J.) was hybridized to a probe corresponding to the GFP open reading frame labeled with the Random Primed DNA Labeling Kit (Roche, Indianapolis, Ind.) and d-CTP $P^{32}$. Blots were visualized after exposure to a phosphorimager screen (GE Healthcare Life Sciences, Piscataway, N.J.).

Densitometry—

Densitometry was performed using the public domain NIH Image program (developed at the U.S. National Institutes of Health available on the Internet at the NIH website). Densitometry analysis of a DpnI resistant band on the agarose gel prior to transfer was used as a loading control to normalize values obtained from the Southern blot. The lowest value (absence of any vector replication) was subtracted from all values to account for background. In order to gauge relative replication efficiency, values for ITR2 vectors were divided by the value obtained from the Rep2-ITR2 control. ITR5 vectors were compared to the Rep5-ITR5 control. All values were obtained in triplicate (n=3). Error bars represent standard error (standard deviation divided by the root of 3). All samples were compared to controls on the same blot.

Molecular Modeling—

Molecular models were generated using Swiss-Model (available at the expasy.org website). The published crystal structure of the N-terminus of Rep5 complexed with the RBE (PDB accession #1rz9) was used as a template for all models. Visualization of protein structure rendering of images were performed with PyMOL (available at pymol.org). DNA folding was performed using the DNA mfold server (available at mfold.bioinfo.rpi.edu).

Example 2

Construction and Characterization of Chimeric ITRs

Previously, AAV replicative specificity was postulated to be driven by the trs sequence (Chiorini et al. (1999) *J. Virol.* 73:4293; Chiorini et al. (1999) *J. Virol.* 73:1309). Rep2 can nick the ITR2 trs (AGT/TGG) and the AAVS1 trs of human chromosome 19 (GGT/TGG) (Wu et al. (2001) *Arch. Biochem. Biophys.* 389:271). Rep5 nicks only the ITR5 trs (AGTG/TGG). However, alignment of the ITR2 and ITR5 sequences revealed several significant sequence and structural differences outside the trs sequence (FIG. 1A). The spacing between the putative RBE and the nicking stem was significantly different; three nucleotides (nt) for ITR2 and 15 nt for ITR5. Additionally, while the trs sequence is not tightly conserved between ITR2 and ITR5, neither is the height or overall length of the putative nicking stem.

A novel method was used to generate mutant ITRs in order to determine which portions of the ITR were responsible for replicative specificity. Previous studies have investigated Rep-ITR interactions in vitro largely due to the difficulty of synthesizing full length ITRs for in vivo assays.

PCR through the secondary structure of the ITR is inefficient and sequencing through these elements typically requires radiolabeled chain-terminator sequencing (Young et al. (2000) *J. Virol.* 74:3953). The AAV ITRs are highly recombinogenic and are frequently mutated even in a plasmid context (Samulski et al. (1983) *Cell* 33:135).

Figure 36A:
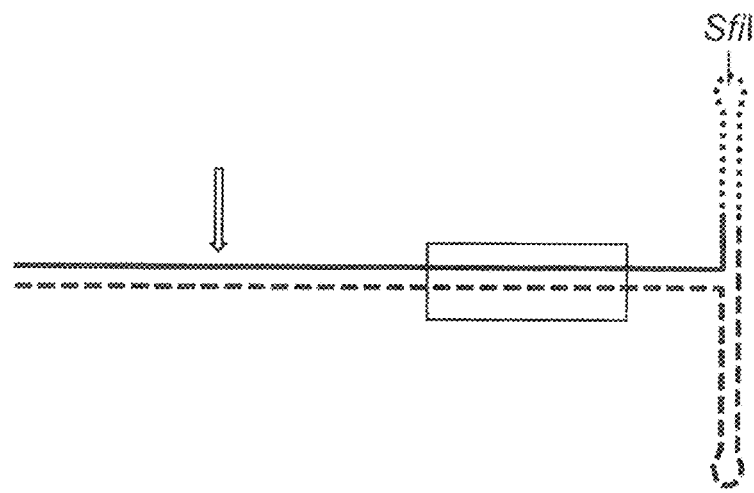
FIGS. 36A-36C shows a diagram of ITR synthesis.
Figure 36B:
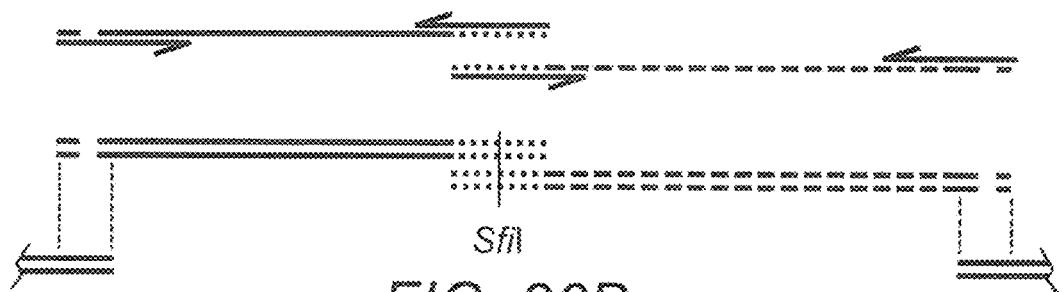
Figure 36C:
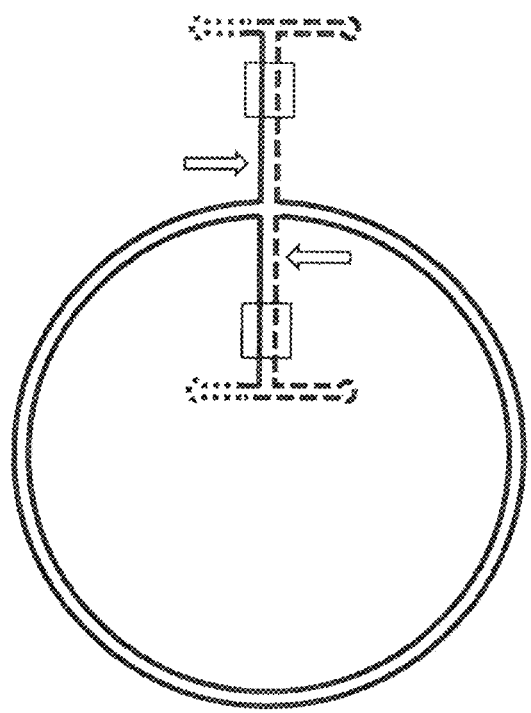

In order to address these concerns, the ITRs were synthesized and amplified in halves (FIGS. 36A-36C). To assemble the halves, a SfiI site was included in one of the hairpin arms of the ITR. SfiI allowed the conservation of the RBE' sequence (Brister and Muzyczka (2000) *J. Virol.* 74:7762). Cloning the ITR in a double D element (DD) format required only one ITR per plasmid for replication (Xiao et al. (1997) *J. Virol.* 71:941). The three core Rep functions necessary for AAV replication (Rep binding, helicase, and nicking) were analyzed by the presence or absence of intracellular replication of the plasmid. This assay provided the ability to quantitate Rep-ITR function in a physiological setting, removing the concern that highly purified Rep protein might take on aberrant function in vitro. This system also avoided concerns that previous in vitro assays used only a fragment of the ITR or that oligos used to recapitulate the ITR might not fold correctly.

An alignment of ITR2 (SEQ ID NO:17) and ITR5 (SEQ ID NO:18) (FIG. 1A) revealed several divergent elements which might confer Rep specificity. The spacer and nicking stem elements appeared to be the most likely candidates for unique interactions with their cognate Rep protein. This hypothesis was supported by low homology of these elements between AAV2 and AAV5.

Figure 1B:
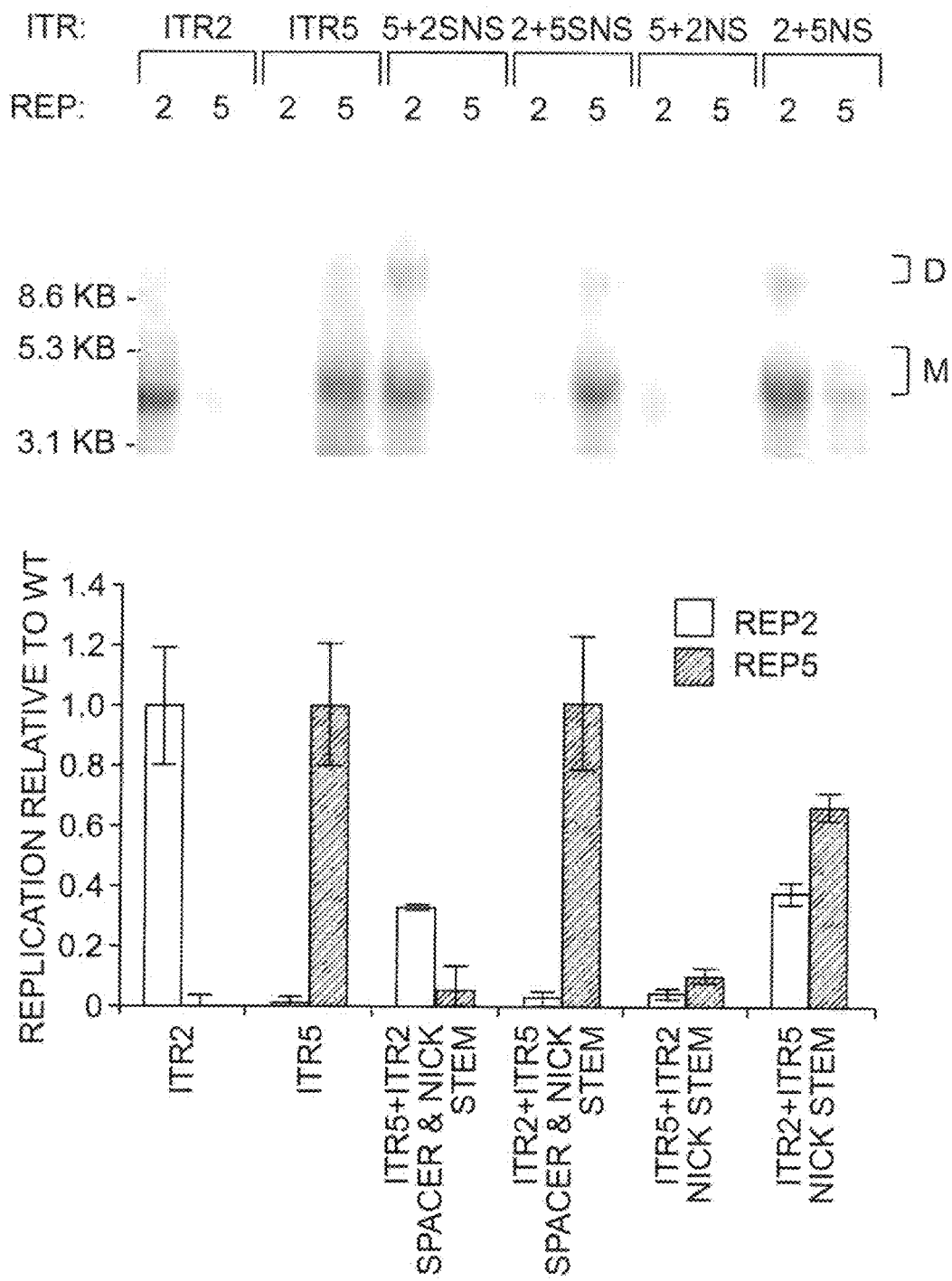

Wt ITRs containing the SfiI site functioned as expected with Rep2 specific to ITR2 and Rep5 specific to ITR5 (FIG. 1B). Rep2-ITR2 replicated approximately 2-fold better than Rep5-ITR5, potentially due to the lower folding energy of ITR5 resulting in reduced plasmid stability prior to replication. Due to this minor difference in replicative fidelity, all ITRs replicated with Rep2 were normalized to Rep2-ITR2, while ITRs replicated with Rep5 were normalized to Rep5-ITR5 (FIG. 1B).

In order to confirm that the RBE and hairpin arms played no role in Rep specificity, we generated a chimeric ITR with ITR5 binding elements and an ITR2 spacer and nicking stem (ITR5+2SNS, SEQ ID NO:19). Only Rep2 replicated this ITR, confirming the determinants of replicative specificity lie in the spacer/nicking stem elements (FIG. 1B). While ITR5+2SNS replication was not as efficient as ITR2–Rep2, it was replicated at ITR5-Rep5 levels. Conversely, Rep5 specifically replicated an ITR comprised of ITR2 hairpins and hairpin spacer and the ITR5 spacer and nicking stem (ITR2+5SNS, SEQ ID NO:20, FIG. 1B). Rep5 replicated this ITR at wt levels. These data demonstrated that Rep-ITR specificity lies outside of the ITR binding regions.

Figure 2A:
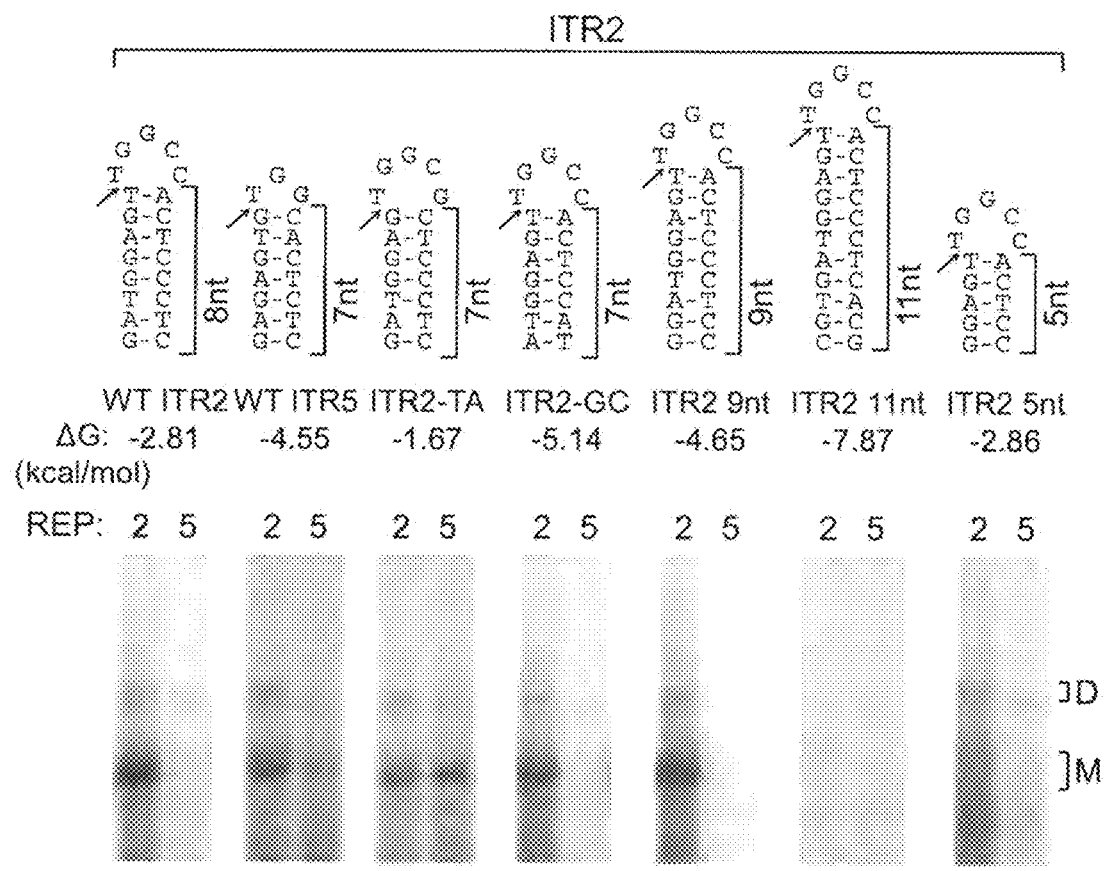
FIGS. 2A-2D show the relation of nicking stem height and sequence to Rep-ITR specificity.

Next, chimeric ITRs were created to explore whether the nicking stem or the spacing between the RBE and nicking stem harbored unique interactions with the Rep protein. An ITR with the ITR5 binding elements and spacer and the ITR2 nicking stem could not be replicated by either Rep2 or Rep5 (ITR5+2NS, SEQ ID NO:21, FIG. 1B). The corresponding chimeric ITR (ITR2 binding elements and spacer with an ITR5 nicking stem) was replicated by both Rep2 and Rep5 (ITR2+5NS, SEQ ID NO:22, FIG. 1B). This disparity suggested that the spacer and nicking stem play different roles in Rep-ITR specificity between AAV2 and AAV5.

that Rep-ITR specificity is not driven exclusively by the trs sequence (FIG. 1B). In order to determine the flexibility of Rep2 toward mutant nicking stems, ITR2s containing altered forms of the hairpin were generated (FIG. 2A). Rep2 is able to replicate an ITR with an ITR5 nicking stem even though the ITR5 nicking stem contains a different trs sequence, is one bp shorter, and has two fewer unpaired nucleotides at its tip (FIG. 2A). The substitution of the ITR5 nicking stem into ITR2 also allowed replication by Rep5.

To determine which element of the ITR2 nicking stem prevented Rep5 activity, specific portions of the ITR2 stem were altered. First, one bp at the top of the putative ITR2 nicking stem was removed to lower the height to that of ITR5 (ITR2-TA, SEQ ID NO:23). Removing the T-A bp also resulted in a trs resembling ITR5, nicking between G/T opposed to T/T. Rep2 continued to function on this ITR as did Rep5, demonstrating that Rep5 can tolerate five unpaired nucleotides at the tip of the stem as long as the stem height and nt sequence are correct. A similar deletion from the base of the ITR2 nicking stem reduced the height to that of ITR5 while retaining the ITR2 nicking site (ITR2-GC, SEQ ID NO:25). Rep2 continued to function efficiently on this ITR while Rep5 activity was ablated. This data suggested that the inability of Rep5 to function on ITR2 is primarily the sequence of the trs, specifically the requirement for a nick to be generated between G/T.

To determine the extent of Rep2 flexibility for different nicking stems, three additional ITR2 mutants were created. Extending the nicking stem by one bp at the base had no effect on replication by Rep2 (ITR2 9 nt, SEQ ID NO:30). However, a three bp extension was sufficient to ablate Rep2 function on the ITR (ITR2 11 nt, SEQ ID NO:32). Surprisingly, Rep2 was able to tolerate a three bp deletion from the base of the stem, underlining the flexibility of Rep2 with respect to nicking stem substrates (ITR2 5 nt, SEQ ID NO:28).

Figure 2B:
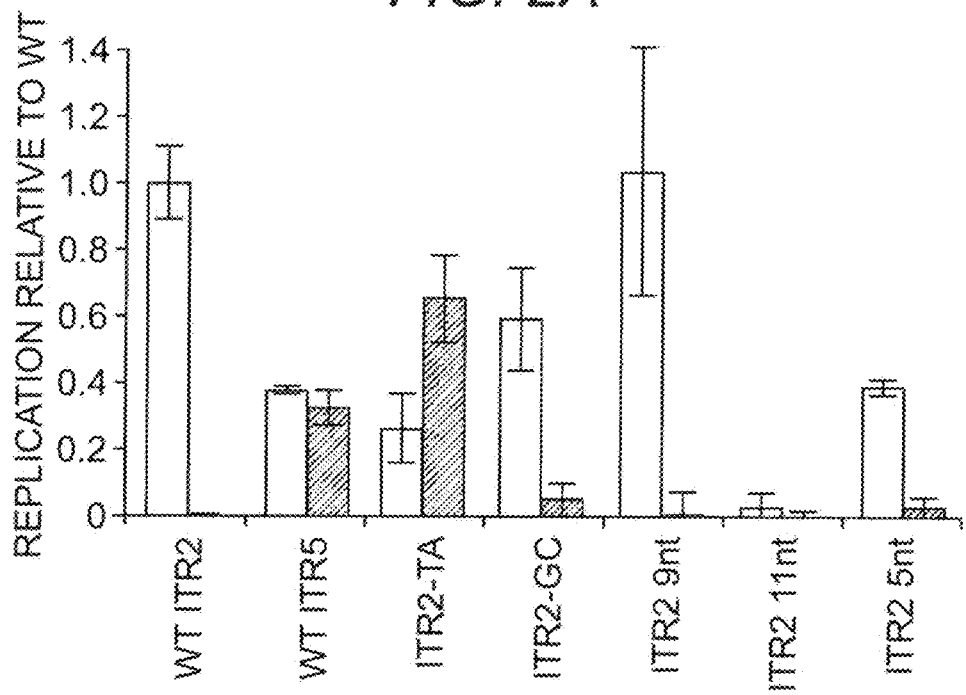
Figure 2C:
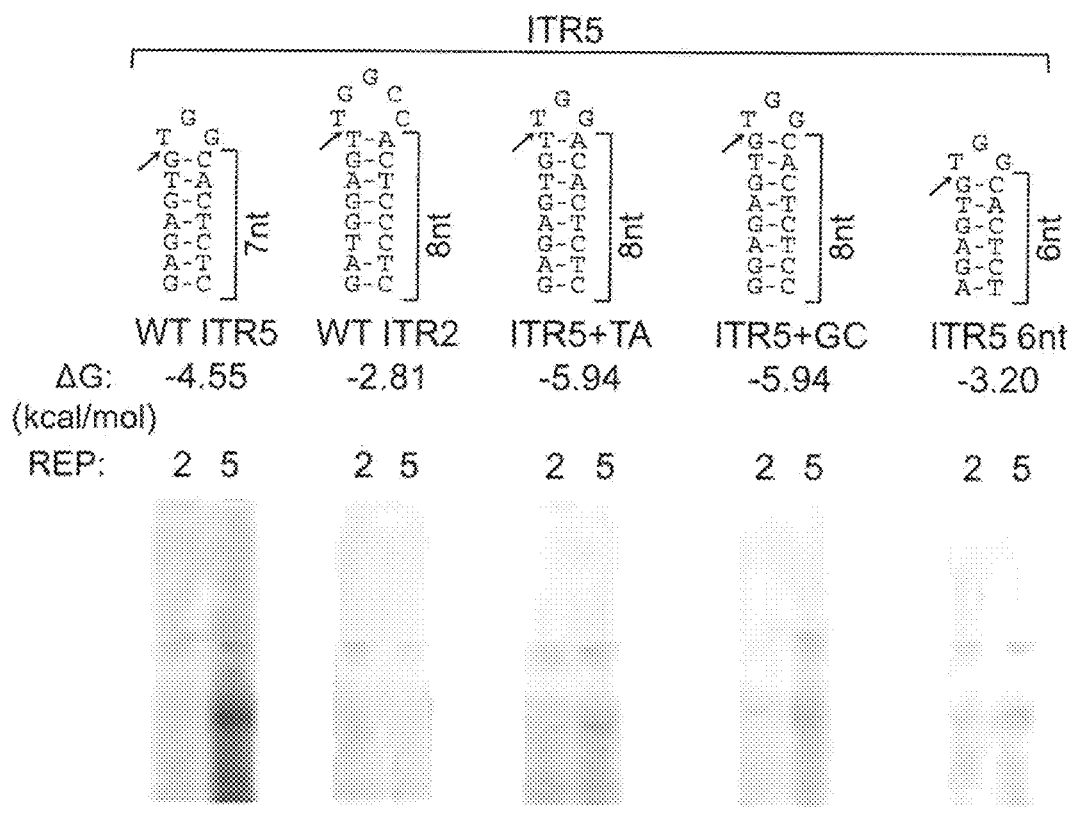
Figure 2D:
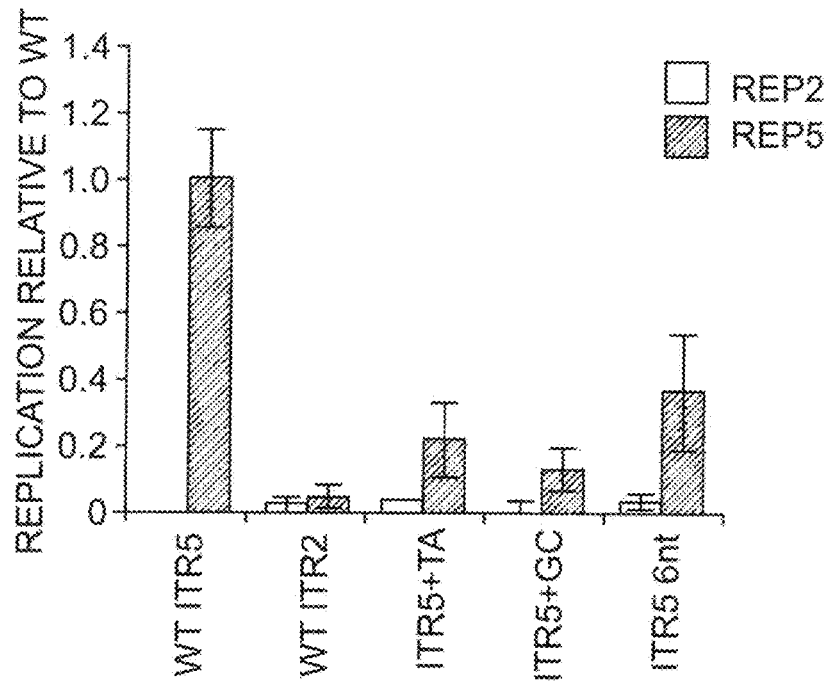

In order to explore the level of flexibility Rep5 possessed toward non-wt nicking stems, a panel of mutant ITR5s harboring altered nicking stems were created (FIG. 2C). Curiously, Rep2 replicated none of these ITRs, suggesting an element outside the ITR5 nicking stem is responsible for preventing Rep2 function. As in FIG. 1B, replacement of the ITR5 nicking stem with that of ITR2 resulted in the ablation of replication by Rep5, attributable to the incompatible trs sequence. The addition of one bp at the top of the ITR5 nicking stem severely decreased the ability of Rep5 to replicate the ITR (ITR5+TA, SEQ ID NO:24, FIG. 2D). This insertion disrupted the ITR5 trs sequence and increased the size of the stem one bp. However, the low level of replication by Rep5 on ITR5+TA suggests that the entire trs site of ITR2 is necessary to confer Rep2 specificity, not just the presence of a T/T nick site.

The addition of one bp to the base of the ITR5 nicking stem, preserving the ITR5 trs at the tip, nearly eliminated replication by Rep5 (ITR5+GC, SEQ ID NO:26). Likewise, the removal of one bp from the base of the ITR5 nicking stem strongly decreased replication by Rep5 (ITR5 6 nt, SEQ ID NO:35, FIG. 2D). This data suggests that Rep5 is sensitive both to the height of the nicking stem as well as to the sequence of the trs. Thus, Rep5 is unable to replicate ITR2 because the ITR2 nicking stem is one bp too tall and has an incompatible trs sequence.

Example 3

The Nicking Stem is Important for ITR5 Specificity

ITR2+5NS (SEQ ID NO:22) established that Rep2 is capable of nicking an ITR with an ITR5 nicking stem and Example 4

Spacer Length is Important for ITR2, not ITR5

While Rep2 can replicate a vector with an ITR5 nicking stem, it can not replicate wt ITR5 (FIG. 1B). The only difference between ITR5+2SNS (which Rep2 can replicate) and ITR5+2NS (which Rep2 cannot replicate) is the ITR5 spacer (FIG. 1B). The wt Rep2 spacer is three nt long while the wt Rep5 spacer is 15 nt long. Thus, we hypothesized that Rep2 may be sensitive to spacer length.

Figure 3A:
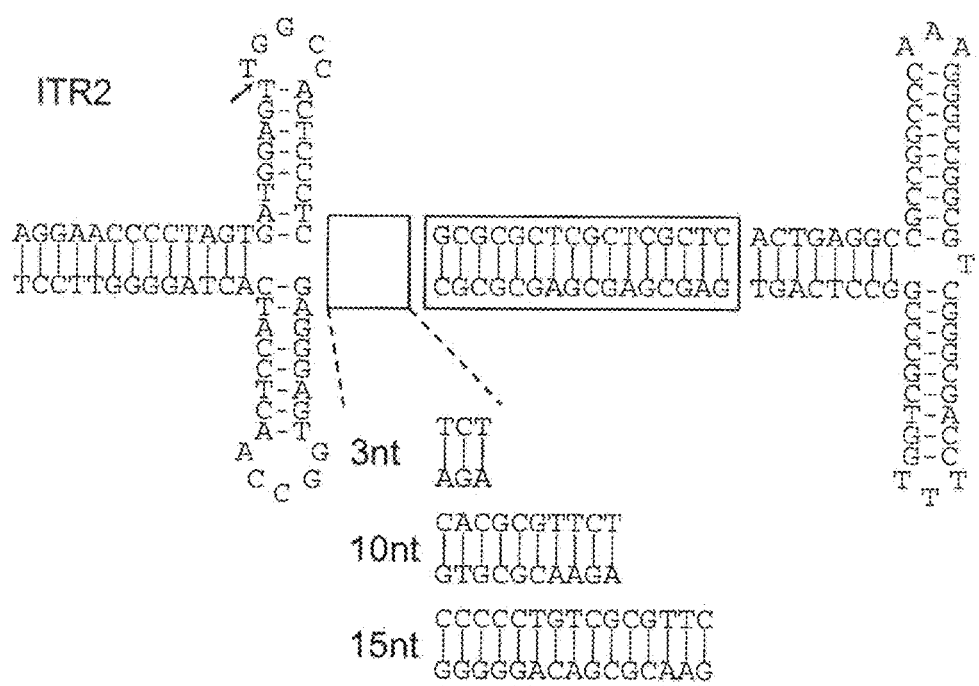
FIGS. 3A-3D show the effect of RBE-nicking stem spacing on Rep-ITR specificity.
Figure 3B:
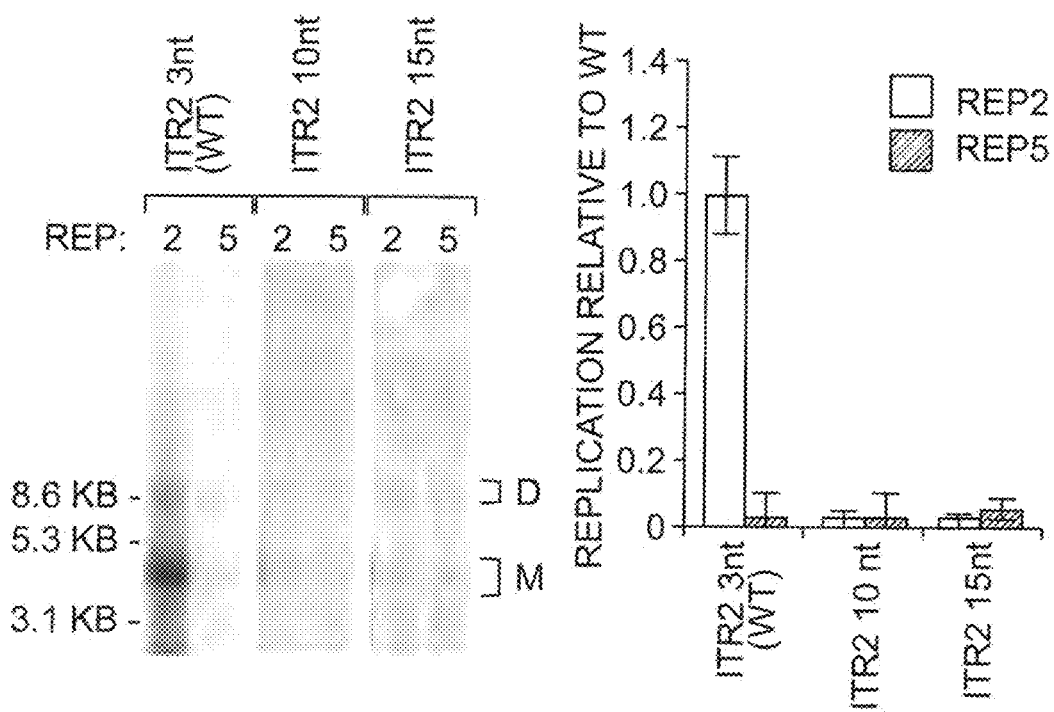
Figure 3C:
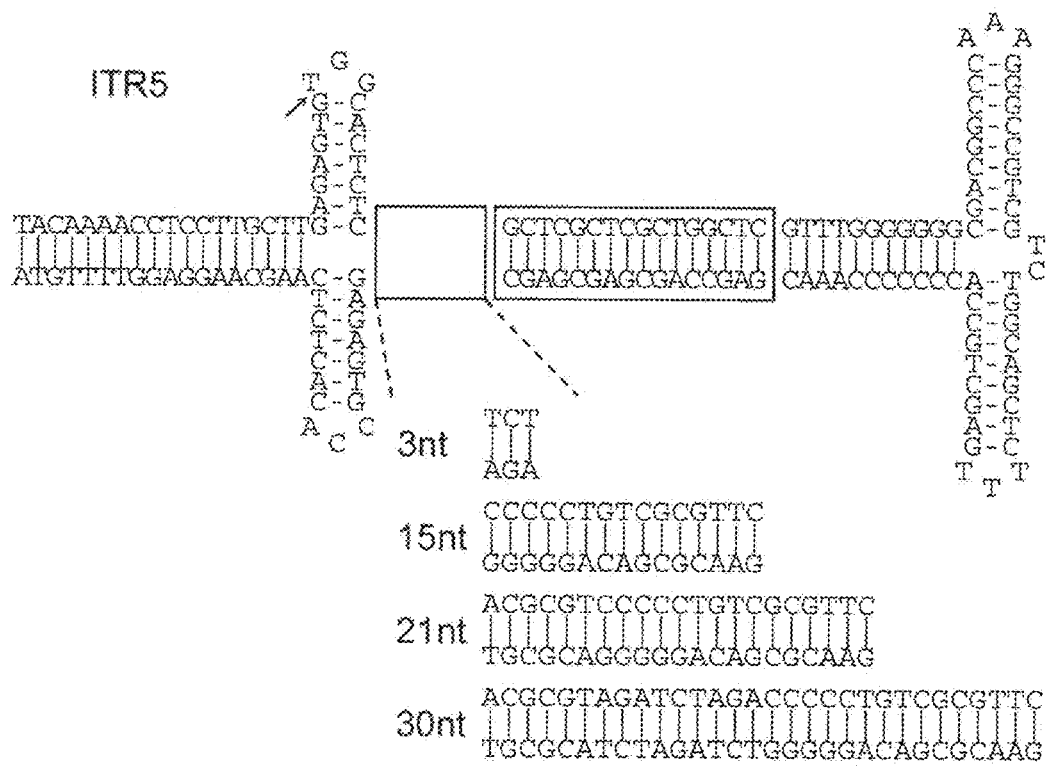

To explore the effect of spacer length on ITR2 and ITR5, a series of mutant ITR2s and ITR5s with differing spacer lengths were generated (FIGS. 3A and 3C). An insertion extending the ITR2 spacer to 10 nt ablated replication by Rep2 (ITR2 10 nt, SEQ ID NO:31, FIG. 3B). Similarly, substitution of the ITR2 spacer with the 15 nt spacer of ITR5 also ablated replication by Rep2 (ITR2 15 nt, SEQ ID NO:33, FIG. 3B). Rep5 was unable to replicate any of these vectors due to the presence of the ITR2 stem loop.

Figure 3D:
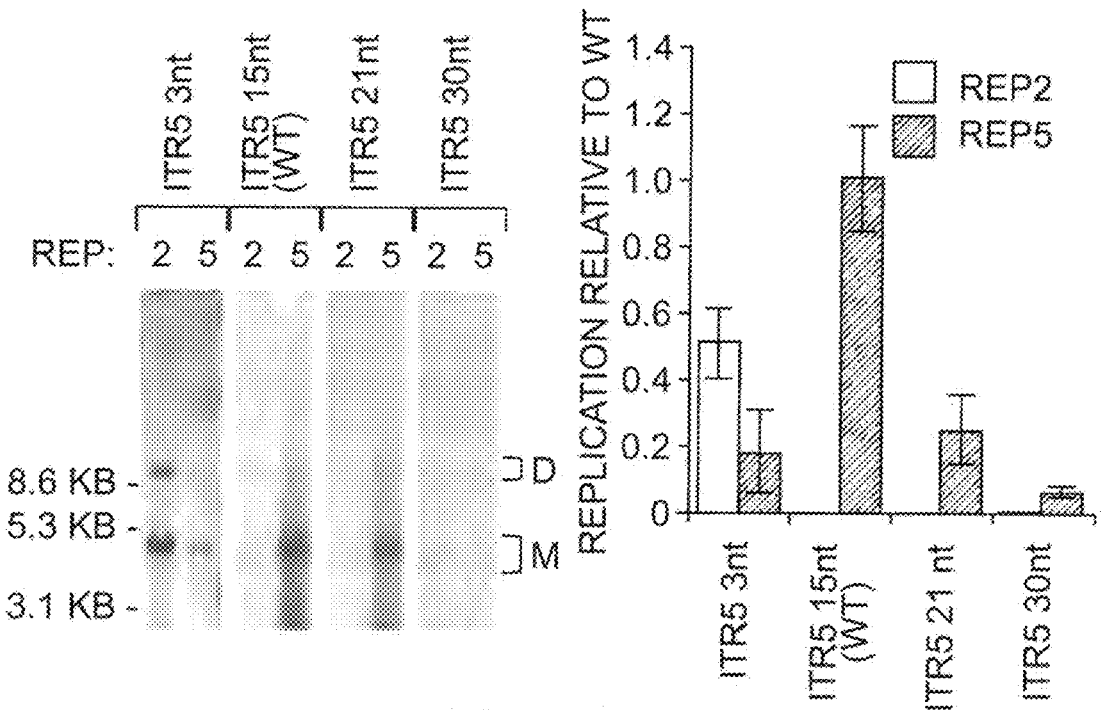

Rep5 displayed greater flexibility toward spacer elements of differing lengths. Replacing the 15 nt ITR5 spacer with that of ITR2 resulted in an ITR in which Rep5 retained the ability to replicate at a reduced level (ITR5 3 nt, SEQ ID NO:34, FIG. 3D). Additionally, the presence of the three nt spacer allowed Rep2 to function on this ITR. The addition of six nt to the ITR5 spacer (for a total spacer length of 21 nt) resulted in an ITR capable of being replicated by Rep5 at an efficient level (ITR5 21 nt, SEQ ID NO:37, FIG. 3D). Replication by Rep5 was effectively abolished only after the insertion of 15 nt into the spacer (ITR5 30 nt, SEQ ID NO:38, FIG. 3D). This panel of mutant ITR5s demonstrates the importance of a three nt spacer element for Rep2 function.

This data confirmed that the length of the ITR5 spacer was important to block Rep2 function. Even small insertions into the ITR2 spacer were not tolerated by Rep2. Meanwhile, Rep5 is flexible in regard to spacer length, demonstrating the ability to function on ITRs with spacers from 3-21 nt.

Example 5

The ITR5 Spacer Acts as a RBE for Rep5

Figure 4A:
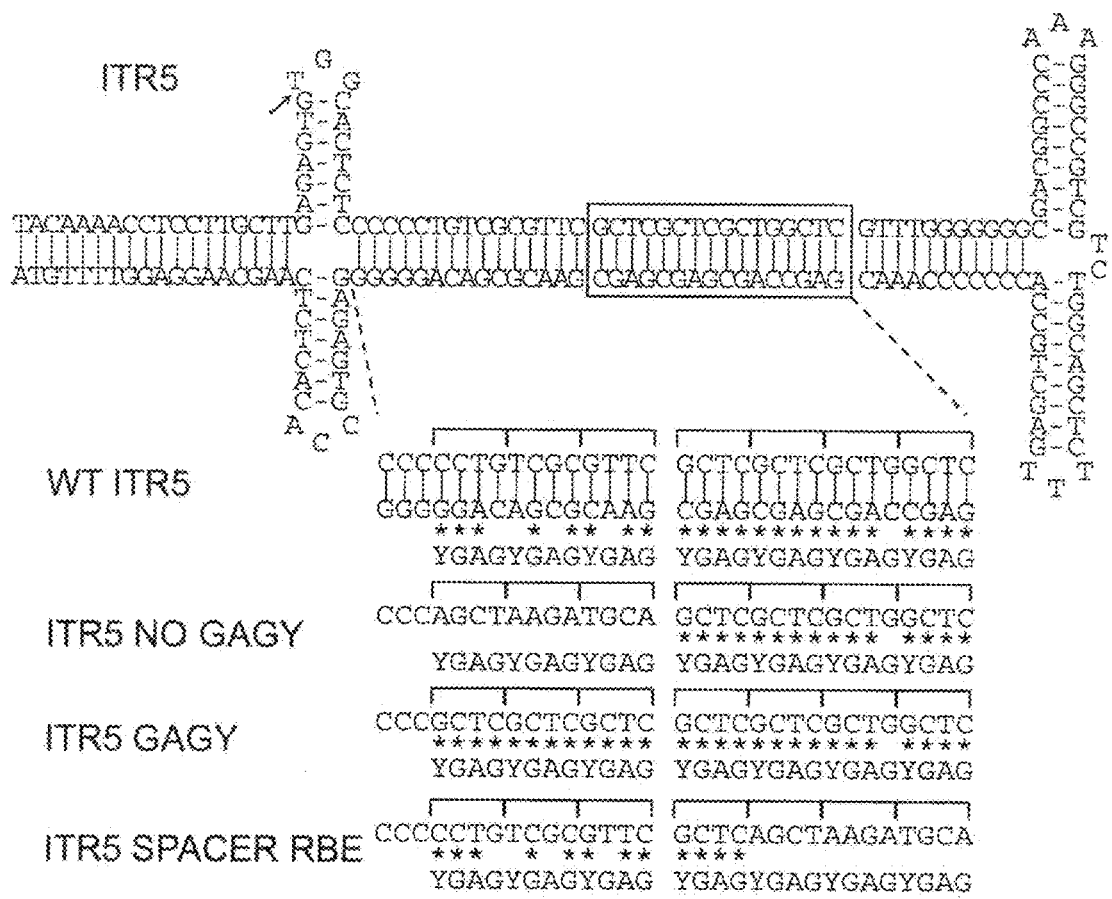

The inability of Rep2 to function on ITRs with spacers longer than three nt led to the question of why Rep5 was so flexible in this regard. It was hypothesized that Rep5 might specifically bind the ITR5 spacer just as it binds the RBE. The inability of Rep2 to bind this sequence would preclude its function on ITR5. Supporting this hypothesis was a moderately conserved GAGY Rep binding motif extending throughout the ITR5 spacer (FIG. 4A). Additionally, as Rep monomers bind every four nt, the binding of three Rep5 monomers to the 15 nt spacer element would result in a three nt spacer, similar to that of ITR2 (Hickman et al. (2004) *Mol. Cell* 13:403).

Figure 4B:
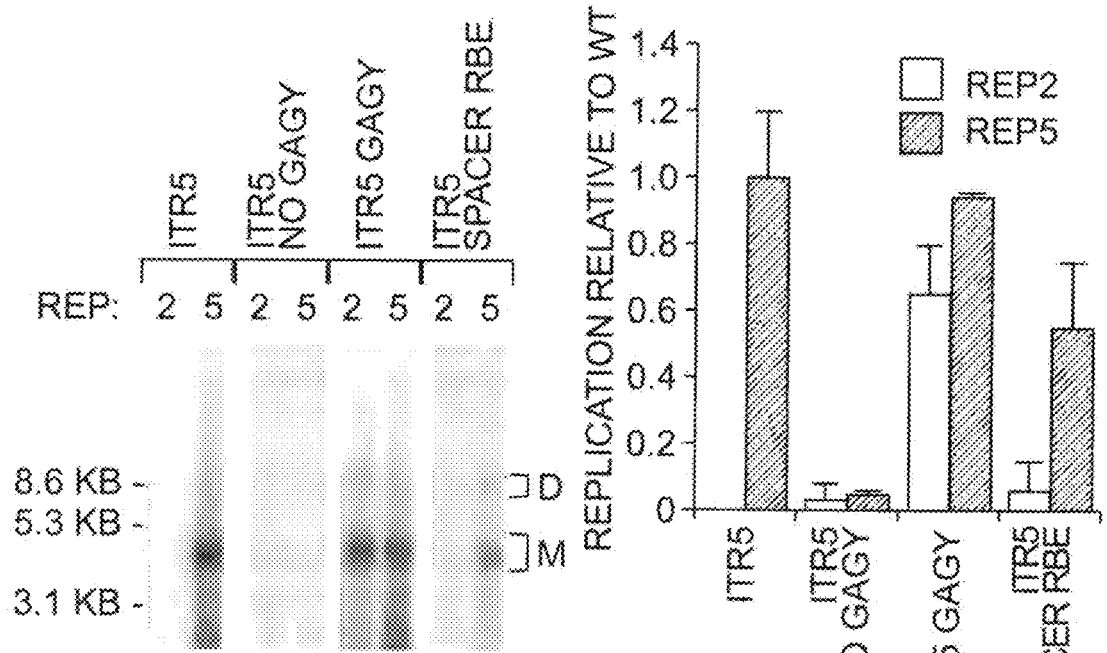

If Rep5 does bind the loosely conserved GAGY motif, the removal of that motif from the spacer should abolish Rep5 function. Indeed, the ITR5 No GAGY mutant (SEQ ID NO:40) could not be replicated by Rep2 or Rep5 (FIG. 4B). This suggested that the specific sequence of the ITR5 spacer plays an active role in the Rep5-ITR5 interaction. Conversely, a spacer with a pure GAGY repeat should not disrupt the ability of Rep5 to function on the ITR. Indeed, Rep5 was able to replicate this ITR at wt levels (ITR5 GAGY, SEQ ID NO:39, FIG. 4B). Rep2 was also able to replicate this ITR efficiently, suggesting the poorly conserved nature of the GAGY repeat within the ITR5 spacer prevents an important DNA-protein interaction with Rep2 necessary for replication.

To explore how the ITR5 spacer functioned as an RBE, we removed three GAGY repeats from the hairpin side of the RBE (ITR5 Spacer RBE, SEQ ID NO:42, FIG. 4A). This essentially shifted the 16 nt RBE 12 nt closer to the nicking stem. Rep5 replicated this ITR efficiently, confirming the ITR5 spacer acts as a RBE (FIG. 4B). The slight reduction in replication fidelity of this ITR, as compared with that of wt ITR5, may signal the inability of Rep to properly interact with the RBE' (Brister and Muzyczka (2000) *J. Virol.* 74:7762). Rep2 was again unable to replicate ITR5 Spacer RBE due to its inability to interact with the ITR5 spacer.

Next, we sought to extend the ITR2 spacer element to function as an extended RBE (FIG. 4C). The seven nt insertion attempted in FIG. 3A possessed essentially no GAGY homology (ITR2+7, SEQ ID NO:29, FIG. 4C). As a result, Rep2 could not replicate this ITR (FIG. 4D). Eight nt (two four nt GAGY repeats) inserted into the ITR2 spacer between the RBE and the existing spacer (ITR2+8 GAGY, SEQ ID NO:41) prevented replication by Rep2, demonstrating that the ITR2 RBE cannot be extended. This suggests that Rep2 may be dependent on RBE' binding or a specific spacer length for proper oligomerization to function on its cognate ITR. Curiously, this requirement does not apply to Rep2 function on ITR5 GAGY (FIG. 4A).

Similar to ITR5 Spacer RBE, we retained the eight nt GAGY insertion into ITR2 while removing eight nt of GAGY from the hairpin side of the RBE (ITR2+8−8 Spacer RBE, SEQ ID NO:43, FIG. 4C). This shifted the RBE eight nt closer to the nicking stem. Rep2 replicated this ITR very inefficiently at a level below the detection threshold of densitometric analysis (FIG. 4D, Southern).

Example 6

Identification of Regions in Rep Responsible for ITR Specificity

Identifying the two elements of the ITR responsible for Rep specificity allowed us to map the regions of Rep2 and Rep5 involved in ITR specificity. We focused exclusively on the N-terminal 208 aa of the large Rep proteins as this region encompasses the DNA binding and endonucleolytic activity of the protein (Yoon et al. (2001) *J. Virol.* 75:3230). This region displays approximately 60% sequence conservation evenly distributed across the protein sequence (FIG. 5A). Residues involved in the active site of the protein are 100% conserved between Rep2 and Rep5 (Hickman et al. (2002) *Mol. Cell* 10:327). Residues implicated in binding the RBE' are highly conserved (Hickman et al. (2004) *Mol. Cell* 13:403). Residues which bind the RBE display nearly perfect conservation except for two conservative substitutions near aa 140.

Figure 5C:
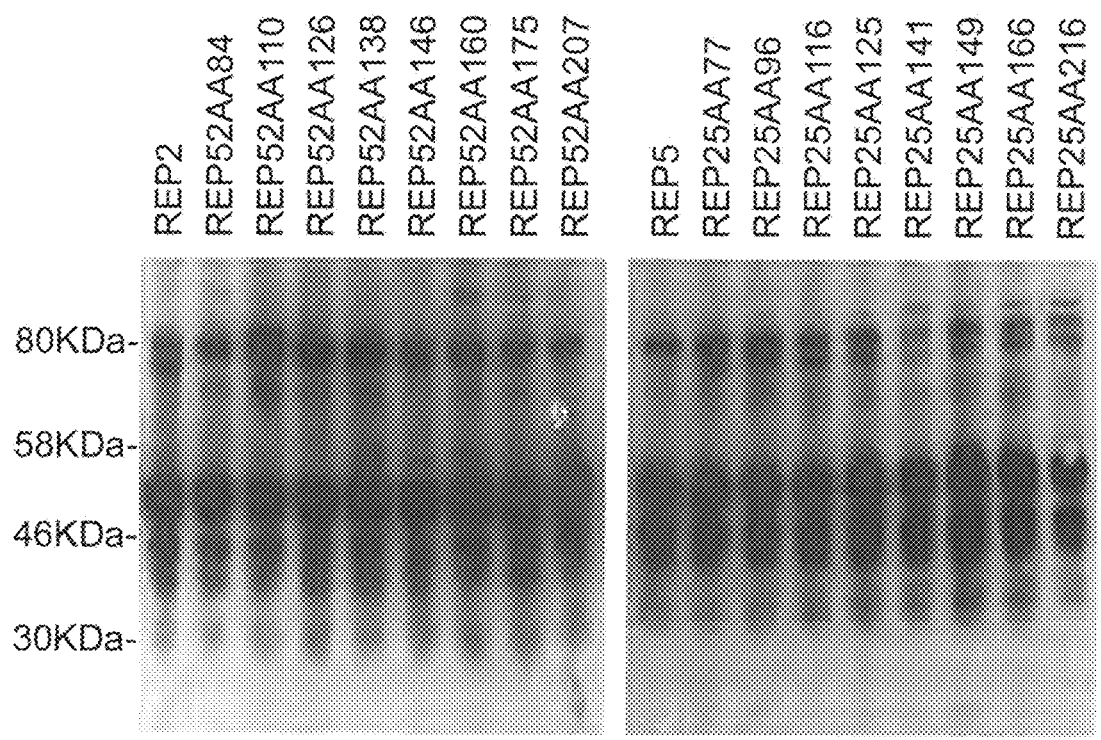
Figure 5D:
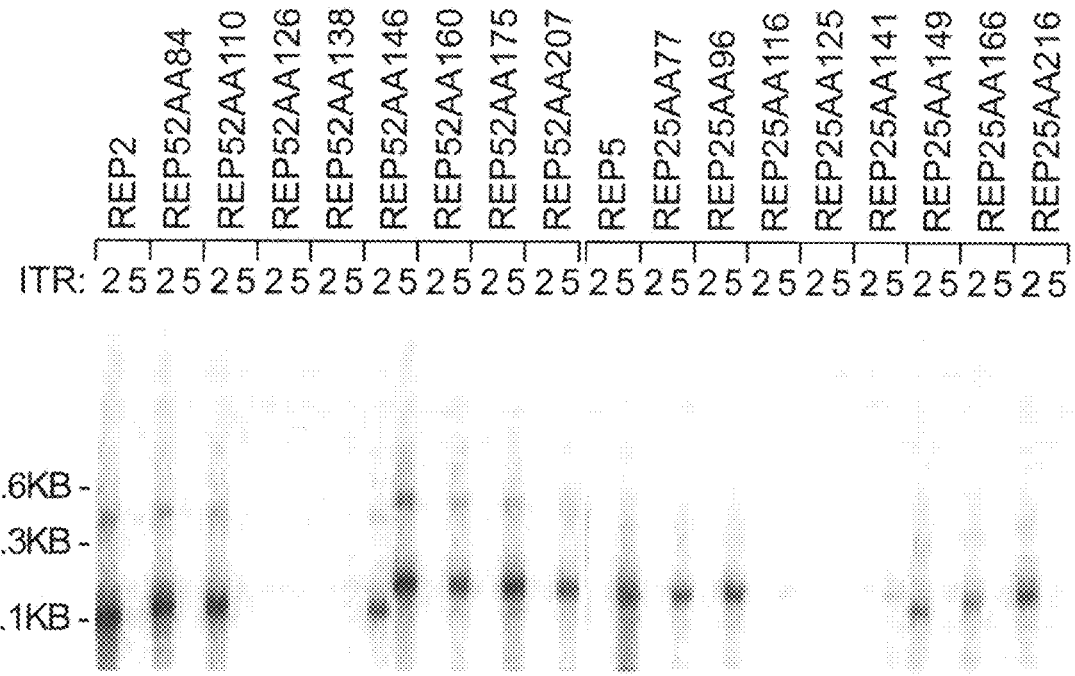

In order to map the regions of Rep involved in ITR specificity, a panel of chimeric Reps derived from Rep2 and Rep5 were generated (FIG. 5B). The ability of each chimeric Rep to replicate an ITR2- or ITR5-flanked vector in HEK 293 cells was determined by Southern blot (FIGS. 5B and 5D). Each Rep in the panel was verified by DNA sequencing and Western blot analysis (FIG. 5C). Every chimeric Rep showed similar protein expression profiles compared to wt. Densitometric analysis provided a comparison of the replication efficiency of each chimeric Rep with that of wt Rep2 or Rep5 (FIG. 5E). Chimeric Reps were named according to the aa location of the swap between serotypes; for instance, Rep25aa77 (SEQ ID NO:63) possesses the N-terminal 76 aa of Rep2 and the C-terminus of Rep5.

In the case of Rep5, replacement of the N-terminal 77 or 97 aa with Rep2 had no effect on ITR specificity nor a significant impact on replicative fidelity (FIGS. 5D and 5E). Larger pieces of Rep2 substituted onto the N-terminus of Rep5 were sufficient to prevent efficient replication of ITRSs (Rep25aa116, SEQ ID NO:65; Rep25aa125, SEQ ID NO:66; Rep25aa141, SEQ ID NO:67). This suggested that these chimeras possessed interruptions of a critical region of Rep5 for ITR5 specificity.

Rep2-based chimeras were unable to replicate ITR5s without the inclusion of the N-terminal 146 aa of Rep5 (Rep52aa146, SEQ ID NO:79, FIG. 5D). Rep52aa146 replicated ITR5 at wt levels, as did the three chimeras with larger portions of Rep5 on the N-terminus (Rep52aa160, SEQ ID NO:58; Rep52aa175, SEQ ID NO:59; Rep52aa207, SEQ ID NO:61). This mapping reveals that the critical region for ITR specificity in Rep5 lies between aa 97-146. Surprisingly, the Rep52aa146 clone also functioned efficiently on ITR2, constituting a Rep capable of replicating ITR2 and ITR5. This suggested that ITR specificity existed in two different regions of Rep.

For Rep2, the N-terminal 83 or 109 aa of Rep5 could be substituted with no effect on ITR specificity or major influence on replicative fidelity (Rep52aa84, SEQ ID NO:54; Rep52aa110, SEQ ID NO:55; FIGS. 5D and 5E). Chimeras including slightly larger portions of Rep5 were unable to replicate either ITR, again suggesting the interruption of a domain critical for ITR specificity (Rep52aa126, SEQ ID NO:56; Rep52aa138, SEQ ID NO:57).

Rep5-based chimeras were unable to replicate ITR2s without the inclusion of the N-terminal 149 aa of Rep2. However, ITR2 replication was inefficient (Rep25aa149, SEQ ID NO:68, FIGS. 5D and 5E). The inclusion of larger portions of Rep2 allowed replication of ITR2s to increase to wt levels (Rep25aa166, SEQ ID NO:69; Rep25aa216, SEQ ID NO:71). This data maps the Rep2 region involved in ITR specificity to aa 110-149. However, unlike Rep5, this was not the only region which played a role in ITR specificity. The ability of the Rep52aa146 chimera to replicate ITR2 and ITR5 vectors demonstrated a second region of Rep2 between aa 138-160 sufficient to allow replication of ITR2s even when the other critical region (aa 110-149) was Rep5. The isolation of two different Rep regions involved in ITR specificity was consistent with the discovery of two independent elements governing specificity within the ITR.

Example 7

Characterization of Rep Regions Involved in ITR Specificity

Figures 6A, 6B:
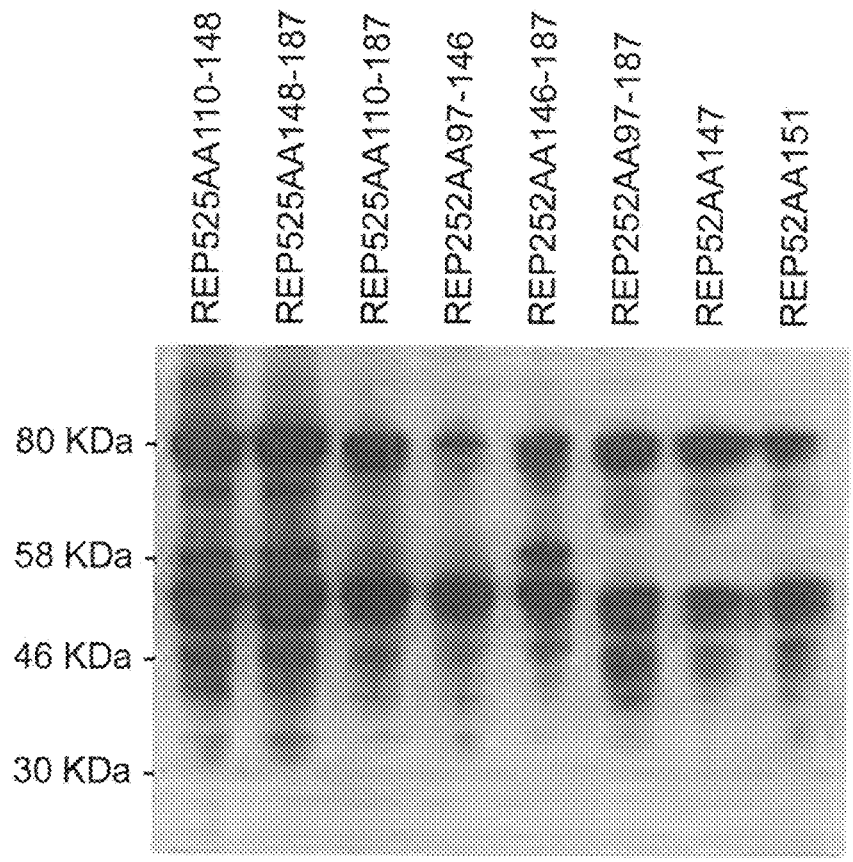
FIGS. 6A-6G show the characterization of Rep regions involved in ITR specificity.

To characterize the Rep domains identified in FIGS. 5A-5E, chimeric Rep proteins which specifically exchanged the regions implicated in ITR specificity were created (FIG. 6A). Region 1 existed in Rep2 from aa 110-149 and in Rep5 from aa 97-146. Region 2 lay within Rep2 from aa 149-187 and Rep5 from aa 146-187. As in FIGS. 5A-5E, all chimeras were verified by DNA sequencing and Western blot analysis (FIG. 6B). Chimeras were then assayed for the ability to replicate ITR2- or ITR5-flanked vectors (FIG. 6C).

Figure 6C:
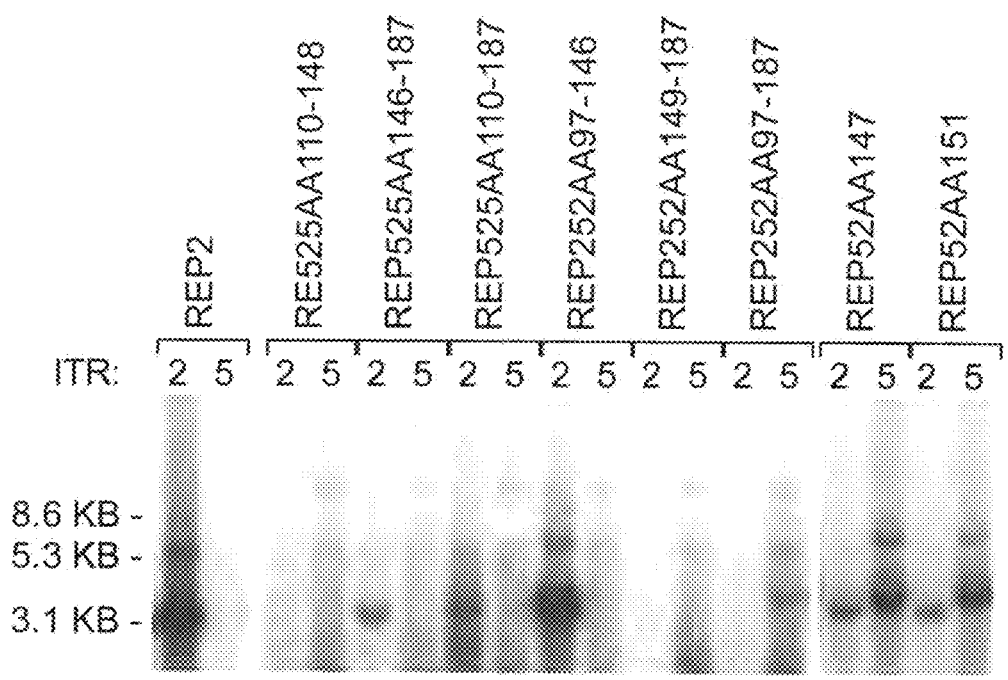

Replacing Rep5 region 1 with Rep2 yielded a clone unable to replicate either vector, suggesting the chimera lacked the ability to bind the ITR5 spacer or nick the ITR2 nicking stem (Rep525aa110-148, SEQ ID NO:72, FIG. 6C). Replacing Rep5 region 2 with that of Rep2 allowed this chimera to replicate an ITR2 vector, suggesting region 2 of Rep2 was critical to nick the ITR2 nicking stem (Rep525aa146-187, SEQ ID NO:73). The inability of this chimera to recognize ITR5 is harder to explain as Rep52aa146 could replicate ITR2 and ITR5 efficiently (FIG. 5B). This result suggests that Rep2 region 2 makes specific contacts within Rep2 aa 188-208 which are necessary in order to function on the ITR5 nicking stem. Replacing regions 1 and 2 of Rep5 with Rep2 resulted in a Rep chimera which replicated only ITR2s (Rep525aa110-187, SEQ ID NO:74).

Replacing Rep2 region 1 with Rep5 resulted in replication of only ITR2s, again demonstrating a connection between Rep2 region 2 and the ITR2 nicking stem (Rep252aa97-146, SEQ ID NO:75). The lack of ITR5 replication by Rep252aa97-146 is difficult to explain based on the Rep52aa146 chimera which replicates ITR2s and ITR5s efficiently (FIG. 5B). This result suggests that Rep5 region 1 makes specific contacts within the preceding 96 aa of Rep5 in order to replicate ITR5. Replacing Rep2 region 2 with Rep5 resulted in a chimera unable to replicate either ITR (Rep252aa149-187, SEQ ID NO:76). This chimeric Rep possesses neither Rep2 region 2 (required to nick the ITR2 nicking stem) nor Rep5 region 1 which appears to interact with the ITR5 spacer. Finally, replacing both Rep2 regions 1 and 2 with Rep5 resulted in a chimera capable of replicating only ITR5 vectors (Rep252aa97-187, SEQ ID NO:77).

Figure 6D:
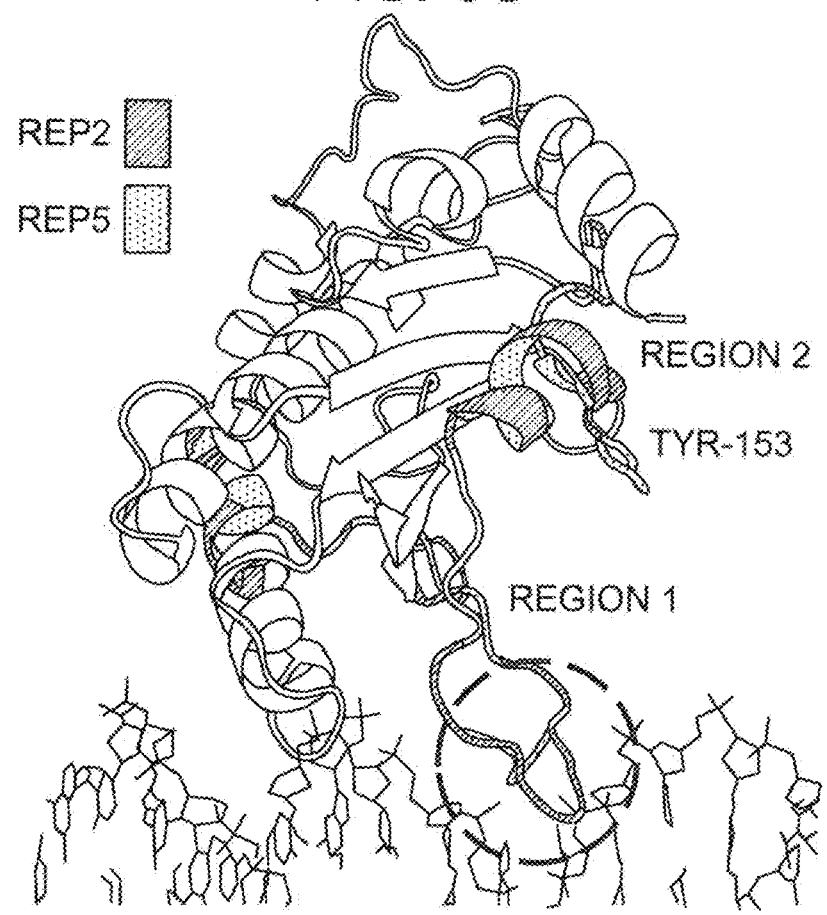

The crystal structure of the N-terminal 193 aa of Rep5 complexed to the RBE allowed the location of these two critical regions to be modeled (Hickman et al. (2004) *Mol. Cell* 13:403). The structure of the N-terminus of Rep2 was modeled with Swiss-Model software using Rep5 as a template. The location of region 1 supports its involvement with the spacer/RBE (FIG. 6D). This region interacts with the major groove of the ITR where one of the most apparent structural differences between Rep2 and Rep5 is predicted (FIG. 6D, hatched circle). Rep2 contains a two aa insertion in this loop with respect to Rep5. This insertion and other non-conservative substitutions are likely responsible for the inability of Rep2 to interact with the ITR5 spacer.

Figure 6E:
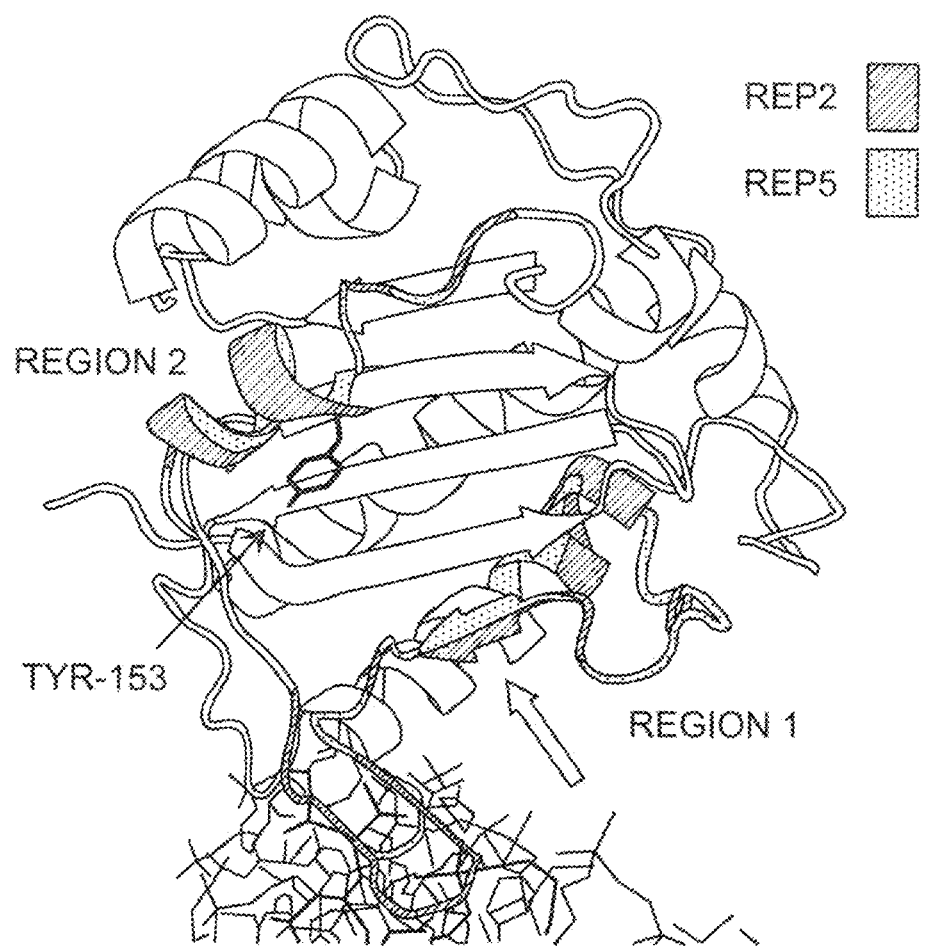
Figure 6F:
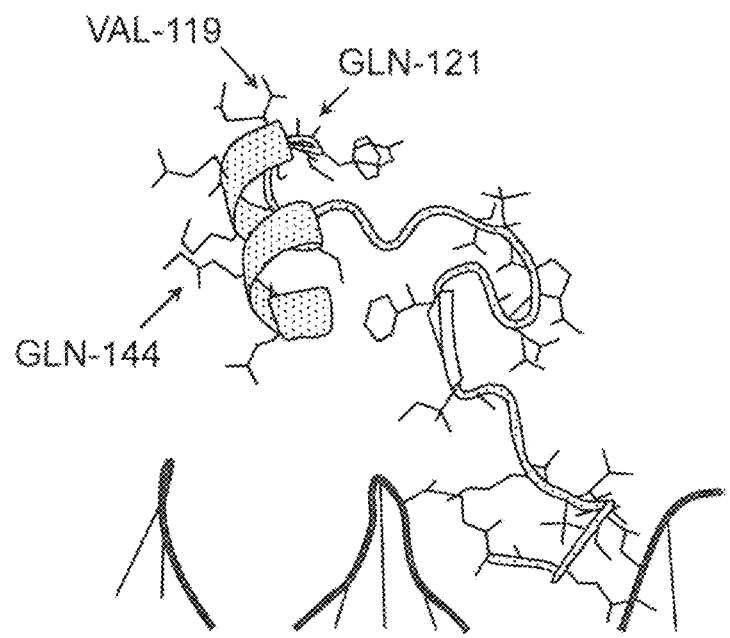

Viewing Rep along the length of the ITR illustrates that region 1 constitutes much of the base of the protein (FIG. 6E). Both Reps are predicted to participate in a β-sheet motif in the center of this region, while areas of reduced homology exist toward either side (the loop interacting with the major groove of the ITR on one side, RBE' interactions on the other). A more detailed look at region 1 reveals the greatest disparity between Rep2 and Rep5 occurs at the RBE binding interface in the major groove of the ITR (FIG. 6F).

Figure 6G:
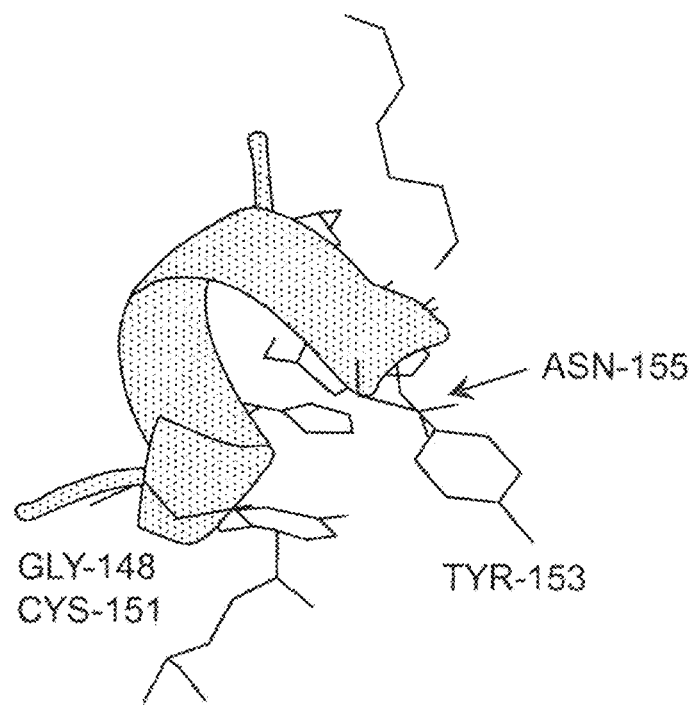

There is very little predicted structural difference between region 2 of Rep2 and Rep5 (FIGS. 6D and 6E). In an effort to dissect this region, we created two additional clones: Rep52aa147 (SEQ ID NO:81) and Rep52aa151 (SEQ ID NO:83) (FIG. 6A). Like Rep52aa146, both of these Reps were able to replicate ITR2 and ITR5 vectors (FIG. 6C). Rep52aa146 and Rep52 aa147 replicated ITR2 and ITR5 vectors with equivalent efficiency, suggesting E147 of Rep2 is not involved in ITR specificity. Rep52aa151 did display a modest reduction in ITR2 replication compared to Rep52aa146, suggesting that C151 of Rep2 plays a role in ITR2 specificity. Because Rep52aa160 cannot replicate ITR2, this leaves only two other non-conserved residues between Rep2 and Rep5 in this region (N155 and T161). Both of these residues lie near the active site and are likely to interact with the nicking stem or active site. N155 lies directly adjacent to Y156, the nucleophilic tyrosine, and may play a major role in ITR2 specificity (FIG. 6G).

Example 8

Structure-Function Model of Rep-ITR Specificity

In order to unify the ITR and Rep elements involved in specificity into a single model, the chimeric Reps separating region 1 and region 2 along with the chimeric ITRs separating the nicking stem and spacer were utilized. Rep2, Rep5, Rep52aa146 (which divides region 1 and 2 of Rep and can replicate ITR2 and ITR5), and Rep25aa149 (essentially no ITR2 or ITR5 replication) were selected. These Reps were tested for their ability to replicate ITR2, ITR5, ITR2+5NS (which is replicated by both Rep2 and Rep5), and ITR5+2NS (which is replicated by neither Rep2 nor Rep5).

Figures 7A, 7B:
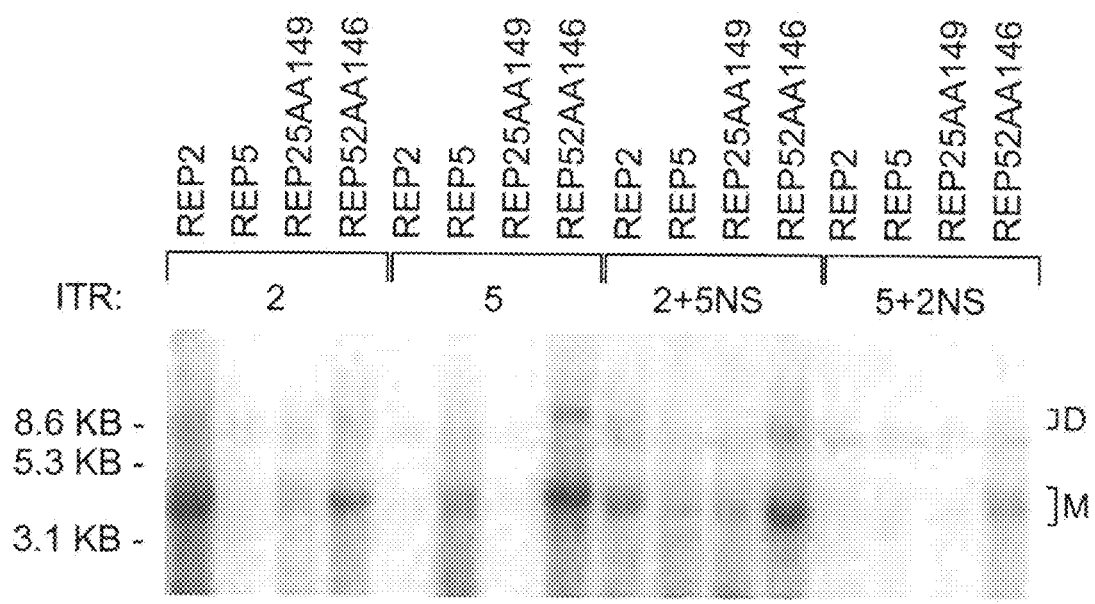
FIGS. 7A-7C show a model of Rep-ITR specificity.

Only Rep2 and Rep52aa146 efficiently replicated ITR2 (FIGS. 7A and 7B). Only Rep5 and Rep52aa146 replicated ITR5. As in FIGS. 1A and 1B, Rep2 and Rep5 replicated ITR2+5NS. Additionally, Rep25aa149 (SEQ ID NO:68) and Rep52aa146 (SEQ ID NO:79) replicated ITR2+5NS. This ITR appears to be universally replicated by every Rep in this assay due to the exclusion of DNA elements involved in protein specificity. The three nt ITR2 spacer is amenable to the DNA binding region 1 of Rep2 and Rep5. The seven bp tall ITR5 nicking stem functions with region 2 of Rep2 and Rep5. Thus, any combination of these regions constitutes a Rep protein capable of replicating ITR2+5NS.

Figure 7C:
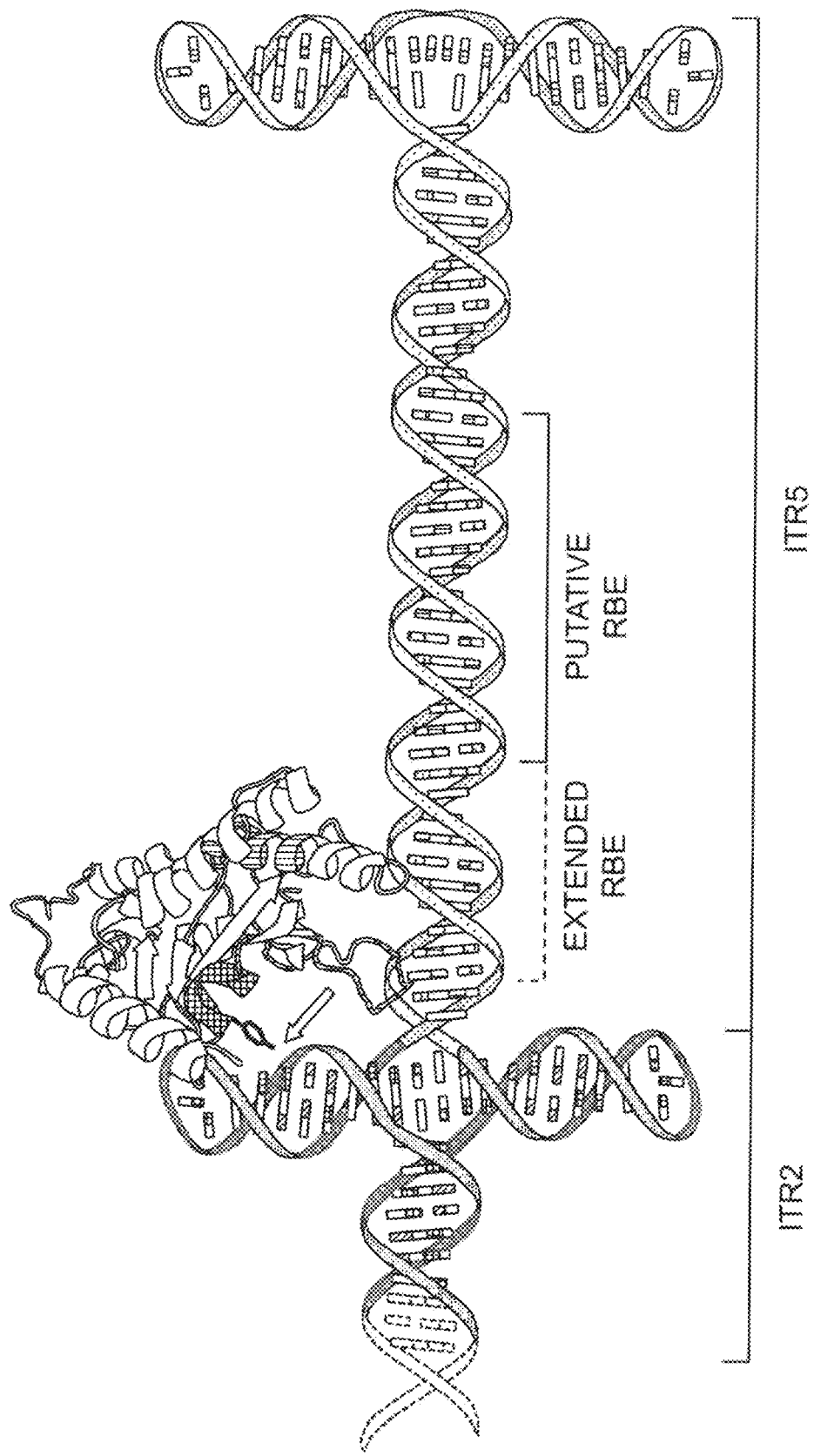

Finally, neither Rep2 nor Rep5 replicated ITR5+2NS. Rep2 is unable to interact properly with the 15 nt ITR5 spacer. Rep5 is unable to function on the ITR2 nicking stem. For these reasons, Rep25aa149 was also unable to catalyze replication. However, Rep52aa146 was able to replicate this ITR due to the proper combination of Rep regions (FIG. 7C). Rep52aa146 possesses Rep5 region 1 which interacts with the 15 nt ITR5 spacer. This chimera also possesses Rep2 region 2, which functions on the ITR2 nicking stem. This recombinant DNA-protein interaction is unique from either AAV2 or AAV5 and constitutes a novel Parvovirus origin of replication.

Taken as a whole, this work illustrates two specific mechanisms of DNA-protein specificity at the Parvovirus origin of replication. Chimeric ITRs narrowed the DNA elements involved in specificity to the spacer and nicking stem sequences (FIG. 1B). These results contradicted previous assertions that Rep-ITR specificity were driven solely by the nicking sequence as Rep2 efficiently nicked an ITR harboring the ITR5 nicking stem (Chiorini et al. (1999) *J. Virol.* 73:4293). Rep2 is highly flexible in the sequence and height of its nicking stem while Rep5 is highly specific to its cognate stem (FIGS. 2A-2D).

Three residues of Rep2 are important to cleave the ITR2 nicking stem (FIGS. 5A-5E and 6A-6G). Residues C151, N155, and T161 all lie in the active site of the protein in a predicted alpha helix along with the nucleophilic tyrosine Y156. How these residues (termed Rep region 2) grant Rep2 flexibility toward mutant nicking stems remains unclear. The corresponding Rep5 residues (G148, A152, and V158) may participate in highly specific interactions which require specific height and sequence considerations for the ITR5 nicking stem.

AAV5 Rep-ITR specificity is mediated by the ITR5 spacer. Replacement of the three nt ITR2 spacer with the 15 nt ITR5 spacer ablated replication by Rep2 (FIG. 2B). A poorly conserved Rep binding element allows Rep5 to interact with the elongated ITR5 spacer (FIG. 4B). Mutating the spacer to include a strong Rep binding element allowed Rep2 and Rep5 to replicate the ITR. However, insertion of a Rep binding element into the ITR2 spacer still largely decreased Rep2 function. While this data might suggest that additional Rep5 molecules bind to ITR5, previous in vitro experiments have not come to this conclusion, although those studies were performed in the absence of hairpins on the ITRs (Chiorini et al. (1999) *J. Virol.* 73:4293).

A 49 aa region of Rep5 interacts with the ITR5 spacer (aa 97-146, FIGS. 5A-5E and 6A-6G). The crystal structure of the N-terminus of Rep5 reveals that this region (region 1) possesses residues which specifically bind to the RBE and RBE' of the ITR. Major structural differences in the Rep5 loop which binds the major groove of the RBE likely account for the majority of ITR5 spacer specificity. While FIG. 1B predicts RBE' binding should not play a role in Rep-ITR specificity, it is possible that RBE' contacts alter the secondary structure of region 1 as it interacts with the RBE.

Because the regions of Rep conferring ITR specificity were separate (region 1 of Rep5 from aa97-146 and region 2 of Rep2 from aa151-161), a chimeric Rep possessing both regions was able to efficiently replicate ITR2 and ITR5. An ITR which could be replicated by any wt or chimeric Rep was constructed by excluding the DNA elements required for specificity; the ITR5 spacer and the ITR2 nicking stem. Most significantly, a novel origin of replication was generated. This ITR contained both of the elements for Rep specificity; the ITR5 spacer and the ITR2 nicking stem. As a result, only a chimeric Rep protein made up of Rep5 region 1 and Rep2 region 2 was able to replicate the ITR. The creation of a unique origin of replication highlights the power of studying the DNA-protein interactions of a viral origin of replication.

The creation of a unique DNA-protein interaction was possible because of the separation of the specific Rep-ITR interactions in AAV2 and AAV5. How and why these two different DNA-protein interactions evolved is unclear. It is likely due to evolutionary divergence in the ITR sequence which may have occurred in different hosts (AAV2 is related to other primate AAVs, AAV5 is related to non-primate AAVs such as goat and bovine). This model of replicative specificity can likely be extended to other parvoviruses such as snake AAV which has a highly conserved T-shaped ITR structure but different spacer and nicking stem lengths (Farkas et al. (2004) *J. Gen. Virol.* 85:555).

These results also stand to improve the safety of future AAV therapeutic vectors. The danger of AAV vector mobilization by wt AAV could be averted if therapeutic vectors harbored ITRs which no wt Rep could replicate (Hewitt et al. (2009) *J. Virol.* 83:3919).

Example 9

Snake ITR Vector Production

HEK 293 cells were cultured in Dulbecco Modified Eagle Medium (DMEM) supplemented with 10% Fetal Bovine Serum (Sigma, St. Louis, Mo.) and 100 units/ml penicillin and 100 µg/ml streptomycin and grown at 37° C. with 5% $CO_2$ saturation. To produce snake (royal python) ITR vectors, 10 µg of each of the following plasmids were transfected by PEI into HEK 293 cells in a 15 cm culture dish: pXX680 (Ad helper plasmid), pSnTR-eGFP (the ITR containing plasmid, SEQ ID NO:124), pSnRepCap2 (AAV helper plasmid containing the snake Rep genes and AAV2 Cap genes, SEQ ID NO:125), and pXR2 (AAV helper plasmid containing the AAV2 Rep and Cap genes). See FIGS. 33-35. Alternately, a plasmid expressing only the small AAV2 Rep proteins (Rep52 and Rep40) could be used in place of pXR2. 48 hours post-transfection, the cells were harvested and vector was purified by CsCl gradient centrifugation as previously described for other AAV vectors.

The foregoing is illustrative of the present invention, and is not to be construed as limiting thereof. The invention is defined by the following claims, with equivalents of the claims to be included therein.

SEQUENCE LISTING

<160> NUMBER OF SEQ ID NOS: 155

<210> SEQ ID NO 1
<211> LENGTH: 4718
<212> TYPE: DNA
<213> ORGANISM: Adeno-associated virus 1

<400> SEQUENCE: 1

| | | | | | | |
|---|---|---|---|---|---|---|
| ttgcccactc | cctctctgcg | cgctcgctcg | ctcggtgggg | cctgcggacc | aaaggtccgc | 60 |
| agacggcaga | gctctgctct | gccggcccca | ccgagcgagc | gagcgcgcag | agagggagtg | 120 |
| ggcaactcca | tcactagggg | taatcgcgaa | gcgcctccca | cgctgccgcg | tcagcgctga | 180 |
| cgtaaattac | gtcatagggg | agtggtcctg | tattagctgt | cacgtgagtg | cttttgcgac | 240 |
| attttgcgac | accacgtggc | catttagggt | atatatggcc | gagtgagcga | gcaggatctc | 300 |
| cattttgacc | gcgaaatttg | aacgagcagc | agccatgccg | gcttctacg | agatcgtgat | 360 |
| caaggtgccg | agcgacctgg | acgagcacct | gccgggcatt | tctgactcgt | ttgtgagctg | 420 |
| ggtggccgag | aaggaatggg | agctgccccc | ggattctgac | atggatctga | atctgattga | 480 |
| gcaggcaccc | ctgaccgtgg | ccgagaagct | gcagcgcgca | ttcctggtcc | aatggcgccg | 540 |
| cgtgagtaag | gccccggagg | ccctcttctt | tgttcagttc | gagaagggcg | agtcctactt | 600 |
| ccacctccat | attctggtgg | agaccacggg | ggtcaaatcc | atggtgctgg | gccgcttcct | 660 |
| gagtcagatt | agggacaagc | tggtgcagac | catctaccgc | gggatcgagc | cgaccctgcc | 720 |
| caactggttc | gcggtgacca | agacgcgtaa | tggcgccgga | gggggaaca | aggtggtgga | 780 |
| cgagtgctac | atccccaact | acctcctgcc | caagactcag | cccgagctgc | agtgggcgtg | 840 |
| gactaacatg | gaggagtata | taagcgcctg | tttgaacctg | gccgagcgca | acggctcgt | 900 |
| ggcgcagcac | ctgacccacg | tcagccagac | ccaggagcag | aacaaggaga | atctgaaccc | 960 |
| caattctgac | gcgcctgtca | tccggtcaaa | aacctccgcg | cgctacatgg | agctggtcgg | 1020 |
| gtggctggtg | gaccggggca | tcacctccga | gaagcagtgg | atccaggagg | accaggcctc | 1080 |
| gtacatctcc | ttcaacgccg | cttccaactc | gcggtcccag | atcaaggccg | ctctggacaa | 1140 |
| tgccggcaag | atcatggcgc | tgaccaaatc | cgcgcccgac | tacctggtag | gccccgctcc | 1200 |
| gcccgcggac | attaaaacca | accgcatcta | ccgcatcctg | gagctgaacg | gctacgaacc | 1260 |
| tgcctacgcc | ggctccgtct | ttctcggctg | ggcccagaaa | aggttcggga | agcgcaacac | 1320 |
| catctggctg | tttgggccgg | ccaccacggg | caagaccaac | atcgcggaag | ccatcgccca | 1380 |
| cgccgtgccc | ttctacggct | gcgtcaactg | gaccaatgag | aactttccct | tcaatgattg | 1440 |
| cgtcgacaag | atggtgatct | ggtgggagga | gggcaagatg | acggccaagg | tcgtggagtc | 1500 |
| cgccaaggcc | attctcggcg | gcagcaaggt | gcgcgtggac | caaaagtgca | agtcgtccgc | 1560 |
| ccagatcgac | cccaccccg | tgatcgtcac | ctccaacacc | aacatgtgcg | ccgtgattga | 1620 |
| cgggaacagc | accaccttcg | agcaccagca | gccgttgcag | gaccggatgt | tcaaatttga | 1680 |
| actcacccgc | cgtctggagc | atgactttgg | caaggtgaca | aagcaggaag | tcaaagagtt | 1740 |
| cttccgctgg | gcgcaggatc | acgtgaccga | ggtggcgcat | gagttctacg | tcagaaaggg | 1800 |
| tggagccaac | aaaagacccg | ccccgatga | cgcggataaa | agcgagccca | gcgggcctg | 1860 |
| cccctcagtc | gcggatccat | cgacgtcaga | gcgcgaagga | gctccggtgg | actttgccga | 1920 |
| caggtaccaa | aacaaatgtt | ctcgtcacgc | gggcatgctt | cagatgctgt | tccctgcaa | 1980 |
| gacatgcgag | agaatgaatc | agaatttcaa | catttgcttc | acgcacggga | cgagagactg | 2040 |
| ttcagagtgc | ttccccggcg | tgtcagaatc | tcaaccggtc | gtcagaaaga | ggacgtatcg | 2100 |

```
gaaactctgt gccattcatc atctgctggg gcgggctccc gagattgctt gctcggcctg    2160
cgatctggtc aacgtggacc tggatgactg tgtttctgag caataaatga cttaaaccag    2220
gtatggctgc cgatggttat cttccagatt ggctcgagga caacctctct gagggcattc    2280
gcgagtggtg ggacttgaaa cctggagccc cgaagcccaa agccaaccag caaaagcagg    2340
acgacggccg gggtctggtg cttcctggct acaagtacct cggacccttc aacggactcg    2400
acaaggggga gcccgtcaac gcggcggacg cagcggccct cgagcacgac aaggcctacg    2460
accagcagct caaagcgggt gacaatccgt acctgcggta taaccacgcc gacgccgagt    2520
ttcaggagcg tctgcaagaa gatacgtctt ttggggcaa cctcgggcga gcagtcttcc    2580
aggccaagaa gcgggttctc gaacctctcg gtctggttga ggaaggcgct aagacggctc    2640
ctggaaagaa acgtccggta gagcagtcgc acaagagcc agactcctcc tcgggcatcg    2700
gcaagacagg ccagcagccc gctaaaaaga gactcaattt tggtcagact ggcgactcag    2760
agtcagtccc cgatccacaa cctctcggag aacctccagc aaccccgct gctgtgggac    2820 ctactacaat ggcttcaggc ggtggcgcac caatggcaga caataacgaa ggcgccgacg    2880
gagtgggtaa tgcctcagga aattggcatt gcgattccac atggctgggc gacagagtca    2940
tcaccaccag cacccgcacc tgggccttgc ccacctacaa taaccacctc tacaagcaaa    3000
tctccagtgc ttcaacgggg gccagcaacg acaaccacta cttcggctac agcaccccct    3060
gggggtattt tgatttcaac agattccact gccactttc accacgtgac tggcagcgac    3120
tcatcaacaa caattgggga ttccggccca agagactcaa cttcaaactc ttcaacatcc    3180
aagtcaagga ggtcacgacg aatgatggcg tcacaaccat cgctaataac cttaccagca    3240
cggttcaagt cttctcggac tcggagtacc agcttccgta cgtcctcggc tctgcgcacc    3300
agggctgcct ccctccgttc ccggcggacg tgttcatgat tccgcaatac ggctacctga    3360
cgctcaacaa tggcagccaa gccgtgggac gttcatcctt ttactgcctg gaatatttcc    3420
cttctcagat gctgagaacg ggcaacaact ttaccttcag ctacacctt gaggaagtgc    3480 cttttccacag cagctacgcg cacagccaga gcctggaccg gctgatgaat cctctcatcg    3540 accaataccct gtattacctg aacagaactc aaaatcagtc cggaagtgcc caaacaagg    3600 acttgctgtt tagccgtggg tctccagctg gcatgtctgt tcagcccaaa aactggctac    3660 ctggacccctg ttatcggcag cagcgcgttt ctaaaacaaa aacagacaac aacaacagca    3720
attttacctg gactggtgct caaaatata acctcaatgg gcgtgaatcc atcatcaacc    3780
ctggcactgc tatggcctca cacaaagacg acgaagacaa gttcttttccc atgagcggtg    3840 tcatgatttt tggaaaagag agcgccggag cttcaaacac tgcattggac aatgtcatga    3900
ttacagacga agaggaaatt aaagccacta accctgtggc caccgaaaga tttgggaccg    3960
tggcagtcaa tttccagagc agcagcacag accctgcgac cggagatgtg catgctatgg    4020
gagcattacc tggcatggtg tggcaagata gagacgtgta cctgcagggt cccatttggg    4080
ccaaaattcc tcacacagat ggacactttc acccgtctcc tcttatgggc ggctttggac    4140
tcaagaaccc gcctcctcag atcctcatca aaaacacgcc tgttcctgcg aatcctccgg    4200
cggagttttc agctacaaag tttgcttcat tcatcaccca atactccaca ggacaagtga    4260
gtgtggaaat tgaatgggag ctgcagaaag aaaacagcaa gcgctggaat cccgaagtgc    4320
agtacacatc caattatgca aaatctgcca acgttgattt tactgtggac aacaatggac    4380
tttatactga gcctcgcccc attggcaccc gttaccttac ccgtcccctg taattacgtg    4440
```

```
ttaatcaata aaccggttga ttcgtttcag ttgaactttg gtctcctgtc cttcttatct    4500
tatcggttac catggttata gcttacacat taactgcttg gttgcgcttc gcgataaaag    4560
acttacgtca tcgggttacc cctagtgatg gagttgccca ctccctctct gcgcgctcgc    4620
tcgctcggtg gggcctgcgg accaaaggtc cgcagacggc agagctctgc tctgccggcc    4680
ccaccgagcg agcgagcgcg cagagaggga gtgggcaa                           4718

<210> SEQ ID NO 2
<211> LENGTH: 4679
<212> TYPE: DNA
<213> ORGANISM: Adeno-associated virus 2

<400> SEQUENCE: 2
ttggccactc cctctctgcg cgctcgctcg ctcactgagg ccgggcgacc aaaggtcgcc      60
cgacgcccgg gctttgcccg gcggcctcca gtgagcgagc gagcgcgcag agagggagtg     120
gccaactcca tcactagggg ttcctggagg ggtggagtcg tgacgtgaat tacgtcatag     180
ggttagggag gtcctgtatt agaggtcacg tgagtgtttt gcgacatttt gcgacaccat     240
gtggtcacgc tgggtattta agcccgagtg agcacgcagg gtctccattt tgaagcggga     300
ggtttgaacg cgcagccgcc atgccggggt tttacgagat tgtgattaag gtccccagcg     360
accttgacga gcatctgccc ggcatttctg acagctttgt gaactgggtg gccgagaagg     420
aatgggagtt gccgccagat tctgacatgg atctgaatct gattgagcag caccccctga     480
ccgtggccga aagctgcag cgcgactttc tgacggaatg cgccgtgtg agtaaggccc      540 cggaggcccc tttctttgtg caatttgaga agggagagag ctactccac atgcacgtgc     600 tcgtggaaac caccggggtg aaatccatgg ttttgggacg tttcctgagt cagattcgcg     660
aaaaactgat tcagagaatt taccgcggga tcgagccgac tttgccaaac tggttcgcgg     720
tcacaaagac cagaaatggc gccggaggcg ggaacaaggt ggtggatgag tgctacatcc     780
ccaattactt gctccccaaa acccagcctg agctccagtg ggcgtggact aatatggaac     840
agtatttaag cgcctgtttg aatctcacgg agcgtaaacg gttggtggcg cagcatctga     900
cgcacgtgtc gcagacgcag gagcagaaca aagagaatca gaatcccaat tctgatgcgc     960
cggtgatcag atcaaaaact tcagccaggt acatggagct ggtcgggtgg ctcgtggaca    1020 agggggattac tcggagaag cagtggatcc aggaggacca ggcctcatac atctccttca    1080
atgcggcctc caactcgcgg tcccaaatca aggctgcctt ggacaatgcg ggaaagatta    1140
tgagcctgac taaaaccgcc cccgactacc tggtgggcca gcagcccgtg gaggacattt    1200
ccagcaatcg gatttataaa attttggaac taaacgggta cgatcccaa tatgcggctt    1260 ccgtctttct gggatgggcc acgaaaaagt tcggcaagag gaacaccatc tggctgtttg    1320
ggcctgcaac taccgggaag accaacatcg cggaggccat agcccacact gtgcccttct    1380
acgggtgcgt aaactggacc aatgagaact tccccttcaa cgactgtgtc gacaagatgg    1440
tgatctggtg ggaggagggg aagatgaccg ccaaggtcgt ggagtcggcc aaagccattc    1500
tcggaggaag caaggtgcgc gtggaccaga atgcaagtc ctcggcccag atagacccga    1560
ctcccgtgat cgtcacctcc aacaccaaca tgtgcgccgt gattgacggg aactcaacga    1620
ccttcgaaca ccagcagccg ttgcaagacc ggatgttcaa atttgaactc acccgccgtc    1680
tggatcatga ctttgggaag gtcaccaagc aggaagtcaa agactttttc cggtgggcaa    1740
aggatcacgt ggttgaggtg gagcatgaat tctacgtcaa aaagggtgga gccaagaaaa    1800
gacccgcccc cagtgacgca gatataagtg agcccaaacg ggtgcgcgag tcagttgcgc    1860
```

-continued

```
agccatcgac gtcagacgcg gaagcttcga tcaactacgc agacaggtac caaaacaaat     1920
gttctcgtca cgtgggcatg aatctgatgc tgtttccctg cagacaatgc gagagaatga     1980
atcagaattc aaatatctgc ttcactcacg gacagaaaga ctgtttagag tgctttcccg     2040
tgtcagaatc tcaacccgtt tctgtcgtca aaaggcgta tcagaaactg tgctacattc      2100
atcatatcat gggaaaggtg ccagacgctt gcactgcctg cgatctggtc aatgtggatt     2160
tggatgactg catctttgaa caataaatga tttaaatcag gtatggctgc cgatggttat     2220
cttccagatt ggctcgagga cactctctct gaaggaataa gacagtggtg gaagctcaaa    2280
cctggcccac caccaccaaa gcccgcagag cggcataagg acgacagcag gggtcttgtg     2340
cttcctgggt acaagtacct cggacccttc aacggactcg acaagggaga gccggtcaac    2400
gaggcagacg ccgcggccct cgagcacgac aaagcctacg accggcagct cgacagcgga    2460
gacaacccgt acctcaagta caaccacgcc gacgcggagt tcaggagcg ccttaaagaa      2520 gatacgtctt ttgggggcaa cctcggacga gcagtcttcc aggcgaaaaa gagggttctt    2580
gaacctctgg gcctggttga ggaacctgtt aagacggctc cgggaaaaaa gaggccggta    2640
gagcactctc ctgtggagcc agactcctcc tcgggaaccg gaaaggcggg ccagcagcct    2700
gcaagaaaaa gattgaattt tggtcagact ggagacgcag actcagtacc tgaccccag     2760 cctctcggac agccaccagc agcccctct ggtctgggaa ctaatacgat ggctacaggc      2820
agtggcgcac caatggcaga caataacgag gcgccgacg gagtgggtaa ttcctcggga     2880
aattggcatt gcgattccac atggatgggc gacagagtca tcaccaccag cacccgaacc    2940
tgggccctgc ccacctacaa caaccacctc tacaaacaaa tttccagcca atcaggagcc    3000
tcgaacgaca atcactactt tggctacagc accccttggg ggtattttga cttcaacaga    3060
ttccactgcc acttttcacc acgtgactgg caaagactca tcaacaacaa ctggggattc    3120
cgacccaaga gactcaactt caagctcttt aacattcaag tcaaagaggt cacgcagaat    3180
gacggtacga cgacgattgc caataacctt accagcacgg ttcaggtgtt tactgactcg    3240
gagtaccagc tcccgtacgt cctcggctcg gcgcatcaag gatgcctccc gccgttccca    3300
gcagacgtct tcatggtgcc acagtatgga tacctcaccc tgaacaacgg gagtcaggca    3360
gtaggacgct cttcatttta ctgcctggag tactttcctt ctcagatgct gcgtaccgga    3420
aacaacttta ccttcagcta cacttttgag gacgttcctt tccacagcag ctacgctcac    3480
agccagagtc tggaccgtct catgaatcct ctcatcgacc agtacctgta ttacttgagc    3540
agaacaaaca ctccaagtgg aaccaccacg cagtcaaggc ttcagttttc tcaggccgga    3600
gcgagtgaca ttcgggacca gtctaggaac tggcttcctg accctgtta ccgccagcag    3660 cgagtatcaa agacatctgc ggataacaac aacagtgaat actcgtggac tggagctacc    3720
aagtaccacc tcaatggcag agactctctg gtgaatccgg gcccggccat ggcaagccac    3780
aaggacgatg aagaaagtt tttttcctcag agcggggttc tcatctttgg gaagcaaggc    3840
tcagagaaaa caaatgtgga cattgaaaag gtcatgatta cagacgaaga ggaaatcagg    3900
acaaccaatc ccgtggctac ggagcagtat ggttctgtat ctaccaacct ccagagaggc    3960
aacagacaag cagctaccgc agatgtcaac acacaaggcg ttcttccagg catggtctgg    4020
caggacagag atgtgtacct tcaggggccc atctgggcaa agattccaca cacggacgga    4080
cattttcacc cctctcccct catggtggga ttcggactta acaccctcc tccacagatt    4140 ctcatcaaga acacccggt acctgcgaat ccttcgacca ccttcagtgc ggcaaagttt    4200
```

| | |
|---|---:|
| gcttccttca tcacacagta ctccacggga caggtcagcg tggagatcga gtgggagctg | 4260 |
| cagaaggaaa acagcaaacg ctggaatccc gaaattcagt acacttccaa ctacaacaag | 4320 |
| tctgttaatg tggactttac tgtggacact aatggcgtgt attcagagcc tcgcccatt | 4380 |
| ggcaccagat acctgactcg taatctgtaa ttgcttgtta atcaataaac cgtttaattc | 4440 |
| gtttcagttg aactttggtc tctgcgtatt tctttcttat ctagtttcca tggctacgta | 4500 |
| gataagtagc atggcgggtt aatcattaac tacaaggaac ccctagtgat ggagttggcc | 4560 |
| actccctctc tgcgcgctcg ctcgctcact gaggccgggc gaccaaaggt cgcccgacgc | 4620 |
| ccgggctttg cccgggcggc ctcagtgagc gagcgagcgc gcagagaggg agtggccaa | 4679 |

<210> SEQ ID NO 3
<211> LENGTH: 4726
<212> TYPE: DNA
<213> ORGANISM: Adeno-associated virus 3A

<400> SEQUENCE: 3

| | |
|---|---:|
| ttggccactc cctctatgcg cactcgctcg ctcggtgggg cctggcgacc aaaggtcgcc | 60 |
| agacggacgt gctttgcacg tccggcccca ccgagcgagc gagtgcgcat agagggagtg | 120 |
| gccaactcca tcactagagg tatggcagtg acgtaacgcg aagcgcgcga agcgagacca | 180 |
| cgcctaccag ctgcgtcagc agtcaggtga ccctttgcg acagtttgcg acaccacgtg | 240 |
| gccgctgagg gtatatattc tcgagtgagc gaaccaggag ctccattttg accgcgaaat | 300 |
| ttgaacgagc agcagccatg ccggggttct acgagattgt cctgaaggtc ccgagtgacc | 360 |
| tggacgagcg cctgccgggc atttctaact cgtttgttaa ctgggtggcc gagaaggaat | 420 |
| gggacgtgcc gccggattct gacatggatc cgaatctgat tgagcaggca cccctgaccg | 480 |
| tggccgaaaa gcttcagcgc gagttcctgg tggagtggcg ccgcgtgagt aaggccccgg | 540 |
| aggccctctt ttttgtccag ttcgaaaagg gggagaccta cttccacctg cacgtgctga | 600 |
| ttgagaccat cggggtcaaa tccatggtgg tcggccgcta cgtgagccag attaaagaga | 660 |
| agctggtgac ccgcatctac cgcggggtcg agccgcagct tccgaactgg ttcgcggtga | 720 |
| ccaaaacgcg aaatggcgcc gggggcggga caaggtggt ggacgactgc tacatcccca | 780 |
| actacctgct ccccaagacc cagcccgagc tccagtgggc gtggactaac atggaccagt | 840 |
| atttaagcgc ctgtttgaat ctcgcggagc gtaaacggct ggtggcgcag catctgacgc | 900 |
| acgtgtcgca gacgcaggag cagaacaaag agaatcagaa ccccaattct gacgcgccgg | 960 |
| tcatcaggtc aaaaacctca gccaggtaca tggagctggt cggtggctg gtggaccgcg | 1020 |
| ggatcacgtc agaaaagcaa tggattcagg aggaccaggc ctcgtacatc tccttcaacg | 1080 |
| ccgcctccaa ctcgcggtcc cagatcaagg ccgcgctgga caatgcctcc aagatcatga | 1140 |
| gcctgacaaa acggctccg gactacctgg tgggcagcaa cccgccggag acattacca | 1200 |
| aaaatcggat ctaccaaatc ctggagctga acgggtacga tccgcagtac gcggcctccg | 1260 |
| tcttcctggg ctgggcgcaa aagaagttcg gaagaggaa caccatctgg ctctttgggc | 1320 |
| cggccacgac gggtaaaacc aacatcgcgg aagccatcgc ccacgccgtg cccttctacg | 1380 |
| gctgcgtaaa ctggaccaat gagaactttc ccttcaacga ttgcgtcgac aagatggtga | 1440 |
| tctggtggga ggagggcaag atgacggcca aggtcgtgga gagcgccaag gccattctgg | 1500 |
| gcggaagcaa ggtgcgcgtg gaccaaaagt gcaagtcatc ggcccagatc gaacccactc | 1560 |
| ccgtgatcgt cacctccaac accaacatgt gcgccgtgat tgacgggaac agcaccacct | 1620 |
| tcgagcatca gcagccgctg caggaccgga tgtttgaatt tgaacttacc cgccgtttgg | 1680 |

```
accatgactt tgggaaggtc accaaacagg aagtaaagga cttttttccgg tgggcttccg   1740 atcacgtgac tgacgtggct catgagttct acgtcagaaa gggtggagct aagaaacgcc   1800
ccgcctccaa tgacgcggat gtaagcgagc caaaacggga gtgcacgtca cttgcgcagc   1860
cgacaacgtc agacgcggaa gcaccggcgg actacgcgga caggtaccaa acaaatgtt    1920 ctcgtcacgt gggcatgaat ctgatgcttt ttccctgtaa aacatgcgag agaatgaatc   1980
aaatttccaa tgtctgtttt acgcatggtc aagagactg tggggaatgc ttccctggaa    2040
tgtcagaatc tcaacccgtt tctgtcgtca aaagaagac ttatcagaaa ctgtgtccaa    2100
ttcatcatat cctgggaagg gcacccgaga ttgcctgttc ggcctgcgat ttggccaatg   2160
tggacttgga tgactgtgtt tctgagcaat aaatgactta aaccaggtat ggctgctgac   2220
ggttatcttc cagattggct cgaggacaac ctttctgaag gcattcgtga gtggtgggct   2280
ctgaaacctg gagtccctca acccaaagcg aaccaacaac accaggacaa ccgtcgggt    2340 cttgtgcttc cgggttacaa atacctcgga cccggtaacg gactcgacaa aggagagccg   2400
gtcaacgagg cggacgcggc agccctcgaa cacgacaaag cttacgacca gcagctcaag   2460
gccggtgaca acccgtacct caagtacaac cacgccgacg ccgagtttca ggagcgtctt   2520
caagaagata cgtcttttgg gggcaacctt ggcagagcag tcttccaggc caaaaagagg   2580
atccttgagc tcttggtct ggttgaggaa gcagctaaaa cggctcctgg aaagaagggg    2640
gctgtagatc agtctcctca ggaaccggac tcatcatctg gtgttggcaa atcgggcaaa   2700
cagcctgcca gaaaaagact aaatttcggt cagactggag actcagagtc agtcccagac   2760
cctcaacctc tcggagaacc accagcagcc cccacaagtt tgggatctaa tacaatggct   2820
tcaggcggtg gcgcaccaat ggcagacaat aacgagggtg ccgatggagt gggtaattcc   2880
tcaggaaatt ggcattgcga ttcccaatgg ctgggcgaca gagtcatcac caccagcacc   2940
agaacctggg ccctgcccac ttacaacaac catctctaca gcaaatctc cagccaatca   3000 ggagcttcaa acgacaacca ctactttggc tacagcaccc cttgggggta ttttgacttt   3060
aacagattcc actgccactt ctcaccacgt gactggcagc gactcattaa caacaactgg   3120
ggattccggc ccaagaaact cagcttcaag ctcttcaaca tccaagttag aggggtcacg   3180
cagaacgatg gcacgacgac tattgccaat aaccttacca gcacggttca agtgtttacg   3240
gactcggagt atcagctccc gtacgtgctc gggtcggcgc accaaggctg tctcccgccg   3300
tttccagcgg acgtcttcat ggtccctcag tatggatacc tcaccctgaa caacggaagt   3360
caagcggtgg gacgctcatc ctttttactgc ctggagtact tcccttcgca gatgctaagg   3420
actggaaata acttccaatt cagctatacc ttcgaggatg taccttttca cagcagctac   3480
gctcacagcc agagtttgga tcgcttgatg aatcctctta ttgatcagta tctgtactac   3540
ctgaacagaa cgcaaggaac aacctctgga acaaccaacc aatcacggct gcttttagc    3600 caggctgggc ctcagtctat gtcttttgcag gccagaaatt ggctacctgg gccctgctac   3660
cggcaacaga gactttcaaa gactgctaac gacaacaaca acagtaactt ccttggaca    3720 gcggccagca aatatcatct caatggccgc gactcgctgg tgaatccagg accagctatg   3780
gccagtcaca aggacgatga agaaaaattt ttccctatgc acggcaatct aatatttggc   3840
aaagaaggga caacggcaag taacgcagaa ttagataatg taatgattac ggatgaagaa   3900
gagattcgta ccaccaatcc tgtggcaaca gagcagtatg gaactgtggc aaataacttg   3960
cagagctcaa atacagctcc cacgactgga actgtcaatc atcagggggc cttacctgg    4020
```

-continued

| | |
|---|---|
| atggtgtggc aagatcgtga cgtgtacctt caaggaccta tctgggcaaa gattcctcac | 4080 |
| acggatggac actttcatcc ttctcctctg atgggaggct ttggactgaa acatccgcct | 4140 |
| cctcaaatca tgatcaaaaa tactccggta ccggcaaatc ctccgacgac tttcagcccg | 4200 |
| gccaagtttg cttcatttat cactcagtac tccactggac aggtcagcgt ggaaattgag | 4260 |
| tgggagctac agaaagaaaa cagcaaacgt tggaatccag agattcagta cacttccaac | 4320 |
| tacaacaagt ctgttaatgt ggactttact gtagacacta atggtgttta tagtgaacct | 4380 |
| cgccctattg aacccggta tctcacacga aacttgtgaa tcctggttaa tcaataaacc | 4440 |
| gtttaattcg tttcagttga actttggctc ttgtgcactt ctttatcttt atcttgtttc | 4500 |
| catggctact gcgtagataa gcagcggcct gcggcgcttg cgcttcgcgg tttacaactg | 4560 |
| ctggttaata tttaactctc gccatacctc tagtgatgga gttggccact ccctctatgc | 4620 |
| gcactcgctc gctcggtggg gcctggcgac caaaggtcgc cagacggacg tgctttgcac | 4680 |
| gtccggcccc accgagcgag cgagtgcgca tagagggagt ggccaa | 4726 |

<210> SEQ ID NO 4
<211> LENGTH: 4722
<212> TYPE: DNA
<213> ORGANISM: Adeno-associated virus 3B

<400> SEQUENCE: 4

| | |
|---|---|
| tggccactcc ctctatgcgc actcgctcgc tcggtggggc ctggcgacca aggtcgcca | 60 |
| gacggacgtg ctttgcacgt ccggccccac cgagcgagcg agtgcgcata gagggagtgg | 120 |
| ccaactccat cactagaggt atggcagtga cgtaacgcga agcgcgcgaa gcgagaccac | 180 |
| gcctaccagc tgcgtcagca gtcaggtgac ccttttgcga cagtttgcga caccacgtgg | 240 |
| ccgctgaggg tatatattct cgagtgagcg aaccaggagc tccattttga ccgcgaaatt | 300 |
| tgaacgagca gcagccatgc cggggttcta cgagattgtc ctgaaggtcc cgagtgacct | 360 |
| ggacgagcac ctgccgggca tttctaactc gtttgttaac tgggtggccg agaaggaatg | 420 |
| ggagctgccg ccggattctg acatggatcc gaatctgatt gagcaggcac ccctgaccgt | 480 |
| ggccgaaaag cttcagcgcg agttcctggt ggagtggcgc gcgtgagta aggccccgga | 540 |
| ggccctcttt tttgtccagt cgaaaagggg ggagacctac ttccacctgc acgtgctgat | 600 |
| tgagaccatc ggggtcaaat ccatggtggt cggccgctac gtgagccaga ttaaagagaa | 660 |
| gctggtgacc cgcatctacc gcggggtcga gccgcagctt ccgaactggt cgcggtgac | 720 |
| caaaacgcga atggcgccg ggggcgggaa caaggtggtg acgactgct acatccccaa | 780 |
| ctacctgctc cccaagaccc agcccgagct ccagtgggcg tggactaaca tggaccagta | 840 |
| tttaagcgcc tgtttgaatc tcgcggagcg taaacggctg gtggcgcagc atctgacgca | 900 |
| cgtgtcgcag acgcaggagc agaacaaaga gaatcagaac cccaattctg acgcgccggt | 960 |
| catcaggtca aaaacctcag ccaggtacat ggagctggtc gggtggctgg tggaccgcgg | 1020 |
| gatcacgtca gaaaagcaat ggattcagga ggaccaggcc tcgtacatct ccttcaacgc | 1080 |
| cgcctccaac tcgcggtccc agatcaaggc cgcgctggac aatgcctcca gatcatgag | 1140 |
| cctgacaaag acggctccgg actacctggt gggcagcaac ccgccggagg acattaccaa | 1200 |
| aaatcggatc taccaaatcc tggagctgaa cgggtacgat ccgcagtacg cggcctccgt | 1260 |
| cttcctgggc tgggcgcaaa agaagttcgg gaagaggaac accatctggc tctttgggcc | 1320 |
| ggccacgacg ggtaaaacca acatcgcgga agccatcgcc cacgccgtgc cttctacgg | 1380 |
| ctgcgtaaac tggaccaatg agaactttcc cttcaacgat tgcgtcgaca gatggtgat | 1440 |

```
ctggtgggag gagggcaaga tgacggccaa ggtcgtggag agcgccaagg ccattctggg    1500
cggaagcaag gtgcgcgtgg accaaaagtg caagtcatcg gcccagatcg aacccactcc    1560
cgtgatcgtc acctccaaca ccaacatgtg cgccgtgatt gacgggaaca gcaccacctt    1620
cgagcatcag cagccgctgc aggaccggat gtttaaattt gaacttaccc gccgtttgga    1680
ccatgacttt gggaaggtca ccaaacagga agtaaaggac ttttccggt gggcttccga     1740
tcacgtgact gacgtggctc atgagttcta cgtcagaaag ggtggagcta agaaacgccc    1800
cgcctccaat gacgcggatg taagcgagcc aaaacggcag tgcacgtcac ttgcgcagcc    1860
gacaacgtca gacgcggaag caccggcgga ctacgcggac aggtaccaaa acaaatgttc    1920
tcgtcacgtg ggcatgaatc tgatgctttt ccctgtaaa acatgcgaga gaatgaatca     1980
aatttccaat gtctgtttta cgcatggtca aagagactgt ggggaatgct tccctggaat    2040
gtcagaatct caacccgttt ctgtcgtcaa aaagaagact tatcagaaac tgtgtccaat    2100
tcatcatatc ctgggaaggg cacccgagat tgcctgttcg gcctgcgatt tggccaatgt    2160
ggacttggat gactgtgttt ctgagcaata aatgacttaa accaggtatg gctgctgacg    2220
gttatcttcc agattggctc gaggacaacc tttctgaagg cattcgtgag tggtgggctc    2280
tgaaacctgg agtccctcaa cccaaagcga accaacaaca ccaggacaac cgtcggggtc    2340
ttgtgcttcc gggttacaaa tacctcggac ccggtaacgg actcgacaaa ggagagccgg    2400
tcaacgaggc ggacgcggca gccctcgaac acgacaaagc ttacgaccag cagctcaagg    2460
ccggtgacaa cccgtacctc aagtacaacc acgccgacgc cgagtttcag gagcgtcttc    2520
aagaagatac gtcttttggg ggcaaccttg gcagagcagt cttccaggcc aaaaagagga    2580
tccttgagcc tcttggtctg gttgaggaag cagctaaaac ggctcctgga agaagaggc     2640
ctgtagatca gtctcctcag gaaccggact catcatctgg tgttggcaaa tcgggcaaac    2700
agcctgccag aaaaagacta aatttcggtc agactggcga ctcagagtca gtcccagacc    2760
ctcaacctct cggagaacca ccagcagccc ccacaagttt gggatctaat acaatggctt    2820
caggcggtgg cgcaccaatg gcagacaata acgagggtgc cgatggagtg ggtaattcct    2880
caggaaattg gcattgcgat tcccaatggc tgggcgacag agtcatcacc accagcacca    2940
gaacctgggc cctgcccact acaacaacc atctctacaa gcaaatctcc agccaatcag     3000
gagcttcaaa cgacaaccac tactttggct acagcacccc ttgggggtat tttgacttta    3060
acagattcca ctgccacttc tcaccacgtg actggcagcg actcattaac aacaactggg    3120
gattccggcc caagaaactc agcttcaagc tcttcaacat ccaagttaaa gaggtcacgc    3180
agaacgatgg cacgacgact attgccaata accttaccag cacggttcaa gtgtttacgg    3240
actcggagta tcagctcccg tacgtgctcg ggtcggcgca ccaaggctgt ctcccgccgt    3300
ttccagcgga cgtcttcatg gtccctcagt atggatacct cacccctgaac aacggaagtc    3360
aagcggtggg acgctcatcc tttttactgcc tggagtactt cccttcgcag atgctaagga    3420
ctggaaataa cttccaattc agctataccgt tcgaggatgt acctttttcac agcagctacg    3480
ctcacagcca gagtttggat cgcttgatga atcctcttat tgatcagtat ctgtactacc    3540
tgaacagaac gcaaggaaca acctctggaa caaccaacca atcacggctg ctttttagcc    3600
aggctgggcc tcagtctatg tctttgcagg ccagaaattg gctacctggg ccctgctacc    3660
ggcaacagag actttcaaag actgctaacg acaacaacaa cagtaacttt ccttggacag    3720
cggccagcaa atatcatctc aatggccgcg actcgctggt gaatccagga ccagctatgg    3780
```

```
ccagtcacaa ggacgatgaa gaaaaatttt tccctatgca cggcaatcta atatttggca    3840
aagaagggac aacggcaagt aacgcagaat tagataatgt aatgattacg gatgaagaag    3900
agattcgtac caccaatcct gtggcaacag agcagtatgg aactgtggca ataacttgc    3960
agagctcaaa tacagctccc acgactagaa ctgtcaatga tcaggggggcc ttacctggca    4020
tggtgtggca agatcgtgac gtgtaccttc aaggacctat ctgggcaaag attcctcaca    4080
cggatggaca ctttcatcct tctcctctga tgggaggctt tggactgaaa catccgcctc    4140
ctcaaatcat gatcaaaaat actccggtac cggcaaatcc tccgacgact ttcagcccgg    4200
ccaagtttgc ttcatttatc actcagtact ccactggaca ggtcagcgtg aaaattgagt    4260
gggagctaca gaaagaaaac agcaaacgtt ggaatccaga gattcagtac acttccaact    4320
acaacaagtc tgttaatgtg gactttactg tagacactaa tggtgtttat agtgaacctc    4380
gccctattgg aacccggtat ctcacacgaa acttgtaatc ctggttaatc aataaaccgt    4440
ttaattcgtt tcagttgaac tttggctctt gtgcacttct tatcttatct tgtttccatg    4500
gctactgcgt agataagcag cggcctgcgg cgcttgcgct tcgcggttta caactgctgg    4560
ttaatattta actctcgcca tacctctagt gatggagttg gccactccct ctatgcgcac    4620
tcgctcgctc ggtggggccg gacgtgcaaa gcacgtccgt ctggcgacct ttggtcgcca    4680
ggccccaccg agcgagcgag tgcgcataga gggagtggcc aa                      4722
```

<210> SEQ ID NO 5
<211> LENGTH: 4767
<212> TYPE: DNA
<213> ORGANISM: Adeno-associated virus 4

<400> SEQUENCE: 5

```
ttggccactc cctctatgcg cgctcgctca ctcactcggc cctggagacc aaaggtctcc     60
agactgccgg cctctggccg gcagggccga gtgagtgagc gagcgcgcat agagggagtg    120
gccaactcca tcatctaggt ttgcccactg acgtcaatgt gacgtcctag ggttagggag    180
gtccctgtat tagcagtcac gtgagtgtcg tatttcgcgg agcgtagcgg agcgcatacc    240
aagctgccac gtcacagcca cgtggtccgt ttgcgacagt ttgcgacacc atgtggtcag    300
gagggtatat aaccgcgagt gagccagcga ggagctccat ttttgcccgcg aattttgaac    360
gagcagcagc catgccgggg ttctacgaga tcgtgctgaa ggtgcccagc gacctggacg    420
agcacctgcc cggcatttct gactcttttg tgagctgggt ggccgagaag gaatgggagc    480
tgccgccgga ttctgacatg gacttgaatc tgattgagca ggcaccctg accgtggccg    540
aaaagctgca acgcgagttc ctggtcgagt ggcgccgcgt gagtaaggcc ccggaggccc    600
tcttctttgt ccagttcgag aagggggaca gctacttcca cctgcacatc ctggtggaga    660
ccgtgggcgt caaatccatg gtggtgggcc gctacgtgag ccagattaaa gagaagctgg    720
tgacccgcat ctaccgcggg gtcgagccgc agcttccgaa ctggttcgcg gtgaccaaga    780
cgcgtaatgg cgccggaggc gggaacaagg tggtggacga ctgctacatc cccaactacc    840
tgctccccaa gacccagccc gagctccagt gggcgtggac taacatggac cagtatataa    900
gcgcctgttt gaatctcgcg gagcgtaaac ggctggtggc gcagcatctg acgcacgtgt    960
cgcagacgca ggagcagaac aaggaaaacc agaacccaa ttctgacgcg ccggtcatca   1020
ggtcaaaaac ctccgccagg tacatggagc tggtcgggtg gctggtggac cgcgggatca   1080
cgtcagaaaa gcaatggatc caggaggacc aggcgtccta catctccttc aacgccgcct   1140
ccaactcgcg gtcacaaatc aaggccgcgc tggacaatgc ctccaaaatc atgagcctga   1200
```

```
caaagacggc tccggactac ctggtgggcc agaacccgcc ggaggacatt tccagcaacc   1260
gcatctaccg aatcctcgag atgaacgggt acgatccgca gtacgcggcc tccgtcttcc   1320
tgggctgggc gcaaaagaag ttcgggaaga ggaacaccat ctggctcttt gggccggcca   1380
cgacgggtaa aaccaacatc gcggaagcca tcgcccacgc cgtgcccttc tacggctgcg   1440
tgaactggac caatgagaac tttccgttca acgattgcgt cgacaagatg gtgatctggt   1500
gggaggaggg caagatgacg gccaaggtcg tagagagcgc caaggccatc ctgggcggaa   1560
gcaaggtgcg cgtggaccaa aagtgcaagt catcggccca gatcgaccca actcccgtga   1620
tcgtcacctc caacaccaac atgtgcgcgg tcatcgacgg aaactcgacc accttcgagc   1680
accaacaacc actccaggac cggatgttca agttcgagct caccaagcgc ctggagcacg   1740
actttggcaa ggtcaccaag caggaagtca aagactttt ccggtgggcg tcagatcacg   1800
tgaccgaggt gactcacgag ttttacgtca gaaagggtgg agctagaaag aggcccgccc   1860
ccaatgacgc agatataagt gagcccaagc ggggcctgtcc gtcagttgcg cagccatcga   1920
cgtcagacgc ggaagctccg gtggactacg cggacaggta ccaaaacaaa tgttctcgtc   1980
acgtgggtat gaatctgatg cttttcccct gccggcaatg cgagagaatg aatcagaatg   2040
tggacatttg cttcacgcac ggggtcatgg actgtgccga gtgcttcccc gtgtcagaat   2100
ctcaacccgt gtctgtcgtc agaaagcgga cgtatcagaa actgtgtccg attcatcaca   2160
tcatggggag ggcgcccgag gtggcctgct cggcctgcga actggccaat gtggacttgg   2220
atgactgtga catggaacaa taaatgactc aaaccagata tgactgacgg ttaccttcca   2280
gattggctag aggacaacct ctctgaaggc gttcgagagt ggtgggcgct gcaacctgga   2340
gcccctaaac ccaaggcaaa tcaacaacat caggacaacg ctcggggtct tgtgcttccg   2400
ggttacaaat acctcggacc cggcaacgga ctcgacaagg gggaacccgt caacgcagcg   2460
gacgcggcag ccctcgagca cgacaaggcc tacgaccagc agctcaaggc cggtgacaac   2520
ccctacctca gtacaaacca cgccgacgcg gagttccagc agcggcttca gggcgacaca   2580
tcgtttgggg gcaacctcgg cagagcagtc ttccaggcca aaagagggt tcttgaacct   2640
cttggtctgg ttgagcaagc gggtgagacg gctcctggaa agaagagacc gttgattgaa   2700
tccccccagc agcccgactc ctccacgggt atcggcaaaa aaggcaagca gccggctaaa   2760
aagaagctcg ttttcgaaga cgaaactgga gcaggcgacg gaccccctga gggatcaact   2820
tccggagcca tgtctgatga cagtgagatg cgtgcagcag ctggcggagc tgcagtcgag   2880
ggcggacaag gtgccgatgg agtgggtaat gcctcgggtg attggcattg cgattccacc   2940
tggtctgagg gccacgtcac gaccaccagc accagaacct gggtcttgcc cacctacaac   3000
aaccacctct acaagcgact cggagagagc ctgcagtcca acacctacaa cggattctcc   3060
accccctggg gatactttga cttcaaccgc ttccactgcc acttctcacc acgtgactgg   3120
cagcgactca tcaacaacaa ctgggggcatg cgacccaaag ccatgcgggt caaaatcttc   3180
aacatccagg tcaaggaggt cacgacgtcg aacggcgaga caacggtggc taataacctt   3240
accagcacgg ttcagatctt tgcggactcg tcgtacgaac tgccgtacgt gatggatgcg   3300
ggtcaagagg gcagcctgcc tccttttccc aacgacgtct ttatggtgcc ccagtacggc   3360
tactgtggac tggtgaccgg caacacttcg cagcaacaga ctgacagaaa tgccttctac   3420
tgcctggagt actttccttc gcagatgctg cggactggca caactttga aattacgtac   3480
agtttgaga aggtgccttt ccactcgatg tacgcgcaca gccagagcct ggaccggctg   3540
```

```
atgaaccctc tcatcgacca gtacctgtgg ggactgcaat cgaccaccac cggaaccacc    3600
ctgaatgccg ggactgccac caccaacttt accaagctgc ggcctaccaa cttttccaac    3660
tttaaaaaga actggctgcc cgggccttca atcaagcagc agggcttctc aaagactgcc    3720
aatcaaaact acaagatccc tgccaccggg tcagacagtc tcatcaaata cgagacgcac    3780
agcactctgg acggaagatg gagtgccctg accccggac  tccaatggc  cacggctgga    3840
cctgcggaca gcaagttcag caacagccag ctcatctttg cggggcctaa acagaacggc    3900
aacacggcca ccgtacccgg gactctgatc ttcacctctg aggaggagct ggcagccacc    3960
aacgccaccg atacggacat gtggggcaac ctacctggcg gtgaccagag caacagcaac    4020
ctgccgaccg tggacagact gacagccttg ggagccgtgc ctggaatggt ctggcaaaac    4080
agagacattt actaccaggg tcccatttgg gccaagattc tcataccga  tggacacttt    4140
cacccctcac cgctgattgg tgggtttggg ctgaaacacc cgcctcctca aattttatc    4200
aagaacaccc cggtacctgc gaatcctgca acgaccttca gctctactcc ggtaaactcc    4260
ttcattactc agtacagcac tggccaggtg tcggtgcaga ttgactggga gatccagaag    4320
gagcggtcca aacgctggaa ccccgaggtc cagtttacct ccaactacgg acagcaaaac    4380
tctctgttgt gggctcccga tgcggctggg aaatacactg agcctaggc  tatcggtacc    4440
cgctacctca cccaccacct gtaataacct gttaatcaat aaaccggttt attcgtttca    4500
gttgaacttt ggtctccgtg tccttcttat cttatctcgt ttccatggct actgcgtaca    4560
taagcagcgg cctgcggcgc ttgcgcttcg cggtttacaa ctgccggtta atcagtaact    4620
tctggcaaac cagatgatgg agttggccac attagctatg cgcgctcgct cactcactcg    4680
gccctggaga ccaaaggtct ccagactgcc ggcctctggc cggcagggcc gagtgagtga    4740
gcgagcgcgc atagagggag tggccaa                                       4767

<210> SEQ ID NO 6
<211> LENGTH: 4642
<212> TYPE: DNA
<213> ORGANISM: Adeno-associated virus 5

<400> SEQUENCE: 6 ctctccccc  tgtcgcgttc gctcgctcgc tggctcgttt ggggggtgg  cagctcaaag     60
agctgccaga cgacggccct ctggccgtcg ccccccaaa  cgagccagcg agcgagcgaa    120
cgcgacaggg gggagagtgc cacactctca agcaagggg  ttttgtaagc agtgatgtca    180
taatgatgta atgcttattg tcacgcgata gttaatgatt aacagtcatg tgatgtgttt    240
atccaatag  gaagaaagcg cgcgtatgag ttctcgcgag acttccgggg tataaaagac    300
cgagtgaacg agcccgccgc cattcttttgc tctggactgc tagaggaccc tcgctgccat    360
ggctaccttc tatgaagtca ttgttcgcgt cccatttgac gtggaggaac atctgcctgg    420
aatttctgac agctttgtgg actgggtaac tggtcaaatt tgggagctgc ctccagagtc    480
agatttaaat ttgactctgg ttgaacagcc tcagttgacg gtggctgata gaattcgccg    540
cgtgttcctg tacgagtgga caaattttc  caagcaggag tccaaattct tgtgcagtt    600
tgaaaaggga tctgaatatt ttcatctgca cacgcttgtg gagacctccg gcatctcttc    660
catggtcctc ggccgctacg tgagtcagat tcgcgcccag ctggtgaaag tggtcttcca    720
gggaattgaa cccgatca   acgactgggt cgccatcacc aaggtaaaga agggcggagc    780
caataaggtg gtggattctg gtatattcc  cgcctacctg ctgccgaagg tccaaccgga    840
gcttcagtgg gcgtggacaa acctggacga gtataaattg gccgccctga atctggagga    900
```

```
gcgcaaacgg ctcgtcgcgc agtttctggc agaatcctcg cagcgctcgc aggaggcggc    960
ttcgcagcgt gagttctcgg ctgacccggt catcaaaagc aagacttccc agaaatacat   1020
ggcgctcgtc aactggctcg tggagcacgg catcacttcc gagaagcagt ggatccagga   1080
aaatcaggag agctacctct ccttcaactc caccggcaac tctcggagcc agatcaaggc   1140
cgcgctcgac aacgcgacca aaattatgag tctgacaaaa agcgcggtgg actacctcgt   1200
ggggagctcc gttcccgagg acatttcaaa aacagaatc tggcaaattt ttgagatgaa   1260
tggctacgac ccggcctacg cgggatccat cctctacggc tggtgtcagc gctccttcaa   1320
caagaggaac accgtctggc tctacggacc cgccacgacc ggcaagacca catcgcgga   1380 ggccatcgcc cacactgtgc ccttttacgg ctgcgtgaac tggaccaatg aaaactttcc   1440
ctttaatgac tgtgtggaca aaatgctcat ttggtgggag gagggaaaga tgaccaacaa   1500
ggtggttgaa tccgccaagg ccatcctggg gggctcaaag gtgcgggtcg atcagaaatg   1560
taaatcctct gttcaaattg attctacccc tgtcattgta acttccaata caaacatgtg   1620
tgtggtggtg gatgggaatt ccacgacctt tgaacaccag cagccgctgg aggaccgcat   1680
gttcaaattt gaactgacta gcggctcccc gccagatttt ggcaagatta ctaagcagga   1740
agtcaaggac ttttttgctt gggcaaaggt caatcaggtg ccggtgactc acgagtttaa   1800
agttcccagg gaattggcgg gaactaaagg ggcggagaaa tctctaaaac gcccactggg   1860
tgacgtcacc aatactagct ataaaagtct ggagaagcgg gccaggctct catttgttcc   1920
cgagacgcct cgcagttcag acgtgactgt tgatcccgct cctctgcgac cgctcaattg   1980
gaattcaagg tatgattgca aatgtgacta tcatgctcaa tttgacaaca tttctaacaa   2040
atgtgatgaa tgtgaatatt tgaatcgggg caaaaatgga tgtatctgtc acaatgtaac   2100
tcactgtcaa atttgtcatg ggattccccc ctgggaaaag gaaaacttgt cagattttgg   2160
ggattttgac gatgccaata agaacagtaa aataaagcga gtagtcatgt cttttgttga   2220
tcaccctcca gattggttgg aagaagttgg tgaaggtctt cgcgagtttt tgggccttga   2280
agcgggccca ccgaaaccaa aacccaatca gcagcatcaa gatcaagccc gtggtcttgt   2340
gctgcctggt tataactatc tcggacccgg aaacggtctc gatcgaggag agcctgtcaa   2400
cagggcagac gaggtcgcgc gagagcacga catctcgtac aacgagcagc ttgaggcggg   2460 agacaaccccc tacctcaagt acaaccacgc ggacgccgag tttcaggaga gctcgccga   2520 cgacacatcc ttcggggaa acctcggaaa ggcagtcttt caggccaaga aagggttct   2580 cgaaccttt ggcctggttg aagagggtgc taagacggcc cctaccggaa agcggataga   2640
cgaccacttt ccaaaaagaa agaaggctcg gaccgaagag gactccaagc cttccaccctc   2700 gtcagacgcc gaagctggac ccagcggatc ccagcagctg caaatcccag cccaaccagc   2760
ctcaagtttg ggagctgata caatgtctgc gggaggtggc ggcccattgg gcgacaataa   2820
ccaaggtgcc gatggagtgg gcaatgcctc gggagattgg cattgcgatt ccacgtggat   2880
gggggacaga gtcgtcacca agtccacccg aacctgggtg ctgcccagct acaacaacca   2940
ccagtaccga gagatcaaaa gcggctccgt cgacggaagc aacgccaacg cctactttgg   3000
atacagcacc ccctgggggt actttgactt taaccgcttc cacagccact ggagcccccg   3060
agactggcaa agactcatca acaactactg gggcttcaga ccccggtccc tcagagtcaa   3120
aatcttcaac attcaagtca agaggtcac ggtgcaggac tccaccacca ccatcgccaa   3180
caacctcacc tccaccgtcc aagtgtttac ggacgacgac taccagctgc cctacgtcgt   3240
```

| | | | | |
|---|---|---|---|---|
| cggcaacggg | accgagggat | gcctgccggc | cttccctccg | caggtctttta cgctgccgca | 3300 |
| gtacggttac | gcgacgctga | accgcgacaa | cacagaaaat | cccaccgaga ggagcagctt | 3360 |
| cttctgccta | gagtactttc | ccagcaagat | gctgagaacg | ggcaacaact ttgagtttac | 3420 |
| ctacaacttt | gaggaggtgc | ccttccactc | cagcttcgct | cccagtcaga acctgttcaa | 3480 |
| gctggccaac | ccgctggtgg | accagtactt | gtaccgcttc | gtgagcacaa ataacactgg | 3540 |
| cggagtccag | ttcaacaaga | acctggccgg | gagatacgcc | aacacctaca aaaactggtt | 3600 |
| cccggggccc | atgggccgaa | cccagggctg | gaacctgggc | tccggggtca accgcgccag | 3660 |
| tgtcagcgcc | ttcgccacga | ccaataggat | ggagctcgag | ggcgcgagtt accaggtgcc | 3720 |
| cccgcagccg | aacggcatga | ccaacaacct | ccagggcagc | aacacctatg ccctggagaa | 3780 |
| cactatgatc | ttcaacagcc | agccggcgaa | cccgggcacc | accgcacgt acctcgaggg | 3840 |
| caacatgctc | atcaccagcg | agagcgagac | gcagccggtg | aaccgcgtgg cgtacaacgt | 3900 |
| cggcgggcag | atggccacca | caaccagag | ctccaccact | gccccgcga ccggcacgta | 3960 |
| caacctccag | gaaatcgtgc | ccggcagcgt | gtggatggag | agggacgtgt acctccaagg | 4020 |
| acccatctgg | gccaagatcc | cagagacggg | ggcgcacttt | caccccctc cggccatggg | 4080 |
| cggattcgga | ctcaaacacc | caccgccat | gatgctcatc | aagaacacgc ctgtgcccgg | 4140 |
| aaatatcacc | agcttctcgg | acgtgcccgt | cagcagcttc | atcacccagt acagcaccgg | 4200 |
| gcaggtcacc | gtggagatgg | agtgggagct | caagaaggaa | aactccaaga ggtggaaccc | 4260 |
| agagatccag | tacacaaaca | actacaacga | cccccagttt | gtggactttg ccccggacag | 4320 |
| caccgggaa | tacagaacca | ccagacctat | cggaacccga | taccttaccc gacccctta | 4380 |
| acccattcat | gtcgcatacc | ctcaataaac | cgtgtattcg | tgtcagtaaa atactgcctc | 4440 |
| ttgtggtcat | tcaatgaata | acagcttaca | acatctacaa | aacctccttg cttgagagtg | 4500 |
| tggcactctc | cccctgtcg | cgttcgctcg | ctcgctggct | cgtttggggg ggtggcagct | 4560 |
| caaagagctg | ccagacgacg | gccctctggc | cgtcgccccc | caaacgagc cagcgagcga | 4620 |
| gcgaacgcga | cagggggag | ag | | | 4642 |

```
<210> SEQ ID NO 7
<211> LENGTH: 4683
<212> TYPE: DNA
<213> ORGANISM: Adeno-associated virus 6

<400> SEQUENCE: 7
```

| | | | | |
|---|---|---|---|---|
| ttggccactc | cctctctgcg | cgctcgctcg | ctcactgagg | ccgggcgacc aaaggtcgcc | 60 |
| cgacgcccgg | gctttgcccg | gcggcctca | gtgagcgagc | gagcgcgcag agagggagtg | 120 |
| gccaactcca | tcactagggg | ttcctggagg | ggtggagtcg | tgacgtgaat tacgtcatag | 180 |
| ggttagggag | gtcctgtatt | agaggtcacg | tgagtgtttt | gcgacatttt gcgacaccat | 240 |
| gtggtcacgc | tgggtattta | agcccgagtg | agcacgcagg | gtctccattt tgaagcggga | 300 |
| ggtttgaacg | cgcagcgcca | tgccggggtt | ttacgagatt | gtgattaagg tccccagcga | 360 |
| ccttgacgag | catctgcccg | gcatttctga | cagctttgtg | aactgggtgg ccgagaagga | 420 |
| atgggagttg | ccgccagatt | ctgacatgga | tctgaatctg | attgagcagg caccctgac | 480 |
| cgtggccgag | aagctgcagc | gcgacttcct | ggtccagtgg | cgccgcgtga gtaaggcccc | 540 |
| ggaggccctc | ttctttgttc | agttcgagaa | gggcgagtcc | tacttccacc tccatattct | 600 |
| ggtggagacc | acggggtca | aatccatggt | gctgggccgc | ttcctgagtc agattaggga | 660 |
| caagctggtg | cagaccatct | accgcgggat | cgagccgacc | ctgcccaact ggttcgcggt | 720 |

```
gaccaagacg cgtaatggcg ccggagggggg gaacaaggtg gtggacgagt gctacatccc    780
caactacctc ctgcccaaga ctcagcccga gctgcagtgg gcgtggacta acatggagga    840
gtatataagc gcgtgtttaa acctggccga gcgcaaacgg ctcgtggcgc acgacctgac    900
ccacgtcagc cagacccagg agcagaacaa ggagaatctg aaccccaatt ctgacgcgcc    960
tgtcatccgg tcaaaaacct ccgcacgcta catggagctg tcgggtggc tggtggaccg    1020 gggcatcacc tccgagaagc agtggatcca ggaggaccag gcctcgtaca tctccttcaa    1080
cgccgcctcc aactcgcggt cccagatcaa ggccgctctg acaatgccg gcaagatcat    1140 ggcgctgacc aaatccgcgc ccgactacct ggtaggcccc gctccgcccg ccgacattaa    1200
aaccaaccgc atttaccgca tcctggagct gaacggctac gaccctgcct acgccggctc    1260
cgtctttctc ggctgggccc agaaaaggtt cggaaaacgc aacaccatct ggctgtttgg    1320
gccggccacc acgggcaaga ccaacatcgc ggaagccatc gcccacgccg tgcccttcta    1380
cggctgcgtc aactgaccca atgagaactt tcccttcaac gattgcgtcg acaagatggt    1440
gatctggtgg gaggagggca agatgacggc caaggtcgtg gagtccgcca aggccattct    1500
cggcggcagc aaggtgcgcg tggaccaaaa gtgcaagtcg tccgcccaga tcgatcccac    1560
ccccgtgatc gtcacctcca acaccaacat gtgcgccgtg attgacggga acagcaccac    1620
cttcgagcac cagcagccgt tgcaggaccg gatgttcaaa tttgaactca cccgccgtct    1680
ggagcatgac tttggcaagg tgacaaagca ggaagtcaaa gagttcttcc gctgggcgca    1740
ggatcacgtg accgaggtgg cgcatgagtt ctacgtcaga aagggtggag ccaacaagag    1800
acccgccccc gatgacgcgg ataaaagcga gcccaagcgg gcctgcccct cagtcgcgga    1860
tccatcgacg tcagacgcgg aaggagctcc ggtggacttt gccgacaggt accaaaaacaa    1920 atgttctcgt cacgcgggca tgcttcagat gctgtttccc tgcaaaacat gcgagagaat    1980
gaatcagaat ttcaacattt gcttcacgca cgggaccaga gactgttcag aatgtttccc    2040
cggcgtgtca gaatctcaac cggtcgtcag aaagaggacg tatcggaaac tctgtgccat    2100
tcatcatctg ctggggcggg ctcccgagat tgcttgctcg gcctgcgatc tggtcaacgt    2160
ggatctggat gactgtgttt ctgagcaata aatgacttaa accaggtatg gctgccgatg    2220
gttatcttcc agattggctc gaggacaacc tctctgaggg cattcgcgag tggtgggact    2280
tgaaacctgg agccccgaaa cccaaagcca accagcaaaa gcaggacgac ggccggggtc    2340
tggtgcttcc tggctacaag tacctcggac ccttcaacgg actcgacaag ggggagcccg    2400
tcaacgcggc ggatgcagcg gccctcgagc acgacaaggc ctacgaccag cagctcaaag    2460
cgggtgacaa tccgtacctg cggtataacc acgccgacgc cgagtttcag gagcgtctgc    2520
aagaagatac gtcttttggg ggcaacctcg gcgagcagt cttccaggcc aagaagaggg    2580
ttctcgaacc ttttggtctg gttgaggaag gtgctaagac ggctcctgga aagaaacgtc    2640
cggtagagca gtcgccacaa gagccagact cctcctcggg cattggcaag acaggccagc    2700
agcccgctaa aaagagactc aattttggtc agactggcga ctcagagtca gtccccgacc    2760
cacaacctct cggagaacct ccagcaaccc ccgctgctgt gggacctact acaatggctt    2820
caggcggtgg cgcaccaatg gcagacaata acgaaggcgc cgacggagtg ggtaatgcct    2880
caggaaattg gcattgcgat tccacatggc tgggcgacag agtcatcacc accagcaccc    2940
gaacatgggc cttgcccacc tataacaacc acctctacaa gcaaatctcc agtgcttcaa    3000 cggggggccag caacgacaac cactacttcg gctacagcac cccctggggg tattttgatt    3060
```

```
tcaacagatt ccactgccat ttctcaccac gtgactggca gcgactcatc aacaacaatt    3120
ggggattccg gcccaagaga ctcaacttca agctcttcaa catccaagtc aaggaggtca    3180
cgacgaatga tggcgtcacg accatcgcta ataaccttac cagcacggtt caagtcttct    3240
cggactcgga gtaccagttg ccgtacgtcc tcggctctgc gcaccagggc tgcctccctc    3300
cgttcccggc ggacgtgttc atgattccgc agtacggcta cctaacgctc aacaatggca    3360
gccaggcagt gggacggtca tccttttact gcctggaata tttcccatcg cagatgctga    3420
gaacgggcaa taactttacc ttcagctaca ccttcgagga cgtgcctttc cacagcagct    3480
acgcgcacag ccagagcctg gaccggctga tgaatcctct catcgaccag tacctgtatt    3540
acctgaacag aactcagaat cagtccggaa gtgcccaaaa caaggacttg ctgtttagcc    3600
gggggtctcc agctggcatg tctgttcagc ccaaaaactg gctacctgga ccctgttacc    3660
ggcagcagcg cgtttctaaa acaaaaacag acaacaacaa cagcaacttt acctggactg    3720
gtgcttcaaa atataacctt aatgggcgtg aatctataat caaccctggc actgctatgg    3780
cctcacacaa agacgacaaa gacaagttct ttcccatgag cggtgtcatg attttttggaa    3840
aggagagcgc cggagcttca aacactgcat tggacaatgt catgatcaca gacgaagagg    3900
aaatcaaagc cactaacccc gtggccaccg aaagatttgg gactgtggca gtcaatctcc    3960
agagcagcag cacagaccct gcgaccggag atgtgcatgt tatgggagcc ttacctggaa    4020
tggtgtggca agacagagac gtatacctgc agggtcctat ttgggccaaa attcctcaca    4080
cggatggaca ctttcacccg tctcctctca tgggcggctt tggacttaag cacccgcctc    4140
ctcagatcct catcaaaaac acgcctgttc ctgcgaatcc tccggcagag ttttcggcta    4200
caaagtttgc ttcattcatc acccagtatt ccacaggaca agtgagcgtg gagattgaat    4260
gggagctgca gaaagaaaac agcaaacgct ggaatcccga agtgcagtat acatctaact    4320
atgcaaaatc tgccaacgtt gatttcactg tggacaacaa tggactttat actgagcctc    4380
gccccattgg cacccgttac ctcacccgtc cctgtaattg tgtgttaat caataaaccg    4440
gttaattcgt gtcagttgaa ctttggtctc atgtcgttat tatcttatct ggtcaccata    4500
gcaaccggtt acacattaac tgcttagttg cgcttcgcga ataccctag tgatggagtt    4560
gcccactccc tctatgcgcg ctcgctcgct cggtggggcc ggcagagcag agctctgccg    4620
tctgcggacc tttggtccgc aggccccacc gagcgagcga gcgcgcatag agggagtggg    4680
caa                                                                   4683

<210> SEQ ID NO 8
<211> LENGTH: 4721
<212> TYPE: DNA
<213> ORGANISM: Adeno-associated virus 7

<400> SEQUENCE: 8
ttggccactc cctctatgcg cgctcgctcg ctcggtgggg cctgcggacc aaaggtccgc      60
agacggcaga gctctgctct gccggcccca ccgagcgagc gagcgcgcat agagggagtg     120
gccaactcca tcactagggg taccgcgaag cgcctcccac gctgccgcgt cagcgctgac     180
gtaaatcacg tcataggga gtggtcctgt attagctgtc acgtgagtgc ttttgcgaca     240
ttttgcgaca ccacgtggcc atttgaggta tatatggccg agtgagcgag caggatctcc     300
attttgaccg cgaaatttga acgagcagca gccatgccgg ttttctacga gatcgtgatc     360
aaggtgccga gcgacctgga cgagcacctg ccgggcattt ctgactcgtt tgtgaactgg     420
gtggccgaga aggaatggga gctgccccg gattctgaca tggatctgaa tctgatcgag     480
```

```
caggcacccc tgaccgtggc cgagaagctg cagcgcgact tcctggtcca atggcgccgc      540
gtgagtaagg ccccggaggc cctgttcttt gttcagttcg agaagggcga gagctacttc      600
caccttcacg ttctggtgga gaccacgggg gtcaagtcca tggtgctagg ccgcttcctg      660
agtcagattc gggagaagct ggtccagacc atctaccgcg gggtcgagcc cacgctgccc      720
aactggttcg cggtgaccaa gacgcgtaat ggcgccggcg gggggaacaa ggtggtggac      780
gagtgctaca tccccaacta cctcctgccc aagacccagc ccgagctgca gtgggcgtgg      840
actaacatgg aggagtatat aagcgcgtgt ttgaacctgg ccgaacgcaa acggctcgtg      900
gcgcagcacc tgacccacgt cagccagacg caggagcaga acaaggagaa tctgaacccc      960
aattctgacg cgcccgtgat caggtcaaaa acctccgcgc gctacatgga gctggtcggg     1020
tggctggtgg accggggcat cacctccgag aagcagtgga tccaggagga ccaggcctcg     1080
tacatctcct tcaacgccgc ctccaactcg cggtcccaga tcaaggccgc gctggacaat     1140
gccggcaaga tcatggcgct gaccaaatcc gcgcccgact acctggtggg gccctcgctg     1200
cccgcggaca ttaaaaccaa ccgcatctac cgcatcctgg agctgaacgg gtacgatcct     1260
gcctacgccg gctccgtctt tctcggctgg gcccagaaaa agttcgggaa gcgcaacacc     1320
atctggctgt ttgggcccgc caccaccggc aagaccaaca ttgcggaagc catcgcccac     1380
gccgtgccct tctacggctg cgtcaactgg accaatgaga ctttcccctt caacgattgc     1440
gtcgacaaga tggtgatctg gtgggaggag ggcaagatga cggccaaggt cgtggagtcc     1500
gccaaggcca ttctcggcgg cagcaaggtg cgcgtggacc aaaagtgcaa gtcgtccgcc     1560
cagatcgacc ccaccccgt gatcgtcacc tccaacacca acatgtgcgc cgtgattgac     1620
gggaacagca ccaccttcga gcaccagcag ccgttgcagg accggatgtt caaatttgaa     1680
ctcacccgcc gtctggagca cgactttggc aaggtgacga agcaggaagt caaagagttc     1740
ttccgctggg ccagtgatca cgtgaccgag gtggcgcatg agttctacgt cagaaagggc     1800
ggagccagca aaagacccgc ccccgatgac gcggatataa gcgagcccaa gcgggcctgc     1860
ccctcagtcg cggatccatc gacgtcagac gcggaaggag ctccggtgga ctttgccgac     1920
aggtaccaaa acaaatgttc tcgtcacgcg ggcatgattc agatgctgtt tccctgcaaa     1980
acgtgcgaga gaatgaatca gaatttcaac atttgcttca cacacggggt cagagactgt     2040
ttagagtgtt tccccggcgt gtcagaatct caaccggtcg tcagaaaaaa gacgtatcgg     2100
aaactctgcg cgattcatca tctgctgggg cgggcgcccg agattgcttg ctcggcctgc     2160
gacctggtca acgtggacct ggacgactgc gtttctgagc aataaatgac ttaaaccagg     2220
tatggctgcc gatggttatc ttccagattg gctcgaggac aacctctctg agggcattcg     2280
cgagtggtgg gacctgaaac ctggagcccc gaaacccaaa gccaaccagc aaaagcagga     2340
caacggccgg ggtctggtgc ttcctggcta caagtacctc ggacccttca acggactcga     2400 caaggggggag cccgtcaacg cggcggacg agcggccctc gagcacgaca aggcctacga     2460
ccagcagctc aaagcgggtg acaatccgta cctgcggtat aaccacgccg acgccgagtt     2520
tcaggagcgt ctgcaagaag atacgtcatt tgggggcaac ctcgggcgag cagtcttcca     2580
ggccaagaag cgggttctcg aacctctcgg tctggttgag gaaggcgcta agacggctcc     2640
tgcaaagaag agaccggtag agccgtcacc tcagcgttcc cccgactcct ccacgggcat     2700
cggcaagaaa ggccagcagc ccgccagaaa gagactcaat ttcggtcaga ctggcgactc     2760
agagtcagtc cccgacccctc aacctctcgg agaacctcca gcagcgccct ctagtgtggg     2820
```

```
atctggtaca gtggctgcag gcggtggcgc accaatggca gacaataacg aaggtgccga      2880
cggagtgggt aatgcctcag gaaattggca ttgcgattcc acatggctgg gcgacagagt      2940
cattaccacc agcacccgaa cctgggccct gcccacctac aacaaccacc tctacaagca      3000
aatctccagt gaaactgcag gtagtaccaa cgacaacacc tacttcggct acagcacccc      3060
ctgggggtat tttgacttta acagattcca ctgccacttc tcaccacgtg actggcagcg      3120
actcatcaac aacaactggg gattccggcc caagaagctg cggttcaagc tcttcaacat      3180
ccaggtcaag gaggtcacga cgaatgacgg cgttacgacc atcgctaata accttaccag      3240
cacgattcag gtattctcgg actcggaata ccagctgccg tacgtcctcg gctctgcgca      3300
ccagggctgc ctgcctccgt tcccggcgga cgtcttcatg attcctcagt acggctacct      3360
gactctcaac aatggcagtc agtctgtggg acgttcctcc ttctactgcc tggagtactt      3420
cccctctcag atgctgagaa cgggcaacaa ctttgagttc agctacagct cgaggacgt      3480
gccttttccac agcagctacg cacacagcca gagcctggac cggctgatga atcccctcat      3540
cgaccagtac ttgtactacc tggccagaac acagagtaac ccaggaggca cagctggcaa      3600
tcgggaactg cagtttttacc agggcgggcc ttcaactatg ccgaacaag ccaagaattg      3660
gttacctgga ccttgcttcc ggcaacaaag agtctccaaa acgctggatc aaaacaacaa      3720
cagcaacttt gcttggactg gtgccaccaa atatcacctg aacggcagaa actcgttggt      3780
taatcccggc gtcgccatgg caactcacaa ggacgacgag gaccgctttt tcccatccag      3840
cggagtcctg attttttggaa aaactggagc aactaacaaa actacattgg aaaatgtgtt      3900
aatgacaaat gaagaagaaa ttcgtcctac taatcctgta gccacggaag aatacgggat      3960
agtcagcagc aacttacaag cggctaatac tgcagcccag acacaagttg tcaacaacca      4020
gggagcctta cctggcatgg tctgcagaa ccgggacgtg tacctgcagg gtcccatctg      4080
ggccaagatt cctcacacgg atggcaactt tcacccgtct cctttgatgg gcggctttgg      4140
acttaaacat ccgcctccatc agatcctgat caagaacact cccgttcccg ctaatcctcc      4200
ggaggtgttt actcctgcca gtttgcttc gttcatcaca cagtacagca ccggacaagt      4260
cagcgtggaa atcgagtggg agctgcagaa ggaaaaacagc aagcgctgga acccggagat      4320
tcagtacacc tccaactttg aaaagcagac tggtgtggac tttgccgttg acagccaggg      4380
tgtttactct gagcctcgcc ctattggcac tcgttacctc acccgtaatc tgtaattgca      4440
tgttaatcaa taaaccggtt gattcgtttc agttgaactt tggtctcctg tgcttcttat      4500
cttatcggtt tccatagcaa ctggttacac attaactgct tgggtgcgct tcacgataag      4560
aacactgacg tcaccgcggt acccctagtg atggagttgg ccactccctc tatgcgcgct      4620
cgctcgctcg gtggggcctg cggaccaaag gtccgcagac ggcagagctc tgctctgccg      4680
gcccaccga gcgagcgagc gcgcatagag ggagtggcca a                          4721
```

<210> SEQ ID NO 9
<211> LENGTH: 4393
<212> TYPE: DNA
<213> ORGANISM: Adeno-associated virus 8

<400> SEQUENCE: 9

```
cagagaggga gtggccaact ccatcactag gggtagcgcg aagcgcctcc cacgctgccg       60
cgtcagcgct gacgtaaatt acgtcatagg ggagtggtcc tgtattagct gtcacgtgag      120
tgcttttgcg gcatttttgcg acaccacgtg gccatttgag gtatatatgg ccgagtgagc      180
gagcaggatc tccatttttga ccgcgaaatt tgaacgagca gcagccatgc cgggcttcta      240
```

```
cgagatcgtg atcaaggtgc cgagcgacct ggacgagcac ctgccgggca tttctgactc    300
gtttgtgaac tgggtggccg agaaggaatg ggagctgccc ccggattctg acatggatcg    360
gaatctgatc gagcaggcac ccctgaccgt ggccgagaag ctgcagcgcg acttcctggt    420
ccaatggcgc cgcgtgagta aggccccgga ggccctcttc tttgttcagt tcgagaaggg    480
cgagagctac tttcacctgc acgttctggt cgagaccacg ggggtcaagt ccatggtgct    540
aggccgcttc ctgagtcaga ttcgggaaaa gcttggtcca gaccatctac ccgcggggtc    600
gagccccacc ttgcccaact ggttcgcggt gaccaaagac gcggtaatgg cgccggcggg    660
ggggaacaag gtggtggacg agtgctacat ccccaactac ctcctgccca agactcagcc    720
cgagctgcag tgggcgtgga ctaacatgga ggagtatata agcgcgtgct gaacctggc    780 cgagcgcaaa cggctcgtgg cgcagcacct gacccacgtc agccagacgc aggagcagaa    840
caaggagaat ctgaaccccca attctgacgc gcccgtgatc aggtcaaaaa cctccgcgcg    900
ctatatggag ctggtcgggt ggctggtgga ccggggcatc acctccgaga agcagtggat    960
ccaggaggac caggcctcgt acatctcctt caacgccgcc tccaactcgc ggtcccagat   1020
caaggccgcg ctggacaatg ccggcaagat catggcgctg accaaatccg cgcccgacta   1080
cctggtgggg ccctcgctgc ccgcggacat tacccagaac cgcatctacc gcatcctcgc   1140
tctcaacggc tacgaccctg cctacgccgg ctccgtcttt ctcggctggg ctcagaaaaa   1200
gttcgggaaa cgcaacacca tctggctgtt tggacccgcc accaccggca agaccaacat   1260
tgcggaagcc atcgcccacg ccgtgcccct ctacggctgc gtcaactgga ccaatgagaa   1320
cttttccttc aatgattgcg tcgacaagat ggtgatctgg tgggaggagg gcaagatgac   1380
ggccaaggtc gtggagtccg ccaaggccat tctcggcggc agcaaggtgc gcgtggacca   1440
aaagtgcaag tcgtccgccc agatcgaccc cacccccgtg atcgtcacct ccaacaccaa   1500
catgtgcgcc gtgattgacg ggaacagcac caccttcgag caccagcagc tctccaggα   1560 ccggatgttt aagttcgaac tcacccgccg tctggagcac gactttggca aggtgacaaa   1620
gcaggaagtc aaagagttct tccgctgggc cagtgatcac gtgaccgagg tggcgcatga   1680
gttttacgtc agaaagggcg gagccagcaa aagacccgcc cccgatgacg cggataaaag   1740
cgagcccaag cgggcctgcc cctcagtcgc ggatccatcg acgtcagacg cggaaggagc   1800
tccggtggac tttgccgaca ggtaccaaaa caaatgttct cgtcacgcgg gcatgcttca   1860
gatgctgttt ccctgcaaaa cgtgcgagag aatgaatcag aatttcaaca tttgcttcac   1920
acacggggtc agagactgct cagagtgttt ccccggcgtg tcagaatctc aaccggtcgt   1980
cagaaagagg acgtatcgga aactctgtgc gattcatcat ctgctggggc gggctcccga   2040
gattgcttgc tcggcctgcg atctggtcaa cgtggacctg gatgactgtg tttctgagca   2100
ataaatgact taaaccaggt atggctgccg atggttatct tccagattgg ctcgaggaca   2160
acctctctga gggcattcgc gagtggtggg cgctgaaacc tggagccccg aagcccaaag   2220
ccaaccagca aaagcaggac gacggccggg gtctggtgct tcctggctac aagtacctcg   2280
gaccctccaa cggactcgac aagggggagc ccgtcaacgc ggcggacgca gcggccctcg   2340
agcacgacaa ggcctacgac cagcagctgc aggcgggtga caatccgtac ctgcggtata   2400
accacgccga cgccgagttt caggagcgtc tgcaagaaga tacgtctttt gggggcaacc   2460
tcgggcgagc agtcttccag gccaagaagc gggttctcga acctctcggt ctggttgagg   2520
aaggcgctaa gacggctcct ggaaagaaga gaccggtaga gccatcaccc cagcgttctc   2580
```

-continued

| | |
|---|---|
| cagactcctc tacgggcatc ggcaagaaag gccaacagcc cgccagaaaa agactcaatt | 2640 |
| ttggtcagac tggcgactca gagtcagttc cagaccctca acctctcgga gaacctccag | 2700 |
| cagcgccctc tggtgtggga cctaatacaa tggctgcagg cggtggcgca ccaatggcag | 2760 |
| acaataacga aggcgccgac ggagtgggta gttcctcggg aaattggcat tgcgattcca | 2820 |
| catggctggg cgacagagtc atcaccacca gcacccgaac ctgggccctg cccacctaca | 2880 |
| acaaccacct ctacaagcaa atctccaacg gacatcggg aggagccacc aacgacaaca | 2940 |
| cctacttcgg ctacagcacc ccctgggggt attttgactt taacagattc cactgccact | 3000 |
| tttcaccacg tgactggcag cgactcatca acaacaactg gggattccgg cccaagagac | 3060 |
| tcagcttcaa gctcttcaac atccaggtca aggaggtcac gcagaatgaa ggcaccaaga | 3120 |
| ccatcgccaa taacctcacc agcaccatcc aggtgtttac ggactcggag taccagctgc | 3180 |
| cgtacgttct cggctctgcc caccagggct gcctgcctcc gttcccggcg acgtgttca | 3240 |
| tgattcccca gtacggctac ctaacactca acaacggtag tcaggccgtg ggacgctcct | 3300 |
| ccttctactg cctggaatac tttccttcgc agatgctgag aaccggcaac aacttccagt | 3360 |
| ttacttacac cttcgaggac gtgccttttc acagcagcta cgcccacagc cagagcttgg | 3420 |
| accggctgat gaatcctctg attgaccagt acctgtacta cttgtctcgg actcaaacaa | 3480 |
| caggaggcac ggcaaatacg cagactctgg gcttcagcca aggtgggcct aatacaatgg | 3540 |
| ccaatcaggc aaagaactgg ctgccaggac cctgttaccg ccaacaacgc gtctcaacga | 3600 |
| caaccgggca aaacaacaat agcaactttg cctggactgc tgggaccaaa taccatctga | 3660 |
| atggaagaaa ttcattggct aatcctggca tcgctatggc aacacacaaa gacgacgagg | 3720 |
| agcgtttttt tcccagtaac gggatcctga ttttgcaa acaaaatgct gccagagaca | 3780 |
| atgcggatta cagcgatgtc atgctcacca gcgaggaaga aatcaaaacc actaaccctg | 3840 |
| tggctacaga ggaatacggt atcgtggcag ataacttgca gcagcaaaac acggctcctc | 3900 |
| aaattggaac tgtcaacagc caggggcct acccggtat ggtctggcag aaccgggacg | 3960 |
| tgtacctgca gggtcccatc tgggccaaga ttcctcacac ggacggcaac ttccacccgt | 4020 |
| ctccgctgat gggcggcttt ggcctgaaac atcctccgcc tcagatcctg atcaagaaca | 4080 |
| cgcctgtacc tgcggatcct ccgaccacct tcaaccagtc aaagctgaac tctttcatca | 4140 |
| cgcaatacag caccggacag gtcagcgtgg aaattgaatg ggagctgcag aaggaaaaca | 4200 |
| gcaagcgctg gaaccccgag atccagtaca cctccaacta ctacaaatct acaagtgtgg | 4260 |
| actttgctgt taatacagaa ggcgtgtact ctgaaccccg ccccattggc accgttacc | 4320 |
| tcaccccgtaa tctgtaattg cctgttaatc aataaaccgg ttgattcgtt tcagttgaac | 4380 |
| tttggtctct gcg | 4393 |

<210> SEQ ID NO 10
<211> LENGTH: 4385
<212> TYPE: DNA
<213> ORGANISM: Adeno-associated virus 9

<400> SEQUENCE: 10

| | |
|---|---|
| cagagaggga gtggccaact ccatcactag gggtaatcgc gaagcgcctc ccacgctgcc | 60 |
| gcgtcagcgc tgacgtagat tacgtcatag gggagtggtc ctgtattagc tgtcacgtga | 120 |
| gtgcttttgc gacattttgc gacaccacat ggccatttga ggtatatatg gccgagtgag | 180 |
| cgagcaggat ctccattttg accgcgaaat ttgaacgagc agcagccatg ccgggcttct | 240 |
| acgagattgt gatcaaggtg ccgagcgacc tggacgagca cctgccgggc atttctgact | 300 |

```
cttttgtgaa ctgggtggcc gagaaggaat gggagctgcc cccgattct gacatggatc    360
ggaatctgat cgagcaggca cccctgaccg tggccgagaa gctgcagcgc gacttcctgg    420
tccaatggcg ccgcgtgagt aaggcccggg aggccctctt ctttgttcag ttcgagaagg    480
gcgagagcta ctttcacctg cacgttctgg tcgagaccac gggggtcaag tccatggtgc    540
taggccgctt cctgagtcag attcgggaga agctggtcca gaccatctac cgcgggatcg    600
agccgaccct gcccaactgg ttcgcggtga ccaagacgcg taatggcgcc ggcgggggga    660
acaaggtggt ggacgagtgc tacatcccca actacctcct gcccaagact cagcccgagc    720
tgcagtgggc gtggactaac atggaggagt atataagcgc gtgcttgaac ctggccgagc    780
gcaaacggct cgtggcgcag cacctgaccc acgtcagcca gacgcaggag cagaacaagg    840
agaatctgaa ccccaattct gacgcgcccg tgatcaggtc aaaaacctcc gcgcgctaca    900
tggagctggt cgggtggctg gtggaccggg gcatcacctc cgagaagcag tggatccagg    960
aggaccaggc ctcgtacatc tccttcaacg ccgcctccaa ctcgcggtcc cagatcaagg   1020
ccgcgctgga caatgccggc aagatcatgg cgctgaccaa atccgcgccc gactacctgg   1080
taggcccttc acttccggtg gacattacgc agaaccgcat ctaccgcatc ctgcagctca   1140
acggctacga ccctgcctac gccggctccg tctttctcgg ctgggcacaa aagaagttcg   1200
ggaaacgcaa caccatctgg ctgtttgggc cggccaccac gggaaagacc aacatcgcag   1260
aagccattgc ccacgccgtg cccttctacg gctgcgtcaa ctggaccaat gagaactttc   1320
ccttcaacga ttgcgtcgac aagatggtga tctggtggga ggagggcaag atgacggcca   1380
aggtcgtgga gtccgccaag gccattctcg gcggcagcaa ggtgcgcgtg gaccaaaagt   1440
gcaagtcgtc cgcccagatc gaccccactc ccgtgatcgt cacctccaac accaacatgt   1500
gcgccgtgat tgacgggaac agcaccacct tcgagcacca gcagcctctc caggaccgga   1560
tgtttaagtt cgaactcacc cgccgtctgg agcacgactt tggcaaggtg acaaagcagg   1620
aagtcaaaga gttcttccgc tgggccagtg atcacgtgac cgaggtggcg catgagtttt   1680
acgtcagaaa gggcggagcc agcaaaagac ccgcccccga tgacgcggat aaaagcgagc   1740
ccaagcgggc ctgcccctca gtcgcggatc catcgacgtc agacgcggaa ggagctccgg   1800
tggactttgc cgacaggtac caaaacaaat gttctcgtca cgcgggcatg cttcagatgc   1860
tgcttccctg caaaacgtgc gagagaatga atcagaattt caacatttgc ttcacacacg   1920
gggtcagaga ctgctcagag tgtttccccg gcgtgtcaga atctcaaccg gtcgtcagaa   1980
agaggacgta tcggaaactc tgtgcgattc atcatctgct ggggcgggct cccgagattg   2040
cttgctcggc ctgcgatctg gtcaacgtgg acctggatga ctgtgtttct gagcaataaa   2100
tgacttaaac caggtatggc tgccgatggt tatcttccag attggctcga ggacaacctc   2160
tctgagggca ttcgcgagtg gtgggcgctg aaacctggag ccccgaagcc aaagccaac    2220
cagcaaaagc aggacgacgg ccgggtctg gtgcttcctg gctacaagta cctcggaccc    2280
ttcaacggac tcgacaaggg ggagcccgtc aacgcggcgg acgcagcggc cctcgagcac    2340
ggcaaggcct acgaccagca gctgcaggcg ggtgacaatc cgtacctgcg gtataaccac    2400
gccgacgccg agtttcagga gcgtctgcaa gaagatacgc ttttgggggg caacctcggg    2460
cgagcagtct tccaggccaa gaagcgggtt ctcgaacctc tcggtctggt tgaggaaggc    2520
gctaagacgc tcctggaaa gaagagaccg gtagagccat caccccagcg ttctccagac    2580
tcctctacgg gcatcggcaa gaaaggccaa cagcccgcca gaaaaagact caattttggt    2640
```

```
cagactggcg actcagagtc agttccagac cctcaacctc tcggagaacc tccagcagcg      2700
ccctctggtg tgggacctaa tacaatggct gcaggcggtg gcgcaccaat ggcagacaat      2760
aacgaaggcg ccgacggagt gggtaattcc tcgggaaatt ggcattgcga ttccacatgg      2820
ctggggacca gagtcatcac caccagcacc cgaacctggg cattgcccac ctacaacaac      2880
cacctctaca agcaaatctc caatggaaca tcgggaggaa gcaccaacga caacacctac      2940
tttggctaca gcaccccctg ggggtatttt gacttcaaca gattccactg ccacttctca      3000
ccacgtgact ggcagcgact catcaacaac aactgggggat ccggccaaa gagactcaac      3060
ttcaagctgt tcaacatcca ggtcaaggag gttacgacga acgaaggcac caagaccatc      3120
gccaataacc ttaccagcac cgtccaggtc tttacggact cggagtacca gctaccgtac      3180
gtcctaggct ctgcccacca aggatgcctg ccaccgtttc ctgcagacgt cttcatggtt      3240
cctcagtacg gctacctgac gctcaacaat ggaagtcaag cgttaggacg ttcttctttc      3300
tactgtctgg aatacttccc ttctcagatg ctgagaaccg gcaacaactt tcagttcagc      3360
tacactttcg aggacgtgcc tttccacagc agctacgcac acagccagag tctagatcga      3420
ctgatgaacc ccctcatcga ccagtaccta tactacctgg tcagaacaca gacaactgga      3480
actggggaa ctcaaacttt ggcattcagc caagcaggcc ctagctcaat ggccaatcag      3540
gctagaaaact gggtacccgg gccttgctac cgtcagcagc gcgtctccac aaccaccaac      3600
caaaataaca cagcaactt tgcgtggacg ggagctgcta aattcaagct gaacgggaga      3660
gactcgctaa tgaatcctgg cgtggctatg gcatcgcaca agacgacga ggaccgcttc      3720
tttccatcaa gtggcgttct catatttggc aagcaaggag ccgggaacga tggagtcgac      3780
tacagccagg tgctgattac agatgaggaa gaaattaaag ccaccaaccc tgtagccaca      3840
gaggaatacg gagcagtggc catcaacaac caggccgcta acacgcaggc gcaaactgga      3900
cttgtgcata accagggagt tattcctggt atggtctggc agaaccggga cgtgtacctg      3960
cagggcccta tttgggctaa aatacctcac acagatggca actttcaccc gtctcctctg      4020
atgggtggat ttggactgaa acaccccacct ccacagattc taattaaaaa tacaccagtg      4080
ccggcagatc ctcctcttac cttcaatcaa gccaagctga actctttcat cacgcagtac      4140
agcacgggac aagtcagcgt ggaaatcgag tgggagctgc agaaagaaaa cagcaagcgc      4200
tggaatccag agatccagta tacttcaaac tactacaaat ctacaaatgt ggactttgct      4260
gtcaatacca aggtgttta ctctgagcct cgccccattg gtactcgtta cctcacccgt      4320
aatttgtaat tgcctgttaa tcaataaacc ggttaattcg tttcagttga actttggtct      4380
ctgcg                                                                4385

<210> SEQ ID NO 11
<211> LENGTH: 4087
<212> TYPE: DNA
<213> ORGANISM: Adeno-associated virus 11

<400> SEQUENCE: 11
atgccgggct ctacgagat cgtgatcaag gtgccgagcg acctggacga gcacctgccg        60
ggcatttctg actcgtttgt gaactggtg gccgagaagg aatgggagct gcccccggat       120
tctgacatgg atcggaatct gatcgagcag gcacccctga ccgtggccga aagctgcag       180
cgcgacttcc tggtccactg gcgccgcgtg agtaaggccc cggaggccct cttctttgtt       240
cagttcgaga agggcgagtc ctacttccac ctccacgttc tcgtcgagac cacggggtc       300
aagtccatgg tcctgggccg cttcctgagt cagatcagag acaggctggt gcagaccatc       360
```

```
taccgcgggg tcgagcccac gctgcccaac tggttcgcgg tgaccaagac gcgaaatggc   420
gccggcgggg ggaacaaggt ggtggacgag tgctacatcc ccaactacct cctgcccaag   480
acccagcccg agctgcagtg ggcgtggact aacatggagg agtatataag cgcgtgtcta   540
aacctcgcgg agcgtaaacg gctcgtggcg cagcacctga cccacgtcag ccagacgcag   600
gagcagaaca aggagaatct gaacccgaat tctgacgcgc ccgtgatcag gtcaaaaacc   660
tccgcgcgct acatggagct ggtcgggtgg ctggtggacc ggggcatcac ctccgagaag   720
cagtggatcc aggaggacca ggcctcgtac atctccttca cgccgcctc caactcgcgg    780 tcccagatca aggccgcgct ggacaatgcc ggaaagatca tggcgctgac caaatccgcg   840
cccgactacc tggtaggccc gtccttaccc gcggacatta aggccaaccg catctaccgc   900
atcctggagc tcaacggcta cgaccccgcc tacgccggct ccgtcttcct gggctgggcg   960
cagaaaaagt tcggtaaacg caacaccatc tggctgtttg ggcccgccac caccggcaag  1020
accaacatcg cggaagccat agcccacgcc gtgcccttct acggctgcgt gaactggacc  1080
aatgagaact ttcccttcaa cgattgcgtc gacaagatgg tgatctggtg ggaggagggc  1140
aagatgaccg ccaaggtcgt ggagtccgcc aaggccattc tgggcggaag caaggtgcgc  1200
gtggaccaaa agtgcaagtc ctcggcccag atcgacccca cgcccgtgat cgtcacctcc  1260
aacaccaaca tgtgcgccgt gatcgacggg aacagcacca ccttcgagca ccagcagccg  1320
ctgcaggacc gcatgttcaa gttcgagctc acccgccgtc tggagcacga ctttggcaag  1380
gtgaccaagc aggaagtcaa agagttcttc cgctgggctc aggatcacgt gactgaggtg  1440
gcgcatgagt tctacgtcag aaagggcgga gccaccaaaa gacccgcccc cagtgacgcg  1500
gatataagcg agcccaagcg ggcctgcccc tcagttccgg agccatcgac gtcagacgcg  1560
gaagcaccgg tggactttgc ggacaggtac caaaacaaat gttctcgtca cgcgggcatg  1620
cttcagatgc tgtttccctg caagacatgc gagagaatga atcagaattt caacgtctgc  1680
ttcacgcacg gggtcagaga ctgctcagag tgcttccccg gcgcgtcaga atctcaaccc  1740
gtcgtcagaa aaaagacgta tcagaaactg tgcgcgattc atcatctgct ggggcgggca  1800
cccgagattg cgtgttcggc ctgcgatctc gtcaacgtgg acttggatga ctgtgtttct  1860
gagcaataaa tgacttaaac caggtatggc tgctgacggt tatcttccag attggctcga  1920
ggacaacctc tctgagggca ttcgcgagtg gtgggacctg aaacctggag ccccgaagcc  1980
caaggccaac cagcagaagc aggacgacgg ccggggtctg gtgcttcctg gctacaagta  2040
cctcggaccc ttcaacggac tcgacaaggg ggagcccgtc aacgcggcgg acgcagcggc  2100
cctcgagcac gacaaggcct acgaccagca gctcaaagcg ggtgacaatc cgtacctgcg  2160
gtataaccac gccgacgccg agtttcagga gcgtctgcaa gaagatacgt cttttggggg  2220
caacctcggg cgagcagtct tccaggccaa gaagagggta ctcgaacctc tgggcctggt  2280
tgaagaaggt gctaaaacgg ctcctggaaa gaagagaccg ttagagtcac acaagagcc   2340 cgactcctcc tcgggcatcg gcaaaaaagg caaacaacca gccagaaaga ggctcaactt  2400
tgaagaggac actggagccg gagacggacc ccctgaagga tcagataccg cgccatgtc   2460 ttcagacatt gaaatgcgtg cagcaccggg cggaaatgct gtcgatgcgg acaaggttc   2520 cgatggagtg ggtaatgcct cgggtgattg gcattgcgat tccacctggt ctgagggcaa  2580
ggtcacaaca acctcgacca gaacctgggt cttgccacc tacaacaacc acttgtacct   2640
gcgtctcgga acaacatcaa gcagcaacac ctacaacgga ttctccaccc cctggggata  2700
```

```
ttttgacttc aacagattcc actgtcactt ctcaccacgt gactggcaaa gactcatcaa   2760
caacaactgg ggactacgac caaaagccat gcgcgttaaa atcttcaata tccaagttaa   2820
ggaggtcaca acgtcgaacg gcgagactac ggtcgctaat aaccttacca gcacggttca   2880
gatatttgcg gactcgtcgt atgagctccc gtacgtgatg gacgctggac aagaggggag   2940
cctgcctcct ttccccaatg acgtgttcat ggtgcctcaa tatggctact gtggcatcgt   3000
gactggcgag aatcagaacc aaacggacag aaacgctttc tactgcctgg agtatttccc   3060
ttcgcaaatg ttgagaactg caacaacttt tgaaatggct acaactttga gaaggtgcc   3120 gttccactca atgtatgctc acagccgag cctggacaga ctgatgaatc ccctcctgga   3180
ccagtacctg tggcacttac agtcgactac ctctggagag actctgaatc aaggcaatgc   3240
agcaaccaca tttggaaaaa tcaggagtgg agactttgcc ttttacagaa agaactggct   3300
gcctgggcct tgtgttaaac agcagagatt ctcaaaaact gccagtcaaa attacaagat   3360
tcctgccagc gggggcaacg ctctgttaaa gtatgacacc cactatacct aaacaaccg   3420 ctggagcaac atcgcgcccg gacctccaat ggccacagcc ggaccttcgg atggggactt   3480
cagtaacgcc cagcttatat tccctggacc atctgttacc ggaaatacaa caacttcagc   3540
caacaatctg ttgtttacat cagaagaaga aattgctgcc accaacccaa gagacacgga   3600
catgtttggc cagattgctg acaataatca gaatgctaca actgctccca taaccggcaa   3660
cgtgactgct atgggagtgc tgcctggcat ggtgtggcaa aacagagaca tttactacca   3720
agggccaatt tgggccaaga tcccacacgc ggacggacat tttcatcctt caccgctgat   3780
tggtgggttt ggactgaaac acccgcctcc ccagatattc atcaagaaca ctcccgtacc   3840
tgccaatcct gcgacaacct tcactgcagc cagagtggac tctttcatca cacaatacag   3900
caccggccag gtcgctgttc agattgaatg ggaaattgaa aaggaacgct ccaaacgctg   3960
gaatcctgaa gtgcagttta cttcaaacta tgggaaccag tcttctatgt tgtgggctcc   4020
tgatacaact gggaagtata cagagccgcg ggttattggc ctctcgttatt tgactaatca   4080 tttgtaa                                                              4087
```

<210> SEQ ID NO 12
<211> LENGTH: 4180
<212> TYPE: DNA
<213> ORGANISM: Adeno-associated virus 13

<400> SEQUENCE: 12

```
ccgcgagtga gcgaaccagg agctccattt tgcccgcgaa ttttgaacga gcagcagcca     60
tgccgggatt ctacgagatt gtcctgaagg tgcccagcga cctggacgag cacctgcctg    120
gcatttctga ctcttttgta aactgggtgg cggagaagga atgggagctg ccgccggatt    180
ctgacatgga tctgaatctg attgagcagg caccccctaac cgtggccgaa aagctgcaac    240
gcgaattcct ggtcgagtgg cgccgcgtga gtaaggcccc ggaggccctc ttctttgttc    300
agttcgagaa gggggacagc tacttccacc tacacattct ggtggagacc gtgggcgtga    360
aatccatggt ggtgggccgc tacgtgagcc agattaaaga gaagctggtg acccgcatct    420
accgcggggt cgagccgcag cttccgaact ggttcgcggt gaccaagacg cgtaatggcg    480
ccggaggcgg gaacaaggtg gtggacgact gctacatccc caactacctg ctccccaaga    540 cccagccga gctccagtgg gcgtggacta atatggacca gtatttaagc gcctgtttga    600
atctcgcgga gcgtaaacgg ctggtggcgc agcatctgac gcacgtgtcg cagacgcagg    660
agcagaacaa agagaaccag aatcccaatt ctgacgcgcc ggtgatcaga tcaaaaacct    720
```

-continued

```
ccgcgaggta catggagctg gtcgggtggc tggtggaccg cgggatcacg tcagaaaagc    780
aatggatcca ggaggaccag gcctcttaca tctccttcaa cgccgcctcc aactcgcggt    840
cacaaatcaa ggccgcactg gacaatgcct ccaaatttat gagcctgaca aaaacggctc    900
cggactacct ggtgggaaac aacccgccgg aggacattac cagcaaccgg atctacaaaa    960
tcctcgagat gaacgggtac gatccgcagt acgcggcctc cgtcttcctg ggctgggcgc   1020
aaaagaagtt cgggaagagg aacaccatct ggctctttgg gccggccacg acgggtaaaa   1080
ccaacatcgc tgaagctatc gcccacgccg tgccttttta cggctgcgtg aactggacca   1140
atgaaactt tccgttcaac gattgcgtcg acaagatggt gatctggtgg gaggagggca   1200
agatgacggc caaggtcgtg gagtccgcca aggccattct gggcggaagc aaggtgcgcg   1260
tggaccaaaa gtgcaagtca tcggcccaga tcgacccaac tcccgtcatc gtcacctcca   1320
acaccaacat gtgcgcggtc atcgacggaa attccaccac cttcgagcac caacaaccac   1380
tccaagaccg gatgttcaag ttcgagctca ccaagcgcct ggagcacgac tttggcaagg   1440
tcaccaagca ggaagtcaag gacttttttcc ggtgggcgtc agatcacgtg actgaggtgt   1500
ctcacgagtt ttacgtcaga aagggtggag ctagaaagag gccgcccccc aatgacgcag   1560
atataagtga gcccaagcgg gcctgtccgt cagttgcgca gccatcgacg tcagacgcgg   1620
aagctccggt ggactacgcg gacaggtacc aaaacaaatg ttctcgtcac gtgggcatga   1680
atctgatgct ttttccctgc cggcaatgcg agagaatgaa tcagaatgtg acatttgct   1740
tcacgcacgg ggtcatggac tgtgccgagt gcttccccgt gtcagaatct caacccgtgt   1800
ctgtcgtcag aaagcggaca tatcagaaac tgtgtccgat tcatcacatc atggggaggg   1860
cgcccgaggt ggcttgttcg gcctgcgatc tggccaatgt ggacttggat gactgtgaca   1920
tggagcaata aatgactcaa accagatatg actgacggtt accttccaga ttggctagag   1980
gacaacctct ctgaaggcgt tcgagagtgg tgggcgctgc aacctggagc ccctaaaccc   2040
aaggcaaatc aacaacatca ggacaacgct cggggtcttg tgcttccggg ttacaaatac   2100
ctcggacccg gcaacggact tgacaagggg gaacccgtca acgcagcgga cgcggcagcc   2160
ctcgaacacg acaaggccta cgaccagcag ctcaaggccg gtgacaaccc ctacctcaag   2220
tacaaccacg ccgacgccga gtttcaggag cgtcttcaag aagatacgtc ttttgggggc   2280
aacctcggac gagcagtctt ccaggccaaa aagaggatcc ttgagcctct gggtctggtt   2340
gaggaagcgg ctaagacggc tcctggaaaa aagagacctg tagagcaatc tccagcagaa   2400
ccggactcct cttcgggcat cggcaaatca ggccagcagc ccgctagaaa agactgaat   2460
tttggtcaga ctggcgacac agagtcagtc ccagaccctc aaccactcgg acaacctccc   2520
gcagcccccct ctggtgtggg atctactaca atggcttcag gcggtggcgc accaatggca   2580
gacaataacg agggtgccga tggagtgggt aattcctcag gaaattggca ttgcgattcc   2640
caatggctgg gcgacagagt catcaccacc agcacccgca cctgggccct gcccacctac   2700
aacaatcacc tctacaagca atctccagc caatcaggag ccaccaacga caaccactac   2760
tttggctaca gcacccctg ggggtatttt gacttcaaca gattccactg ccactttta   2820
ccacgtgact ggcaaagact catcaacaac aactggggat tccgacccaa gagactcaac   2880
ttcaagctct ttaacattca agtcaaagag gtcacgcaga atgacggtac gacgacgatt   2940
gccaataacc ttaccagcac ggttcaggtg tttactgact ccgagtacca gctcccgtac   3000
gtcctcggct cggcgcatca gggatgcctc ccgccgttcc cagcagacgt cttcatggtc   3060
```

-continued

```
ccacagtatg gatacctcac cctgaacaac gggagtcagg cggtaggacg ctcttcctt      3120 tactgcctgg agtactttcc ttctcagatg ctgcgtactg gaaacaactt tcagtttagc      3180 tacactttg aagacgtgcc tttccacagc agctacgctc acagccaaag tctggaccgt       3240
ctcatgaatc ctctgatcga ccagtacctg tactatctga acaggacaca aacagccagt     3300
ggaactcagc agtctcggct actgtttagc caagctggac ccaccagtat gtctcttcaa     3360
gctaaaaact ggctgcctgg accttgctac agacagcagc gtctgtcaaa gcaggcaaac     3420
gacaacaaca acagcaactt tccctggact ggtgccacca atatcatct gaatggccgg      3480 gactcattgg tgaacccggg ccctgctatg ccagtcaca aggatgacaa agaaaagttt      3540
ttccccatgc atggaaccct gatatttggt aaagaaggaa caaatgccaa caacgcggat     3600
ttggaaaatg tcatgattac agatgaagaa gaaatccgca ccaccaatcc cgtggctacg     3660
gagcagtacg ggactgtgtc aaataatttg caaaactcaa acgctggtcc aactactgga     3720
actgtcaatc accaaggagc gttacctggt atggtgtggc aggatcgaga cgtgtacctg     3780
cagggaccca tttgggccaa gattcctcac accgatggac actttcatcc ttctccactg     3840
atgggaggtt ttgggctcaa acacccgcct cctcagatca tgatcaaaaa cactcccgtt     3900
ccagccaatc ctcccacaaa ctttagtgcg gcaaagtttg cttccttcat cacacagtac     3960
tccacggggc aggtcagcgt ggagatcgag tgggagctgc agaaggagaa cagcaaacgc     4020
tggaatcccg aaattcagta cacttccaac tacaacaaat ctgttaatgt ggactttact     4080
gtggacacta atggtgtgta ttcagagcct cgccccattg gcaccagata cctgactcgt     4140
aatctgtaat tgcttgttaa tcaataaacc ggttaattcg                           4180

<210> SEQ ID NO 13
<211> LENGTH: 5594
<212> TYPE: DNA
<213> ORGANISM: Human parvovirus B19

<400> SEQUENCE: 13
ccaaatcaga tgccgccggt cgccgccggt aggcgggact tccggtacaa gatggcggac       60
aattacgtca tttcctgtga cgtcatttcc tgtgacgtca cttccggtgg gcgggacttc      120
cggaattagg gttggctctg ggccagcttg cttggggttg ccttgacact aagacaagcg      180
gcgcgccgct tgtcttagtg gcacgtcaac cccaagcgct ggcccagagc caaccctaat      240
tccggaagtc ccgcccaccg gaagtgacgt cacaggaaat gacgtcacag gaaatgacgt      300
aattgtccgc catcttgtac cggaagtccc gcctaccggc ggcgaccggc ggcatctgat      360
ttggtgtctt cttttaaatt ttagcgggct ttttcccgc cttatgcaaa tgggcagcca      420
ttttaagtgt ttcactataa ttttattggt cagttttgta acggttaaaa tgggcggagc      480
gtaggcgggg actacagtat atatagcacg gcactgccgc agctctttct ttctgggctg     540 cttttcctg gactttcttg ctgttttttg tgagctaact aacaggtatt tatactactt      600
gttaacatac taacatggag ctatttagag gggtgcttca gtttcttct aatgttctgg       660 actgtgctaa cgataactgg tggtgctctt tactggattt agacacttct gactgggaac     720
cactaactca tactaacaga ctaatggcaa tatacttaag cagtgtggct tctaagcttg     780
actttaccgg ggggccacta gcggggtgct tgtacttttt tcaagtagaa tgtaacaaat     840
ttgaagaagg ctatcatatt catgtggtta ttggggggcc agggttaaac cccagaaacc      900
tcacagtgtg tgtagagggg ttattaata atgtacttta tcaccttgta actgaaaatg     960
taaagctaaa attttgcca ggaatgacta caaaaggcaa atactttaga gatggagagc      1020
```

```
agtttataga aaactattta atgaaaaaaa tacctttaaa tgttgtatgg tgtgttacta   1080
atattgatgg atatatagat acctgtattt ctgctacttt tagaagggga gcttgccatg   1140
ccaagaaacc ccgcattacc acagccataa atgacactag tagtgatgct ggggagtcta   1200
gcggcacagg ggcagaggtt gtgccaatta atgggaaggg aactaaggct agcataaagt   1260
ttcaaactat ggtaaactgg ttgtgtgaaa acagagtgtt tacagaggat aagtggaaac   1320
tagttgactt taaccagtac actttactaa gcagtagtca cagtggaagt tttcaaattc   1380
aaagtgcact aaaactagca atttataaag caactaattt agtgcctaca agcacatttc   1440
tattgcatac agactttgag caggttatgt gtattaaaga caataaaatt gttaaattgt   1500
tactttgtca aaactatgac cccctattag tggggcagca tgtgttaaag tggattgata   1560
aaaaatgtgg caagaaaaat acactgtggt tttatgggcc gccaagtaca ggaaaaacaa   1620
acttggcaat ggccattgct aaaagtgttc cagtatatgg catggttaac tggaataatg   1680
aaaactttcc atttaatgat gtagcaggga aaagcttggt ggtctgggat gaaggtatta   1740
ttaagtctac aattgtagaa gctgcaaaag ccattttagg cgggcaaccc accagggtag   1800
atcaaaaaat gcgtggaagt gtagctgtgc ctggagtacc tgtggttata accagcaatg   1860
gtgacattac ttttgttgta agcgggaaca ctacaacaac tgtacatgct aaagccttaa   1920
aagagcgaat ggtaaagtta aactttactg taagatgcag ccctgacatg gggttactaa   1980
cagaggctga tgtacaacag tggcttacat ggtgtaatgc acaaagctgg gaccactatg   2040
aaaactgggc aataaactac actttttgatt tccctggaat taatgcagat gccctccacc   2100
cagacctcca aaccacccca attgtcacag acaccagtat cagcagcagt ggtggtgaaa   2160
gctctgaaga actcagtgaa agcagctttt ttaacctcat cacccaggc gcctggaaca   2220
ctgaaacccc gcgctctagt acgcccatcc ccgggaccag ttcaggagaa tcatttgtcg   2280
gaagctcagt ttcctccgaa gttgtagctg catcgtggga agaagccttc tacacacctt   2340
tggcagacca gtttcgtgaa ctgttagttg gggttgatta tgtgtgggac ggtgtaaggg   2400
gtttacctgt gtgttgtgtg caacatatta acaatagtgg gggaggcttg ggactttgtc   2460
cccattgcat taatgtaggg gcttggtata atggatggaa atttcgagaa tttaccccag   2520
atttggtgcg gtgtagctgc catgtgggag cttctaatcc cttttctgtg ctaacctgca   2580
aaaaatgtgc ttacctgtct ggattgcaaa gctttgtaga ttatgagtaa agaaagtggc   2640
aaatggtggg aaagtgatga taaatttgct aaagctgtgt atcagcaatt tgtggaattt   2700
tatgaaaagg ttactggaac agacttagag cttattcaaa tattaaaaga tcactataat   2760
atttctttag ataatcccct agaaaaccca tcctctctgt ttgacttagt tgctcgtatt   2820
aaaaataacc ttaaaaactc tccagactta tatagtcatc attttcaaag tcatggacag   2880
ttatctgacc accccccatgc cttatcatcc agtagcagtc atgcagaacc tagaggagaa   2940
aatgcagtat tatctagtga agacttacac aagcctgggc aagttagcgt acaactaccc   3000
ggtactaact atgttgggcc tggcaatgag ctacaagctg gccccccgca aagtgctgtt   3060
gacagtgctg caaggattca tgactttagg tatagccaac tggctaagtt gggaataaat   3120
ccatatactc attggactgt agcagatgaa gagcttttaa aaatataaa aaatgaaact   3180
gggtttcaag cacaagtagt aaaagactac tttacttttaa aaggtgcagc tgcccctgtg   3240
gcccatttttc aaggaagttt gccggaagtt cccgcttaca acgcctcaga aaaataccca   3300
agcatgactt cagttaattc tgcagaagcc agcactggtg caggagggg tggcagtaat   3360
```

```
cctgtcaaaa gcatgtggag tgaggggggcc acttttagtg ccaactctgt aacttgtaca    3420
ttttccagac agttttaat  tccttatgac ccagagcacc attataaggt gttttctccc     3480
gcagcaagca gctgccacaa tgccagtgga aaggaggcaa aggtttgcac aattagtccc    3540
ataatgggat actcaacccc atggagatat ttagatttta atgctttaaa tttattttt    3600
tcacctttag agtttcagca cttaattgaa aattatggaa gtatagctcc tgatgcttta    3660
actgtaacca tatcagaaat tgctgttaag gatgttacag acaaaactgg agggggggta    3720
caggttactg acagcactac agggcgccta tccatgttag tagaccatga atacaagtac    3780
ccatatgtgt taggacaagg tcaggatact ttagccccag aacttcctat ttgggtatac    3840
tttccccctc aatatgctta cttaacagta ggagatgtta acacacaagg aatctctgga    3900
gacagcaaaa aattagcaag tgaagaatca gcattttatg ttttggaaca cagttctttt    3960
cagcttttag gtacaggagg tacagcaact atgtcttata agtttcctcc agtgcccca     4020
gaaaatttag agggctgcag tcaacacttt tatgaaatgt acaatccctt atacggatcc    4080
cgcttagggg ttcctgacac attaggaggt gacccaaaat ttagatcttt aacacatgaa    4140
gaccatgcaa ttcagcccca aaacttcatg ccagggccac tagtaaactc agtgtctaca    4200
aaggagggag acagctctaa tactggagct ggaaaagcct taacaggcct tagcacaggc    4260
acctctcaaa acactagaat atccttacgc cctgggccag tgtcacagcc ataccaccac    4320
tgggacacag ataaatatgt tccaggaata aatgccattt ctcatggtca gaccacttat    4380
ggtaacgctg aagacaaaga gtatcagcaa ggagtgggta gatttccaaa tgaaaaagaa    4440
cagctaaaac agttacaggg tttaaacatg cacacctatt tccccaataa aggaacccag    4500
caatatacag atcaaattga gcgccccta  atggtgggtt ctgtatggaa cagaagagcc    4560
cttcactatg aaagccagct gtggagtaaa attccaaatt tagatgacag ttttaaaact    4620
cagtttgcag ccttaggagg atgggggtttg catcagccac ctcctcaaat atttttaaaa    4680
atattaccac aaagtgggcc aattggaggt attaaatcaa tgggaattac taccttagtt    4740
cagtatgccg tgggaattat gacagtaact atgacatta  aattgggggcc ccgtaaagct    4800
acgggacggt ggaatcctca acctggagta tatccccgc  acgcagcagg tcatttacca    4860
tatgtactat atgaccccac agctacagat gcaaacaac  accacaggca tggatacgaa    4920
aagcctgaag aattgtggac agccaaaagc cgtgtgcacc cattgtaaac actccccacc    4980
gtgccctcag ccaggatgcg taactaaacg cccaccagta ccacccagac tgtacctgcc    5040
ccctcctgta cctataagac agcctaacac aaaagatata gacaatgtag aatttaagta    5100
cttaaccaga tatgaacaac atgttattag aatgttaaga ttgtgtaata tgtatcaaaa    5160
tttagaaaaa taaacatttg ttgtggttaa aaaattatgt tgttcgcgtt taaaaattta    5220
aaagaagaca ccaaatcaga tgccgccggt cgccgccggt aggcgggact tccggtacaa    5280
gatgcggac  aattacgtca tttcctgtga cgtcatttcc tgtgacgtca cttccggtgg    5340
gcgggacttc cggaattagg gttggctctg gccagcgct  tgggggttgac gtgccactaa    5400
gacaagcggc gcgccgcttg tcttagtgtc aaggcaaccc caagcaagct ggcccagagc    5460
caacccta at tccggaagtc ccgcccaccg gaagtgacgt cacaggaaat gacgtcacag    5520
gaaatgacgt aattgtccgc catcttgtac cggaagtccc gcctaccggc ggcgaccggc    5580
ggcatctgat ttgg                                                      5594
```

<210> SEQ ID NO 14
<211> LENGTH: 5149

<212> TYPE: DNA
<213> ORGANISM: Minute virus of mice

<400> SEQUENCE: 14

```
atttttagaa ctgaccaacc atgttcacgt aagtgacgtg atgacgcgcg ctgcgcgcgc      60
gccttcggac gtcacacgtc acttacgttt cacatggttg gtcagttcta aaaatgataa     120
gcggttcagg gagtttaaac caaggcgcga aaaggaagtg ggcgtggttt aaagtatata     180
agcaactact gaagtcagtt acttatcttt tctttcattc tgtgagtcga gacgcacaga     240
aagagagtaa ccaactaacc atggctggaa atgcttactc tgatgaagtt ttgggagcaa     300
ccaactggtt aaaggaaaaa agtaaccagg aagtgttctc atttgttttt aaaaatgaaa     360
atgttcaact gaatggaaaa gatatcggat ggaatagtta caaaaaagag ctgcaggagg     420
acgagctgaa atctttacaa cgaggagcgg aaactacttg ggaccaaagc gaggacatgg     480
aatgggaaac cacagtggat gaaatgacca aaaagcaagt attcattttt gattctttgg     540
ttaaaaaatg tttatttgaa gtgcttaaca caaagaatat atttcctggt gatgttaatt     600
ggtttgtgca acatgaatgg ggaaaagacc aaggctggca ctgccatgta ctaattggag     660
gaaaggactt tagtcaagct caagggaaat ggtggagaag gcaactaaat gtttactgga     720
gcagatggtt ggtaacagcc tgtaatgtgc aactaacacc agctgaaaga attaaactaa     780
gagaaatagc agaagacaat gagtgggtta ctctacttac ttataagcat aagcaaacca     840
aaaaagacta taccaagtgt gttctttttg gaaacatgat tgcttactat tttttaacta     900
aaaagaaaat aagcactagt ccaccaagag acggaggcta ttttcttagc agtgactctg     960
gctggaaaac taacttttta aagaaggcg agcgccatct agtgagcaaa ctatacactg    1020
atgacatgcg gccagaaacg gttgaaacca cagtaaccac tgcgcaggaa actaagcgcg    1080
gcagaattca aactaaaaaa gaagtttcta ttaaaactac acttaaagag ctggtgcata    1140
aaagagtaac ctcaccagag gactggatga tgatgcagcc agacagttac attgaaatga    1200
tggctcaacc aggtggagaa aacctgctga aaaatacgct agagatttgt acactaactc    1260
tagccagaac caaaacagca tttgacttaa ttttagaaaa agctgaaacc agcaaactaa    1320
ccaacttttc actgcctgac acaagaacct gcagaatttt tgcttttcat ggctggaact    1380
atgttaaagt ttgccatgct atttgctgtg ttttaaacag acaaggaggc aaaagaaata    1440
ctgttttatt tcatggacca gccagcacag gcaaatctat tattgcacaa gccatagcac    1500
aagcagttgg caatgttggt tgctataatg cagccaatgt aaactttcca tttaatgact    1560
gtaccaacaa gaacttgatt tgggtagaag aagctggtaa ctttggacag caagtaaacc    1620
agtttaaagc catttgctct ggtcaaacta ttcgcattga tcaaaaagga aaaggcagca    1680
aacagattga accaacacca gtcatcatga ccacaaatga aacattaca gtggtcagaa    1740
taggctgcga agaaagacca gaacacactc aaccaatcag agacagaatg cttaacattc    1800
atctaacaca taccttgcct ggtgactttg gtttggttga caaaaatgaa tggcccatga    1860
tttgtgcttg gttggtaaag aatggttacc aatctaccat ggcaagctac tgtgctaaat    1920
ggggcaaagt tcctgattgg tcagaaaact gggcggagcc aaaggtgcca actcctataa    1980
atttactagg ttcggcacgc tcaccattca cgacaccgaa agtacgcct tcagccaga     2040
actatgcact aactccactt gcatcggatc tcgaggacct ggctttagag ccttggagca    2100
caccaaatac tcctgttgcg ggcactgcag aaacccagaa cactgggaa gctggttcca    2160
aagcctgcca agatggtcaa ctgagcccaa cttggtcaga gatcgaggag gatttgagag    2220
```

```
cgtgcttcgg tgcggaaccg ttgaagaaag acttcagcga gccgctgaac ttggactaag    2280
gtacgatggc gcctccagct aaaagagcta aaagaggtaa gggtttaagg gatggttggt    2340
tggtggggta ttaatgttta attacctgtt ttacaggcct gaaatcactt ggttttaggt    2400
tgggtgcctc ctggctacaa gtacctggga ccagggaaca gccttgacca aggagaacca    2460
accaatccat ctgacgccgc tgccaaagag cacgacgagg cctatgatca atacatcaaa    2520
tctggaaaaa atccttacct gtacttctct gctgctgatc aacgctttat tgaccaaacc    2580
aaggacgcca aagactgggg aggcaaggtt ggtcactact ttttagaac caagcgcgct     2640 tttgcaccta agcttgctac tgactctgaa cctggaactt ctggtgtaag cagagctggt    2700
aaacgcacta gaccacctgc ttacattttt attaaccaag ccagagctaa aaaaaaactt    2760
acttcttctg ctgcacagca aagcagtcaa accatgagtg atggcaccag ccaacctgac    2820
agcggaaacg ctgtccactc agctgcaaga gttgaacgag cagctgacgg ccctggaggc    2880 tctggggtg ggggctctgg cggggtgg gttggtgttt ctactgggtc ttatgataat       2940
caaacgcatt atagattctt gggtgacggc tgggtagaaa ttactgcact agcaactaga    3000
ctagtacatt taaacatgcc taaatcagaa aactattgca gaatcagagt tcacaataca    3060
acagacacat cagtcaaagg caacatggca aaagatgatg ctcatgagca aatttggaca    3120
ccatggagct tggtggatgc taatgcttgg ggagtttggc tccagccaag tgactggcaa    3180
tacatttgca acaccatgag ccagcttaac ttggtatcac ttgatcaaga aatattcaat    3240
gtagtgctga aaactgttac agagcaagac ttaggaggtc aagctataaa aatatacaac    3300
aatgacctta cagcttgcat gatggttgca gtagactcaa acaacatttt gccatacaca    3360
cctgcagcaa actcaatgga aacacttggt ttctacccct ggaaaccaac catagcatca    3420
ccatacaggt actattttg cgttgacaga gatctttcag tgacctacga aaatcaagaa    3480
ggcacagttg aacataatgt gatgggaaca ccaaaaggaa tgaattctca atttttacc     3540 attgagaaca cacaacaaat cacattgctc agaacagggg acgaatttgc cacaggtact    3600
tactactttg acacaaattc agttaaactc acacacacgt ggcaaaccaa ccgtcaactt    3660
ggacagcctc cactgctgtc aacctttcct gaagctgaca ctgatgcagg tacacttact    3720
gctcaaggga gcagacatgg aacaacacaa atgggggtta actgggtgag tgaagcaatc    3780
agaaccagac ctgctcaagt aggattttgt caaccacaca atgactttga agccagcaga    3840
gctggaccat ttgctgcccc aaaagttcca gcagatatta ctcaaggagt agacaaagaa    3900
gccaatggca gtgttagata cagttatggc aaacagcatg gtgaaaattg gcttcacat     3960 ggaccagcac cagagcgcta cacatgggat gaaacaagct ttggttcagg tagagacacc    4020
aaagatggtt ttattcaatc agcaccacta gttgttccac caccactaaa tggcattctt    4080
acaaatgcaa accctattgg gactaaaaat gacattcatt tttcaaatgt ttttaacagc    4140
tatggtccac taactgcatt tcacacccca gtcctgtat accctcaagg acaaatatgg     4200
gacaaagaac tagatcttga acacaaacct agacttcaca taactgctcc atttgtttgt    4260
aaaaacaatg cacctggaca aatgttggtt agattaggac caaacctaac tgaccaatat    4320
gatccaaacg gagccacact ttctagaatt gttacatacg gtacatttt ctggaaagga    4380 aaactaacca tgagagcaaa acttagagct aacaccactt ggaacccagt gtaccaagta    4440
agtgctgaag acaatggcaa ctcatacatg agtgtaacta aatggttacc aactgctact    4500
ggaaacatgc agtctgtgcc gcttataaca agacctgttg ctagaaatac ttactaacta    4560
accatgcttt ttctttctgt acttcatata ttattaagac taataaagat acaacataga    4620
```

```
aatataatat tacgtataga tttaagaaat agaataatat ggtacttagt aactgttaaa    4680
aataatagaa cctttggaat aacaagatag ttagttggtt aatgttagat agaataagaa    4740
gatcatgtat aatgaataaa agggtggaag ggtggttggt aggttaatgt tagatagaat    4800
aagaagatca tgtataatga ataaaagggt ggaagggtgg ttggtaggta ttcccttaga    4860
cttgatgtta aggaccaaaa aaataataaa actttttttaa aactcaacca agactactgt    4920
ctattcagtg aaccaactga accattagta ttactatgtt tttagggtgg gagggtggga    4980
gatacatgtg ttcgctatga gcgaactggt actggttggt tgctctgctc aaccaaccag    5040
accggcaaag ccggtctggt tggttgagcg caaccaacca gtaccagttc gctcatagcg    5100
aacacatgta tctcccaccc tcccacccta aaaacatagt aatactaat              5149
```

```
<210> SEQ ID NO 15
<211> LENGTH: 5106
<212> TYPE: DNA
<213> ORGANISM: Goose parvovirus

<400> SEQUENCE: 15
```

```
ctcattggag ggttcgttcg ttcgaaccag ccaatcaggg gaggggaag tgacgcaagt       60 tccggtcaca tgcttccggt gacgcacatc cggtgacgta gttccggtca cgtgcttcct    120
gtcacgtgtt tccggtcacg tgacttccgg tcatgtgact tccggtgacg tgtttccggc    180
tgttaggttg accacgcgca tgccgcgcgg tcagcccaat agttaagccg gaaacacgtc    240
accggaagtc acatgaccgg aagtcacgtg accggaaaca cgtgacagga agcacgtgac    300
cggaactacg tcaccggatg tgcgtcaccg gaagcatgtg accggaactt gcgtcacttc    360
cccctcccct gattggctgg ttcgaacgaa cgaaccctcc aatgagactc aaggacaaga    420
ggatattttg cgcgccagga agtgacgtgc aatgccaccc tatataagcc aggaaacttc    480
cggtttagtt cattcgttac tctgctctca gagagaacgg acctcaggtc ggagagatgg    540
cactttctag gcctcttcag atttcttctg ataaattcta tgaagttatt attagattat    600
catcggatat tgatcaagat gtccccggtc tgtctcttaa cttttgtagaa tggctttcta    660 ccggagtttg ggagcccacg ggcatctgga acatggagca tgtgaatcta ccgatggtga    720
ccttggcaga aagatcaag aacatttttca tacaaagatg gaatcagttc aaccaggacg    780
aaacggactt cttctttcaa ctggaagaag gcagtagta cattcatctt cattgctgta    840
ttgcccaggg caatgtacgg tcttttgttc tcgggagata tatgtctcag ataaaagact    900
ctatcataag agatgtatat gaagggaaac aaatcaagat ccccgattgg tttgctatta    960
ctaaaaccaa gaggggagga cagaataaga ccgtgactgc agcatacata ctgcattacc   1020
ttattcctaa aaagcaacct gaactgcaat gggcctttac caatatgcct ttattcactg   1080
ctgctgctct ttgtctgcaa aagcggcaag aattgctgga tgcatttcaa gaaagtgatt   1140
tggctgcccc tttacctgat cctcaagcat caactgtggc accgcttatt ccaacagag    1200 cggcaaagaa ctatagcaac cttgttgatt ggctcattga aatggggata acatctgaga   1260
agcaatggct cactgagaac cgagagagct acagaagctt tcaagcaact tcttcaaata   1320
atagacaagt gaaagctgca ctggaaaatg cccgtgctga aatgttattg acaaagactg   1380
caactgatta cctgatagga aaagaccctg tcctggatat aactaagaat agggtctatc   1440
aaattctgaa aatgaataac tacaaccctc aatacatagg aagtatcctg tgcggctggg   1500
tgaagagaga gttcaacaaa agaaacgcca tatggctcta cggacctgcc accaccggga   1560
```

```
agaccaacat tgcagaagct attgcccatg ctgtacccct ctatggctgt gttaactgga    1620
ctaatgagaa ctttcctttt aatgattgtg ttgataaaat gctgatttgg tgggaggagg    1680
gaaaaatgac taataaggtt gttgaatctg caaaagcaat tttgggaggg tctgctgtcc    1740
gggtagacca gaaatgtaaa ggatctgttt gtattgaacc tactcctgta attattacta    1800
gtaatactga tatgtgtatg attgttgatg gcaactctac tacaatggaa catagaatac    1860
cattagagga gcgtatgttt caaattgtcc tatcacataa attggagcct tcttttggaa    1920
aaatttctaa aaagaagtc agagaatttt tcaaatgggc caatgacaat ctagttcctg    1980
ttgtgtctga gttcaaagtc cgaactaatg aacaaaccaa cttgccagag cccgttcctg    2040
aacgagcgaa cgagccggag gagcctccta agatctgggc tcctcctact agggaggagt    2100
tagaagagct tttaagagcc agcccagaat tgttctcatc agtcgctcca attcctgtga    2160
ctcctcagaa ctcccctgag cctaagagaa gcaggaacaa ttaccaggta cgctgcgctt    2220
tgcatactta tgacaattct atggatgtat ttgaatgtat ggaatgtgag aaagcaaact    2280
ttcctgaatt tcaacctctg ggagaaaatt attgtgatga catgggtgg tatgattgtg    2340 ctatatgtaa agagttgaaa aatgaacttg cagaaattga gcatgtgttt gagcttgatg    2400
atgctgaaaa tgaacaataa agatgactca agcagatat gtctactttt ttagattctt    2460
ttgaagagtg gtatgagact gcagccgcct cgtggcggaa tctgaaagct ggagcccctc    2520
agccaaaacc aaaccagcag tctcagtctg tgtctccaga cagagaaccc gaacgaaaag    2580
ataataatcg gggctttgta cttcctggct ataagtatct tgggcctggt aacggcctgg    2640
ataaaggccc acctgtcaat aaggcggaca gcgtcgcgct tgaacacgac aaggcctatg    2700
accagcagct taaagcggga gacaacccat atataaaatt caatcacgct gaccaggact    2760
ttatagatag cctccaagac gaccagtcat tcggaggtaa tcttggaaag gctgtatttc    2820
aggccaaaaa acgtatctta gagccatttg gcctagtaga agatcctgtc aacacggcac    2880
ctgcaaaaaa aaatacaggg aagcttactg accattaccc ggtagttaag aagcctaaac    2940
ttaccgagga agtcagtgcg ggaggtggta gcagtgccgt acaagacgga ggagccaccg    3000
cggagggcac cgaacctgtg gcagcatctg aaatggcaga gggaggaggc ggagctatgg    3060
gcgactcttc aggggtgcc gatggagtgg gtaatgcctc gggaaattgg cattgcgatt    3120
cccaatggat gggaaacaca gtcatcacaa agaccaccag aacctgggtc ctgccaagct    3180
acaacaacca catctacaaa gcaattacca gcggaacctc tcaagatgca aatgtccagt    3240
atgcaggata cagtaccccc tgggggtact ttgatttcaa ccgcttccac tgccacttct    3300
cccctagaga ctggcagaga cttatcaaca accattgggg aatcagaccc aagtctctta    3360
aattcaagat cttcaatgtc caagtcaaag aagtcacaac gcaggatcag acaaagacca    3420
ttgcaaacaa tctcacctca acaattcaag tctttacgga tgatgagcat caactcccgt    3480
atgtcctggg ctcggctacg gaaggcacca tgccgccgtt cccgtcggat gtctatgccc    3540
tgccgcagta cgggtactgc acaatgcaca ccaaccagaa tggagcacgg ttcaatgacc    3600
gtagtgcatt ctactgctta gagtacttcc ctagtcagat gctaagaaca ggcaacaact    3660
ttgagttcac atttgacttt gaagaagttc ctttccatag catgttcgct cattcacagg    3720
acttagacag gctgatgaac cccctagtgg atcaatacct ctggaatttc aatgaggtag    3780
acagcagcag aaatgctcaa tttaaaaagg ctgtgaaagg ggcttatggc accatgggcc    3840
gcaattggct gccaggacct aaattcctgg atcaaagagt tagggcctac acaggaggaa    3900
cagacaacta tgcaaactgg aacatctgga gtaatgggaa caaggtgaat ttgaaagaca    3960
```

```
gacagtatct cctacaaccc ggacctgtgt cagctactta cacagaaggg gaggcttcca    4020
gccttccagc tcaaaatatt ttagggatag ctaaagatcc atacagatca ggcagcacta    4080
cagcaggaat aagtgacatt atggtcacgg aagaacaaga agtagcacct acaaatggag    4140
tagggtggaa accatatggt aggactgtaa cgaatgaaca aaacactact acagctccta    4200
caagttcaga tctggatgtt cttggagctt taccaggaat ggtttggcag aacagggata    4260
tatatctgca gggaccctatt ggggcaaaaa taccgaagac tgatggtaaa ttccatcctt    4320
ctccgaatct cggaggattt ggcctgcaca atccaccacc gcaggtgttc atcaagaata    4380
caccagtgcc tgcagaccct ccagtagaat acgtgcacca gaagtggaat tcctacataa    4440
cccagtactc tacgggccag tgtacagtag agatggtgtg ggagctgaga aaagagaatt    4500
caaagagatg gaacccagaa atccagttca ccagtaattt cagtaacaga caagcataa    4560 tgtttgcacc taatgaaact ggtggatatg tagaagatag attgattgga accagatatc    4620
taactcaaaa tctgtaaatt ctgtgtaaaa attcaaataa agcacttcct ggcgcgcaaa    4680
atatcctctt gtccttgagt ctcattggag ggttcgttcg ttcgaaccag ccaatcaggg    4740
gagggggaag tgacgcaagt tccggtcaca tgcttccggt gacgcacatc cggtgacgta    4800
gttccggtca cgtgcttcct gtcacgtgtt tccggtcacg tgacttccgg tcatgtgact    4860
tccggtgacg tgtttccggc ttaactattg ggctgaccgc gcgcatgcgc gtggtcaacc    4920
taacagccgg aaacacgtca ccggaagtca catgaccgga agtcacgtga ccggaaacac    4980
gtgacaggaa gcacgtgacc ggaactacgt caccggatgt gcgtcaccgg aagcatgtga    5040
ccggaacttg cgtcacttcc ccctcccctg attggctggt tcgaacgaac gaaccctcca    5100
atgaga                                                              5106

<210> SEQ ID NO 16
<211> LENGTH: 4432
<212> TYPE: DNA
<213> ORGANISM: Snake parvovirus 1

<400> SEQUENCE: 16
cgccccaccc ctagtgatcg cgcgcgctct ctcttggggc ctgacggccg aaggccgtca      60
gctgccgagc ttcgctcggc aggccccaag agagagcgcg cgcgatcact aggggtgggg     120
cgagtgccct gctcaacggg ttttttggtg ggcggagcaa tgacgtcagc ggacatgtct     180
ggacatgtct ttgagcaagt ccatataagg agttccgccg gatatgcaaa tgagcaatcg     240
cgcaaagcat tttgggtagt caccatgaat aaaaaggaca gcaagaaaga tgacgcccca     300 taatttttaat aggaattta accatggcgt tttacgaggt tgtgtttcgt ttgccaagag     360
acaataacaa cttgttggat gaagatagat atcagccaga gttgaaagaa gagatgact     420 ggcctgagga atatttaacc agtgaagatg ccagctttat cggactagcg tatgctgtgc     480
taagtgaaat tcgagagatc tttggaaagg aactacaatg gtttgcccag gttgaatggt     540
gtcctactgc tggttaccac atgcatgttt tgttgaacca tcctaagctg agtaaccaga     600
cttatggaag aaaggtcaat gaactggctt gccgtatagt cgataccttt ggcctaatta     660
atccagaaga agtcatcagt acccattatg ttaaaagcaa ctatggacat aaaaaggtga     720
gagtcattca cctagagtct tatttgaaga actactttt cagaaagact ttagctcctc     780
ccaattatac cgaggaagga gactataaaa gagaggaaga agtcgtgctg tgggcattta     840
cgaatatcgt cgcttggaag ccattcgtgc ggaatctcat caagagatcg gagctagcga     900
```

```
ctgttcctaa gcaaccagag aatccggcgg gagacggacc ggcacctcga gtgactgcag   960
gaacccgcca ttttatggaa accatcgact ggttggtgaa acatggaatt actacagaac  1020
gagaattctg ccacgccaac cgccctttgt acctgtctat gctggcttct acttcgggtg  1080
ctgggcagat taaaagagcg ctggaccagg cgaaacacat gatgaccagc accatgtcag  1140
cagaggatta cctgacaaca aagaggatg tgatcgaacc acctactgaa aatagaatct   1200
acaagattat gaaactgaat cgctatgatc cagaactagc agctgctctc ttctacggct  1260
ggacctgcaa gaactttggc aagagaaaca ccatctggct gtatggtcca gctactaccg  1320
gcaaaaccat catcgctcaa gctattgcac atgctgttaa actgtttgct ggtgttaatt  1380
ggactaatga aaactttccc ttctgtaact gtccagggaa actgcttatc tggtgggagg  1440
agggcaagat gacaaacaaa atggtggaga cggctaaatg tatactgggg ggatctgctg  1500
tacctgtaga catcaaaggc aaacccgctg aaatgtgtcc tcaaacaccc tgtattatta  1560
ctagcaatac taacatgtgt caagtatatg atggtaatag ttctagcttt gagcaccaag  1620 aaccccctaga ggaacgcatg tttatgttca gacttaatac taaactgcca tcgacctttg  1680
gcaagatcac agaagaggaa gtcaaacagt ttattacctg ggggaggagc ttaaaggttc  1740
aagttccaca tcagttcaga gtgcctacca caggagagta taaaaggcca gcccccgagg  1800
cgaaagctca ttcttcggat gagccgccaa agagaaggt cgcgcgtatt gatgactctc   1860
taaccaggta tgttaacaat attgatgagt cagctaccag tagagaaatg tttctagaga  1920
ttgctaatac taatcaatgt atgttgcatc attgcttttc ttgtaccgaa tgttatcctg  1980
aattgcttga tgacatggac aaggaacaat aaacttactg ataacagata tggattttct  2040
cgatgatttc tttgcagata aatataaaga gactgttaac gaactcggta accggtcaa   2100 tcctaaacct gtaaaacaca ttagcgaagc tcactcgcaa cctggcagca ggaggggctt  2160
tgtggtgcct gggtatcggt atcttgggcc tggtaatagc ttggaccgtg aaagcccgt   2220 taacaaagca gacgaggctg ctaaaaagca cgatcaagaa tacgatcaac agcttaaagc  2280
gggagacaat ccctacataa aatataatca cgcggacgaa cagttccaga agacctaca   2340 aggtgatacc agtctagccg gcaacgcggc taacgctcta tttcaaggca aaaagactct  2400
actagcgccc cttggcctag tagagacccc tgtcggcaaa acgtctgaaa agcacaaatt  2460
agacgaatac tatcctaaag ctaaaaaggc caaacaaggc ttgcagatac cagctccacc  2520
taaaggcgga gaagaagaag ctacatcgtc acaatctgga gggagcccag caggttccga  2580
tactagcggc acatctgtca tggctacagg aggaggcgt ccgatggcag acgataacca   2640
gggcgccgag ggagtgggta attcctcagg tgattggcat tgcgatacca agtggatggg  2700
agaccacgtc attacaaagt caaccagaac ttgggtgctc cccacttacg ggaatcatct  2760
ctacgggcct atcaactttg acggcaccac aggttcgggt gctaatgcag cctatgcagg  2820
atacaagact ccctggggt actttgactt caatcgattc cattgccact tctccccccg   2880
agactggcaa agactcatca caaccacac aggcatcagg ccgaaaggac tcaaaatcaa   2940
agtctttaac gtccaagtca agaagttac aacacaagat tcaacgaaaa caattgccaa   3000
caatctcacc agcaccgtac agatctttgc ggacgagaac tacgacttac catatgtatt  3060
aggcagtgct acacaaggca catttcctcc atttcccaat gatgtatta tgttaccaca   3120 atatgcttat tgtacacttc aaggaaattc ggggaaattt gtagatagaa gtgccttta   3180 ttgtttagaa tattttcctt cacaaatgct gagaacagga aacaattttg agttccagtt  3240
taaatttgaa gaagttccct ttcattctgg atgggcacag agtcaaagcc tagacagatt  3300
```

-continued

```
gatgaatccg ttgcttgatc aatatctgat aggagactat ggaacagatg catcaggaaa      3360
ccttatttat cacagagctg gtccaaatga tttgaatgaa ttctacaaga attgggcacc      3420
tgcaccctat gaatgtatcc agaatattaa cagcagtgat aataccaaga atgctaattc      3480
tataaatggt tcaaattcta ccaacaaatg gggactacaa ggaagacaag catgggatgc      3540
tccaggattt gttcaagcta gtacctatga aggtgcagca gcaggacaat ctcttcttaa      3600
tggcgtactt actttcgata aaagttcagc tactacttca tctccagctg ctactgcagt      3660
aaacagaaca attgaagacg aaatacaggg taccaataat tttggtaatg ctagaaataa      3720
cattgttgct atcaatcaac aaacgaaagg aacaaatcca acaacaggta gtacatctca      3780
atttgagaca atgccaggta tggtgtggtc taatagagac atttacttac aggggcctat      3840
ttgggctaaa attccaaata cagatggaca ttttcatcct tctcccagaa tgggtggttt      3900
tggattaaaa catcctccgc ctatgattct gatcaaaaat acaccagttc ctgctgatcc      3960
tccaactacc ttcaatccaa tgccacagac tagtttcatt actgaataca gtacaggaca      4020
agtaactgtt gaaatgttgt gggaggtaca gaaagaatcc tccaaaagat ggaatccaga      4080
agtacagttt acttccaatt ttggaacttc agatccagct gttgatggaa taccgtttgg      4140
aattaataat ttgggtactt atgttgaatc tagaccatat ggaactcgtt atatttctaa      4200
acacttgtaa ataataaaaa ttgtcaaatt tgcactaaga attgttgtca cgtggttgtt      4260
tacatgcttg ctaaaacacg cccaccaaaa aacccgttga gcagggcact cgccccaccc      4320
ctagtgatcg cgcgcgctct ctcttggggc ctgccgagcg aagctcggca gctgacggcc      4380
ttcggccgtc aggccccaag agagagcgcg cgcgatcact aggggtgggg cg              4432
```

<210> SEQ ID NO 17
<211> LENGTH: 165
<212> TYPE: DNA
<213> ORGANISM: Artificial
<220> FEATURE:
<223> OTHER INFORMATION: Chimeric ITR sequence

<400> SEQUENCE: 17

```
aggaacccct agtgatggag ttggccactc cctctctgcg cgctcgctcg ctcactgagg       60
gcgggcgacc aaaggtcgcc cgagcccggc cctttgggcc gggccccctca gtgagcgagc     120 gagcgcgcag agagggagtg gccaactcca tcactagggg ttcct                      165
```

<210> SEQ ID NO 18
<211> LENGTH: 198
<212> TYPE: DNA
<213> ORGANISM: Artificial
<220> FEATURE:
<223> OTHER INFORMATION: Chimeric ITR sequence

<400> SEQUENCE: 18

```
tacaaaacct ccttgcttga gagtgtggca ctctcccccc tgtcgcgttc gctcgctcgc       60
tggctcgttt ggggggggcga cggcccaaag ggccgtcgtc tggcagctct ttgagctgcc     120 accccccccaa acgagccagc gagcgagcga acgcgacagg ggggagagtg ccacactctc     180
aagcaaggag gttttgta                                                    198
```

<210> SEQ ID NO 19
<211> LENGTH: 189
<212> TYPE: DNA
<213> ORGANISM: Artificial
<220> FEATURE:

<223> OTHER INFORMATION: Chimeric ITR sequence

<400> SEQUENCE: 19

```
aggaacccct agtgatggag ttggccactc cctcccccct gtcgcgttcg cgcgctcgct    60
cgctcactga gggcgggcga ccaaaggtcg cccgagcccg gcccttt ggg ccgggcccct   120
cagtgagcga gcgagcgcgc gaacgcgaca gggggaggg agtggccaac tccatcacta   180
ggggttcct                                                            189
```

<210> SEQ ID NO 20
<211> LENGTH: 190
<212> TYPE: DNA
<213> ORGANISM: Artificial
<220> FEATURE:
<223> OTHER INFORMATION: Chimeric ITR sequence

<400> SEQUENCE: 20

```
tacaaaacct ccttgcttga gagtgtggca ctctccccc tgtcgcgttc gcgcgctcgc    60
tcgctcactg agggcgggcg accaaaggtc gcccgagccc ggccctttgg gccgggcccc   120
tcagtgagcg agcgagcgcg cgaacgcgac aggggggaga gtgccacact ctcaagcaag   180
gaggttttgt                                                           190
```

<210> SEQ ID NO 21
<211> LENGTH: 196
<212> TYPE: DNA
<213> ORGANISM: Artificial
<220> FEATURE:
<223> OTHER INFORMATION: Chimeric ITR sequence

<400> SEQUENCE: 21

```
aggaacccct agtgatggag ttggccactc cctcccccct gtcgcgttcg ctcgctcgct    60
ggctcgtttg ggggggcgac ggcccaaagg gccgtcgtct ggcagctctt tgagctgcca   120
ccccccaaa cgagccagcg agcgagcgaa cgcgacaggg gggagggagt ggccaactcc   180
atcactaggg gttcct                                                   196
```

<210> SEQ ID NO 22
<211> LENGTH: 170
<212> TYPE: DNA
<213> ORGANISM: Artificial
<220> FEATURE:
<223> OTHER INFORMATION: Chimeric ITR sequence

<400> SEQUENCE: 22

```
tacaaaacct ccttgcttga gagtgtggca ctctctctgc gcgctcgctc gctcactgag    60
ggcgggcgac caaaggtcgc ccgacgcccg gcccttt ggg ccgggcggcc ctcagtgagc   120
gagcgagcgc gcagagagag tgccacactc tcaagcaagg aggttttgta               170
```

<210> SEQ ID NO 23
<211> LENGTH: 164
<212> TYPE: DNA
<213> ORGANISM: Artificial
<220> FEATURE:
<223> OTHER INFORMATION: Chimeric ITR sequence

<400> SEQUENCE: 23

```
aggaacccct agtgatggag tggccctccc tctctgcgcg ctcgctcgct cactgagggc    60
gggcgaccaa aggtcgcccg acgccgggcc ctttgggccg gcggccctc agtgagcgag   120
cgagcgcgca gagggagg gccactccat cactaggggt tcct                      164
```

<210> SEQ ID NO 24
<211> LENGTH: 202
<212> TYPE: DNA
<213> ORGANISM: Artificial
<220> FEATURE:
<223> OTHER INFORMATION: Chimeric ITR sequence

<400> SEQUENCE: 24

```
tacaaaacct ccttgcttga gagtgttgga cactctcccc cctgtcgcgt tcgctcgctc      60
gctggctcgt ttggggggc gacggcccaa agggccgtcg tctggcagct ctttgagctg     120
ccaccccccc aaacgagcca gcgagcgagc gaacgcgaca gggggagag tgtccaacac     180 tctcaagcaa ggaggttttg ta                                             202
```

<210> SEQ ID NO 25
<211> LENGTH: 161
<212> TYPE: DNA
<213> ORGANISM: Artificial
<220> FEATURE:
<223> OTHER INFORMATION: Chimeric ITR sequence

<400> SEQUENCE: 25

```
aggaacccct agtatggagt tggccactcc attctgcgcg ctcgctcgct cactgagggc      60
gggcgaccaa aggtcgcccg agcccggccc tttgggccgg gcccctcagt gagcgagcga     120
gcgcgcagaa tggagtggcc aactccatac taggggttcc t                        161
```

<210> SEQ ID NO 26
<211> LENGTH: 202
<212> TYPE: DNA
<213> ORGANISM: Artificial
<220> FEATURE:
<223> OTHER INFORMATION: Chimeric ITR sequence

<400> SEQUENCE: 26

```
tacaaaacct ccttgcttgg agagtgtggc actctcccc cctgtcgcgt tcgctcgctc       60
gctggctcgt ttggggggc gacggcccaa agggccgtcg tctggcagct ctttgagctg     120
ccaccccccc aaacgagcca gcgagcgagc gaacgcgaca gggggggaga gtgccacact    180
ctccaagcaa ggaggttttg ta                                             202
```

<210> SEQ ID NO 27
<211> LENGTH: 155
<212> TYPE: DNA
<213> ORGANISM: Artificial
<220> FEATURE:
<223> OTHER INFORMATION: Chimeric ITR sequence

<400> SEQUENCE: 27

```
aggaacccct agtgctggag ttggccactc ccgcgcgctc gctcgctcac tgagggcggg      60
cgaccaaagg tcgcccgagc ccggcccttt gggccgggcc cctcagtgag cgagcgagcg     120
cgcgggagtg gccaactcca gcactagggg ttcct                                155
```

<210> SEQ ID NO 28
<211> LENGTH: 153
<212> TYPE: DNA
<213> ORGANISM: Artificial
<220> FEATURE:
<223> OTHER INFORMATION: Chimeric ITR sequence

<400> SEQUENCE: 28

```
aggaacccct agtggagttg ccactcctc tgcgcgctcg ctcgctcact gagggcgggc    60
gaccaaaggt cgcccgagcc cggcccttg ggccgggccc ctcagtgagc gagcgagcgc   120
gcagaggagt ggccaactcc actagggtt cct                                153
```

<210> SEQ ID NO 29
<211> LENGTH: 182
<212> TYPE: DNA
<213> ORGANISM: Artificial
<220> FEATURE:
<223> OTHER INFORMATION: Chimeric ITR sequence

<400> SEQUENCE: 29

```
aggaacccct agtgatggag ttggccactc cctccacgcg ttctgcgcgc tcgctcgctc    60
actgagggcg gcgaccaaa ggtcgcccga cgcccggccc tttgggccgg gcggccctca   120
gtgagcgagc gagcgcgcag aacgcgtgga gggagtggcc aactccatca ctaggggttc   180
ct                                                                 182
```

<210> SEQ ID NO 30
<211> LENGTH: 161
<212> TYPE: DNA
<213> ORGANISM: Artificial
<220> FEATURE:
<223> OTHER INFORMATION: Chimeric ITR sequence

<400> SEQUENCE: 30

```
aggaacccct agtggatgga gttggccact ccctcctctg cgcgctcgct cgctcactga    60
gggcgggcga ccaaaggtcg cccgagcccg gcccttggg ccgggcccct cagtgagcga   120
gcgagcgcgc agaggagtgg ccaactccac tagggggttcc t                      161
```

<210> SEQ ID NO 31
<211> LENGTH: 182
<212> TYPE: DNA
<213> ORGANISM: Artificial
<220> FEATURE:
<223> OTHER INFORMATION: Chimeric ITR sequence

<400> SEQUENCE: 31

```
aggaacccct agtgatggag ttggccactc cctccacgcg ttctgcgcgc tcgctcgctc    60
actgagggcg gcgaccaaa ggtcgcccga cgcccggccc tttgggccgg gcggccctca   120
gtgagcgagc gagcgcgcag aacgcgtgga gggagtggcc aactccatca ctaggggttc   180
ct                                                                 182
```

<210> SEQ ID NO 32
<211> LENGTH: 177
<212> TYPE: DNA
<213> ORGANISM: Artificial
<220> FEATURE:
<223> OTHER INFORMATION: Chimeric ITR sequence

<400> SEQUENCE: 32

```
aggaacccct agtcgtgatg gagttggcca ctccctcacg tctgcgcgct cgctcgctca    60
ctgagggcgg gcgaccaaag gtcgcccgag cccggcccct tgggccgggc ccctcagtga   120
gcgagcgagc gcgcagacgt gagggagtgg ccaactccat cacgactagg ggttcct      177
```

<210> SEQ ID NO 33
<211> LENGTH: 177
<212> TYPE: DNA
<213> ORGANISM: Artificial

```
<220> FEATURE:
<223> OTHER INFORMATION: Chimeric ITR sequence

<400> SEQUENCE: 33
aggaacccct agtgatggag ttggccactc cctcccccct gtcgcgttcg cgcgctcgct      60
cgctcactga gggcgggcga ccaaaggtcg cccgagcccg gcccttggg ccgggcccct     120 cagtgagcga gcgagcgcgc agagagggag tggccaactc catcactagg ggttcct      177

<210> SEQ ID NO 34
<211> LENGTH: 173
<212> TYPE: DNA
<213> ORGANISM: Artificial
<220> FEATURE:
<223> OTHER INFORMATION: Chimeric ITR sequence

<400> SEQUENCE: 34
tacaaaacct ccttgcttga gagtgtggca ctcttctgct cgctcgctgg ctcgtttggg      60
ggggcgacgg cccaaagggc cgtcgtctgg cagctctttg agctgccacc cccccaaacg     120
agccagcgag cgagcagaga gagtgccaca ctctcaagca aggaggtttt gta           173

<210> SEQ ID NO 35
<211> LENGTH: 194
<212> TYPE: DNA
<213> ORGANISM: Artificial
<220> FEATURE:
<223> OTHER INFORMATION: Chimeric ITR sequence

<400> SEQUENCE: 35
tacaaaacct ccttgcttag agtgtggcac tctcccctg tcgcgttcgc tcgctcgctg      60
gctcgtttgg gggggcgacg gcccaaaggg ccgtcgtctg gcagctcttt gagctgccac    120 cccccaaac gagccagcga gcgagcgaac gcgacagggg gagagtgcca cactctaagc    180
aaggaggttt tgta                                                       194

<210> SEQ ID NO 36
<211> LENGTH: 206
<212> TYPE: DNA
<213> ORGANISM: Artificial
<220> FEATURE:
<223> OTHER INFORMATION: Chimeric ITR sequence

<400> SEQUENCE: 36
tacaaaacct ccttgcttga gagagtgtgg cactctctcc ccctgtcgc gttcgctcgc      60 tcgctggctc gtttggggg gcgacggccc aaagggccgt cgtctggcag ctctttgagc    120
tgccaccccc ccaaacgagc cagcgagcga gcgaacgcga caggggggag agagtgccac    180
actctctcaa gcaaggaggt tttgta                                          206

<210> SEQ ID NO 37
<211> LENGTH: 210
<212> TYPE: DNA
<213> ORGANISM: Artificial
<220> FEATURE:
<223> OTHER INFORMATION: Chimeric ITR sequence

<400> SEQUENCE: 37
tacaaaacct ccttgcttga gagtgtggca ctctacgcgt cccccctgtc gcgttcgctc      60
gctcgctggc tcgtttgggg gggcgacggc ccaaagggcc gtcgtctggc agctctttga    120
gctgccaccc ccccaaacga gccagcgagc gagcgaacgc gacaggggggc gcgtggagag    180
```

```
tgccacactc tcaagcaagg aggttttgta                                      210
```

<210> SEQ ID NO 38
<211> LENGTH: 227
<212> TYPE: DNA
<213> ORGANISM: Artificial
<220> FEATURE:
<223> OTHER INFORMATION: Chimeric ITR sequence

<400> SEQUENCE: 38

```
tacaaaacct ccttgcttga gagtgtggca ctctcacgcg tagatctaga ccccctgtcg      60
cgttcgctcg ctcgctggct cgtttggggg ggcgacggcc caaagggccg tcgtctggca     120
gctctttgag ctgccacccc cccaaacgag ccagcgagcg agcgaacgcg acaggggtc      180 tagatctacg gtgagagtgc cacactctca agcaaggagg ttttgta                   227
```

<210> SEQ ID NO 39
<211> LENGTH: 198
<212> TYPE: DNA
<213> ORGANISM: Artificial
<220> FEATURE:
<223> OTHER INFORMATION: Chimeric ITR sequence

<400> SEQUENCE: 39

```
tacaaaacct ccttgcttga gagtgtggca ctctccccgc tcgctcgctc gctcgctcgc      60
tggctcgttt ggggggcga cggcccaaag gccgtcgtc tggcagctct ttgagctgcc      120 accccccaa acgagccagc gagcgagcga gcgagcgagc ggggagagtg ccacactctc     180
aagcaaggag gttttgta                                                   198
```

<210> SEQ ID NO 40
<211> LENGTH: 198
<212> TYPE: DNA
<213> ORGANISM: Artificial
<220> FEATURE:
<223> OTHER INFORMATION: Chimeric ITR sequence

<400> SEQUENCE: 40

```
tacaaaacct ccttgcttga gagtgtggca ctctccccag ctaagatgca gctcgctcgc      60
tggctcgttt ggggggcga cggcccaaag gccgtcgtc tggcagctct ttgagctgcc      120 accccccaa acgagccagc gagcgagctg catcttagct ggggagagtg ccacactctc     180
aagcaaggag gttttgta                                                   198
```

<210> SEQ ID NO 41
<211> LENGTH: 181
<212> TYPE: DNA
<213> ORGANISM: Artificial
<220> FEATURE:
<223> OTHER INFORMATION: Chimeric ITR sequence

<400> SEQUENCE: 41

```
aggaacccct agtgatggag ttggccactc cctctctgct cgctcgcgcg ctcgctcgct      60
cactgagggc gggcgaccaa aggtcgcccg agccggccc tttgggccgg gccctcagt      120 gagcgagcga gcgcgcgagc gagcagagag ggagtggcca actccatcac taggggttcc     180
t                                                                     181
```

<210> SEQ ID NO 42
<211> LENGTH: 198
<212> TYPE: DNA
<213> ORGANISM: Artificial

```
<220> FEATURE:
<223> OTHER INFORMATION: Chimeric ITR sequence

<400> SEQUENCE: 42
tacaaaacct ccttgcttga gagtgtggca ctctcccccc tgtcgcgttc gctcagctaa      60
gatgcagttt gggggggcga cggcccaaag ggccgtcgtc tggcagctct ttgagctgcc     120 accccccaa actgcatctt agctgagcga acgcgacagg ggggagagtg ccacactctc      180
aagcaaggag gttttgta                                                   198

<210> SEQ ID NO 43
<211> LENGTH: 180
<212> TYPE: DNA
<213> ORGANISM: Artificial
<220> FEATURE:
<223> OTHER INFORMATION: Chimeric ITR sequence

<400> SEQUENCE: 43
aggaacccct agtgatggag ttggccactc cctctctgct cgctcgcgcg ctcaagatgc      60
actgagggcg ggcgaccaaa ggtcgcccga gcccggccct ttgggccggg ccctcagtt      120 gcatcttgag cgcgcgagcg agcagagagg gagtggccaa ctccatcact agggggttcct    180

<210> SEQ ID NO 44
<211> LENGTH: 197
<212> TYPE: DNA
<213> ORGANISM: Artificial
<220> FEATURE:
<223> OTHER INFORMATION: Chimeric ITR sequence

<400> SEQUENCE: 44
tacaaaacct ccttgcttga gagtgtggca ctctcccccc tgtcgcgttc gctcgctcgc      60
tggctcgttt gggggggcgg gcgaccaaag gtcgcccgag cccggccctt tgggccgggc     120
cccccccaaa cgagccagcg agcgagcgaa cgcgacaggg gggagagtgc cacactctca     180
agcaaggagg ttttgta                                                    197

<210> SEQ ID NO 45
<211> LENGTH: 135
<212> TYPE: DNA
<213> ORGANISM: Artificial
<220> FEATURE:
<223> OTHER INFORMATION: Chimeric ITR sequence

<400> SEQUENCE: 45
aggaacccct agtgatggag ttggccactc cctctctgcg cgctcgctcg ctcactgagg      60 cggcccttg ggccgcctca gtgagcgagc gagcgcgcag agagggagtg gccaactcca     120
tcactagggg ttcct                                                      135

<210> SEQ ID NO 46
<211> LENGTH: 153
<212> TYPE: DNA
<213> ORGANISM: Artificial
<220> FEATURE:
<223> OTHER INFORMATION: Chimeric ITR sequence

<400> SEQUENCE: 46
aggaacccct agtgatggag ttggggtctg cgcgcgctcg ctcgctcact gagggcgggc      60
gaccaaaggt cgcccgagcc cggccctttg ggccgggccc ctcagtgagc gagcgagcgc     120
gcgcagaccc caactccatc actagggggtt cct                                 153
```

<210> SEQ ID NO 47
<211> LENGTH: 164
<212> TYPE: DNA
<213> ORGANISM: Artificial
<220> FEATURE:
<223> OTHER INFORMATION: Chimeric ITR sequence

<400> SEQUENCE: 47
aggaacccct agtgatggag ttgggactcc ctctctgcgc gctcgctcgc tcactgaggg      60
cgggcgacca aaggtcgccc gagcccggcc cttgggccg ggcccctcag tgagcgagcg     120
agcgcgcaga gagggagtcc ccaactccat cactaggggt tcct                     164

<210> SEQ ID NO 48
<211> LENGTH: 159
<212> TYPE: DNA
<213> ORGANISM: Artificial
<220> FEATURE:
<223> OTHER INFORMATION: Chimeric ITR sequence

<400> SEQUENCE: 48
aggaacccct agtgatggag ttggggttaa ctctgcgcgc tcgctcgctc actgagggcg      60 gcgaccaaa ggtcgcccga gcccggccct ttgggccggg ccctcagtg agcgagcgag     120 cgcgcagagt taaccccaac tccatcacta ggggttcct                            159

<210> SEQ ID NO 49
<211> LENGTH: 157
<212> TYPE: DNA
<213> ORGANISM: Artificial
<220> FEATURE:
<223> OTHER INFORMATION: Chimeric ITR sequence

<400> SEQUENCE: 49
aggaacccct agtgatggag ttggtccctc tctgcgcgct cgctcgctca ctgagggcgg      60
gcgaccaaag gtcgcccgag cccggccctt tgggccgggc ccctcagtga gcgagcgagc    120
gcgcagagag ggaccaactc catcactagg ggttcct                              157

<210> SEQ ID NO 50
<211> LENGTH: 165
<212> TYPE: DNA
<213> ORGANISM: Artificial
<220> FEATURE:
<223> OTHER INFORMATION: Chimeric ITR sequence

<400> SEQUENCE: 50
aggaacccct agtgatggag ttggggttaa ccctctgcg cgctcgctcg ctcactgagg       60
gcgggcgacc aaaggtcgcc cgagcccggc cctttgggcc gggcccctca gtgagcgagc    120
gagcgcgcag aggggttaac cccaactcca tcactagggg ttcct                     165

<210> SEQ ID NO 51
<211> LENGTH: 172
<212> TYPE: DNA
<213> ORGANISM: Artificial
<220> FEATURE:
<223> OTHER INFORMATION: Chimeric ITR sequence

<400> SEQUENCE: 51
aggaacccct agtgatggag ttggccactc cctcttcgct cgctcgctgg ctcgtttggg      60
ggggcgacgg cccaaagggc cgtcgtctgg cagctctttg agctgccacc ccccaaacg     120 agccagcgag cgagcgaaga gggagtggcc aactccatca ctagggggttc ct            172

<210> SEQ ID NO 52
<211> LENGTH: 181
<212> TYPE: DNA
<213> ORGANISM: Artificial
<220> FEATURE:
<223> OTHER INFORMATION: Chimeric ITR sequence

<400> SEQUENCE: 52

```
aggaacccct agtgatggag ttggggttaa ccccactccc tctctgcgcg ctcgctcgct    60
cactgagggc gggcgaccaa aggtcgcccg agcccggccc tttgggccgg gcccctcagt   120
gagcgagcga gcgcgcagag agggagtggg gttaacccca actccatcac tagggttcc   180 t                                                                   181
```

<210> SEQ ID NO 53
<211> LENGTH: 621
<212> TYPE: PRT
<213> ORGANISM: Artificial
<220> FEATURE:
<223> OTHER INFORMATION: Chimeric Rep protein sequence

<400> SEQUENCE: 53

```
Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270
```

```
Ile Met Ser Leu Thr Lys Thr Ala Pro Asp Tyr Leu Val Gly Gln Gln
            275                 280                 285

Pro Val Glu Asp Ile Ser Ser Asn Arg Ile Tyr Lys Ile Leu Glu Leu
        290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
        515                 520                 525

Arg Tyr Gln Asn Lys Cys Ser Arg His Val Gly Met Asn Leu Met Leu
    530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
            580                 585                 590

Ile His His Ile Met Gly Lys Val Pro Asp Ala Cys Thr Ala Cys Asp
        595                 600                 605

Leu Val Asn Val Asp Leu Asp Asp Cys Ile Phe Glu Gln
    610                 615                 620

<210> SEQ ID NO 54
<211> LENGTH: 620
<212> TYPE: PRT
<213> ORGANISM: Artificial
<220> FEATURE:
<223> OTHER INFORMATION: Chimeric Rep protein sequence

<400> SEQUENCE: 54

Met Ala Thr Phe Tyr Glu Val Ile Val Arg Val Pro Phe Asp Val Glu
1               5                   10                  15
```

```
Glu His Leu Pro Gly Ile Ser Asp Ser Phe Val Asp Trp Val Thr Gly
             20                  25                  30

Gln Ile Trp Glu Leu Pro Pro Glu Ser Asp Leu Asn Leu Thr Leu Val
         35                  40                  45

Glu Gln Pro Gln Leu Thr Val Ala Asp Arg Ile Arg Arg Val Phe Leu
 50                  55                  60

Tyr Glu Trp Asn Lys Phe Ser Lys Gln Glu Ser Lys Phe Phe Val Gln
 65                  70                  75                  80

Phe Glu Lys Gly Glu Ser Tyr Phe His Met His Val Leu Val Glu Thr
                 85                  90                  95

Thr Gly Val Lys Ser Met Val Leu Gly Arg Phe Leu Ser Gln Ile Arg
                100                 105                 110

Glu Lys Leu Ile Gln Arg Ile Tyr Arg Gly Ile Glu Pro Thr Leu Pro
             115                 120                 125

Asn Trp Phe Ala Val Thr Lys Thr Arg Asn Gly Ala Gly Gly Gly Asn
 130                 135                 140

Lys Val Val Asp Glu Cys Tyr Ile Pro Asn Tyr Leu Leu Pro Lys Thr
145                 150                 155                 160

Gln Pro Glu Leu Gln Trp Ala Trp Thr Asn Met Glu Gln Tyr Leu Ser
                165                 170                 175

Ala Cys Leu Asn Leu Thr Glu Arg Lys Arg Leu Val Ala Gln His Leu
                180                 185                 190

Thr His Val Ser Gln Thr Gln Glu Gln Asn Lys Glu Asn Gln Asn Pro
             195                 200                 205

Asn Ser Asp Ala Pro Val Ile Arg Ser Lys Thr Ser Ala Arg Tyr Met
 210                 215                 220

Glu Leu Val Gly Trp Leu Val Asp Lys Gly Ile Thr Ser Glu Lys Gln
225                 230                 235                 240

Trp Ile Gln Glu Asp Gln Ala Ser Tyr Ile Ser Phe Asn Ala Ala Ser
                245                 250                 255

Asn Ser Arg Ser Gln Ile Lys Ala Ala Leu Asp Asn Ala Gly Lys Ile
                260                 265                 270

Met Ser Leu Thr Lys Thr Ala Pro Asp Tyr Leu Val Gly Gln Gln Pro
             275                 280                 285

Val Glu Asp Ile Ser Ser Asn Arg Ile Tyr Lys Ile Leu Glu Leu Asn
 290                 295                 300

Gly Tyr Asp Pro Gln Tyr Ala Ala Ser Val Phe Leu Gly Trp Ala Thr
305                 310                 315                 320

Lys Lys Phe Gly Lys Arg Asn Thr Ile Trp Leu Phe Gly Pro Ala Thr
                325                 330                 335

Thr Gly Lys Thr Asn Ile Ala Gly Ala Ile Ala His Thr Val Pro Phe
                340                 345                 350

Tyr Gly Cys Val Asn Trp Thr Asn Glu Asn Phe Pro Phe Asn Asp Cys
             355                 360                 365

Val Asp Lys Met Val Ile Trp Trp Glu Glu Gly Lys Met Thr Ala Lys
 370                 375                 380

Val Val Glu Ser Ala Lys Ala Ile Leu Gly Gly Ser Lys Val Arg Val
385                 390                 395                 400

Asp Gln Lys Cys Lys Ser Ser Ala Gln Ile Asp Pro Thr Pro Val Ile
                405                 410                 415

Val Thr Ser Asn Thr Asn Met Cys Ala Val Ile Asp Gly Asn Ser Thr
             420                 425                 430
```

```
Thr Phe Glu His Gln Gln Pro Leu Gln Asp Arg Met Phe Lys Phe Glu
            435                 440                 445

Leu Thr Arg Arg Leu Asp His Asp Phe Gly Lys Val Thr Lys Gln Glu
450                 455                 460

Val Lys Asp Phe Phe Arg Trp Ala Lys Asp His Val Val Glu Val Glu
465                 470                 475                 480

His Glu Phe Tyr Val Lys Lys Gly Ala Lys Lys Arg Pro Ala Pro
                485                 490                 495

Ser Asp Ala Asp Ile Ser Glu Pro Lys Arg Val Arg Glu Ser Val Ala
            500                 505                 510

Gln Pro Ser Thr Ser Asp Ala Glu Ala Ser Ile Asn Tyr Ala Asp Arg
        515                 520                 525

Tyr Gln Asn Lys Cys Ser Arg His Val Gly Met Asn Leu Met Leu Phe
530                 535                 540

Pro Cys Arg Gln Cys Glu Arg Met Asn Gln Asn Ser Asn Ile Cys Phe
545                 550                 555                 560

Thr His Gly Gln Lys Asp Cys Leu Glu Cys Phe Pro Val Ser Glu Ser
                565                 570                 575

Gln Pro Val Ser Val Lys Lys Ala Tyr Gln Lys Leu Cys Tyr Ile
            580                 585                 590

His His Ile Met Gly Lys Val Pro Asp Ala Cys Thr Ala Cys Asp Leu
        595                 600                 605

Val Asn Val Asp Leu Asp Asp Cys Ile Phe Glu Gln
    610                 615                 620

<210> SEQ ID NO 55
<211> LENGTH: 620
<212> TYPE: PRT
<213> ORGANISM: Artificial
<220> FEATURE:
<223> OTHER INFORMATION: Chimeric Rep protein sequence

<400> SEQUENCE: 55

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Glu Lys Leu Ile Gln Arg Ile Tyr Arg Gly Ile Glu Pro Thr Leu Pro
        115                 120                 125

Asn Trp Phe Ala Val Thr Lys Thr Arg Asn Gly Ala Gly Gly Asn
    130                 135                 140

Lys Val Val Asp Glu Cys Tyr Ile Pro Asn Tyr Leu Leu Pro Lys Thr
145                 150                 155                 160

Gln Pro Glu Leu Gln Trp Ala Trp Thr Asn Met Glu Gln Tyr Leu Ser
                165                 170                 175
```

```
Ala Cys Leu Asn Leu Thr Glu Arg Lys Arg Leu Val Ala Gln His Leu
            180                 185                 190

Thr His Val Ser Gln Thr Gln Glu Gln Asn Lys Glu Asn Gln Asn Pro
            195                 200                 205

Asn Ser Asp Ala Pro Val Ile Arg Ser Lys Thr Ser Ala Arg Tyr Met
            210                 215                 220

Glu Leu Val Gly Trp Leu Val Asp Lys Gly Ile Thr Ser Glu Lys Gln
225                 230                 235                 240

Trp Ile Gln Glu Asp Gln Ala Ser Tyr Ile Ser Phe Asn Ala Ala Ser
            245                 250                 255

Asn Ser Arg Ser Gln Ile Lys Ala Ala Leu Asp Asn Ala Gly Lys Ile
            260                 265                 270

Met Ser Leu Thr Lys Thr Ala Pro Asp Tyr Leu Val Gly Gln Gln Pro
            275                 280                 285

Val Glu Asp Ile Ser Ser Asn Arg Ile Tyr Lys Ile Leu Glu Leu Asn
            290                 295                 300

Gly Tyr Asp Pro Gln Tyr Ala Ala Ser Val Phe Leu Gly Trp Ala Thr
305                 310                 315                 320

Lys Lys Phe Gly Lys Arg Asn Thr Ile Trp Leu Phe Gly Pro Ala Thr
            325                 330                 335

Thr Gly Lys Thr Asn Ile Ala Glu Ala Ile Ala His Thr Val Pro Phe
            340                 345                 350

Tyr Gly Cys Val Asn Trp Thr Asn Glu Asn Phe Pro Phe Asn Asp Cys
            355                 360                 365

Val Asp Lys Met Val Ile Trp Trp Glu Glu Lys Met Thr Ala Lys
370                 375                 380

Val Val Glu Ser Ala Lys Ala Ile Leu Gly Gly Ser Lys Val Arg Val
385                 390                 395                 400

Asp Gln Lys Cys Lys Ser Ser Ala Gln Ile Asp Pro Thr Pro Val Ile
            405                 410                 415

Val Thr Ser Asn Thr Asn Met Cys Ala Val Ile Asp Gly Asn Ser Thr
            420                 425                 430

Thr Phe Glu His Gln Gln Pro Leu Gln Asp Arg Met Phe Lys Phe Glu
            435                 440                 445

Leu Thr Arg Arg Leu Asp His Asp Phe Gly Lys Val Thr Lys Gln Glu
    450                 455                 460

Val Lys Asp Phe Phe Arg Trp Ala Lys Asp His Val Val Glu Val Glu
465                 470                 475                 480

His Glu Phe Tyr Val Lys Lys Gly Gly Ala Lys Lys Arg Pro Ala Pro
            485                 490                 495

Ser Asp Ala Asp Ile Ser Glu Pro Lys Arg Val Arg Glu Ser Val Ala
            500                 505                 510

Gln Pro Ser Thr Ser Asp Ala Glu Ala Ser Ile Asn Tyr Ala Asp Arg
            515                 520                 525

Tyr Gln Asn Lys Cys Ser Arg His Val Gly Met Asn Leu Met Leu Phe
            530                 535                 540

Pro Cys Arg Gln Cys Glu Arg Met Asn Gln Asn Ser Asn Ile Cys Phe
545                 550                 555                 560

Thr His Gly Gln Lys Asp Cys Leu Glu Cys Phe Pro Val Ser Glu Ser
            565                 570                 575

Gln Pro Val Ser Val Val Lys Lys Ala Tyr Gln Lys Leu Cys Tyr Ile
            580                 585                 590

His His Ile Met Gly Lys Val Pro Asp Ala Cys Thr Ala Cys Asp Leu
```

```
            595                 600                 605
Val Asn Val Asp Leu Asp Asp Cys Ile Phe Glu Gln
    610                 615                 620

<210> SEQ ID NO 56
<211> LENGTH: 620
<212> TYPE: PRT
<213> ORGANISM: Artificial
<220> FEATURE:
<223> OTHER INFORMATION: Chimeric Rep protein sequence

<400> SEQUENCE: 56

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Thr Leu Pro
        115                 120                 125

Asn Trp Phe Ala Val Thr Lys Thr Arg Asn Gly Ala Gly Gly Gly Asn
    130                 135                 140

Lys Val Val Asp Glu Cys Tyr Ile Pro Asn Tyr Leu Leu Pro Lys Thr
145                 150                 155                 160

Gln Pro Glu Leu Gln Trp Ala Trp Thr Asn Met Glu Gln Tyr Leu Ser
                165                 170                 175

Ala Cys Leu Asn Leu Thr Glu Arg Lys Arg Leu Val Ala Gln His Leu
            180                 185                 190

Thr His Val Ser Gln Thr Gln Glu Gln Asn Lys Glu Asn Gln Asn Pro
        195                 200                 205

Asn Ser Asp Ala Pro Val Ile Arg Ser Lys Thr Ser Ala Arg Tyr Met
    210                 215                 220

Glu Leu Val Gly Trp Leu Val Asp Lys Gly Ile Thr Ser Glu Lys Gln
225                 230                 235                 240

Trp Ile Gln Glu Asp Gln Ala Ser Tyr Ile Ser Phe Asn Ala Ala Ser
                245                 250                 255

Asn Ser Arg Ser Gln Ile Lys Ala Ala Leu Asp Asn Ala Gly Lys Ile
            260                 265                 270

Met Ser Leu Thr Lys Thr Ala Pro Asp Tyr Leu Val Gly Gln Gln Pro
        275                 280                 285

Val Glu Asp Ile Ser Ser Asn Arg Ile Tyr Lys Ile Leu Glu Leu Asn
    290                 295                 300

Gly Tyr Asp Pro Gln Tyr Ala Ala Ser Val Phe Leu Gly Trp Ala Thr
305                 310                 315                 320

Lys Lys Phe Gly Lys Arg Asn Thr Ile Trp Leu Phe Gly Pro Ala Thr
                325                 330                 335

Thr Gly Lys Thr Asn Ile Ala Glu Ala Ile Ala His Thr Val Pro Phe
```

```
                340                 345                 350
Tyr Gly Cys Val Asn Trp Thr Asn Glu Asn Phe Pro Phe Asn Asp Cys
            355                 360                 365
Val Asp Lys Met Val Ile Trp Trp Glu Glu Gly Lys Met Thr Ala Lys
        370                 375                 380
Val Val Glu Ser Ala Lys Ala Ile Leu Gly Gly Ser Lys Val Arg Val
385                 390                 395                 400
Asp Gln Lys Cys Lys Ser Ser Ala Gln Ile Asp Pro Thr Pro Val Ile
                405                 410                 415
Val Thr Ser Asn Thr Asn Met Cys Ala Val Ile Asp Gly Asn Ser Thr
            420                 425                 430
Thr Phe Glu His Gln Gln Pro Leu Gln Asp Arg Met Phe Lys Phe Glu
        435                 440                 445
Leu Thr Arg Arg Leu Asp His Asp Phe Gly Lys Val Thr Lys Gln Glu
        450                 455                 460
Val Lys Asp Phe Phe Arg Trp Ala Lys Asp His Val Val Glu Val Glu
465                 470                 475                 480
His Glu Phe Tyr Val Lys Lys Gly Gly Ala Lys Lys Arg Pro Ala Pro
                485                 490                 495
Ser Asp Ala Asp Ile Ser Glu Pro Lys Arg Val Arg Glu Ser Val Ala
            500                 505                 510
Gln Pro Ser Thr Ser Asp Ala Glu Ala Ser Ile Asn Tyr Ala Asp Arg
        515                 520                 525
Tyr Gln Asn Lys Cys Ser Arg His Val Gly Met Asn Leu Met Leu Phe
        530                 535                 540
Pro Cys Arg Gln Cys Glu Arg Met Asn Gln Asn Ser Asn Ile Cys Phe
545                 550                 555                 560
Thr His Gly Gln Lys Asp Cys Leu Glu Cys Phe Pro Val Ser Glu Ser
                565                 570                 575
Gln Pro Val Ser Val Val Lys Lys Ala Tyr Gln Lys Leu Cys Tyr Ile
            580                 585                 590
His His Ile Met Gly Lys Val Pro Asp Ala Cys Thr Ala Cys Asp Leu
        595                 600                 605
Val Asn Val Asp Leu Asp Asp Cys Ile Phe Glu Gln
        610                 615                 620
```

<210> SEQ ID NO 57
<211> LENGTH: 618
<212> TYPE: PRT
<213> ORGANISM: Artificial
<220> FEATURE:
<223> OTHER INFORMATION: Chimeric Rep protein sequence

<400> SEQUENCE: 57

```
Met Ala Thr Phe Tyr Glu Val Ile Val Arg Val Pro Phe Asp Val Glu
1               5                   10                  15
Glu His Leu Pro Gly Ile Ser Asp Ser Phe Val Asp Trp Val Thr Gly
                20                  25                  30
Gln Ile Trp Glu Leu Pro Pro Glu Ser Asp Leu Asn Leu Thr Leu Val
        35                  40                  45
Glu Gln Pro Gln Leu Thr Val Ala Asp Arg Ile Arg Arg Val Phe Leu
        50                  55                  60
Tyr Glu Trp Asn Lys Phe Ser Lys Gln Glu Ser Lys Phe Phe Val Gln
65                  70                  75                  80
Phe Glu Lys Gly Ser Glu Tyr Phe His Leu His Thr Leu Val Glu Thr
```

```
                    85                  90                  95
Ser Gly Ile Ser Ser Met Val Leu Gly Arg Tyr Val Ser Gln Ile Arg
                100                 105                 110
Ala Gln Leu Val Lys Val Val Phe Gln Gly Ile Glu Pro Gln Ile Asn
                115                 120                 125
Asp Trp Val Ala Ile Thr Lys Val Lys Lys Gly Gly Asn Lys Val
                130                 135                 140
Val Asp Glu Cys Tyr Ile Pro Asn Tyr Leu Leu Pro Lys Thr Gln Pro
145                 150                 155                 160
Glu Leu Gln Trp Ala Trp Thr Asn Met Glu Gln Tyr Leu Ser Ala Cys
                165                 170                 175
Leu Asn Leu Thr Glu Arg Lys Arg Leu Val Ala Gln His Leu Thr His
                180                 185                 190
Val Ser Gln Thr Gln Glu Gln Asn Lys Glu Asn Gln Asn Pro Asn Ser
                195                 200                 205
Asp Ala Pro Val Ile Arg Ser Lys Thr Ser Ala Arg Tyr Met Glu Leu
                210                 215                 220
Val Gly Trp Leu Val Asp Lys Gly Ile Thr Ser Glu Lys Gln Trp Ile
225                 230                 235                 240
Gln Glu Asp Gln Ala Ser Tyr Ile Ser Phe Asn Ala Ala Ser Asn Ser
                245                 250                 255
Arg Ser Gln Ile Lys Ala Ala Leu Asp Asn Ala Gly Lys Ile Met Ser
                260                 265                 270
Leu Thr Lys Thr Ala Pro Asp Tyr Leu Val Gly Gln Gln Pro Val Glu
                275                 280                 285
Asp Ile Ser Ser Asn Arg Ile Tyr Lys Ile Leu Glu Leu Asn Gly Tyr
                290                 295                 300
Asp Pro Gln Tyr Ala Ala Ser Val Phe Leu Gly Trp Ala Thr Lys Lys
305                 310                 315                 320
Phe Gly Lys Arg Asn Thr Ile Trp Leu Phe Gly Pro Ala Thr Gly
                325                 330                 335
Lys Thr Asn Ile Ala Glu Ala Ile Ala His Thr Val Pro Phe Tyr Gly
                340                 345                 350
Cys Val Asn Trp Thr Asn Glu Asn Phe Pro Phe Asn Asp Cys Val Asp
                355                 360                 365
Lys Met Val Ile Trp Trp Glu Glu Gly Lys Met Thr Ala Lys Val Val
                370                 375                 380
Glu Ser Ala Lys Ala Ile Leu Gly Gly Ser Lys Val Arg Val Asp Gln
385                 390                 395                 400
Lys Cys Lys Ser Ser Ala Gln Ile Asp Pro Thr Pro Val Ile Val Thr
                405                 410                 415
Ser Asn Thr Asn Met Cys Ala Val Ile Asp Gly Asn Ser Thr Thr Phe
                420                 425                 430
Glu His Gln Gln Pro Leu Gln Asp Arg Met Phe Lys Phe Glu Leu Thr
                435                 440                 445
Arg Arg Leu Asp His Asp Phe Gly Lys Val Thr Lys Gln Glu Val Lys
                450                 455                 460
Asp Phe Phe Arg Trp Ala Lys Asp His Val Val Glu Val Glu His Glu
465                 470                 475                 480
Phe Tyr Val Lys Lys Gly Gly Ala Lys Lys Arg Pro Ala Pro Ser Asp
                485                 490                 495
Ala Asp Ile Ser Glu Pro Lys Arg Val Arg Glu Ser Val Ala Gln Pro
                500                 505                 510
```

```
Ser Thr Ser Asp Ala Glu Ala Ser Ile Asn Tyr Ala Asp Arg Tyr Gln
        515                 520                 525

Asn Lys Cys Ser Arg His Val Gly Met Asn Leu Met Leu Phe Pro Cys
    530                 535                 540

Arg Gln Cys Glu Arg Met Asn Gln Asn Ser Asn Ile Cys Phe Thr His
545                 550                 555                 560

Gly Gln Lys Asp Cys Leu Glu Cys Phe Pro Val Ser Glu Ser Gln Pro
                565                 570                 575

Val Ser Val Val Lys Lys Ala Tyr Gln Lys Leu Cys Tyr Ile His His
            580                 585                 590

Ile Met Gly Lys Val Pro Asp Ala Cys Thr Ala Cys Asp Leu Val Asn
        595                 600                 605

Val Asp Leu Asp Asp Cys Ile Phe Glu Gln
        610                 615

<210> SEQ ID NO 58
<211> LENGTH: 617
<212> TYPE: PRT
<213> ORGANISM: Artificial
<220> FEATURE:
<223> OTHER INFORMATION: Chimeric Rep protein sequence

<400> SEQUENCE: 58

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Phe Gln Gly Ile Glu Pro Gln Ile Asn
        115                 120                 125

Asp Trp Val Ala Ile Thr Lys Val Lys Lys Gly Gly Ala Asn Lys Val
    130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Met Glu Gln Tyr Leu Ser Ala Cys
                165                 170                 175

Leu Asn Leu Thr Glu Arg Lys Arg Leu Val Ala Gln His Leu Thr His
            180                 185                 190

Val Ser Gln Thr Gln Glu Gln Asn Lys Glu Asn Gln Asn Pro Asn Ser
        195                 200                 205

Asp Ala Pro Val Ile Arg Ser Lys Thr Ala Arg Tyr Met Glu Leu Val
    210                 215                 220

Gly Trp Leu Val Asp Lys Gly Ile Thr Ser Glu Lys Gln Trp Ile Gln
225                 230                 235                 240

Glu Asp Gln Ala Ser Tyr Ile Ser Phe Asn Ala Ala Ser Asn Ser Arg
                245                 250                 255
```

-continued

Ser Gln Ile Lys Ala Ala Leu Asp Asn Ala Gly Lys Ile Met Ser Leu
            260                 265                 270

Thr Lys Thr Ala Pro Asp Tyr Leu Val Gly Gln Pro Val Glu Asp
        275                 280                 285

Ile Ser Ser Asn Arg Ile Tyr Lys Ile Leu Glu Leu Asn Gly Tyr Asp
            290                 295                 300

Pro Gln Tyr Ala Ala Ser Val Phe Leu Gly Trp Ala Thr Lys Lys Phe
305                 310                 315                 320

Gly Lys Arg Asn Thr Ile Trp Leu Phe Gly Pro Ala Thr Thr Gly Lys
                325                 330                 335

Thr Asn Ile Ala Glu Ala Ile Ala His Thr Val Pro Phe Tyr Gly Cys
            340                 345                 350

Val Asn Trp Thr Asn Glu Asn Phe Pro Phe Asn Asp Cys Val Asp Lys
            355                 360                 365

Met Val Ile Trp Trp Glu Glu Gly Lys Met Thr Ala Lys Val Val Glu
    370                 375                 380

Ser Ala Lys Ala Ile Leu Gly Gly Ser Lys Val Arg Val Asp Gln Lys
385                 390                 395                 400

Cys Lys Ser Ser Ala Gln Ile Asp Pro Thr Pro Val Ile Val Thr Ser
                405                 410                 415

Asn Thr Asn Met Cys Ala Val Ile Asp Gly Asn Ser Thr Thr Phe Glu
            420                 425                 430

His Gln Gln Pro Leu Gln Asp Arg Met Phe Lys Phe Glu Leu Thr Arg
            435                 440                 445

Arg Leu Asp His Asp Phe Gly Lys Val Thr Lys Gln Glu Val Lys Asp
    450                 455                 460

Phe Phe Arg Trp Ala Lys Asp His Val Val Glu Val Glu His Glu Phe
465                 470                 475                 480

Tyr Val Lys Lys Gly Gly Ala Lys Lys Arg Pro Ala Pro Ser Asp Ala
                485                 490                 495

Asp Ile Ser Glu Pro Lys Arg Val Arg Glu Ser Val Ala Gln Pro Ser
            500                 505                 510

Thr Ser Asp Ala Glu Ala Ser Ile Asn Tyr Ala Asp Arg Tyr Gln Asn
        515                 520                 525

Lys Cys Ser Arg His Val Gly Met Asn Leu Met Leu Phe Pro Cys Arg
530                 535                 540

Gln Cys Glu Arg Met Asn Gln Asn Ser Asn Ile Cys Phe Thr His Gly
545                 550                 555                 560

Gln Lys Asp Cys Leu Glu Cys Phe Pro Val Ser Glu Ser Gln Pro Val
                565                 570                 575

Ser Val Val Lys Lys Ala Tyr Gln Lys Leu Cys Tyr Ile His His Ile
            580                 585                 590

Met Gly Lys Val Pro Asp Ala Cys Thr Ala Cys Asp Leu Val Asn Val
        595                 600                 605

Asp Leu Asp Asp Cys Ile Phe Glu Gln
    610                 615

<210> SEQ ID NO 59
<211> LENGTH: 616
<212> TYPE: PRT
<213> ORGANISM: Artificial
<220> FEATURE:
<223> OTHER INFORMATION: Chimeric Rep protein sequence

<400> SEQUENCE: 59

```
Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
                20                  25                  30

Gln Ile Trp Glu Leu Pro Pro Glu Ser Asp Leu Asn Leu Thr Leu Val
            35              40                  45

Glu Gln Pro Gln Leu Thr Val Ala Asp Arg Ile Arg Arg Val Phe Leu
50                      55                  60

Tyr Glu Trp Asn Lys Phe Ser Lys Gln Glu Ser Lys Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Gly Gly Ala Asn Lys Val
    130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Cys
                165                 170                 175

Leu Asn Leu Thr Glu Arg Lys Arg Leu Val Ala Gln His Leu Thr His
            180                 185                 190

Val Ser Gln Thr Gln Glu Gln Asn Lys Glu Asn Gln Asn Pro Asn Asp
        195                 200                 205

Ala Pro Val Ile Arg Ser Lys Thr Ala Arg Tyr Met Glu Leu Val Gly
    210                 215                 220

Trp Leu Val Asp Lys Gly Ile Thr Ser Glu Lys Gln Trp Ile Gln Glu
225                 230                 235                 240

Asp Gln Ala Ser Tyr Ile Ser Phe Asn Ala Ala Ser Asn Ser Arg Ser
                245                 250                 255

Gln Ile Lys Ala Ala Leu Asp Asn Ala Gly Lys Ile Met Ser Leu Thr
            260                 265                 270

Lys Thr Ala Pro Asp Tyr Leu Val Gly Gln Gln Pro Val Glu Asp Ile
        275                 280                 285

Ser Ser Asn Arg Ile Tyr Lys Ile Leu Glu Leu Asn Gly Tyr Asp Pro
    290                 295                 300

Gln Tyr Ala Ala Ser Val Phe Leu Gly Trp Ala Thr Lys Lys Phe Gly
305                 310                 315                 320

Lys Arg Asn Thr Ile Trp Leu Phe Gly Pro Ala Thr Thr Gly Lys Thr
                325                 330                 335

Asn Ile Ala Glu Ala Ile Ala His Thr Val Pro Phe Tyr Gly Cys Val
            340                 345                 350

Asn Trp Thr Asn Glu Asn Phe Pro Phe Asn Asp Cys Val Asp Lys Met
        355                 360                 365

Val Ile Trp Trp Glu Glu Gly Lys Met Thr Ala Lys Val Val Glu Ser
    370                 375                 380

Ala Lys Ala Ile Leu Gly Gly Ser Lys Val Arg Val Asp Gln Lys Cys
385                 390                 395                 400

Lys Ser Ser Ala Gln Ile Asp Pro Thr Pro Val Ile Val Thr Ser Asn
                405                 410                 415
```

-continued

```
Thr Asn Met Cys Ala Val Ile Asp Gly Asn Ser Thr Thr Phe Glu His
            420                 425                 430

Gln Gln Pro Leu Gln Asp Arg Met Phe Lys Phe Glu Leu Thr Arg Arg
            435                 440                 445

Leu Asp His Asp Phe Gly Lys Val Thr Lys Gln Glu Val Lys Asp Phe
450                 455                 460

Phe Arg Trp Ala Lys Asp His Val Val Glu Val Glu His Glu Phe Tyr
465                 470                 475                 480

Val Lys Lys Gly Gly Ala Lys Lys Arg Pro Ala Pro Ser Asp Ala Asp
            485                 490                 495

Ile Ser Glu Pro Lys Arg Val Arg Glu Ser Val Ala Gln Pro Ser Thr
            500                 505                 510

Ser Asp Ala Glu Ala Ser Ile Asn Tyr Ala Asp Arg Tyr Gln Asn Lys
            515                 520                 525

Cys Ser Arg His Val Gly Met Asn Leu Met Leu Phe Pro Cys Arg Gln
            530                 535                 540

Cys Glu Arg Met Asn Gln Asn Ser Asn Ile Cys Phe Thr His Gly Gln
545                 550                 555                 560

Lys Asp Cys Leu Glu Cys Phe Pro Val Ser Glu Ser Gln Pro Val Ser
            565                 570                 575

Val Val Lys Lys Ala Tyr Gln Lys Leu Cys Tyr Ile His His Ile Met
            580                 585                 590

Gly Lys Val Pro Asp Ala Cys Thr Ala Cys Asp Leu Val Asn Val Asp
            595                 600                 605

Leu Asp Asp Cys Ile Phe Glu Gln
610                 615

<210> SEQ ID NO 60
<211> LENGTH: 621
<212> TYPE: PRT
<213> ORGANISM: Artificial
<220> FEATURE:
<223> OTHER INFORMATION: Chimeric Rep protein sequence

<400> SEQUENCE: 60

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
            35                  40                  45

Glu Gln Pro Gln Leu Thr Val Ala Asp Arg Ile Arg Arg Val Phe Leu
            50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
            85                  90                  95

Ser Gly Ile Ser Ser Met Val Leu Gly Arg Tyr Val Ser Gln Ile Arg
            100                 105                 110

Ala Gln Leu Val Lys Val Phe Gln Gly Ile Glu Pro Gln Ile Asn
            115                 120                 125

Asp Trp Val Ala Ile Thr Lys Val Lys Lys Gly Gly Ala Asn Lys Val
            130                 135                 140

Val Asp Ser Gly Tyr Ile Pro Ala Tyr Leu Leu Pro Lys Val Gln Pro
145                 150                 155                 160
```

-continued

```
Glu Leu Gln Trp Ala Trp Thr Asn Leu Asp Glu Tyr Lys Leu Ala Ala
                165                 170                 175
Leu Asn Leu Glu Glu Arg Lys Arg Arg Lys Arg Leu Val Ala Gln His
            180                 185                 190
Leu Thr His Val Ser Gln Thr Gln Glu Gln Asn Lys Glu Asn Gln Asn
            195                 200                 205
Pro Asn Ser Asp Ala Pro Val Ile Arg Ser Lys Thr Ser Ala Arg Tyr
            210                 215                 220
Met Glu Leu Val Gly Trp Leu Val Asp Lys Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Gly Lys
            260                 265                 270
Ile Met Ser Leu Thr Lys Thr Ala Pro Asp Tyr Leu Val Gly Gln Gln
            275                 280                 285
Pro Val Glu Asp Ile Ser Ser Asn Arg Ile Tyr Lys Ile Leu Glu Leu
            290                 295                 300
Asn Gly Tyr Asp Pro Gln Tyr Ala Ala Ser Val Phe Leu Gly Trp Ala
305                 310                 315                 320
Thr Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Thr Val Pro
            340                 345                 350
Phe Tyr Gly Cys Val Asn Trp Thr Asn Glu Asn Phe Pro Phe Asn Asp
            355                 360                 365
Cys Val Asp Lys Met Val Ile Trp Trp Glu Glu Gly Lys Met Thr Ala
            370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
            420                 425                 430
Thr Thr Phe Glu His Gln Gln Pro Leu Gln Asp Arg Met Phe Lys Phe
            435                 440                 445
Glu Leu Thr Arg Arg Leu Asp His Asp Phe Gly Lys Val Thr Lys Gln
            450                 455                 460
Glu Val Lys Asp Phe Phe Arg Trp Ala Lys Asp His Val Val Glu Val
465                 470                 475                 480
Glu His Glu Phe Tyr Val Lys Lys Gly Gly Ala Lys Lys Arg Pro Ala
                485                 490                 495
Pro Ser Asp Ala Asp Ile Ser Glu Pro Lys Arg Val Arg Glu Ser Val
            500                 505                 510
Ala Gln Pro Ser Thr Ser Asp Ala Glu Ala Ser Ile Asn Tyr Ala Asp
            515                 520                 525
Arg Tyr Gln Asn Lys Cys Ser Arg His Val Gly Met Asn Leu Met Leu
            530                 535                 540
Phe Pro Cys Arg Gln Cys Glu Arg Met Asn Gln Asn Ser Asn Ile Cys
545                 550                 555                 560
Phe Thr His Gly Gln Lys Asp Cys Leu Glu Cys Phe Pro Val Ser Glu
                565                 570                 575
Ser Gln Pro Val Ser Val Val Lys Lys Ala Tyr Gln Lys Leu Cys Tyr
```

-continued

```
                580                 585                 590
Ile His His Ile Met Gly Lys Val Pro Asp Ala Cys Thr Ala Cys Asp
            595                 600                 605

Leu Val Asn Val Asp Leu Asp Asp Cys Ile Phe Glu Gln
    610                 615                 620

<210> SEQ ID NO 61
<211> LENGTH: 617
<212> TYPE: PRT
<213> ORGANISM: Artificial
<220> FEATURE:
<223> OTHER INFORMATION: Chimeric Rep protein sequence

<400> SEQUENCE: 61

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Lys Gly Gly Ala Asn Lys Val
130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175

Leu Asn Leu Glu Glu Arg Lys Arg Leu Val Ala Gln Phe Leu Ala Glu
            180                 185                 190

Ser Ser Gln Arg Ser Glu Gln Asn Lys Glu Asn Gln Asn Pro Asn Ser
        195                 200                 205

Asp Ala Pro Val Ile Arg Ser Lys Ser Ala Arg Tyr Met Glu Leu Val
    210                 215                 220

Gly Trp Leu Val Asp Lys Gly Ile Thr Ser Glu Lys Gln Trp Ile Gln
225                 230                 235                 240

Glu Asp Gln Ala Ser Tyr Ile Ser Phe Asn Ala Ala Ser Asn Ser Arg
                245                 250                 255

Ser Gln Ile Lys Ala Ala Leu Asp Asn Ala Gly Lys Ile Met Ser Leu
            260                 265                 270

Thr Lys Thr Ala Pro Asp Tyr Leu Val Gly Gln Gln Pro Val Glu Asp
        275                 280                 285

Ile Ser Ser Asn Arg Ile Tyr Lys Ile Leu Glu Leu Asn Gly Tyr Asp
    290                 295                 300

Pro Gln Tyr Ala Ala Ser Val Phe Leu Gly Trp Ala Thr Lys Lys Phe
305                 310                 315                 320

Gly Lys Arg Asn Thr Ile Trp Leu Phe Gly Pro Ala Thr Thr Gly Lys
```

```
                    325                 330                 335
Thr Asn Ile Ala Glu Ala Ile Ala His Thr Val Pro Phe Tyr Gly Cys
                340                 345                 350
Val Asn Trp Thr Asn Glu Asn Phe Pro Phe Asn Asp Cys Val Asp Lys
                355                 360                 365
Met Val Ile Trp Trp Glu Glu Gly Lys Met Thr Ala Lys Val Val Glu
                370                 375                 380
Ser Ala Lys Ala Ile Leu Gly Gly Ser Lys Val Arg Val Asp Gln Lys
385                 390                 395                 400
Cys Lys Ser Ser Ala Gln Ile Asp Pro Thr Pro Val Ile Val Thr Ser
                405                 410                 415
Asn Thr Asn Met Cys Ala Val Ile Asp Gly Asn Ser Thr Thr Phe Glu
                420                 425                 430
His Gln Gln Pro Leu Gln Asp Arg Met Phe Lys Phe Glu Leu Thr Arg
                435                 440                 445
Arg Leu Asp His Asp Phe Gly Lys Val Thr Lys Gln Glu Val Lys Asp
                450                 455                 460
Phe Phe Arg Trp Ala Lys Asp His Val Val Glu Val Glu His Glu Phe
465                 470                 475                 480
Tyr Val Lys Lys Gly Gly Ala Lys Lys Arg Pro Ala Pro Ser Asp Ala
                485                 490                 495
Asp Ile Ser Glu Pro Lys Arg Val Arg Glu Ser Val Ala Gln Pro Ser
                500                 505                 510
Thr Ser Asp Ala Glu Ala Ser Ile Asn Tyr Ala Asp Arg Tyr Gln Asn
                515                 520                 525
Lys Cys Ser Arg His Val Gly Met Asn Leu Met Leu Phe Pro Cys Arg
                530                 535                 540
Gln Cys Glu Arg Met Asn Gln Asn Ser Asn Ile Cys Phe Thr His Gly
545                 550                 555                 560
Gln Lys Asp Cys Leu Glu Cys Phe Pro Val Ser Glu Ser Gln Pro Val
                565                 570                 575
Ser Val Val Lys Lys Ala Tyr Gln Lys Leu Cys Tyr Ile His His Ile
                580                 585                 590
Met Gly Lys Val Pro Asp Ala Cys Thr Ala Cys Asp Leu Val Asn Val
                595                 600                 605
Asp Leu Asp Asp Cys Ile Phe Glu Gln
    610                 615

<210> SEQ ID NO 62
<211> LENGTH: 610
<212> TYPE: PRT
<213> ORGANISM: Artificial
<220> FEATURE:
<223> OTHER INFORMATION: Chimeric Rep protein sequence

<400> SEQUENCE: 62

Met Pro Gly Phe Tyr Glu Ile Val Ile Lys Val Pro Ser Asp Leu Asp
1               5                   10                  15
Gly His Leu Pro Gly Ile Ser Asp Ser Phe Val Asn Trp Val Ala Glu
                20                  25                  30
Lys Glu Trp Glu Leu Pro Pro Asp Ser Asp Met Asp Leu Asn Leu Ile
                35                  40                  45
Glu Gln Ala Pro Leu Thr Val Ala Glu Lys Leu Gln Arg Asp Phe Leu
                50                  55                  60
Thr Glu Trp Arg Arg Val Ser Lys Gln Glu Ser Lys Phe Phe Val Gln
```

```
              65                  70                  75                  80
        Phe Glu Lys Gly Ser Glu Tyr Phe His Leu His Thr Leu Val Glu Thr
                            85                  90                  95
        Ser Gly Ile Ser Ser Met Val Leu Gly Arg Tyr Val Ser Gln Ile Arg
                        100                 105                 110
        Ala Gln Leu Val Lys Val Val Phe Gln Gly Ile Glu Pro Gln Ile Asn
                    115                 120                 125
        Asp Trp Val Ala Ile Thr Lys Val Lys Lys Gly Gly Ala Asn Lys Val
                130                 135                 140
        Val Asp Ser Gly Tyr Ile Pro Ala Tyr Leu Leu Pro Lys Val Gln Pro
        145                 150                 155                 160
        Glu Leu Gln Trp Ala Trp Thr Asn Leu Asp Glu Tyr Lys Leu Ala Ala
                        165                 170                 175
        Leu Asn Leu Glu Glu Arg Lys Arg Leu Val Ala Gln Phe Leu Ala Glu
                    180                 185                 190
        Ser Ser Gln Arg Ser Gln Glu Ala Ala Ser Gln Arg Glu Phe Ser Ala
                195                 200                 205
        Asp Pro Val Ile Lys Ser Lys Thr Ser Gln Lys Tyr Met Ala Leu Val
            210                 215                 220
        Asn Trp Leu Val Glu His Gly Ile Thr Ser Glu Lys Gln Trp Ile Gln
        225                 230                 235                 240
        Glu Asn Gln Glu Ser Tyr Leu Ser Phe Asn Ser Thr Gly Asn Ser Arg
                        245                 250                 255
        Ser Gln Ile Lys Ala Ala Leu Asp Asn Ala Thr Lys Ile Met Ser Leu
                    260                 265                 270
        Thr Lys Ser Ala Val Asp Tyr Leu Val Gly Ser Ser Val Pro Glu Asp
                275                 280                 285
        Ile Ser Lys Asn Arg Ile Trp Gln Ile Phe Glu Met Asn Gly Tyr Asp
            290                 295                 300
        Pro Ala Tyr Ala Gly Ser Ile Leu Tyr Gly Trp Cys Gln Arg Ser Phe
        305                 310                 315                 320
        Asn Lys Arg Asn Thr Val Trp Leu Tyr Gly Pro Ala Thr Thr Gly Lys
                        325                 330                 335
        Thr Asn Ile Ala Glu Ala Ile Ala His Thr Val Pro Phe Tyr Gly Cys
                    340                 345                 350
        Val Asn Trp Thr Asn Glu Asn Phe Pro Phe Asn Asp Cys Val Asp Lys
                355                 360                 365
        Met Leu Ile Trp Trp Glu Glu Gly Lys Met Thr Asn Lys Val Val Glu
            370                 375                 380
        Ser Ala Lys Ala Ile Leu Gly Gly Ser Lys Val Arg Val Asp Gln Lys
        385                 390                 395                 400
        Cys Lys Ser Ser Val Gln Ile Asp Ser Thr Pro Val Ile Val Thr Ser
                        405                 410                 415
        Asn Thr Asn Met Cys Val Val Asp Gly Asn Ser Thr Thr Phe Glu
                    420                 425                 430
        His Gln Gln Pro Leu Glu Asp Arg Met Phe Lys Phe Glu Leu Thr Lys
                435                 440                 445
        Arg Leu Pro Pro Asp Phe Gly Lys Ile Thr Lys Gln Glu Val Lys Asp
            450                 455                 460
        Phe Phe Ala Trp Ala Lys Val Asn Gln Val Pro Val Thr His Glu Phe
        465                 470                 475                 480
        Lys Val Pro Arg Glu Leu Ala Gly Thr Lys Gly Ala Glu Lys Ser Leu
                        485                 490                 495
```

```
Lys Arg Pro Leu Gly Asp Val Thr Asn Thr Ser Tyr Lys Ser Leu Glu
            500                 505                 510

Lys Arg Ala Arg Leu Ser Phe Val Pro Glu Thr Pro Arg Ser Ser Asp
            515                 520                 525

Val Thr Val Asp Pro Ala Pro Leu Arg Pro Leu Asn Trp Asn Ser Arg
530                 535                 540

Tyr Asp Cys Lys Cys Asp Tyr His Ala Gln Phe Asp Asn Ile Ser Asn
545                 550                 555                 560

Lys Cys Asp Glu Cys Glu Tyr Leu Asn Arg Gly Lys Asn Gly Cys Ile
            565                 570                 575

Cys His Asn Val Thr His Cys Gln Ile Cys His Gly Ile Pro Pro Trp
            580                 585                 590

Glu Lys Glu Asn Leu Ser Asp Phe Gly Asp Phe Asp Asp Ala Asn Lys
            595                 600                 605

Glu Gln
    610

<210> SEQ ID NO 63
<211> LENGTH: 611
<212> TYPE: PRT
<213> ORGANISM: Artificial
<220> FEATURE:
<223> OTHER INFORMATION: Chimeric Rep protein sequence

<400> SEQUENCE: 63

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
        50                  55                  60

Thr Glu Trp Arg Arg Val Ser Lys Ala Pro Glu Ala Leu Phe Phe Val
65                  70                  75                  80

Gln Phe Glu Lys Gly Ser Glu Tyr Phe His Leu His Thr Leu Val Glu
            85                  90                  95

Thr Ser Gly Ile Ser Ser Met Val Leu Gly Arg Tyr Val Ser Gln Ile
            100                 105                 110

Arg Ala Gln Leu Val Lys Val Val Phe Gln Gly Ile Glu Pro Gln Ile
        115                 120                 125

Asn Asp Trp Val Ala Ile Thr Lys Val Lys Lys Gly Gly Ala Asn Lys
130                 135                 140

Val Val Asp Ser Gly Tyr Ile Pro Ala Tyr Leu Leu Pro Lys Val Gln
145                 150                 155                 160

Pro Glu Leu Gln Trp Ala Trp Thr Asn Leu Asp Glu Tyr Lys Leu Ala
            165                 170                 175

Ala Leu Asn Leu Glu Glu Arg Lys Arg Leu Val Ala Gln Phe Leu Ala
            180                 185                 190

Glu Ser Ser Gln Arg Ser Gln Glu Ala Ala Ser Gln Arg Glu Phe Ser
        195                 200                 205

Ala Asp Pro Val Ile Lys Ser Lys Thr Ser Gln Lys Tyr Met Ala Leu
        210                 215                 220

Val Asn Trp Leu Val Glu His Gly Ile Thr Ser Glu Lys Gln Trp Ile
225                 230                 235                 240
```

```
Gln Glu Asn Gln Glu Ser Tyr Leu Ser Phe Asn Ser Thr Gly Asn Ser
                245                 250                 255
Arg Ser Gln Ile Lys Ala Ala Leu Asp Asn Ala Thr Lys Ile Met Ser
            260                 265                 270
Leu Thr Lys Ser Ala Val Asp Tyr Leu Val Gly Ser Ser Val Pro Glu
        275                 280                 285
Asp Ile Ser Lys Asn Arg Ile Trp Gln Ile Phe Glu Met Asn Gly Tyr
    290                 295                 300
Asp Pro Ala Tyr Ala Gly Ser Ile Leu Tyr Gly Trp Cys Gln Arg Ser
305                 310                 315                 320
Phe Asn Lys Arg Asn Thr Val Trp Leu Tyr Gly Pro Ala Thr Thr Gly
                325                 330                 335
Lys Thr Asn Ile Ala Glu Ala Ile Ala His Thr Val Pro Phe Tyr Gly
            340                 345                 350
Cys Val Asn Trp Thr Asn Glu Asn Phe Pro Phe Asn Asp Cys Val Asp
        355                 360                 365
Lys Met Leu Ile Trp Trp Glu Glu Gly Lys Met Thr Asn Lys Val Val
    370                 375                 380
Glu Ser Ala Lys Ala Ile Leu Gly Gly Ser Lys Val Arg Val Asp Gln
385                 390                 395                 400
Lys Cys Lys Ser Ser Val Gln Ile Asp Ser Thr Pro Val Ile Val Thr
                405                 410                 415
Ser Asn Thr Asn Met Cys Val Val Asp Gly Asn Ser Thr Thr Phe
            420                 425                 430
Glu His Gln Gln Pro Leu Glu Asp Arg Met Phe Lys Phe Glu Leu Thr
        435                 440                 445
Lys Arg Leu Pro Pro Asp Phe Gly Lys Ile Thr Lys Gln Glu Val Lys
    450                 455                 460
Asp Phe Phe Ala Trp Ala Lys Val Asn Gln Val Pro Val Thr His Glu
465                 470                 475                 480
Phe Lys Val Pro Arg Glu Leu Ala Gly Thr Lys Gly Ala Glu Lys Ser
                485                 490                 495
Leu Lys Arg Pro Leu Gly Asp Val Thr Asn Thr Ser Tyr Lys Ser Leu
            500                 505                 510
Glu Lys Arg Ala Arg Leu Ser Phe Val Pro Glu Thr Pro Arg Ser Ser
        515                 520                 525
Asp Val Thr Val Asp Pro Ala Pro Leu Arg Pro Leu Asn Trp Asn Ser
    530                 535                 540
Arg Tyr Asp Cys Lys Cys Asp Tyr His Ala Gln Phe Asp Asn Ile Ser
545                 550                 555                 560
Asn Lys Cys Asp Glu Cys Glu Tyr Leu Asn Arg Gly Lys Asn Gly Cys
                565                 570                 575
Ile Cys His Asn Val Thr His Cys Gln Ile Cys His Gly Ile Pro Pro
            580                 585                 590
Trp Glu Lys Glu Asn Leu Ser Asp Phe Gly Asp Phe Asp Asp Ala Asn
        595                 600                 605
Lys Glu Gln
    610

<210> SEQ ID NO 64
<211> LENGTH: 611
<212> TYPE: PRT
<213> ORGANISM: Artificial
<220> FEATURE:
```

<223> OTHER INFORMATION: Chimeric Rep protein sequence

<400> SEQUENCE: 64

```
Met Pro Gly Phe Tyr Glu Ile Val Ile Lys Val Pro Ser Asp Leu Asp
1               5                   10                  15
Gly His Leu Pro Gly Ile Ser Asp Ser Phe Val Asn Trp Val Ala Glu
            20                  25                  30
Lys Glu Trp Glu Leu Pro Pro Asp Ser Asp Met Asp Leu Asn Leu Ile
        35                  40                  45
Glu Gln Ala Pro Leu Thr Val Ala Glu Lys Leu Gln Arg Asp Phe Leu
    50                  55                  60
Thr Glu Trp Arg Arg Val Ser Lys Ala Pro Glu Ala Leu Phe Phe Val
65                  70                  75                  80
Gln Phe Glu Lys Gly Glu Ser Tyr Phe His Met His Val Leu Val Glu
                85                  90                  95
Thr Ser Gly Ile Ser Ser Met Val Leu Gly Arg Tyr Val Ser Gln Ile
            100                 105                 110
Arg Ala Gln Leu Val Lys Val Val Phe Gln Gly Ile Glu Pro Gln Ile
        115                 120                 125
Asn Asp Trp Val Ala Ile Thr Lys Val Lys Lys Gly Gly Ala Asn Lys
    130                 135                 140
Val Val Asp Ser Gly Tyr Ile Pro Ala Tyr Leu Leu Pro Lys Val Gln
145                 150                 155                 160
Pro Glu Leu Gln Trp Ala Trp Thr Asn Leu Asp Glu Tyr Lys Leu Ala
                165                 170                 175
Ala Leu Asn Leu Glu Glu Arg Lys Arg Leu Val Ala Gln Phe Leu Ala
            180                 185                 190
Glu Ser Ser Gln Arg Ser Gln Glu Ala Ala Ser Gln Arg Glu Phe Ser
        195                 200                 205
Ala Asp Pro Val Ile Lys Ser Lys Thr Ser Gln Lys Tyr Met Ala Leu
    210                 215                 220
Val Asn Trp Leu Val Glu His Gly Ile Thr Ser Glu Lys Gln Trp Ile
225                 230                 235                 240
Gln Glu Asn Gln Glu Ser Tyr Leu Ser Phe Asn Ser Thr Gly Asn Ser
                245                 250                 255
Arg Ser Gln Ile Lys Ala Ala Leu Asp Asn Ala Thr Lys Ile Met Ser
            260                 265                 270
Leu Thr Lys Ser Ala Val Asp Tyr Leu Val Gly Ser Ser Val Pro Glu
        275                 280                 285
Asp Ile Ser Lys Asn Arg Ile Trp Gln Ile Phe Glu Met Asn Gly Tyr
    290                 295                 300
Asp Pro Ala Tyr Ala Gly Ser Ile Leu Tyr Gly Trp Cys Gln Arg Ser
305                 310                 315                 320
Phe Asn Lys Arg Asn Thr Val Trp Leu Tyr Gly Pro Ala Thr Thr Gly
                325                 330                 335
Lys Thr Asn Ile Ala Glu Ala Ile Ala His Thr Val Pro Phe Tyr Gly
            340                 345                 350
Cys Val Asn Trp Thr Asn Glu Asn Phe Pro Phe Asn Asp Cys Val Asp
        355                 360                 365
Lys Met Leu Ile Trp Trp Glu Glu Gly Lys Met Thr Asn Lys Val Val
    370                 375                 380
Glu Ser Ala Lys Ala Ile Leu Gly Gly Ser Lys Val Arg Val Asp Gln
385                 390                 395                 400
```

```
Lys Cys Lys Ser Ser Val Gln Ile Asp Ser Thr Pro Val Ile Val Thr
            405                 410                 415

Ser Asn Thr Asn Met Cys Val Val Asp Gly Asn Ser Thr Thr Phe
        420                 425                 430

Glu His Gln Gln Pro Leu Glu Asp Arg Met Phe Lys Phe Glu Leu Thr
            435                 440                 445

Lys Arg Leu Pro Pro Asp Phe Gly Lys Ile Thr Lys Gln Glu Val Lys
450                 455                 460

Asp Phe Phe Ala Trp Ala Lys Val Asn Gln Val Pro Val Thr His Glu
465                 470                 475                 480

Phe Lys Val Pro Arg Glu Leu Ala Gly Thr Lys Gly Ala Glu Lys Ser
                485                 490                 495

Leu Lys Arg Pro Leu Gly Asp Val Thr Asn Thr Ser Tyr Lys Ser Leu
            500                 505                 510

Glu Lys Arg Ala Arg Leu Ser Phe Val Pro Glu Thr Pro Arg Ser Ser
        515                 520                 525

Asp Val Thr Val Asp Pro Ala Pro Leu Arg Pro Leu Asn Trp Asn Ser
        530                 535                 540

Arg Tyr Asp Cys Lys Cys Asp Tyr His Ala Gln Phe Asp Asn Ile Ser
545                 550                 555                 560

Asn Lys Cys Asp Glu Cys Glu Tyr Leu Asn Arg Gly Lys Asn Gly Cys
                565                 570                 575

Ile Cys His Asn Val Thr His Cys Gln Ile Cys His Gly Ile Pro Pro
            580                 585                 590

Trp Glu Lys Glu Asn Leu Ser Asp Phe Gly Asp Phe Asp Asp Ala Asn
        595                 600                 605

Lys Glu Gln
    610

<210> SEQ ID NO 65
<211> LENGTH: 611
<212> TYPE: PRT
<213> ORGANISM: Artificial
<220> FEATURE:
<223> OTHER INFORMATION: Chimeric Rep protein sequence

<400> SEQUENCE: 65

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Val Lys Val Phe Gln Gly Ile Glu Pro Gln Ile
        115                 120                 125

Asn Asp Trp Val Ala Ile Thr Lys Val Lys Lys Gly Gly Ala Asn Lys
    130                 135                 140
```

-continued

Val Val Asp Ser Gly Tyr Ile Pro Ala Tyr Leu Leu Pro Lys Val Gln
145                 150                 155                 160

Pro Glu Leu Gln Trp Ala Trp Thr Asn Leu Asp Glu Tyr Lys Leu Ala
            165                 170                 175

Ala Leu Asn Leu Glu Glu Arg Lys Arg Leu Val Ala Gln Phe Leu Ala
        180                 185                 190

Glu Ser Ser Gln Arg Ser Gln Glu Ala Ala Ser Gln Arg Glu Phe Ser
    195                 200                 205

Ala Asp Pro Val Ile Lys Ser Lys Thr Ser Gln Lys Tyr Met Ala Leu
210                 215                 220

Val Asn Trp Leu Val Glu His Gly Ile Thr Ser Glu Lys Gln Trp Ile
225                 230                 235                 240

Gln Glu Asn Gln Glu Ser Tyr Leu Ser Phe Asn Ser Thr Gly Asn Ser
            245                 250                 255

Arg Ser Gln Ile Lys Ala Ala Leu Asp Asn Ala Thr Lys Ile Met Ser
        260                 265                 270

Leu Thr Lys Ser Ala Val Asp Tyr Leu Val Gly Ser Ser Val Pro Glu
    275                 280                 285

Asp Ile Ser Lys Asn Arg Ile Trp Gln Ile Phe Glu Met Asn Gly Tyr
290                 295                 300

Asp Pro Ala Tyr Ala Gly Ser Ile Leu Tyr Gly Trp Cys Gln Arg Ser
305                 310                 315                 320

Phe Asn Lys Arg Asn Thr Val Trp Leu Tyr Gly Pro Ala Thr Thr Gly
            325                 330                 335

Lys Thr Asn Ile Ala Glu Ala Ile Ala His Thr Val Pro Phe Tyr Gly
        340                 345                 350

Cys Val Asn Trp Thr Asn Glu Asn Phe Pro Phe Asn Asp Cys Val Asp
    355                 360                 365

Lys Met Leu Ile Trp Trp Glu Glu Gly Lys Met Thr Asn Lys Val Val
370                 375                 380

Glu Ser Ala Lys Ala Ile Leu Gly Gly Ser Lys Val Arg Val Asp Gln
385                 390                 395                 400

Lys Cys Lys Ser Ser Val Gln Ile Asp Ser Thr Pro Val Ile Val Thr
            405                 410                 415

Ser Asn Thr Asn Met Cys Val Val Asp Gly Asn Ser Thr Thr Phe
        420                 425                 430

Glu His Gln Gln Pro Leu Glu Asp Arg Met Phe Lys Phe Glu Leu Thr
    435                 440                 445

Lys Arg Leu Pro Pro Asp Phe Gly Lys Ile Thr Lys Gln Glu Val Lys
450                 455                 460

Asp Phe Phe Ala Trp Ala Lys Val Asn Gln Val Pro Val Thr His Glu
465                 470                 475                 480

Phe Lys Val Pro Arg Glu Leu Ala Gly Thr Lys Gly Ala Glu Lys Ser
            485                 490                 495

Leu Lys Arg Pro Leu Gly Asp Val Thr Asn Thr Ser Tyr Lys Ser Leu
        500                 505                 510

Glu Lys Arg Ala Arg Leu Ser Phe Val Pro Glu Thr Pro Arg Ser Ser
    515                 520                 525

Asp Val Thr Val Asp Pro Ala Pro Leu Arg Pro Leu Asn Trp Asn Ser
530                 535                 540

Arg Tyr Asp Cys Lys Cys Asp Tyr His Ala Gln Phe Asp Asn Ile Ser
545                 550                 555                 560

Asn Lys Cys Asp Glu Cys Glu Tyr Leu Asn Arg Gly Lys Asn Gly Cys

```
                        565                 570                 575
Ile Cys His Asn Val Thr His Cys Gln Ile Cys His Gly Ile Pro Pro
                    580                 585                 590

Trp Glu Lys Glu Asn Leu Ser Asp Phe Gly Asp Phe Asp Asp Ala Asn
                595                 600                 605

Lys Glu Gln
    610

<210> SEQ ID NO 66
<211> LENGTH: 611
<212> TYPE: PRT
<213> ORGANISM: Artificial
<220> FEATURE:
<223> OTHER INFORMATION: Chimeric Rep protein sequence

<400> SEQUENCE: 66

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Gln Ile
        115                 120                 125

Asn Asp Trp Val Ala Ile Thr Lys Val Lys Lys Gly Gly Ala Asn Lys
    130                 135                 140

Val Val Asp Ser Gly Tyr Ile Pro Ala Tyr Leu Leu Pro Lys Val Gln
145                 150                 155                 160

Pro Glu Leu Gln Trp Ala Trp Thr Asn Leu Asp Glu Tyr Lys Leu Ala
                165                 170                 175

Ala Leu Asn Leu Glu Glu Arg Lys Arg Leu Val Ala Gln Phe Leu Ala
            180                 185                 190

Glu Ser Ser Gln Arg Ser Gln Glu Ala Ala Ser Gln Arg Glu Phe Ser
        195                 200                 205

Ala Asp Pro Val Ile Lys Ser Lys Thr Ser Gln Lys Tyr Met Ala Leu
    210                 215                 220

Val Asn Trp Leu Val Glu His Gly Ile Thr Ser Glu Lys Gln Trp Ile
225                 230                 235                 240

Gln Glu Asn Gln Glu Ser Tyr Leu Ser Phe Asn Ser Thr Gly Asn Ser
                245                 250                 255

Arg Ser Gln Ile Lys Ala Ala Leu Asp Asn Ala Thr Lys Ile Met Ser
            260                 265                 270

Leu Thr Lys Ser Ala Val Asp Tyr Leu Val Gly Ser Ser Val Pro Glu
        275                 280                 285

Asp Ile Ser Lys Asn Arg Ile Trp Gln Ile Phe Glu Met Asn Gly Tyr
    290                 295                 300

Asp Pro Ala Tyr Ala Gly Ser Ile Leu Tyr Gly Trp Cys Gln Arg Ser
```

```
                305                 310                 315                 320
            Phe Asn Lys Arg Asn Thr Val Trp Leu Tyr Gly Pro Ala Thr Thr Gly
                        325                 330                 335

Lys Thr Asn Ile Ala Glu Ala Ile Ala His Thr Val Pro Phe Tyr Gly
                        340                 345                 350

Cys Val Asn Trp Thr Asn Glu Asn Phe Pro Phe Asn Asp Cys Val Asp
                        355                 360                 365

Lys Met Leu Ile Trp Trp Glu Glu Gly Lys Met Thr Asn Lys Val Val
                        370                 375                 380

Glu Ser Ala Lys Ala Ile Leu Gly Gly Ser Lys Val Arg Val Asp Gln
            385                 390                 395                 400

Lys Cys Lys Ser Ser Val Gln Ile Asp Ser Thr Pro Val Ile Val Thr
                        405                 410                 415

Ser Asn Thr Asn Met Cys Val Val Val Asp Gly Asn Ser Thr Thr Phe
                        420                 425                 430

Glu His Gln Gln Pro Leu Glu Asp Arg Met Phe Lys Phe Glu Leu Thr
                        435                 440                 445

Lys Arg Leu Pro Pro Asp Phe Gly Lys Ile Thr Lys Gln Glu Val Lys
                        450                 455                 460

Asp Phe Phe Ala Trp Ala Lys Val Asn Gln Val Pro Val Thr His Glu
            465                 470                 475                 480

Phe Lys Val Pro Arg Glu Leu Ala Gly Thr Lys Gly Ala Glu Lys Ser
                        485                 490                 495

Leu Lys Arg Pro Leu Gly Asp Val Thr Asn Thr Ser Tyr Lys Ser Leu
                        500                 505                 510

Glu Lys Arg Ala Arg Leu Ser Phe Val Pro Glu Thr Pro Arg Ser Ser
                        515                 520                 525

Asp Val Thr Val Asp Pro Ala Pro Leu Arg Pro Leu Asn Trp Asn Ser
                        530                 535                 540

Arg Tyr Asp Cys Lys Cys Asp Tyr His Ala Gln Phe Asp Asn Ile Ser
            545                 550                 555                 560

Asn Lys Cys Asp Glu Cys Glu Tyr Leu Asn Arg Gly Lys Asn Gly Cys
                        565                 570                 575

Ile Cys His Asn Val Thr His Cys Gln Ile Cys His Gly Ile Pro Pro
                        580                 585                 590

Trp Glu Lys Glu Asn Leu Ser Asp Phe Gly Asp Phe Asp Asp Ala Asn
                        595                 600                 605

Lys Glu Gln
                610

<210> SEQ ID NO 67
<211> LENGTH: 613
<212> TYPE: PRT
<213> ORGANISM: Artificial
<220> FEATURE:
<223> OTHER INFORMATION: Chimeric Rep protein sequence

<400> SEQUENCE: 67

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
```

```
                50                  55                  60
Thr Glu Trp Arg Arg Val Ser Lys Ala Pro Glu Ala Leu Phe Phe Val
 65                  70                  75                  80

Gln Phe Glu Lys Gly Glu Ser Tyr Phe His Met His Val Leu Val Glu
                 85                  90                  95

Thr Thr Gly Val Lys Ser Met Val Leu Gly Arg Phe Leu Ser Gln Ile
                100                 105                 110

Arg Glu Lys Leu Ile Gln Arg Ile Tyr Arg Gly Ile Glu Pro Thr Leu
                115                 120                 125

Pro Asn Trp Phe Ala Val Thr Lys Thr Arg Asn Gly Ala Gly Gly Ala
130                 135                 140

Asn Lys Val Val Asp Ser Gly Tyr Ile Pro Ala Tyr Leu Leu Pro Lys
145                 150                 155                 160

Val Gln Pro Glu Leu Gln Trp Ala Trp Thr Asn Leu Asp Glu Tyr Lys
                165                 170                 175

Leu Ala Ala Leu Asn Leu Glu Glu Arg Lys Arg Leu Val Ala Gln Phe
                180                 185                 190

Leu Ala Glu Ser Ser Gln Arg Ser Gln Glu Ala Ala Ser Gln Arg Glu
                195                 200                 205

Phe Ser Ala Asp Pro Val Ile Lys Ser Lys Thr Ser Gln Lys Tyr Met
210                 215                 220

Ala Leu Val Asn Trp Leu Val Glu His Gly Ile Thr Ser Glu Lys Gln
225                 230                 235                 240

Trp Ile Gln Glu Asn Gln Glu Ser Tyr Leu Ser Phe Asn Ser Thr Gly
                245                 250                 255

Asn Ser Arg Ser Gln Ile Lys Ala Ala Leu Asp Asn Ala Thr Lys Ile
                260                 265                 270

Met Ser Leu Thr Lys Ser Ala Val Asp Tyr Leu Val Gly Ser Ser Val
                275                 280                 285

Pro Glu Asp Ile Ser Lys Asn Arg Ile Trp Gln Ile Phe Glu Met Asn
                290                 295                 300

Gly Tyr Asp Pro Ala Tyr Ala Gly Ser Ile Leu Tyr Gly Trp Cys Gln
305                 310                 315                 320

Arg Ser Phe Asn Lys Arg Asn Thr Val Trp Leu Tyr Gly Pro Ala Thr
                325                 330                 335

Thr Gly Lys Thr Asn Ile Ala Glu Ala Ile Ala His Thr Val Pro Phe
                340                 345                 350

Tyr Gly Cys Val Asn Trp Thr Asn Glu Asn Phe Pro Phe Asn Asp Cys
                355                 360                 365

Val Asp Lys Met Leu Ile Trp Trp Glu Glu Gly Lys Met Thr Asn Lys
370                 375                 380

Val Val Glu Ser Ala Lys Ala Ile Leu Gly Gly Ser Lys Val Arg Val
385                 390                 395                 400

Asp Gln Lys Cys Lys Ser Ser Val Gln Ile Asp Ser Thr Pro Val Ile
                405                 410                 415

Val Thr Ser Asn Thr Asn Met Cys Val Val Asp Gly Asn Ser Thr
                420                 425                 430

Thr Phe Glu His Gln Gln Pro Leu Glu Asp Arg Met Phe Lys Phe Glu
                435                 440                 445

Leu Thr Lys Arg Leu Pro Pro Asp Phe Gly Lys Ile Thr Lys Gln Glu
                450                 455                 460

Val Lys Asp Phe Phe Ala Trp Ala Lys Val Asn Gln Val Pro Val Thr
465                 470                 475                 480
```

-continued

```
His Glu Phe Lys Val Pro Arg Glu Leu Ala Gly Thr Lys Gly Ala Glu
            485                 490                 495

Lys Ser Leu Lys Arg Pro Leu Gly Asp Val Thr Asn Thr Ser Tyr Lys
            500                 505                 510

Ser Leu Glu Lys Arg Ala Arg Leu Ser Phe Val Pro Glu Thr Pro Arg
            515                 520                 525

Ser Ser Asp Val Thr Val Asp Pro Ala Pro Leu Arg Pro Leu Asn Trp
            530                 535                 540

Asn Ser Arg Tyr Asp Cys Lys Cys Asp Tyr His Ala Gln Phe Asp Asn
545                 550                 555                 560

Ile Ser Asn Lys Cys Asp Glu Cys Glu Tyr Leu Asn Arg Gly Lys Asn
            565                 570                 575

Gly Cys Ile Cys His Asn Val Thr His Cys Gln Ile Cys His Gly Ile
            580                 585                 590

Pro Pro Trp Glu Lys Glu Asn Leu Ser Asp Phe Gly Asp Phe Asp Asp
            595                 600                 605

Ala Asn Lys Glu Gln
            610

<210> SEQ ID NO 68
<211> LENGTH: 613
<212> TYPE: PRT
<213> ORGANISM: Artificial
<220> FEATURE:
<223> OTHER INFORMATION: Chimeric Rep protein sequence

<400> SEQUENCE: 68

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
            85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
            115                 120                 125

Pro Asn Trp Phe Ala Val Thr Lys Thr Arg Asn Gly Ala Gly Gly Gly
            130                 135                 140

Asn Lys Val Val Asp Ser Gly Tyr Ile Pro Ala Tyr Leu Leu Pro Lys
145                 150                 155                 160

Val Gln Pro Glu Leu Gln Trp Ala Trp Thr Asn Leu Asp Glu Tyr Lys
            165                 170                 175

Leu Ala Ala Leu Asn Leu Glu Glu Arg Lys Arg Leu Val Ala Gln Phe
            180                 185                 190

Leu Ala Glu Ser Ser Gln Arg Ser Gln Glu Ala Ala Ser Gln Arg Glu
            195                 200                 205

Phe Ser Ala Asp Pro Val Ile Lys Ser Lys Thr Ser Gln Lys Tyr Met
            210                 215                 220
```

-continued

Ala Leu Val Asn Trp Leu Val Glu His Gly Ile Thr Ser Glu Lys Gln
225                 230                 235                 240

Trp Ile Gln Glu Asn Gln Glu Ser Tyr Leu Ser Phe Asn Ser Thr Gly
            245                 250                 255

Asn Ser Arg Ser Gln Ile Lys Ala Ala Leu Asp Asn Ala Thr Lys Ile
        260                 265                 270

Met Ser Leu Thr Lys Ser Ala Val Asp Tyr Leu Val Gly Ser Ser Val
    275                 280                 285

Pro Glu Asp Ile Ser Lys Asn Arg Ile Trp Gln Ile Phe Glu Met Asn
290                 295                 300

Gly Tyr Asp Pro Ala Tyr Ala Gly Ser Ile Leu Tyr Gly Trp Cys Gln
305                 310                 315                 320

Arg Ser Phe Asn Lys Arg Asn Thr Val Trp Leu Tyr Gly Pro Ala Thr
            325                 330                 335

Thr Gly Lys Thr Asn Ile Ala Glu Ala Ile Ala His Thr Val Pro Phe
        340                 345                 350

Tyr Gly Cys Val Asn Trp Thr Asn Glu Asn Phe Pro Phe Asn Asp Cys
    355                 360                 365

Val Asp Lys Met Leu Ile Trp Trp Glu Glu Gly Lys Met Thr Asn Lys
370                 375                 380

Val Val Glu Ser Ala Lys Ala Ile Leu Gly Gly Ser Lys Val Arg Val
385                 390                 395                 400

Asp Gln Lys Cys Lys Ser Ser Val Gln Ile Asp Ser Thr Pro Val Ile
            405                 410                 415

Val Thr Ser Asn Thr Asn Met Cys Val Val Asp Gly Asn Ser Thr
        420                 425                 430

Thr Phe Glu His Gln Gln Pro Leu Glu Asp Arg Met Phe Lys Phe Glu
    435                 440                 445

Leu Thr Lys Arg Leu Pro Pro Asp Phe Gly Lys Ile Thr Lys Gln Glu
450                 455                 460

Val Lys Asp Phe Phe Ala Trp Ala Lys Val Asn Gln Val Pro Val Thr
465                 470                 475                 480

His Glu Phe Lys Val Pro Arg Glu Leu Ala Gly Thr Lys Gly Ala Glu
            485                 490                 495

Lys Ser Leu Lys Arg Pro Leu Gly Asp Val Thr Asn Thr Ser Tyr Lys
        500                 505                 510

Ser Leu Glu Lys Arg Ala Arg Leu Ser Phe Val Pro Glu Thr Pro Arg
    515                 520                 525

Ser Ser Asp Val Thr Val Asp Pro Ala Pro Leu Arg Pro Leu Asn Trp
530                 535                 540

Asn Ser Arg Tyr Asp Cys Lys Cys Asp Tyr His Ala Gln Phe Asp Asn
545                 550                 555                 560

Ile Ser Asn Lys Cys Asp Glu Cys Glu Tyr Leu Asn Arg Gly Lys Asn
            565                 570                 575

Gly Cys Ile Cys His Asn Val Thr His Cys Gln Ile Cys His Gly Ile
        580                 585                 590

Pro Pro Trp Glu Lys Glu Asn Leu Ser Asp Phe Gly Asp Phe Asp Asp
    595                 600                 605

Ala Asn Lys Glu Gln
610

<210> SEQ ID NO 69
<211> LENGTH: 613

```
<212> TYPE: PRT
<213> ORGANISM: Artificial
<220> FEATURE:
<223> OTHER INFORMATION: Chimeric Rep protein sequence

<400> SEQUENCE: 69
```

| | | | | | | | | | | | | | | |
|---|---|---|---|---|---|---|---|---|---|---|---|---|---|---|
| Met | Pro | Gly | Phe | Tyr | Glu | Ile | Val | Ile | Lys | Val | Pro | Ser | Asp | Leu | Asp |
| 1 | | | | 5 | | | | | 10 | | | | | 15 | |
| Gly | His | Leu | Pro | Gly | Ile | Ser | Asp | Ser | Phe | Val | Asn | Trp | Val | Ala | Glu |
| | | | 20 | | | | | 25 | | | | | 30 | | |
| Lys | Glu | Trp | Glu | Leu | Pro | Pro | Asp | Ser | Asp | Met | Asp | Leu | Asn | Leu | Ile |
| | | | 35 | | | | | 40 | | | | | 45 | | |
| Glu | Gln | Ala | Pro | Leu | Thr | Val | Ala | Glu | Lys | Leu | Gln | Arg | Asp | Phe | Leu |
| | 50 | | | | | 55 | | | | | 60 | | | | |
| Thr | Glu | Trp | Arg | Arg | Val | Ser | Lys | Ala | Pro | Glu | Ala | Leu | Phe | Phe | Val |
| 65 | | | | | 70 | | | | | 75 | | | | | 80 |
| Gln | Phe | Glu | Lys | Gly | Glu | Ser | Tyr | Phe | His | Met | His | Val | Leu | Val | Glu |
| | | | | 85 | | | | | 90 | | | | | 95 | |
| Thr | Thr | Gly | Val | Lys | Ser | Met | Val | Leu | Gly | Arg | Phe | Leu | Ser | Gln | Ile |
| | | | 100 | | | | | 105 | | | | | 110 | | |
| Arg | Glu | Lys | Leu | Ile | Gln | Arg | Ile | Tyr | Arg | Gly | Ile | Glu | Pro | Thr | Leu |
| | | | 115 | | | | | 120 | | | | | 125 | | |
| Pro | Asn | Trp | Phe | Ala | Val | Thr | Lys | Thr | Arg | Asn | Gly | Ala | Gly | Gly | Gly |
| | 130 | | | | | 135 | | | | | 140 | | | | |
| Asn | Lys | Val | Val | Asp | Glu | Cys | Tyr | Ile | Pro | Asn | Tyr | Leu | Leu | Pro | Lys |
| 145 | | | | | 150 | | | | | 155 | | | | | 160 |
| Thr | Gln | Pro | Glu | Leu | Gln | Trp | Ala | Trp | Thr | Asn | Leu | Asp | Glu | Tyr | Lys |
| | | | | 165 | | | | | 170 | | | | | 175 | |
| Leu | Ala | Ala | Leu | Asn | Leu | Glu | Glu | Arg | Lys | Arg | Leu | Val | Ala | Gln | Phe |
| | | | 180 | | | | | 185 | | | | | 190 | | |
| Leu | Ala | Glu | Ser | Ser | Gln | Arg | Ser | Gln | Glu | Ala | Ala | Ser | Gln | Arg | Glu |
| | | | 195 | | | | | 200 | | | | | 205 | | |
| Phe | Ser | Ala | Asp | Pro | Val | Ile | Lys | Ser | Lys | Thr | Ser | Gln | Lys | Tyr | Met |
| | 210 | | | | | 215 | | | | | 220 | | | | |
| Ala | Leu | Val | Asn | Trp | Leu | Val | Glu | His | Gly | Ile | Thr | Ser | Glu | Lys | Gln |
| 225 | | | | | 230 | | | | | 235 | | | | | 240 |
| Trp | Ile | Gln | Glu | Asn | Gln | Glu | Ser | Tyr | Leu | Ser | Phe | Asn | Ser | Thr | Gly |
| | | | | 245 | | | | | 250 | | | | | 255 | |
| Asn | Ser | Arg | Ser | Gln | Ile | Lys | Ala | Ala | Leu | Asp | Asn | Ala | Thr | Lys | Ile |
| | | | 260 | | | | | 265 | | | | | 270 | | |
| Met | Ser | Leu | Thr | Lys | Ser | Ala | Val | Asp | Tyr | Leu | Val | Gly | Ser | Ser | Val |
| | | | 275 | | | | | 280 | | | | | 285 | | |
| Pro | Glu | Asp | Ile | Ser | Lys | Asn | Arg | Ile | Trp | Gln | Ile | Phe | Glu | Met | Asn |
| | 290 | | | | | 295 | | | | | 300 | | | | |
| Gly | Tyr | Asp | Pro | Ala | Tyr | Ala | Gly | Ser | Ile | Leu | Tyr | Gly | Trp | Cys | Gln |
| 305 | | | | | 310 | | | | | 315 | | | | | 320 |
| Arg | Ser | Phe | Asn | Lys | Arg | Asn | Thr | Val | Trp | Leu | Tyr | Gly | Pro | Ala | Thr |
| | | | | 325 | | | | | 330 | | | | | 335 | |
| Thr | Gly | Lys | Thr | Asn | Ile | Ala | Glu | Ala | Ile | Ala | His | Thr | Val | Pro | Phe |
| | | | 340 | | | | | 345 | | | | | 350 | | |
| Tyr | Gly | Cys | Val | Asn | Trp | Thr | Asn | Glu | Asn | Phe | Pro | Phe | Asn | Asp | Cys |
| | | | 355 | | | | | 360 | | | | | 365 | | |
| Val | Asp | Lys | Met | Leu | Ile | Trp | Trp | Glu | Glu | Gly | Lys | Met | Thr | Asn | Lys |
| | 370 | | | | | 375 | | | | | 380 | | | | |

-continued

```
Val Val Glu Ser Ala Lys Ala Ile Leu Gly Gly Ser Lys Val Arg Val
385                 390                 395                 400

Asp Gln Lys Cys Lys Ser Ser Val Gln Ile Asp Ser Thr Pro Val Ile
            405                 410                 415

Val Thr Ser Asn Thr Asn Met Cys Val Val Asp Gly Asn Ser Thr
        420                 425                 430

Thr Phe Glu His Gln Gln Pro Leu Glu Asp Arg Met Phe Lys Phe Glu
        435                 440                 445

Leu Thr Lys Arg Leu Pro Pro Asp Phe Gly Lys Ile Thr Lys Gln Glu
        450                 455                 460

Val Lys Asp Phe Phe Ala Trp Ala Lys Val Asn Gln Val Pro Val Thr
465                 470                 475                 480

His Glu Phe Lys Val Pro Arg Glu Leu Ala Gly Thr Lys Gly Ala Glu
            485                 490                 495

Lys Ser Leu Lys Arg Pro Leu Gly Asp Val Thr Asn Thr Ser Tyr Lys
        500                 505                 510

Ser Leu Glu Lys Arg Ala Arg Leu Ser Phe Val Pro Glu Thr Pro Arg
        515                 520                 525

Ser Ser Asp Val Thr Val Asp Pro Ala Pro Leu Arg Pro Leu Asn Trp
530                 535                 540

Asn Ser Arg Tyr Asp Cys Lys Cys Asp Tyr His Ala Gln Phe Asp Asn
545                 550                 555                 560

Ile Ser Asn Lys Cys Asp Glu Cys Glu Tyr Leu Asn Arg Gly Lys Asn
            565                 570                 575

Gly Cys Ile Cys His Asn Val Thr His Cys Gln Ile Cys His Gly Ile
        580                 585                 590

Pro Pro Trp Glu Lys Glu Asn Leu Ser Asp Phe Gly Asp Phe Asp Asp
        595                 600                 605

Ala Asn Lys Glu Gln
610

<210> SEQ ID NO 70
<211> LENGTH: 613
<212> TYPE: PRT
<213> ORGANISM: Artificial
<220> FEATURE:
<223> OTHER INFORMATION: Chimeric Rep protein sequence

<400> SEQUENCE: 70

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125
```

```
Pro Asn Trp Phe Ala Val Thr Lys Thr Arg Asn Gly Ala Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln Phe
            180                 185                 190

Leu Ala Glu Ser Ser Gln Arg Ser Gln Glu Ala Ala Ser Gln Arg Glu
                195                 200                 205

Phe Ser Ala Asp Pro Val Ile Lys Ser Lys Thr Ser Gln Lys Tyr Met
210                 215                 220

Ala Leu Val Asn Trp Leu Val Glu His Gly Ile Thr Ser Glu Lys Gln
225                 230                 235                 240

Trp Ile Gln Glu Asn Gln Glu Ser Tyr Leu Ser Phe Asn Ser Thr Gly
                245                 250                 255

Asn Ser Arg Ser Gln Ile Lys Ala Ala Leu Asp Asn Ala Thr Lys Ile
            260                 265                 270

Met Ser Leu Thr Lys Ser Ala Val Asp Tyr Leu Val Gly Ser Ser Val
        275                 280                 285

Pro Glu Asp Ile Ser Lys Asn Arg Ile Trp Gln Ile Phe Glu Met Asn
    290                 295                 300

Gly Tyr Asp Pro Ala Tyr Ala Gly Ser Ile Leu Tyr Gly Trp Cys Gln
305                 310                 315                 320

Arg Ser Phe Asn Lys Arg Asn Thr Val Trp Leu Tyr Gly Pro Ala Thr
                325                 330                 335

Thr Gly Lys Thr Asn Ile Ala Glu Ala Ile Ala His Thr Val Pro Phe
            340                 345                 350

Tyr Gly Cys Val Asn Trp Thr Asn Glu Asn Phe Pro Phe Asn Asp Cys
        355                 360                 365

Val Asp Lys Met Leu Ile Trp Trp Glu Glu Gly Lys Met Thr Asn Lys
    370                 375                 380

Val Val Glu Ser Ala Lys Ala Ile Leu Gly Gly Ser Lys Val Arg Val
385                 390                 395                 400

Asp Gln Lys Cys Lys Ser Ser Val Gln Ile Asp Ser Thr Pro Val Ile
                405                 410                 415

Val Thr Ser Asn Thr Asn Met Cys Val Val Asp Gly Asn Ser Thr
            420                 425                 430

Thr Phe Glu His Gln Gln Pro Leu Glu Asp Arg Met Phe Lys Phe Glu
        435                 440                 445

Leu Thr Lys Arg Leu Pro Pro Asp Phe Gly Lys Ile Thr Lys Gln Glu
    450                 455                 460

Val Lys Asp Phe Phe Ala Trp Ala Lys Val Asn Gln Val Pro Val Thr
465                 470                 475                 480

His Glu Phe Lys Val Pro Arg Glu Leu Ala Gly Thr Lys Gly Ala Glu
                485                 490                 495

Lys Ser Leu Lys Arg Pro Leu Gly Asp Val Thr Asn Thr Ser Tyr Lys
            500                 505                 510

Ser Leu Glu Lys Arg Ala Arg Leu Ser Phe Val Pro Glu Thr Pro Arg
        515                 520                 525

Ser Ser Asp Val Thr Val Asp Pro Ala Pro Leu Arg Pro Leu Asn Trp
    530                 535                 540

Asn Ser Arg Tyr Asp Cys Lys Cys Asp Tyr His Ala Gln Phe Asp Asn
```

```
                545                 550                 555                 560
        Ile Ser Asn Lys Cys Asp Glu Cys Glu Tyr Leu Asn Arg Gly Lys Asn
                            565                 570                 575
        Gly Cys Ile Cys His Asn Val Thr His Cys Gln Ile Cys His Gly Ile
                            580                 585                 590
        Pro Pro Trp Glu Lys Glu Asn Leu Ser Asp Phe Gly Asp Phe Asp Asp
                            595                 600                 605
        Ala Asn Lys Glu Gln
                            610

<210> SEQ ID NO 71
<211> LENGTH: 614
<212> TYPE: PRT
<213> ORGANISM: Artificial
<220> FEATURE:
<223> OTHER INFORMATION: Chimeric Rep protein sequence

<400> SEQUENCE: 71

Met Pro Gly Phe Tyr Glu Ile Val Ile Lys Val Pro Ser Asp Leu Asp
        1               5                   10                  15

Gly His Leu Pro Gly Ile Ser Asp Ser Phe Val Asn Trp Val Ala Glu
                            20                  25                  30

Lys Glu Trp Glu Leu Pro Pro Asp Ser Asp Met Asp Leu Asn Leu Ile
                            35                  40                  45

Glu Gln Ala Pro Leu Thr Val Ala Glu Lys Leu Gln Arg Asp Phe Leu
                    50                  55                  60

Thr Glu Trp Arg Arg Val Ser Lys Ala Pro Glu Ala Leu Phe Phe Val
        65                  70                  75                  80

Gln Phe Glu Lys Gly Glu Ser Tyr Phe His Met His Val Leu Val Glu
                            85                  90                  95

Thr Thr Gly Val Lys Ser Met Val Leu Gly Arg Phe Leu Ser Gln Ile
                            100                 105                 110

Arg Glu Lys Leu Ile Gln Arg Ile Tyr Arg Gly Ile Glu Pro Thr Leu
                            115                 120                 125

Pro Asn Trp Phe Ala Val Thr Lys Thr Arg Asn Gly Ala Gly Gly Gly
                    130                 135                 140

Asn Lys Val Val Asp Glu Cys Tyr Ile Pro Asn Tyr Leu Leu Pro Lys
        145                 150                 155                 160

Thr Gln Pro Glu Leu Gln Trp Ala Trp Thr Asn Met Glu Gln Tyr Leu
                            165                 170                 175

Ser Ala Cys Leu Asn Leu Thr Glu Arg Lys Arg Leu Val Ala Gln His
                            180                 185                 190

Leu Thr His Val Ser Gln Thr Gln Glu Gln Asn Lys Glu Asn Gln Asn
                            195                 200                 205

Pro Asn Ser Asp Ala Pro Val Ile Lys Ser Lys Thr Ser Gln Lys Tyr
                    210                 215                 220

Met Ala Leu Val Asn Trp Leu Val Glu His Gly Ile Thr Ser Glu Lys
        225                 230                 235                 240

Gln Trp Ile Gln Glu Asn Gln Glu Ser Tyr Leu Ser Phe Asn Ser Thr
                            245                 250                 255

Gly Asn Ser Arg Ser Gln Ile Lys Ala Ala Leu Asp Asn Ala Thr Lys
                            260                 265                 270

Ile Met Ser Leu Thr Lys Ser Ala Val Asp Tyr Leu Val Gly Ser Ser
                            275                 280                 285

Val Pro Glu Asp Ile Ser Lys Asn Arg Ile Trp Gln Ile Phe Glu Met
```

```
            290                 295                 300
Asn Gly Tyr Asp Pro Ala Tyr Ala Gly Ser Ile Leu Tyr Gly Trp Cys
305                 310                 315                 320

Gln Arg Ser Phe Asn Lys Arg Asn Thr Val Trp Leu Tyr Gly Pro Ala
                325                 330                 335

Thr Thr Gly Lys Thr Asn Ile Ala Glu Ala Ile Ala His Thr Val Pro
                340                 345                 350

Phe Tyr Gly Cys Val Asn Trp Thr Asn Glu Asn Phe Pro Phe Asn Asp
                355                 360                 365

Cys Val Asp Lys Met Leu Ile Trp Trp Glu Glu Gly Lys Met Thr Asn
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Val Gln Ile Asp Ser Thr Pro Val
                405                 410                 415

Ile Val Thr Ser Asn Thr Asn Met Cys Val Val Val Asp Gly Asn Ser
                420                 425                 430

Thr Thr Phe Glu His Gln Gln Pro Leu Glu Asp Arg Met Phe Lys Phe
                435                 440                 445

Glu Leu Thr Lys Arg Leu Pro Pro Asp Phe Gly Lys Ile Thr Lys Gln
450                 455                 460

Glu Val Lys Asp Phe Phe Ala Trp Ala Lys Val Asn Gln Val Pro Val
465                 470                 475                 480

Thr His Glu Phe Lys Val Pro Arg Glu Leu Ala Gly Thr Lys Gly Ala
                485                 490                 495

Glu Lys Ser Leu Lys Arg Pro Leu Gly Asp Val Thr Asn Thr Ser Tyr
                500                 505                 510

Lys Ser Leu Glu Lys Arg Ala Arg Leu Ser Phe Val Pro Glu Thr Pro
                515                 520                 525

Arg Ser Ser Asp Val Thr Val Asp Pro Ala Pro Leu Arg Pro Leu Asn
530                 535                 540

Trp Asn Ser Arg Tyr Asp Cys Lys Cys Asp Tyr His Ala Gln Phe Asp
545                 550                 555                 560

Asn Ile Ser Asn Lys Cys Asp Glu Cys Glu Tyr Leu Asn Arg Gly Lys
                565                 570                 575

Asn Gly Cys Ile Cys His Asn Val Thr His Cys Gln Ile Cys His Gly
                580                 585                 590

Ile Pro Pro Trp Glu Lys Glu Asn Leu Ser Asp Phe Gly Asp Phe Asp
                595                 600                 605

Asp Ala Asn Lys Glu Gln
610

<210> SEQ ID NO 72
<211> LENGTH: 612
<212> TYPE: PRT
<213> ORGANISM: Artificial
<220> FEATURE:
<223> OTHER INFORMATION: Chimeric Rep protein sequence

<400> SEQUENCE: 72

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
                20                  25                  30

Gln Ile Trp Glu Leu Pro Pro Glu Ser Asp Leu Asn Leu Thr Leu Val
```

```
            35                  40                  45
Glu Gln Pro Gln Leu Thr Val Ala Asp Arg Ile Arg Arg Val Phe Leu
 50                  55                  60

Tyr Glu Trp Asn Lys Phe Ser Lys Gln Glu Ser Lys Phe Phe Val Gln
 65                  70                  75                  80

Phe Glu Lys Gly Ser Glu Tyr Phe His Leu His Thr Leu Val Glu Thr
                 85                  90                  95

Ser Gly Ile Ser Ser Met Val Leu Gly Arg Tyr Val Ser Gln Ile Arg
                100                 105                 110

Glu Lys Leu Ile Gln Arg Ile Tyr Arg Gly Ile Glu Pro Thr Leu Pro
            115                 120                 125

Asn Trp Phe Ala Val Thr Lys Thr Arg Asn Gly Ala Gly Gly Gly Asn
            130                 135                 140

Lys Val Val Asp Ser Gly Tyr Ile Pro Ala Tyr Leu Leu Pro Lys Val
145                 150                 155                 160

Gln Pro Glu Leu Gln Trp Ala Trp Thr Asn Leu Asp Glu Tyr Lys Leu
                165                 170                 175

Ala Ala Leu Asn Leu Glu Glu Arg Lys Arg Leu Val Ala Gln Phe Leu
            180                 185                 190

Ala Glu Ser Ser Gln Arg Ser Gln Glu Ala Ala Ser Gln Arg Glu Phe
            195                 200                 205

Ser Ala Asp Pro Val Ile Lys Ser Lys Thr Ser Gln Lys Tyr Met Ala
210                 215                 220

Leu Val Asn Trp Leu Val Glu His Gly Ile Thr Ser Glu Lys Gln Trp
225                 230                 235                 240

Ile Gln Glu Asn Gln Glu Ser Tyr Leu Ser Phe Asn Ser Thr Gly Asn
                245                 250                 255

Ser Arg Ser Gln Ile Lys Ala Ala Leu Asp Asn Ala Thr Lys Ile Met
            260                 265                 270

Ser Leu Thr Lys Ser Ala Val Asp Tyr Leu Val Gly Ser Ser Val Pro
            275                 280                 285

Glu Asp Ile Ser Lys Asn Arg Ile Trp Gln Ile Phe Glu Met Asn Gly
290                 295                 300

Tyr Asp Pro Ala Tyr Ala Gly Ser Ile Leu Tyr Gly Trp Cys Gln Arg
305                 310                 315                 320

Ser Phe Asn Lys Arg Asn Thr Val Trp Leu Tyr Gly Pro Ala Thr Thr
                325                 330                 335

Gly Lys Thr Asn Ile Ala Glu Ala Ile Ala His Thr Val Pro Phe Tyr
            340                 345                 350

Gly Cys Val Asn Trp Thr Asn Glu Asn Phe Pro Phe Asn Asp Cys Val
            355                 360                 365

Asp Lys Met Leu Ile Trp Trp Glu Glu Gly Lys Met Thr Asn Lys Val
            370                 375                 380

Val Glu Ser Ala Lys Ala Ile Leu Gly Gly Ser Lys Val Arg Val Asp
385                 390                 395                 400

Gln Lys Cys Lys Ser Ser Val Gln Ile Asp Ser Thr Pro Val Ile Val
                405                 410                 415

Thr Ser Asn Thr Asn Met Cys Val Val Val Asp Gly Asn Ser Thr Thr
            420                 425                 430

Phe Glu His Gln Gln Pro Leu Glu Asp Arg Met Phe Lys Phe Glu Leu
            435                 440                 445

Thr Lys Arg Leu Pro Pro Asp Phe Gly Lys Ile Thr Lys Gln Glu Val
450                 455                 460
```

```
Lys Asp Phe Phe Ala Trp Ala Lys Val Asn Gln Val Pro Val Thr His
465                 470                 475                 480

Glu Phe Lys Val Pro Arg Glu Leu Ala Gly Thr Lys Gly Ala Glu Lys
            485                 490                 495

Ser Leu Lys Arg Pro Leu Gly Asp Val Thr Asn Thr Ser Tyr Lys Ser
            500                 505                 510

Leu Glu Lys Arg Ala Arg Leu Ser Phe Val Pro Glu Thr Pro Arg Ser
            515                 520                 525

Ser Asp Val Thr Val Asp Pro Ala Pro Leu Arg Pro Leu Asn Trp Asn
            530                 535                 540

Ser Arg Tyr Asp Cys Lys Cys Asp Tyr His Ala Gln Phe Asp Asn Ile
545                 550                 555                 560

Ser Asn Lys Cys Asp Glu Cys Glu Tyr Leu Asn Arg Gly Lys Asn Gly
            565                 570                 575

Cys Ile Cys His Asn Val Thr His Cys Gln Ile Cys His Gly Ile Pro
            580                 585                 590

Pro Trp Glu Lys Glu Asn Leu Ser Asp Phe Gly Asp Phe Asp Asp Ala
            595                 600                 605

Asn Lys Glu Gln
        610

<210> SEQ ID NO 73
<211> LENGTH: 610
<212> TYPE: PRT
<213> ORGANISM: Artificial
<220> FEATURE:
<223> OTHER INFORMATION: Chimeric Rep protein sequence

<400> SEQUENCE: 73

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Phe Gln Gly Ile Glu Pro Gln Ile Asn
            115                 120                 125

Asp Trp Val Ala Ile Thr Lys Val Lys Gly Gly Ala Asn Lys Val
        130                 135                 140

Val Asp Glu Cys Tyr Ile Pro Asn Tyr Leu Leu Pro Lys Thr Gln Pro
145                 150                 155                 160

Glu Leu Gln Trp Ala Trp Thr Asn Met Glu Gln Tyr Leu Ser Ala Cys
                165                 170                 175

Leu Asn Leu Thr Glu Arg Lys Arg Leu Val Ala Gln Phe Leu Ala Glu
            180                 185                 190

Ser Ser Gln Arg Ser Gln Glu Ala Ala Ser Gln Arg Glu Phe Ser Ala
        195                 200                 205
```

Asp Pro Val Ile Lys Ser Lys Thr Ser Gln Lys Tyr Met Ala Leu Val
    210                 215                 220

Asn Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
                245                 250                 255

Ser Gln Ile Lys Ala Ala Leu Asp Asn Ala Thr Lys Ile Met Ser Leu
            260                 265                 270

Thr Lys Ser Ala Val Asp Tyr Leu Val Gly Ser Ser Val Pro Glu Asp
        275                 280                 285

Ile Ser Lys Asn Arg Ile Trp Gln Ile Phe Glu Met Asn Gly Tyr Asp
    290                 295                 300

Pro Ala Tyr Ala Gly Ser Ile Leu Tyr Gly Trp Cys Gln Arg Ser Phe
305                 310                 315                 320

Asn Lys Arg Asn Thr Val Trp Leu Tyr Gly Pro Ala Thr Thr Gly Lys
                325                 330                 335

Thr Asn Ile Ala Glu Ala Ile Ala His Thr Val Pro Phe Tyr Gly Cys
            340                 345                 350

Val Asn Trp Thr Asn Glu Asn Phe Pro Phe Asn Asp Cys Val Asp Lys
        355                 360                 365

Met Leu Ile Trp Trp Glu Glu Gly Lys Met Thr Asn Lys Val Val Glu
    370                 375                 380

Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
                405                 410                 415

Asn Thr Asn Met Cys Val Val Asp Gly Asn Ser Thr Thr Phe Glu
            420                 425                 430

His Gln Gln Pro Leu Glu Asp Arg Met Phe Lys Phe Glu Leu Thr Lys
        435                 440                 445

Arg Leu Pro Pro Asp Phe Gly Lys Ile Thr Lys Gln Glu Val Lys Asp
    450                 455                 460

Phe Phe Ala Trp Ala Lys Val Asn Gln Val Pro Val Thr His Glu Phe
465                 470                 475                 480

Lys Val Pro Arg Glu Leu Ala Gly Thr Lys Gly Ala Glu Lys Ser Leu
                485                 490                 495

Lys Arg Pro Leu Gly Asp Val Thr Asn Thr Ser Tyr Lys Ser Leu Glu
            500                 505                 510

Lys Arg Ala Arg Leu Ser Phe Val Pro Glu Thr Pro Arg Ser Ser Asp
        515                 520                 525

Val Thr Val Asp Pro Ala Pro Leu Arg Pro Leu Asn Trp Asn Ser Arg
    530                 535                 540

Tyr Asp Cys Lys Cys Asp Tyr His Ala Gln Phe Asp Asn Ile Ser Asn
545                 550                 555                 560

Lys Cys Asp Glu Cys Glu Tyr Leu Asn Arg Gly Lys Asn Gly Cys Ile
                565                 570                 575

Cys His Asn Val Thr His Cys Gln Ile Cys His Gly Ile Pro Pro Trp
            580                 585                 590

Glu Lys Glu Asn Leu Ser Asp Phe Gly Asp Phe Asp Asp Ala Asn Lys
        595                 600                 605

Glu Gln
    610

<210> SEQ ID NO 74
<211> LENGTH: 612
<212> TYPE: PRT
<213> ORGANISM: Artificial
<220> FEATURE:
<223> OTHER INFORMATION: Chimeric Rep protein sequence

<400> SEQUENCE: 74

```
Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Glu Lys Leu Ile Gln Arg Ile Tyr Arg Gly Ile Glu Pro Thr Leu Pro
        115                 120                 125

Asn Trp Phe Ala Val Thr Lys Thr Arg Asn Gly Ala Gly Gly Gly Asn
130                 135                 140

Lys Val Val Asp Glu Cys Tyr Ile Pro Asn Tyr Leu Leu Pro Lys Thr
145                 150                 155                 160

Gln Pro Glu Leu Gln Trp Ala Trp Thr Asn Met Glu Gln Tyr Leu Ser
                165                 170                 175

Ala Cys Leu Asn Leu Thr Glu Arg Lys Arg Leu Val Ala Gln Phe Leu
            180                 185                 190

Ala Glu Ser Ser Gln Arg Ser Gln Glu Ala Ala Ser Gln Arg Glu Phe
        195                 200                 205

Ser Ala Asp Pro Val Ile Lys Ser Lys Thr Ser Gln Lys Tyr Met Ala
    210                 215                 220

Leu Val Asn Trp Leu Val Glu His Gly Ile Thr Ser Glu Lys Gln Trp
225                 230                 235                 240

Ile Gln Glu Asn Gln Glu Ser Tyr Leu Ser Phe Asn Ser Thr Gly Asn
                245                 250                 255

Ser Arg Ser Gln Ile Lys Ala Ala Leu Asp Asn Ala Thr Lys Ile Met
            260                 265                 270

Ser Leu Thr Lys Ser Ala Val Asp Tyr Leu Val Gly Ser Ser Val Pro
        275                 280                 285

Glu Asp Ile Ser Lys Asn Arg Ile Trp Gln Ile Phe Glu Met Asn Gly
    290                 295                 300

Tyr Asp Pro Ala Tyr Ala Gly Ser Ile Leu Tyr Gly Trp Cys Gln Arg
305                 310                 315                 320

Ser Phe Asn Lys Arg Asn Thr Val Trp Leu Tyr Gly Pro Ala Thr Thr
                325                 330                 335

Gly Lys Thr Asn Ile Ala Glu Ala Ile Ala His Thr Val Pro Phe Tyr
            340                 345                 350

Gly Cys Val Asn Trp Thr Asn Glu Asn Phe Pro Phe Asn Asp Cys Val
        355                 360                 365
```

Asp Lys Met Leu Ile Trp Trp Glu Glu Gly Lys Met Thr Asn Lys Val
    370                 375                 380

Val Glu Ser Ala Lys Ala Ile Leu Gly Gly Ser Lys Val Arg Val Asp
385                 390                 395                 400

Gln Lys Cys Lys Ser Ser Val Gln Ile Asp Ser Thr Pro Val Ile Val
                405                 410                 415

Thr Ser Asn Thr Asn Met Cys Val Val Val Asp Gly Asn Ser Thr Thr
            420                 425                 430

Phe Glu His Gln Gln Pro Leu Glu Asp Arg Met Phe Lys Phe Glu Leu
        435                 440                 445

Thr Lys Arg Leu Pro Pro Asp Phe Gly Lys Ile Thr Lys Gln Glu Val
450                 455                 460

Lys Asp Phe Phe Ala Trp Ala Lys Val Asn Gln Val Pro Val Thr His
465                 470                 475                 480

Glu Phe Lys Val Pro Arg Glu Leu Ala Gly Thr Lys Gly Ala Glu Lys
                485                 490                 495

Ser Leu Lys Arg Pro Leu Gly Asp Val Thr Asn Thr Ser Tyr Lys Ser
            500                 505                 510

Leu Glu Lys Arg Ala Arg Leu Ser Phe Val Pro Glu Thr Pro Arg Ser
        515                 520                 525

Ser Asp Val Thr Val Asp Pro Ala Pro Leu Arg Pro Leu Asn Trp Asn
530                 535                 540

Ser Arg Tyr Asp Cys Lys Cys Asp Tyr His Ala Gln Phe Asp Asn Ile
545                 550                 555                 560

Ser Asn Lys Cys Asp Glu Cys Glu Tyr Leu Asn Arg Gly Lys Asn Gly
                565                 570                 575

Cys Ile Cys His Asn Val Thr His Cys Gln Ile Cys His Gly Ile Pro
            580                 585                 590

Pro Trp Glu Lys Glu Asn Leu Ser Asp Phe Gly Asp Phe Asp Asp Ala
        595                 600                 605

Asn Lys Glu Gln
    610

<210> SEQ ID NO 75
<211> LENGTH: 619
<212> TYPE: PRT
<213> ORGANISM: Artificial
<220> FEATURE:
<223> OTHER INFORMATION: Chimeric Rep protein sequence

<400> SEQUENCE: 75

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Ser Gly Ile Ser Ser Met Val Leu Gly Arg Tyr Val Ser Gln Ile
            100                 105                 110

-continued

Arg Ala Gln Leu Val Lys Val Val Phe Gln Gly Ile Glu Pro Gln Ile
            115                 120                 125

Asn Asp Trp Val Ala Ile Thr Lys Val Lys Gly Gly Ala Asn Lys
130                 135                 140

Val Val Asp Glu Cys Tyr Ile Pro Asn Tyr Leu Leu Pro Lys Thr Gln
145                 150                 155                 160

Pro Glu Leu Gln Trp Ala Trp Thr Asn Met Glu Gln Tyr Leu Ser Ala
                165                 170                 175

Cys Leu Asn Leu Thr Glu Arg Lys Arg Leu Val Ala Gln His Leu Thr
            180                 185                 190

His Val Ser Gln Thr Gln Glu Gln Asn Lys Glu Asn Gln Asn Pro Asn
        195                 200                 205

Ser Asp Ala Pro Val Ile Arg Ser Lys Thr Ser Ala Arg Tyr Met Glu
    210                 215                 220

Leu Val Gly Trp Leu Val Asp Lys Gly Ile Thr Ser Glu Lys Gln Trp
225                 230                 235                 240

Ile Gln Glu Asp Gln Ala Ser Tyr Ile Ser Phe Asn Ala Ala Ser Asn
                245                 250                 255

Ser Arg Ser Gln Ile Lys Ala Ala Leu Asp Asn Ala Gly Lys Ile Met
            260                 265                 270

Ser Leu Thr Lys Thr Ala Pro Asp Tyr Leu Val Gly Gln Gln Pro Val
        275                 280                 285

Glu Asp Ile Ser Ser Asn Arg Ile Tyr Lys Ile Leu Glu Leu Asn Gly
    290                 295                 300

Tyr Asp Pro Gln Tyr Ala Ala Ser Val Phe Leu Gly Trp Ala Thr Lys
305                 310                 315                 320

Lys Phe Gly Lys Arg Asn Thr Ile Trp Leu Phe Gly Pro Ala Thr Thr
                325                 330                 335

Gly Lys Thr Asn Ile Ala Glu Ala Ile Ala His Thr Val Pro Phe Tyr
            340                 345                 350

Gly Cys Val Asn Trp Thr Asn Glu Asn Phe Pro Phe Asn Asp Cys Val
        355                 360                 365

Asp Lys Met Val Ile Trp Trp Glu Glu Gly Lys Met Thr Ala Lys Val
    370                 375                 380

Val Glu Ser Ala Lys Ala Ile Leu Gly Gly Ser Lys Val Arg Val Asp
385                 390                 395                 400

Gln Lys Cys Lys Ser Ser Ala Gln Ile Asp Pro Thr Pro Val Ile Val
                405                 410                 415

Thr Ser Asn Thr Asn Met Cys Ala Val Ile Asp Gly Asn Ser Thr Thr
            420                 425                 430

Phe Glu His Gln Gln Pro Leu Gln Asp Arg Met Phe Lys Phe Glu Leu
        435                 440                 445

Thr Arg Arg Leu Asp His Asp Phe Gly Lys Val Thr Lys Gln Glu Val
    450                 455                 460

Lys Asp Phe Phe Arg Trp Ala Lys Asp His Val Val Glu Val Glu His
465                 470                 475                 480

Glu Phe Tyr Val Lys Lys Gly Gly Ala Lys Lys Arg Pro Ala Pro Ser
                485                 490                 495

Asp Ala Asp Ile Ser Glu Pro Lys Arg Val Arg Glu Ser Val Ala Gln
            500                 505                 510

Pro Ser Thr Ser Asp Ala Glu Ala Ser Ile Asn Tyr Ala Asp Arg Tyr
        515                 520                 525

Gln Asn Lys Cys Ser Arg His Val Gly Met Asn Leu Met Leu Phe Pro

```
            530                 535                 540
Cys Arg Gln Cys Glu Arg Met Asn Gln Asn Ser Asn Ile Cys Phe Thr
545                 550                 555                 560

His Gly Gln Lys Asp Cys Leu Glu Cys Phe Pro Val Ser Glu Ser Gln
                565                 570                 575

Pro Val Ser Val Val Lys Lys Ala Tyr Gln Lys Leu Cys Tyr Ile His
                580                 585                 590

His Ile Met Gly Lys Val Pro Asp Ala Cys Thr Ala Cys Asp Leu Val
                595                 600                 605

Asn Val Asp Leu Asp Asp Cys Ile Phe Glu Gln
                610                 615

<210> SEQ ID NO 76
<211> LENGTH: 624
<212> TYPE: PRT
<213> ORGANISM: Artificial
<220> FEATURE:
<223> OTHER INFORMATION: Chimeric Rep protein sequence

<400> SEQUENCE: 76

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
                35                  40                  45

Glu Gln Ala Pro Leu Thr Val Ala Glu Lys Leu Gln Arg Asp Phe Leu
50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
                100                 105                 110

Arg Glu Lys Leu Ile Gln Arg Ile Tyr Arg Gly Ile Glu Pro Thr Leu
                115                 120                 125

Pro Asn Trp Phe Ala Val Thr Lys Thr Arg Asn Gly Ala Gly Gly Gly
                130                 135                 140

Asn Lys Val Val Asp Ser Gly Tyr Ile Pro Ala Tyr Leu Leu Pro Lys
145                 150                 155                 160

Val Gln Pro Glu Leu Gln Trp Ala Trp Thr Asn Leu Asp Glu Tyr Lys
                165                 170                 175

Leu Ala Ala Leu Asn Leu Glu Glu Arg Lys Arg Arg Lys Arg Leu Val
                180                 185                 190

Ala Gln His Leu Thr His Val Ser Gln Thr Gln Glu Gln Asn Lys Glu
                195                 200                 205

Asn Gln Asn Pro Asn Ser Asp Ala Pro Val Ile Arg Ser Lys Thr Ser
                210                 215                 220

Ala Arg Tyr Met Glu Leu Val Gly Trp Leu Val Asp Lys Gly Ile Thr
225                 230                 235                 240

Ser Glu Lys Gln Trp Ile Gln Glu Asp Gln Ala Ser Tyr Ile Ser Phe
                245                 250                 255

Asn Ala Ala Ser Asn Ser Arg Ser Gln Ile Lys Ala Ala Leu Asp Asn
                260                 265                 270

Ala Gly Lys Ile Met Ser Leu Thr Lys Thr Ala Pro Asp Tyr Leu Val
```

```
            275                 280                 285
Gly Gln Gln Pro Val Glu Asp Ile Ser Ser Asn Arg Ile Tyr Lys Ile
    290                 295                 300

Leu Glu Leu Asn Gly Tyr Asp Pro Gln Tyr Ala Ala Ser Val Phe Leu
305                 310                 315                 320

Gly Trp Ala Thr Lys Phe Gly Lys Arg Asn Thr Ile Trp Leu Phe
                325                 330                 335

Gly Pro Ala Thr Thr Gly Lys Thr Asn Ile Ala Glu Ala Ile Ala His
                340                 345                 350

Thr Val Pro Phe Tyr Gly Cys Val Asn Trp Thr Asn Glu Asn Phe Pro
                355                 360                 365

Phe Asn Asp Cys Val Asp Lys Met Val Ile Trp Trp Glu Glu Gly Lys
                370                 375                 380

Met Thr Ala Lys Val Val Glu Ser Ala Lys Ala Ile Leu Gly Gly Ser
385                 390                 395                 400

Lys Val Arg Val Asp Gln Lys Cys Lys Ser Ser Ala Gln Ile Asp Pro
                405                 410                 415

Thr Pro Val Ile Val Thr Ser Asn Thr Asn Met Cys Ala Val Ile Asp
                420                 425                 430

Gly Asn Ser Thr Thr Phe Glu His Gln Gln Pro Leu Gln Asp Arg Met
                435                 440                 445

Phe Lys Phe Glu Leu Thr Arg Arg Leu Asp His Asp Phe Gly Lys Val
    450                 455                 460

Thr Lys Gln Glu Val Lys Asp Phe Phe Arg Trp Ala Lys Asp His Val
465                 470                 475                 480

Val Glu Val Glu His Glu Phe Tyr Val Lys Lys Gly Gly Ala Lys Lys
                485                 490                 495

Arg Pro Ala Pro Ser Asp Ala Asp Ile Ser Glu Pro Lys Arg Val Arg
                500                 505                 510

Glu Ser Val Ala Gln Pro Ser Thr Ser Asp Ala Glu Ala Ser Ile Asn
                515                 520                 525

Tyr Ala Asp Arg Tyr Gln Asn Lys Cys Ser Arg His Val Gly Met Asn
                530                 535                 540

Leu Met Leu Phe Pro Cys Arg Gln Cys Glu Arg Met Asn Gln Asn Ser
545                 550                 555                 560

Asn Ile Cys Phe Thr His Gly Gln Lys Asp Cys Leu Glu Cys Phe Pro
                565                 570                 575

Val Ser Glu Ser Gln Pro Val Ser Val Lys Lys Ala Tyr Gln Lys
                580                 585                 590

Leu Cys Tyr Ile His His Ile Met Gly Lys Val Pro Asp Ala Cys Thr
                595                 600                 605

Ala Cys Asp Leu Val Asn Val Asp Leu Asp Asp Cys Ile Phe Glu Gln
                610                 615                 620

<210> SEQ ID NO 77
<211> LENGTH: 622
<212> TYPE: PRT
<213> ORGANISM: Artificial
<220> FEATURE:
<223> OTHER INFORMATION: Chimeric Rep protein sequence

<400> SEQUENCE: 77

Met Pro Gly Phe Tyr Glu Ile Val Ile Lys Val Pro Ser Asp Leu Asp
1               5                   10                  15

Gly His Leu Pro Gly Ile Ser Asp Ser Phe Val Asn Trp Val Ala Glu
```

-continued

```
                20                  25                  30
Lys Glu Trp Glu Leu Pro Pro Asp Ser Asp Met Asp Leu Asn Leu Ile
            35                  40                  45
Glu Gln Ala Pro Leu Thr Val Ala Glu Lys Leu Gln Arg Asp Phe Leu
        50                  55                  60
Thr Glu Trp Arg Arg Val Ser Lys Ala Pro Glu Ala Leu Phe Phe Val
65                  70                  75                  80
Gln Phe Glu Lys Gly Glu Ser Tyr Phe His Met His Val Leu Val Glu
                85                  90                  95
Thr Ser Gly Ile Ser Ser Met Val Leu Gly Arg Tyr Val Ser Gln Ile
            100                 105                 110
Arg Ala Gln Leu Val Lys Val Val Phe Gln Gly Ile Glu Pro Gln Ile
        115                 120                 125
Asn Asp Trp Val Ala Ile Thr Lys Val Lys Gly Gly Ala Asn Lys
        130                 135                 140
Val Val Asp Ser Gly Tyr Ile Pro Ala Tyr Leu Leu Pro Lys Val Gln
145                 150                 155                 160
Pro Glu Leu Gln Trp Ala Trp Thr Asn Leu Asp Glu Tyr Lys Leu Ala
                165                 170                 175
Ala Leu Asn Leu Glu Glu Arg Lys Arg Arg Lys Arg Leu Val Ala Gln
            180                 185                 190
His Leu Thr His Val Ser Gln Thr Gln Glu Gln Asn Lys Glu Asn Gln
        195                 200                 205
Asn Pro Asn Ser Asp Ala Pro Val Ile Arg Ser Lys Thr Ser Ala Arg
        210                 215                 220
Tyr Met Glu Leu Val Gly Trp Leu Val Asp Lys Gly Ile Thr Ser Glu
225                 230                 235                 240
Lys Gln Trp Ile Gln Glu Asp Gln Ala Ser Tyr Ile Ser Phe Asn Ala
                245                 250                 255
Ala Ser Asn Ser Arg Ser Gln Ile Lys Ala Ala Leu Asp Asn Ala Gly
            260                 265                 270
Lys Ile Met Ser Leu Thr Lys Thr Ala Pro Asp Tyr Leu Val Gly Gln
        275                 280                 285
Gln Pro Val Glu Asp Ile Ser Ser Asn Arg Ile Tyr Lys Ile Leu Glu
        290                 295                 300
Leu Asn Gly Tyr Asp Pro Gln Tyr Ala Ala Ser Val Phe Leu Gly Trp
305                 310                 315                 320
Ala Thr Lys Lys Phe Gly Lys Arg Asn Thr Ile Trp Leu Phe Gly Pro
                325                 330                 335
Ala Thr Thr Gly Lys Thr Asn Ile Ala Glu Ala Ile Ala His Thr Val
            340                 345                 350
Pro Phe Tyr Gly Cys Val Asn Trp Thr Asn Glu Asn Phe Pro Phe Asn
        355                 360                 365
Asp Cys Val Asp Lys Met Val Ile Trp Trp Glu Glu Gly Lys Met Thr
        370                 375                 380
Ala Lys Val Val Glu Ser Ala Lys Ala Ile Leu Gly Gly Ser Lys Val
385                 390                 395                 400
Arg Val Asp Gln Lys Cys Lys Ser Ser Ala Gln Ile Asp Pro Thr Pro
                405                 410                 415
Val Ile Val Thr Ser Asn Thr Asn Met Cys Ala Val Ile Asp Gly Asn
            420                 425                 430
Ser Thr Thr Phe Glu His Gln Gln Pro Leu Gln Asp Arg Met Phe Lys
        435                 440                 445
```

```
Phe Glu Leu Thr Arg Arg Leu Asp His Asp Phe Gly Lys Val Thr Lys
    450                 455                 460
Gln Glu Val Lys Asp Phe Phe Arg Trp Ala Lys Asp His Val Val Glu
465                 470                 475                 480
Val Glu His Glu Phe Tyr Val Lys Lys Gly Gly Ala Lys Lys Arg Pro
                485                 490                 495
Ala Pro Ser Asp Ala Asp Ile Ser Glu Pro Lys Arg Val Arg Glu Ser
            500                 505                 510
Val Ala Gln Pro Ser Thr Ser Asp Ala Glu Ala Ser Ile Asn Tyr Ala
        515                 520                 525
Asp Arg Tyr Gln Asn Lys Cys Ser Arg His Val Gly Met Asn Leu Met
    530                 535                 540
Leu Phe Pro Cys Arg Gln Cys Glu Arg Met Asn Gln Asn Ser Asn Ile
545                 550                 555                 560
Cys Phe Thr His Gly Gln Lys Asp Cys Leu Glu Cys Phe Pro Val Ser
                565                 570                 575
Glu Ser Gln Pro Val Ser Val Val Lys Lys Ala Tyr Gln Lys Leu Cys
            580                 585                 590
Tyr Ile His His Ile Met Gly Lys Val Pro Ala Cys Thr Ala Cys
        595                 600                 605
Asp Leu Val Asn Val Asp Leu Asp Asp Cys Ile Phe Glu Gln
    610                 615                 620
```

<210> SEQ ID NO 78
<211> LENGTH: 1857
<212> TYPE: DNA
<213> ORGANISM: Artificial
<220> FEATURE:
<223> OTHER INFORMATION: Chimeric Rep protein coding sequence

<400> SEQUENCE: 78

| | | | | | |
|---|---|---|---|---|---|
| atggctacct | tctatgaagt | cattgttcgc | gtcccatttg | acgtggagga | acatctgcct | 60 |
| ggaatttctg | acagctttgt | ggactgggta | actggtcaaa | tttgggagct | gcctccagag | 120 |
| tcagatttaa | atttgactct | ggttgaacag | cctcagttga | cggtggctga | tagaattcgc | 180 |
| cgcgtgttcc | tgtacgagtg | gaacaaattt | ccaagcagg | agtccaaatt | ctttgtgcag | 240 |
| tttgaaaagg | gatctgaata | ttttcatctg | cacacgcttg | tggagacctc | cggcatctct | 300 |
| tccatggtcc | tcggccgcta | cgtgagtcag | attcgcgccc | agctggtgaa | agtggtcttc | 360 |
| cagggaattg | aacccagat | caacgactgg | gtcgccatca | ccaaggtaaa | gaagggcgga | 420 |
| gccaataagg | tggtggatga | gtgctacatc | cccaattact | tgctccccaa | acccagcct | 480 |
| gagctccagt | gggcgtggac | taatatggaa | cagtatttaa | cgcctgtttt | gaatctcacg | 540 |
| gagcgtaaac | ggttggtggc | gcagcatctg | acgcacgtgt | cgcagacgca | ggagcagaac | 600 |
| aaagagaatc | agaatcccaa | ttctgatgcg | ccggtgatca | gatcaaaaac | ttcagccagg | 660 |
| tacatggagc | tggtcgggtg | gctcgtggac | aagggattac | cctcggagaa | gcagtggatc | 720 |
| caggaggacc | aggcctcata | catctccttc | aatgcggcct | ccaactcgcg | gtcccaaatc | 780 |
| aaggctgcct | tggacaatgc | gggaaagatt | atgagcctga | ctaaaaccgc | cccgactac | 840 |
| ctggtgggcc | agcagcccgt | ggaggacatt | tccagcaatc | ggatttataa | aattttggaa | 900 |
| ctaaacgggt | acgatcccca | atatgcggct | tccgtctttc | tgggatgggc | cacgaaaag | 960 |
| ttcggcaaga | gaacaccat | ctggctgttt | gggcctgcaa | ctaccgggaa | gaccaacatc | 1020 |
| gcggaggcca | tagcccacac | tgtgcccttc | tacgggtgcg | taaactggac | caatgagaac | 1080 |

```
tttcccttca acgactgtgt cgacaagatg gtgatctggt gggaggaggg gaagatgacc    1140
gccaaggtcg tggagtcggc caaagccatt ctcggaggaa gcaaggtgcg cgtggaccag    1200
aaatgcaagt cctcggccca gatagacccg actcccgtga tcgtcacctc caacaccaac    1260
atgtgcgccg tgattgacgg gaactcaacg accttcgaac accagcagcc gttgcaagac    1320
cggatgttca aatttgaact cacccgccgt ctggatcatg actttgggaa ggtcaccaag    1380
caggaagtca aagactttt ccggtgggca aaggatcacg tggttgaggt ggagcatgaa    1440
ttctacgtca aaagggtgg agccaagaaa agacccgccc ccagtgacgc agatataagt    1500
gagcccaaac gggtgcgcga gtcagttgcg cagccatcga cgtcagacgc ggaagcttcg    1560
atcaactacg cagacaggta ccaaaacaaa tgttctcgtc acgtgggcat gaatctgatg    1620
ctgtttccct gcagacaatg cgagagaatg aatcagaatt caaatatctg cttcactcac    1680
ggacagaaag actgtttaga gtgctttccc gtgtcagaat ctcaacccgt ttctgtcgtc    1740
aaaaaggcgt atcagaaact gtgctacatt catcatatca tgggaaaggt gccagacgct    1800
tgcactgcct gcgatctggt caatgtggat ttggatgact gcatctttga acaataa      1857
```

<210> SEQ ID NO 79
<211> LENGTH: 618
<212> TYPE: PRT
<213> ORGANISM: Artificial
<220> FEATURE:
<223> OTHER INFORMATION: Chimeric Rep protein sequence

<400> SEQUENCE: 79

```
Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Lys Gly Gly Ala Asn Lys Val
    130                 135                 140

Val Asp Glu Cys Tyr Ile Pro Asn Tyr Leu Leu Pro Lys Thr Gln Pro
145                 150                 155                 160

Glu Leu Gln Trp Ala Trp Thr Asn Met Glu Gln Tyr Leu Ser Ala Cys
                165                 170                 175

Leu Asn Leu Thr Glu Arg Lys Arg Leu Val Ala Gln His Leu Thr His
            180                 185                 190

Val Ser Gln Thr Gln Glu Gln Asn Lys Glu Asn Gln Asn Pro Asn Ser
        195                 200                 205

Asp Ala Pro Val Ile Arg Ser Lys Thr Ser Ala Arg Tyr Met Glu Leu
    210                 215                 220
```

Val Gly Trp Leu Val Asp Lys Gly Ile Thr Ser Glu Lys Gln Trp Ile
225                 230                 235                 240

Gln Glu Asp Gln Ala Ser Tyr Ile Ser Phe Asn Ala Ala Ser Asn Ser
            245                 250                 255

Arg Ser Gln Ile Lys Ala Ala Leu Asp Asn Ala Gly Lys Ile Met Ser
        260                 265                 270

Leu Thr Lys Thr Ala Pro Asp Tyr Leu Val Gly Gln Pro Val Glu
    275                 280                 285

Asp Ile Ser Ser Asn Arg Ile Tyr Lys Ile Leu Glu Leu Asn Gly Tyr
290                 295                 300

Asp Pro Gln Tyr Ala Ala Ser Val Phe Leu Gly Trp Ala Thr Lys Lys
305                 310                 315                 320

Phe Gly Lys Arg Asn Thr Ile Trp Leu Phe Gly Pro Ala Thr Gly
            325                 330                 335

Lys Thr Asn Ile Ala Glu Ala Ile Ala His Thr Val Pro Phe Tyr Gly
            340                 345                 350

Cys Val Asn Trp Thr Asn Glu Asn Phe Pro Phe Asn Asp Cys Val Asp
            355                 360                 365

Lys Met Val Ile Trp Trp Glu Glu Gly Lys Met Thr Ala Lys Val Val
370                 375                 380

Glu Ser Ala Lys Ala Ile Leu Gly Gly Ser Lys Val Arg Val Asp Gln
385                 390                 395                 400

Lys Cys Lys Ser Ser Ala Gln Ile Asp Pro Thr Pro Val Ile Val Thr
            405                 410                 415

Ser Asn Thr Asn Met Cys Ala Val Ile Asp Gly Asn Ser Thr Thr Phe
            420                 425                 430

Glu His Gln Gln Pro Leu Gln Asp Arg Met Phe Lys Phe Glu Leu Thr
            435                 440                 445

Arg Arg Leu Asp His Asp Phe Gly Lys Val Thr Lys Gln Glu Val Lys
450                 455                 460

Asp Phe Phe Arg Trp Ala Lys Asp His Val Val Glu Val Glu His Glu
465                 470                 475                 480

Phe Tyr Val Lys Lys Gly Gly Ala Lys Lys Arg Pro Ala Pro Ser Asp
            485                 490                 495

Ala Asp Ile Ser Glu Pro Lys Arg Val Arg Glu Ser Val Ala Gln Pro
            500                 505                 510

Ser Thr Ser Asp Ala Glu Ala Ser Ile Asn Tyr Ala Asp Arg Tyr Gln
            515                 520                 525

Asn Lys Cys Ser Arg His Val Gly Met Asn Leu Met Leu Phe Pro Cys
530                 535                 540

Arg Gln Cys Glu Arg Met Asn Gln Asn Ser Asn Ile Cys Phe Thr His
545                 550                 555                 560

Gly Gln Lys Asp Cys Leu Glu Cys Phe Pro Val Ser Glu Ser Gln Pro
            565                 570                 575

Val Ser Val Lys Lys Ala Tyr Gln Lys Leu Cys Tyr Ile His His
            580                 585                 590

Ile Met Gly Lys Val Pro Asp Ala Cys Thr Ala Cys Asp Leu Val Asn
            595                 600                 605

Val Asp Leu Asp Asp Cys Ile Phe Glu Gln
    610                 615

<210> SEQ ID NO 80
<211> LENGTH: 1857
<212> TYPE: DNA

<213> ORGANISM: Artificial
<220> FEATURE:
<223> OTHER INFORMATION: Chimeric Rep protein coding sequence

<400> SEQUENCE: 80

```
atggctacct tctatgaagt cattgttcgc gtcccatttg acgtggagga acatctgcct      60
ggaatttctg acagctttgt ggactgggta actggtcaaa tttgggagct gcctccagag     120
tcagatttaa atttgactct ggttgaacag cctcagttga cggtggctga tagaattcgc     180
cgcgtgttcc tgtacgagtg aacaaattt tccaagcagg agtccaaatt ctttgtgcag      240
tttgaaaagg gatctgaata ttttcatctg cacacgcttg tggagacctc cggcatctct     300
tccatggtcc tcggccgcta cgtgagtcag attcgcgccc agctggtgaa agtggtcttc     360
cagggaattg aacccagat caacgactgg gtcgccatca ccaaggtaaa gaagggcgga     420
gccaataagg tggtggattc ttgctacatc cccaattact tgctcccaa acccagcct      480
gagctccagt gggcgtggac taatatggaa cagtatttaa gcgcctgttt gaatctcacg     540
gagcgtaaac ggttggtggc gcagcatctg acgcacgtgt cgcagacgca ggagcagaac     600
aaagagaatc agaatcccaa ttctgatgcg ccggtgatca gatcaaaaac ttcagccagg     660
tacatggagc tggtcgggtg gctcgtggac aaggggatta cctcggagaa gcagtggatc     720
caggaggacc aggcctcata catctccttc aatgcggcct ccaactcgcg gtcccaaatc     780
aaggctgcct tggacaatgc gggaaagatt atgagcctga ctaaaaccgc cccgactac      840
ctggtgggcc agcagcccgt ggaggacatt ccagcaatc ggatttataa aattttggaa      900
ctaaacgggt acgatcccca atatgcggct ccgtctttc tgggatgggc cacgaaaaag     960
ttcggcaaga ggaacaccat ctggctgttt gggcctgcaa ctaccgggaa gaccaacatc   1020
gcggaggcca tagcccacac tgtgccttc tacgggtgcg taaactggac caatgagaac   1080
tttcccttca cgactgtgt cgacaagatg gtgatctggt gggaggaggg gaagatgacc   1140
gccaaggtcg tggagtcggc caaagccatt ctcggaggaa gcaaggtgcg cgtgaccag   1200
aaatgcaagt cctcggccca gatagaccg actcccgtga tcgtcacctc caacaccaac   1260
atgtgcgccg tgattgacgg gaactcaacg accttcgaac accagcagcc gttgcaagac   1320
cggatgttca atttgaact cacccgccgt ctggatcatg actttgggaa ggtcaccaag   1380
caggaagtca agacttttt ccggtgggca aaggatcacg tggttgaggt ggagcatgaa   1440
ttctacgtca aaagggtgg agccaagaaa agacccgccc ccagtgacgc agatataagt   1500
gagcccaaac gggtgcgcga gtcagttgcg cagccatcga cgtcagacgc ggaagcttcg   1560
atcaactacg cagacaggta ccaaaacaaa tgttctcgtc acgtgggcat gaatctgatg   1620
ctgtttccct gcagacaatg cgagagaatg aatcagaatt caaatatctg cttcactcac   1680
ggacagaaag actgtttaga gtgctttccc gtgtcagaat ctcaacccgt ttctgtcgtc   1740
aaaaaggcgt atcagaaact gtgctacatt catcatatca tgggaaaggt gccagacgct   1800
tgcactgcct gcgatctggt caatgtggat ttggatgact gcatctttga acaataa       1857
```

<210> SEQ ID NO 81
<211> LENGTH: 618
<212> TYPE: PRT
<213> ORGANISM: Artificial
<220> FEATURE:
<223> OTHER INFORMATION: Chimeric Rep protein sequence

<400> SEQUENCE: 81

Met Ala Thr Phe Tyr Glu Val Ile Val Arg Val Pro Phe Asp Val Glu

-continued

```
1               5                   10                  15
Glu His Leu Pro Gly Ile Ser Asp Ser Phe Val Asp Trp Val Thr Gly
            20                  25                  30
Gln Ile Trp Glu Leu Pro Pro Glu Ser Asp Leu Asn Leu Thr Leu Val
            35                  40                  45
Glu Gln Pro Gln Leu Thr Val Ala Asp Arg Ile Arg Arg Val Phe Leu
            50                  55                  60
Tyr Glu Trp Asn Lys Phe Ser Lys Gln Glu Ser Lys Phe Phe Val Gln
65                  70                  75                  80
Phe Glu Lys Gly Ser Glu Tyr Phe His Leu His Thr Leu Val Glu Thr
                85                  90                  95
Ser Gly Ile Ser Ser Met Val Leu Gly Arg Tyr Val Ser Gln Ile Arg
            100                 105                 110
Ala Gln Leu Val Lys Val Phe Gln Gly Ile Glu Pro Gln Ile Asn
            115                 120                 125
Asp Trp Val Ala Ile Thr Lys Val Lys Lys Gly Gly Ala Asn Lys Val
    130                 135                 140
Val Asp Ser Cys Tyr Ile Pro Asn Tyr Leu Leu Pro Lys Thr Gln Pro
145                 150                 155                 160
Glu Leu Gln Trp Ala Trp Thr Asn Met Glu Gln Tyr Leu Ser Ala Cys
                165                 170                 175
Leu Asn Leu Thr Glu Arg Lys Arg Leu Val Ala Gln His Leu Thr His
            180                 185                 190
Val Ser Gln Thr Gln Glu Gln Asn Lys Glu Asn Gln Asn Pro Asn Ser
            195                 200                 205
Asp Ala Pro Val Ile Arg Ser Lys Thr Ser Ala Arg Tyr Met Glu Leu
    210                 215                 220
Val Gly Trp Leu Val Asp Lys Gly Ile Thr Ser Glu Lys Gln Trp Ile
225                 230                 235                 240
Gln Glu Asp Gln Ala Ser Tyr Ile Ser Phe Asn Ala Ala Ser Asn Ser
                245                 250                 255
Arg Ser Gln Ile Lys Ala Ala Leu Asp Asn Ala Gly Lys Ile Met Ser
            260                 265                 270
Leu Thr Lys Thr Ala Pro Asp Tyr Leu Val Gly Gln Pro Val Glu
            275                 280                 285
Asp Ile Ser Ser Asn Arg Ile Tyr Lys Ile Leu Glu Leu Asn Gly Tyr
    290                 295                 300
Asp Pro Gln Tyr Ala Ala Ser Val Phe Leu Gly Trp Ala Thr Lys Lys
305                 310                 315                 320
Phe Gly Lys Arg Asn Thr Ile Trp Leu Phe Gly Pro Ala Thr Thr Gly
                325                 330                 335
Lys Thr Asn Ile Ala Glu Ala Ile Ala His Thr Val Pro Phe Tyr Gly
            340                 345                 350
Cys Val Asn Trp Thr Asn Glu Asn Phe Pro Phe Asn Asp Cys Val Asp
            355                 360                 365
Lys Met Val Ile Trp Trp Glu Glu Gly Lys Met Thr Ala Lys Val Val
    370                 375                 380
Glu Ser Ala Lys Ala Ile Leu Gly Gly Ser Lys Val Arg Val Asp Gln
385                 390                 395                 400
Lys Cys Lys Ser Ser Ala Gln Ile Asp Pro Thr Pro Val Ile Val Thr
                405                 410                 415
Ser Asn Thr Asn Met Cys Ala Val Ile Asp Gly Asn Ser Thr Thr Phe
            420                 425                 430
```

```
Glu His Gln Gln Pro Leu Gln Asp Arg Met Phe Lys Phe Glu Leu Thr
            435                 440                 445

Arg Arg Leu Asp His Asp Phe Gly Lys Val Thr Lys Gln Glu Val Lys
    450                 455                 460

Asp Phe Phe Arg Trp Ala Lys Asp His Val Val Glu Val Glu His Glu
465                 470                 475                 480

Phe Tyr Val Lys Lys Gly Gly Ala Lys Lys Arg Pro Ala Pro Ser Asp
                485                 490                 495

Ala Asp Ile Ser Glu Pro Lys Arg Val Arg Glu Ser Val Ala Gln Pro
            500                 505                 510

Ser Thr Ser Asp Ala Glu Ala Ser Ile Asn Tyr Ala Asp Arg Tyr Gln
            515                 520                 525

Asn Lys Cys Ser Arg His Val Gly Met Asn Leu Met Leu Phe Pro Cys
    530                 535                 540

Arg Gln Cys Glu Arg Met Asn Gln Asn Ser Asn Ile Cys Phe Thr His
545                 550                 555                 560

Gly Gln Lys Asp Cys Leu Glu Cys Phe Pro Val Ser Glu Ser Gln Pro
                565                 570                 575

Val Ser Val Val Lys Lys Ala Tyr Gln Lys Leu Cys Tyr Ile His His
            580                 585                 590

Ile Met Gly Lys Val Pro Asp Ala Cys Thr Ala Cys Asp Leu Val Asn
            595                 600                 605

Val Asp Leu Asp Asp Cys Ile Phe Glu Gln
610                 615

<210> SEQ ID NO 82
<211> LENGTH: 1857
<212> TYPE: DNA
<213> ORGANISM: Artificial
<220> FEATURE:
<223> OTHER INFORMATION: Chimeric Rep protein coding sequence

<400> SEQUENCE: 82
atggctacct tctatgaagt cattgttcgc gtcccatttg acgtggagga acatctgcct     60
ggaatttctg acagctttgt ggactgggta actggtcaaa tttgggagct gcctccagag    120
tcagatttaa atttgactct ggttgaacag cctcagttga cggtggctga tagaattcgc    180
cgcgtgttcc tgtacgagtg gaacaaattt ccaagcagg agtccaaatt ctttgtgcag    240
tttgaaaagg gatctgaata ttttcatctg cacacgcttg tggagacctc cggcatctct    300
tccatggtcc tcggccgcta cgtgagtcag attcgcgccc agctggtgaa agtggtcttc    360
cagggaattg aaccccagat caacgactgg gtcgccatca ccaaggtaaa gaagggcgga    420
gccaataagg tggtggattc tgggtatatt cccaattact tgctccccaa acccagcct    480 gagctccagt gggcgtggac taatatggaa cagtatttaa gcgcctgttt gaatctcacg    540
gagcgtaaac ggttggtggc gcagcatctg acgcacgtgt cgcagacgca ggagcagaac    600
aaagagaatc agaatcccaa ttctgatgcg ccggtgatca gatcaaaaac ttcagccagg    660
tacatggagc tggtcgggtg gctcgtggac aaggggatta cctcggagaa gcagtggatc    720
caggaggacc aggcctcata catctccttc aatgcggcct ccaactcgcg gtcccaaatc    780
aaggctgcct ggacaatgc gggaaagatt atgagcctga ctaaaaccgc cccgactac    840 ctggtgggcc agcagcccgt ggaggacatt tccagcaatc ggatttataa aattttggaa    900
ctaaacgggt acgatcccca atatgcggct tccgtctttc tgggatgggc cacgaaaaag    960
```

```
ttcggcaaga ggaacaccat ctggctgttt gggcctgcaa ctaccgggaa gaccaacatc   1020
gcggaggcca tagcccacac tgtgcccttc tacgggtgcg taaactggac caatgagaac   1080
tttcccttca acgactgtgt cgacaagatg gtgatctggt gggaggaggg gaagatgacc   1140
gccaaggtcg tggagtcggc caaagccatt ctcggaggaa gcaaggtgcg cgtggaccag   1200
aaatgcaagt cctcggccca gatagacccg actcccgtga tcgtcacctc caacaccaac   1260
atgtgcgccg tgattgacgg gaactcaacg accttcgaac accagcagcc gttgcaagac   1320
cggatgttca aatttgaact cacccgccgt ctggatcatg actttgggaa ggtcaccaag   1380
caggaagtca aagacttttt ccggtgggca aggatcacg tggttgaggt ggagcatgaa   1440
ttctacgtca aaaagggtgg agccaagaaa agacccgccc ccagtgacgc agatataagt   1500
gagcccaaac gggtgcgcga gtcagttgcg cagccatcga cgtcagacgc ggaagcttcg   1560
atcaactacg cagacaggta ccaaaacaaa tgttctcgtc acgtgggcat gaatctgatg   1620
ctgtttccct gcagacaatg cgagagaatg aatcagaatt caaatatctg cttcactcac   1680
ggacagaaag actgtttaga gtgctttccc gtgtcagaat ctcaacccgt ttctgtcgtc   1740
aaaaaggcgt atcagaaact gtgctacatt catcatatca tgggaaaggt gccagacgct   1800
tgcactgcct gcgatctggt caatgtggat ttggatgact gcatctttga acaataa     1857
```

<210> SEQ ID NO 83
<211> LENGTH: 618
<212> TYPE: PRT
<213> ORGANISM: Artificial
<220> FEATURE:
<223> OTHER INFORMATION: Chimeric Rep protein sequence

<400> SEQUENCE: 83

```
Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Glu Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Lys Gly Gly Ala Asn Lys Val
    130                 135                 140

Val Asp Ser Gly Tyr Ile Pro Asn Tyr Leu Leu Pro Lys Thr Gln Pro
145                 150                 155                 160

Glu Leu Gln Trp Ala Trp Thr Asn Met Glu Gln Tyr Leu Ser Ala Cys
                165                 170                 175

Leu Asn Leu Thr Glu Arg Lys Arg Leu Val Ala Gln His Leu Thr His
            180                 185                 190

Val Ser Gln Thr Gln Glu Gln Asn Lys Glu Asn Gln Asn Pro Asn Ser
        195                 200                 205
```

```
Asp Ala Pro Val Ile Arg Ser Lys Thr Ser Ala Arg Tyr Met Glu Leu
210                 215                 220

Val Gly Trp Leu Val Asp Lys Gly Ile Thr Ser Glu Lys Gln Trp Ile
225                 230                 235                 240

Gln Glu Asp Gln Ala Ser Tyr Ile Ser Phe Asn Ala Ala Ser Asn Ser
            245                 250                 255

Arg Ser Gln Ile Lys Ala Ala Leu Asp Asn Ala Gly Lys Ile Met Ser
            260                 265                 270

Leu Thr Lys Thr Ala Pro Asp Tyr Leu Val Gly Gln Pro Val Glu
        275                 280                 285

Asp Ile Ser Ser Asn Arg Ile Tyr Lys Ile Leu Glu Leu Asn Gly Tyr
290                 295                 300

Asp Pro Gln Tyr Ala Ala Ser Val Phe Leu Gly Trp Ala Thr Lys Lys
305                 310                 315                 320

Phe Gly Lys Arg Asn Thr Ile Trp Leu Phe Gly Pro Ala Thr Thr Gly
            325                 330                 335

Lys Thr Asn Ile Ala Glu Ala Ile Ala His Thr Val Pro Phe Tyr Gly
            340                 345                 350

Cys Val Asn Trp Thr Asn Glu Asn Phe Pro Phe Asn Asp Cys Val Asp
            355                 360                 365

Lys Met Val Ile Trp Trp Glu Glu Gly Lys Met Thr Ala Lys Val Val
370                 375                 380

Glu Ser Ala Lys Ala Ile Leu Gly Gly Ser Lys Val Arg Val Asp Gln
385                 390                 395                 400

Lys Cys Lys Ser Ser Ala Gln Ile Asp Pro Thr Pro Val Ile Val Thr
            405                 410                 415

Ser Asn Thr Asn Met Cys Ala Val Ile Asp Gly Asn Ser Thr Thr Phe
            420                 425                 430

Glu His Gln Gln Pro Leu Gln Asp Arg Met Phe Lys Phe Glu Leu Thr
            435                 440                 445

Arg Arg Leu Asp His Asp Phe Gly Lys Val Thr Lys Gln Glu Val Lys
            450                 455                 460

Asp Phe Phe Arg Trp Ala Lys Asp His Val Val Glu Val Glu His Glu
465                 470                 475                 480

Phe Tyr Val Lys Lys Gly Gly Ala Lys Lys Arg Pro Ala Pro Ser Asp
            485                 490                 495

Ala Asp Ile Ser Glu Pro Lys Arg Val Arg Glu Ser Val Ala Gln Pro
            500                 505                 510

Ser Thr Ser Asp Ala Glu Ala Ser Ile Asn Tyr Ala Asp Arg Tyr Gln
            515                 520                 525

Asn Lys Cys Ser Arg His Val Gly Met Asn Leu Met Leu Phe Pro Cys
            530                 535                 540

Arg Gln Cys Glu Arg Met Asn Gln Asn Ser Asn Ile Cys Phe Thr His
545                 550                 555                 560

Gly Gln Lys Asp Cys Leu Glu Cys Phe Pro Val Ser Glu Ser Gln Pro
            565                 570                 575

Val Ser Val Val Lys Lys Ala Tyr Gln Lys Leu Cys Tyr Ile His His
            580                 585                 590

Ile Met Gly Lys Val Pro Asp Ala Cys Thr Ala Cys Asp Leu Val Asn
            595                 600                 605

Val Asp Leu Asp Asp Cys Ile Phe Glu Gln
        610                 615
```

<210> SEQ ID NO 84
<211> LENGTH: 312
<212> TYPE: PRT
<213> ORGANISM: Adeno-associated virus 1

<400> SEQUENCE: 84

```
Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ala
    50                  55                  60

Pro Pro Ala Asp Ile Lys Thr Asn Arg Ile Tyr Arg Ile Leu Glu Leu
65                  70                  75                  80

Asn Gly Tyr Glu Pro Ala Tyr Ala Gly Ser Val Phe Leu Gly Trp Ala
                85                  90                  95

Gln Lys Arg Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Gln Asp His Val Thr Glu Val
                245                 250                 255

Ala His Glu Phe Tyr Val Arg Lys Gly Gly Ala Asn Lys Arg Pro Ala
            260                 265                 270

Pro Asp Asp Ala Asp Lys Ser Glu Pro Lys Arg Ala Cys Pro Ser Val
        275                 280                 285

Ala Asp Pro Ser Thr Ser Asp Ala Glu Gly Ala Pro Val Asp Phe Ala
    290                 295                 300

Asp Leu Ala Arg Gly Gln Pro Leu
305                 310
```

<210> SEQ ID NO 85
<211> LENGTH: 312
<212> TYPE: PRT
<213> ORGANISM: Adeno-associated virus 2

<400> SEQUENCE: 85

```
Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
```

```
            20                  25                  30
Ser Asn Ser Arg Ser Gln Ile Lys Ala Ala Leu Asp Asn Ala Gly Lys
        35                  40                  45

Ile Met Ser Leu Thr Lys Thr Ala Pro Asp Tyr Leu Val Gly Gln Gln
    50                  55                  60

Pro Val Glu Asp Ile Ser Ser Asn Arg Ile Tyr Lys Ile Leu Glu Leu
65                  70                  75                  80

Asn Gly Tyr Asp Pro Gln Tyr Ala Ala Ser Val Phe Leu Gly Trp Ala
                85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255

Glu His Glu Phe Tyr Val Lys Lys Gly Gly Ala Lys Lys Arg Pro Ala
            260                 265                 270

Pro Ser Asp Ala Asp Ile Ser Glu Pro Lys Arg Val Arg Glu Ser Val
        275                 280                 285

Ala Gln Pro Ser Thr Ser Asp Ala Glu Ala Ser Ile Asn Tyr Ala Asp
    290                 295                 300

Arg Leu Ala Arg Gly His Ser Leu
305                 310

<210> SEQ ID NO 86
<211> LENGTH: 311
<212> TYPE: PRT
<213> ORGANISM: Adeno-associated virus 3A

<400> SEQUENCE: 86

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Ser Asn
    50                  55                  60

Pro Pro Glu Asp Ile Thr Lys Asn Arg Ile Tyr Gln Ile Leu Glu Leu
65                  70                  75                  80
```

```
Asn Gly Tyr Asp Pro Gln Tyr Ala Ala Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Glu Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Glu Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Ser Asp His Val Thr Asp Val
                245                 250                 255

Ala His Glu Phe Tyr Val Arg Lys Gly Ala Lys Lys Arg Pro Ala
            260                 265                 270

Ser Asn Asp Ala Asp Val Ser Glu Pro Lys Arg Glu Cys Thr Ser Leu
        275                 280                 285

Ala Gln Pro Thr Thr Ser Asp Ala Glu Ala Pro Ala Asp Tyr Ala Asp
    290                 295                 300

Leu Ala Arg Gly Gln Pro Phe
305                 310

<210> SEQ ID NO 87
<211> LENGTH: 311
<212> TYPE: PRT
<213> ORGANISM: Adeno-associated virus 3B

<400> SEQUENCE: 87

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Ser Asn
    50                  55                  60

Pro Pro Glu Asp Ile Thr Lys Asn Arg Ile Tyr Gln Ile Leu Glu Leu
65                  70                  75                  80

Asn Gly Tyr Asp Pro Gln Tyr Ala Ala Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140
```

-continued

```
Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Glu Pro Thr Pro Val
            180                 185                 190

Ile Val Thr Ser Asn Thr Asn Met Cys Ala Val Ile Asp Gly Asn Ser
            195                 200                 205

Thr Thr Phe Glu His Gln Gln Pro Leu Gln Asp Arg Met Phe Lys Phe
210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Ser Asp His Val Thr Asp Val
                245                 250                 255

Ala His Glu Phe Tyr Val Arg Lys Gly Gly Ala Lys Lys Arg Pro Ala
            260                 265                 270

Ser Asn Asp Ala Asp Val Ser Glu Pro Lys Arg Gln Cys Thr Ser Leu
            275                 280                 285

Ala Gln Pro Thr Thr Ser Asp Ala Glu Ala Pro Ala Asp Tyr Ala Asp
            290                 295                 300

Leu Ala Arg Gly Gln Pro Phe
305                 310

<210> SEQ ID NO 88
<211> LENGTH: 311
<212> TYPE: PRT
<213> ORGANISM: Adeno-associated virus 4

<400> SEQUENCE: 88

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Gln Asn
    50                  55                  60

Pro Pro Glu Asp Ile Ser Ser Asn Arg Ile Tyr Arg Ile Leu Glu Met
65                  70                  75                  80

Asn Gly Tyr Asp Pro Gln Tyr Ala Ala Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
```

```
                195                 200                 205
Thr Thr Phe Glu His Gln Gln Pro Leu Gln Asp Arg Met Phe Lys Phe
210                 215                 220

Glu Leu Thr Lys Arg Leu Glu His Asp Phe Gly Lys Val Thr Lys Gln
225                 230                 235                 240

Glu Val Lys Asp Phe Phe Arg Trp Ala Ser Asp His Val Thr Glu Val
                245                 250                 255

Thr His Glu Phe Tyr Val Arg Lys Gly Gly Ala Arg Lys Arg Pro Ala
                260                 265                 270

Pro Asn Asp Ala Asp Ile Ser Glu Pro Lys Arg Ala Cys Pro Ser Val
                275                 280                 285

Ala Gln Pro Ser Thr Ser Asp Ala Glu Ala Pro Val Asp Tyr Ala Asp
290                 295                 300

Leu Ala Arg Gly Gln Pro Leu
305                 310

<210> SEQ ID NO 89
<211> LENGTH: 329
<212> TYPE: PRT
<213> ORGANISM: Adeno-associated virus 5

<400> SEQUENCE: 89

Met Ala Leu Val Asn Trp Leu Val Glu His Gly Ile Thr Ser Glu Lys
1               5                   10                  15

Gln Trp Ile Gln Glu Asn Gln Glu Ser Tyr Leu Ser Phe Asn Ser Thr
                20                  25                  30

Gly Asn Ser Arg Ser Gln Ile Lys Ala Ala Leu Asp Asn Ala Thr Lys
            35                  40                  45

Ile Met Ser Leu Thr Lys Ser Ala Val Asp Tyr Leu Val Gly Ser Ser
        50                  55                  60

Val Pro Glu Asp Ile Ser Lys Asn Arg Ile Trp Gln Ile Phe Glu Met
65                  70                  75                  80

Asn Gly Tyr Asp Pro Ala Tyr Ala Gly Ser Ile Leu Tyr Gly Trp Cys
                85                  90                  95

Gln Arg Ser Phe Asn Lys Arg Asn Thr Val Trp Leu Tyr Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
130                 135                 140

Cys Val Asp Lys Met Leu Ile Trp Trp Glu Gly Lys Met Thr Ala Asn
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Val Gln Ile Asp Ser Thr Pro Val
            180                 185                 190

Ile Val Thr Ser Asn Thr Asn Met Cys Val Val Val Asp Gly Asn Ser
        195                 200                 205

Thr Thr Phe Glu His Gln Gln Pro Leu Glu Asp Arg Met Phe Lys Phe
210                 215                 220

Glu Leu Thr Lys Arg Leu Pro Pro Asp Phe Gly Lys Ile Thr Lys Gln
225                 230                 235                 240

Glu Val Lys Asp Phe Phe Ala Trp Ala Lys Val Asn Gln Val Pro Val
                245                 250                 255
```

```
Thr His Glu Phe Lys Val Pro Arg Glu Leu Ala Gly Thr Lys Gly Ala
            260                 265                 270

Glu Lys Ser Leu Lys Arg Pro Leu Gly Asp Val Thr Asn Thr Ser Tyr
        275                 280                 285

Lys Ser Leu Glu Lys Arg Ala Arg Leu Ser Phe Val Pro Glu Thr Pro
    290                 295                 300

Arg Ser Ser Asp Val Thr Val Asp Pro Ala Pro Leu Arg Pro Leu Asn
305                 310                 315                 320

Trp Asn Ser Leu Val Gly Pro Ser Trp
                325

<210> SEQ ID NO 90
<211> LENGTH: 312
<212> TYPE: PRT
<213> ORGANISM: Adeno-associated virus 6

<400> SEQUENCE: 90

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ala
    50                  55                  60

Pro Pro Ala Asp Ile Lys Thr Asn Arg Ile Tyr Arg Ile Leu Glu Leu
65                  70                  75                  80

Asn Gly Tyr Asp Pro Ala Tyr Ala Gly Ser Val Phe Leu Gly Trp Ala
                85                  90                  95

Gln Lys Arg Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Gln Asp His Val Thr Glu Val
                245                 250                 255

Ala His Glu Phe Tyr Val Arg Lys Gly Gly Ala Asn Lys Arg Pro Ala
            260                 265                 270

Pro Asp Asp Ala Asp Lys Ser Glu Pro Lys Arg Ala Cys Pro Ser Val
        275                 280                 285

Ala Asp Pro Ser Thr Ser Asp Ala Glu Gly Ala Pro Val Asp Phe Ala
    290                 295                 300
```

Asp Leu Ala Arg Gly Gln Pro Leu
305                 310

<210> SEQ ID NO 91
<211> LENGTH: 312
<212> TYPE: PRT
<213> ORGANISM: Adeno-associated virus 7

<400> SEQUENCE: 91

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ser
    50                  55                  60

Leu Pro Ala Asp Ile Lys Thr Asn Arg Ile Tyr Arg Ile Leu Glu Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Ser Asp His Val Thr Glu Val
                245                 250                 255

Ala His Glu Phe Tyr Val Arg Lys Gly Gly Ala Ser Lys Arg Pro Ala
            260                 265                 270

Pro Asp Asp Ala Asp Ile Ser Glu Pro Lys Arg Ala Cys Pro Ser Val
        275                 280                 285

Ala Asp Pro Ser Thr Ser Asp Ala Glu Gly Ala Pro Val Asp Phe Ala
    290                 295                 300

Asp Leu Ala Arg Gly Gln Pro Leu
305                 310

<210> SEQ ID NO 92
<211> LENGTH: 312
<212> TYPE: PRT
<213> ORGANISM: Adeno-associated virus 8

<400> SEQUENCE: 92

```
Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ser
50                  55                  60

Leu Pro Ala Asp Ile Thr Gln Asn Arg Ile Tyr Arg Ile Leu Ala Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Ser Asp His Val Thr Glu Val
                245                 250                 255

Ala His Glu Phe Tyr Val Arg Lys Gly Gly Ala Ser Lys Arg Pro Ala
            260                 265                 270

Pro Asp Asp Ala Asp Lys Ser Glu Pro Lys Arg Ala Cys Pro Ser Val
        275                 280                 285

Ala Asp Pro Ser Thr Ser Asp Ala Glu Gly Ala Pro Val Asp Phe Ala
290                 295                 300

Asp Leu Ala Arg Gly Gln Pro Leu
305                 310
```

<210> SEQ ID NO 93
<211> LENGTH: 311
<212> TYPE: PRT
<213> ORGANISM: Artificial
<220> FEATURE:
<223> OTHER INFORMATION: AAV Rep40 consensus sequence
<220> FEATURE:
<221> NAME/KEY: MISC_FEATURE
<222> LOCATION: (63)..(63)
<223> OTHER INFORMATION: Xaa can be Gln, Pro or Ser
<220> FEATURE:
<221> NAME/KEY: MISC_FEATURE
<222> LOCATION: (290)..(290)
<223> OTHER INFORMATION: Xaa can be Asp, Gln or Thr

<400> SEQUENCE: 93

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Xaa Ser
50                  55                  60

Pro Pro Glu Asp Ile Ser Thr Asn Arg Ile Tyr Arg Ile Leu Ala Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
            130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Ser Asp His Val Thr Glu Val
                245                 250                 255

Ala His Glu Phe Tyr Val Arg Lys Gly Gly Ala Lys Lys Arg Pro Ala
            260                 265                 270

Pro Asp Asp Ala Asp Lys Ser Glu Pro Lys Arg Ala Cys Pro Ser Val
        275                 280                 285

Ala Xaa Pro Ser Thr Ser Asp Ala Glu Ala Pro Val Asp Phe Ala Asp
        290                 295                 300

Leu Ala Arg Gly Gln Pro Leu
305                 310

<210> SEQ ID NO 94
<211> LENGTH: 399
<212> TYPE: PRT
<213> ORGANISM: Adeno-associated virus 1

<400> SEQUENCE: 94

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ala
50                  55                  60

Pro Pro Ala Asp Ile Lys Thr Asn Arg Ile Tyr Arg Ile Leu Glu Leu
65                  70                  75                  80

Asn Gly Tyr Glu Pro Ala Tyr Ala Gly Ser Val Phe Leu Gly Trp Ala
            85                  90                  95

Gln Lys Arg Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
            115                 120                 125

Phe Tyr Gly Cys Val Asn Trp Thr Asn Glu Asn Phe Pro Phe Asn Asp
            130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
            165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
            195                 200                 205

Thr Thr Phe Glu His Gln Gln Pro Leu Gln Asp Arg Met Phe Lys Phe
            210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Gln Asp His Val Thr Glu Val
            245                 250                 255

Ala His Glu Phe Tyr Val Arg Lys Gly Gly Ala Asn Lys Arg Pro Ala
            260                 265                 270

Pro Asp Asp Ala Asp Lys Ser Glu Pro Lys Arg Ala Cys Pro Ser Val
            275                 280                 285

Ala Asp Pro Ser Thr Ser Asp Ala Glu Gly Ala Pro Val Asp Phe Ala
            290                 295                 300

Asp Arg Tyr Gln Asn Lys Cys Ser Arg His Ala Gly Met Leu Gln Met
305                 310                 315                 320

Leu Phe Pro Cys Lys Thr Cys Glu Arg Met Asn Gln Asn Phe Asn Ile
            325                 330                 335

Cys Phe Thr His Gly Thr Arg Asp Cys Ser Glu Cys Phe Pro Gly Val
            340                 345                 350

Ser Glu Ser Gln Pro Val Val Arg Lys Arg Thr Tyr Arg Lys Leu Cys
            355                 360                 365

Ala Ile His His Leu Leu Gly Arg Ala Pro Glu Ile Ala Cys Ser Ala
            370                 375                 380

Cys Asp Leu Val Asn Val Asp Leu Asp Asp Cys Val Ser Glu Gln
385                 390                 395

<210> SEQ ID NO 95
<211> LENGTH: 397
<212> TYPE: PRT
<213> ORGANISM: Adeno-associated virus 2

<400> SEQUENCE: 95

Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys

```
            35                  40                  45
Ile Met Ser Leu Thr Lys Thr Ala Pro Asp Tyr Leu Val Gly Gln Gln
 50                  55                  60

Pro Val Glu Asp Ile Ser Ser Asn Arg Ile Tyr Lys Ile Leu Glu Leu
 65                  70                  75                  80

Asn Gly Tyr Asp Pro Gln Tyr Ala Ala Ser Val Phe Leu Gly Trp Ala
                 85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
            115                 120                 125

Phe Tyr Gly Cys Val Asn Trp Thr Asn Glu Asn Phe Pro Phe Asn Asp
130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
            195                 200                 205

Thr Thr Phe Glu His Gln Gln Pro Leu Gln Asp Arg Met Phe Lys Phe
210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Lys Asp His Val Val Glu Val
                245                 250                 255

Glu His Glu Phe Tyr Val Lys Lys Gly Gly Ala Lys Lys Arg Pro Ala
            260                 265                 270

Pro Ser Asp Ala Asp Ile Ser Glu Pro Lys Arg Val Arg Glu Ser Val
            275                 280                 285

Ala Gln Pro Ser Thr Ser Asp Ala Glu Ala Ser Ile Asn Tyr Ala Asp
290                 295                 300

Arg Tyr Gln Asn Lys Cys Ser Arg His Val Gly Met Asn Leu Met Leu
305                 310                 315                 320

Phe Pro Cys Arg Gln Cys Glu Arg Met Asn Gln Asn Ser Asn Ile Cys
                325                 330                 335

Phe Thr His Gly Gln Lys Asp Cys Leu Glu Cys Phe Pro Val Ser Glu
            340                 345                 350

Ser Gln Pro Val Ser Val Val Lys Lys Ala Tyr Gln Lys Leu Cys Tyr
            355                 360                 365

Ile His His Ile Met Gly Lys Val Pro Asp Ala Cys Thr Ala Cys Asp
370                 375                 380

Leu Val Asn Val Asp Leu Asp Asp Cys Ile Phe Glu Gln
385                 390                 395

<210> SEQ ID NO 96
<211> LENGTH: 400
<212> TYPE: PRT
<213> ORGANISM: Adeno-associated virus 3A

<400> SEQUENCE: 96

Met Glu Leu Val Gly Trp Leu Val Asp Arg Gly Ile Thr Ser Glu Lys
 1               5                  10                  15
```

```
Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Ser Asn
    50                  55                  60

Pro Pro Glu Asp Ile Thr Lys Asn Arg Ile Tyr Gln Ile Leu Glu Leu
65              70                  75                  80

Asn Gly Tyr Asp Pro Gln Tyr Ala Ala Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Glu Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Glu Phe
    210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Ser Asp His Val Thr Asp Val
                245                 250                 255

Ala His Glu Phe Tyr Val Arg Lys Gly Gly Ala Lys Lys Arg Pro Ala
            260                 265                 270

Ser Asn Asp Ala Asp Val Ser Glu Pro Lys Arg Glu Cys Thr Ser Leu
        275                 280                 285

Ala Gln Pro Thr Thr Ser Asp Ala Glu Ala Pro Ala Asp Tyr Ala Asp
    290                 295                 300

Arg Tyr Gln Asn Lys Cys Ser Arg His Val Gly Met Asn Leu Met Leu
305                 310                 315                 320

Phe Pro Cys Lys Thr Cys Glu Arg Met Asn Gln Ile Ser Asn Val Cys
                325                 330                 335

Phe Thr His Gly Gln Arg Asp Cys Gly Glu Cys Phe Pro Gly Met Ser
            340                 345                 350

Glu Ser Gln Pro Val Ser Val Val Lys Lys Thr Tyr Gln Lys Leu
        355                 360                 365

Cys Pro Ile His His Ile Leu Gly Arg Ala Pro Glu Ile Ala Cys Ser
    370                 375                 380

Ala Cys Asp Leu Ala Asn Val Asp Leu Asp Asp Cys Val Ser Glu Gln
385                 390                 395                 400

<210> SEQ ID NO 97
<211> LENGTH: 400
<212> TYPE: PRT
<213> ORGANISM: Adeno-associated virus 3B

<400> SEQUENCE: 97
```

```
Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
            35                  40                  45

Ile Met Ser Leu Thr Lys Thr Ala Pro Asp Tyr Leu Val Gly Ser Asn
50                  55                  60

Pro Pro Glu Asp Ile Thr Lys Asn Arg Ile Tyr Gln Ile Leu Glu Leu
65                  70                  75                  80

Asn Gly Tyr Asp Pro Gln Tyr Ala Ala Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
            115                 120                 125

Phe Tyr Gly Cys Val Asn Trp Thr Asn Glu Asn Phe Pro Phe Asn Asp
130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Glu Pro Thr Pro Val
            180                 185                 190

Ile Val Thr Ser Asn Thr Asn Met Cys Ala Val Ile Asp Gly Asn Ser
            195                 200                 205

Thr Thr Phe Glu His Gln Gln Pro Leu Gln Asp Arg Met Phe Lys Phe
210                 215                 220

Glu Leu Thr Arg Arg Leu Asp His Asp Phe Gly Lys Val Thr Lys Gln
225                 230                 235                 240

Glu Val Lys Asp Phe Phe Arg Trp Ala Ser Asp His Val Thr Asp Val
                245                 250                 255

Ala His Glu Phe Tyr Val Arg Lys Gly Gly Ala Lys Lys Arg Pro Ala
            260                 265                 270

Ser Asn Asp Ala Asp Val Ser Glu Pro Lys Arg Gln Cys Thr Ser Leu
            275                 280                 285

Ala Gln Pro Thr Thr Ser Asp Ala Glu Ala Pro Ala Asp Tyr Ala Asp
290                 295                 300

Arg Tyr Gln Asn Lys Cys Ser Arg His Val Gly Met Asn Leu Met Leu
305                 310                 315                 320

Phe Pro Cys Lys Thr Cys Glu Arg Met Asn Gln Ile Ser Asn Val Cys
                325                 330                 335

Phe Thr His Gly Gln Arg Asp Cys Gly Glu Cys Phe Pro Gly Met Ser
            340                 345                 350

Glu Ser Gln Pro Val Ser Val Lys Lys Lys Thr Tyr Gln Lys Leu
            355                 360                 365

Cys Pro Ile His His Ile Leu Gly Arg Ala Pro Glu Ile Ala Cys Ser
370                 375                 380

Ala Cys Asp Leu Ala Asn Val Asp Leu Asp Asp Cys Val Ser Glu Gln
385                 390                 395                 400

<210> SEQ ID NO 98
<211> LENGTH: 399
```

<212> TYPE: PRT
<213> ORGANISM: Adeno-associated virus 4

<400> SEQUENCE: 98

```
Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Ser Lys
        35                  40                  45

Ile Met Ser Leu Thr Lys Thr Ala Pro Asp Tyr Leu Val Gly Gln Asn
50                  55                  60

Pro Pro Glu Asp Ile Ser Ser Asn Arg Ile Tyr Arg Ile Leu Glu Met
65                  70                  75                  80

Asn Gly Tyr Asp Pro Gln Tyr Ala Ala Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
210                 215                 220

Glu Leu Thr Lys Arg Leu Glu His Asp Phe Gly Lys Val Thr Lys Gln
225                 230                 235                 240

Glu Val Lys Asp Phe Phe Arg Trp Ala Ser Asp His Val Thr Glu Val
                245                 250                 255

Thr His Glu Phe Tyr Val Arg Lys Gly Gly Ala Arg Lys Arg Pro Ala
            260                 265                 270

Pro Asn Asp Ala Asp Ile Ser Glu Pro Lys Arg Ala Cys Pro Ser Val
        275                 280                 285

Ala Gln Pro Ser Thr Ser Asp Ala Glu Ala Pro Val Asp Tyr Ala Asp
290                 295                 300

Arg Tyr Gln Asn Lys Cys Ser Arg His Val Gly Met Asn Leu Met Leu
305                 310                 315                 320

Phe Pro Cys Arg Gln Cys Glu Arg Met Asn Gln Asn Val Asp Ile Cys
                325                 330                 335

Phe Thr His Gly Val Met Asp Cys Ala Glu Cys Phe Pro Val Ser Glu
            340                 345                 350

Ser Gln Pro Val Ser Val Val Arg Lys Arg Thr Tyr Gln Lys Leu Cys
        355                 360                 365

Pro Ile His His Ile Met Gly Arg Ala Pro Glu Val Ala Cys Ser Ala
370                 375                 380

Cys Glu Leu Ala Asn Val Asp Leu Asp Asp Cys Asp Met Glu Gln
385                 390                 395
```

<210> SEQ ID NO 99
<211> LENGTH: 390
<212> TYPE: PRT
<213> ORGANISM: Adeno-associated virus 5

<400> SEQUENCE: 99

Met Ala Leu Val Asn Trp Leu Val Glu His Gly Ile Thr Ser Glu Lys
1               5                   10                  15

Gln Trp Ile Gln Glu Asn Gln Glu Ser Tyr Leu Ser Phe Asn Ser Thr
            20                  25                  30

Gly Asn Ser Arg Ser Gln Ile Lys Ala Ala Leu Asp Asn Ala Thr Lys
        35                  40                  45

Ile Met Ser Leu Thr Lys Ser Ala Val Asp Tyr Leu Val Gly Ser Ser
    50                  55                  60

Val Pro Glu Asp Ile Ser Lys Asn Arg Ile Trp Gln Ile Phe Glu Met
65                  70                  75                  80

Asn Gly Tyr Asp Pro Ala Tyr Ala Gly Ser Ile Leu Tyr Gly Trp Cys
                85                  90                  95

Gln Arg Ser Phe Asn Lys Arg Asn Thr Val Trp Leu Tyr Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
    130                 135                 140

Cys Val Asp Lys Met Leu Ile Trp Trp Glu Glu Gly Lys Met Thr Asn
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Val Gln Ile Asp Ser Thr Pro Val
            180                 185                 190

Ile Val Thr Ser Asn Thr Asn Met Cys Val Val Val Asp Gly Asn Ser
        195                 200                 205

Thr Thr Phe Glu His Gln Gln Pro Leu Glu Asp Arg Met Phe Lys Phe
    210                 215                 220

Glu Leu Thr Lys Arg Leu Pro Pro Asp Phe Gly Lys Ile Thr Lys Gln
225                 230                 235                 240

Glu Val Lys Asp Phe Phe Ala Trp Ala Lys Val Asn Gln Val Pro Val
                245                 250                 255

Thr His Glu Phe Lys Val Pro Arg Glu Leu Ala Gly Thr Lys Gly Ala
            260                 265                 270

Glu Lys Ser Leu Lys Arg Pro Leu Gly Asp Val Thr Asn Thr Ser Tyr
        275                 280                 285

Lys Ser Leu Glu Lys Arg Ala Arg Leu Ser Phe Val Pro Glu Thr Pro
    290                 295                 300

Arg Ser Ser Asp Val Thr Val Asp Pro Ala Pro Leu Arg Pro Leu Asn
305                 310                 315                 320

Trp Asn Ser Arg Tyr Asp Cys Lys Cys Asp Tyr His Ala Gln Phe Asp
                325                 330                 335

Asn Ile Ser Asn Lys Cys Asp Glu Cys Glu Tyr Leu Asn Arg Gly Lys
            340                 345                 350

Asn Gly Cys Ile Cys His Asn Val Thr His Cys Gln Ile Cys His Gly
        355                 360                 365

Ile Pro Pro Trp Glu Lys Glu Asn Leu Ser Asp Phe Gly Asp Phe Asp

```
                    370                 375                 380
Asp Ala Asn Lys Glu Gln
385                 390

<210> SEQ ID NO 100
<211> LENGTH: 399
<212> TYPE: PRT
<213> ORGANISM: Adeno-associated virus 6

<400> SEQUENCE: 100

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ala
    50                  55                  60

Pro Pro Ala Asp Ile Lys Thr Asn Arg Ile Tyr Arg Ile Leu Glu Leu
65                  70                  75                  80

Asn Gly Tyr Asp Pro Ala Tyr Ala Gly Ser Val Phe Leu Gly Trp Ala
                85                  90                  95

Gln Lys Arg Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Gln Asp His Val Thr Glu Val
                245                 250                 255

Ala His Glu Phe Tyr Val Arg Lys Gly Gly Ala Asn Lys Arg Pro Ala
            260                 265                 270

Pro Asp Asp Ala Asp Lys Ser Glu Pro Lys Arg Ala Cys Pro Ser Val
        275                 280                 285

Ala Asp Pro Ser Thr Ser Asp Ala Glu Gly Ala Pro Val Asp Phe Ala
    290                 295                 300

Asp Arg Tyr Gln Asn Lys Cys Ser Arg His Ala Gly Met Leu Gln Met
305                 310                 315                 320

Leu Phe Pro Cys Lys Thr Cys Glu Arg Met Asn Gln Asn Phe Asn Ile
                325                 330                 335

Cys Phe Thr His Gly Thr Arg Asp Cys Ser Glu Cys Phe Pro Gly Val
            340                 345                 350
```

Ser Glu Ser Gln Pro Val Val Arg Lys Arg Thr Tyr Arg Lys Leu Cys
            355                 360                 365

Ala Ile His His Leu Leu Gly Arg Ala Pro Glu Ile Ala Cys Ser Ala
        370                 375                 380

Cys Asp Leu Val Asn Val Asp Leu Asp Asp Cys Val Ser Glu Gln
385                 390                 395

<210> SEQ ID NO 101
<211> LENGTH: 399
<212> TYPE: PRT
<213> ORGANISM: Adeno-associated virus 7

<400> SEQUENCE: 101

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ser
    50                  55                  60

Leu Pro Ala Asp Ile Lys Thr Asn Arg Ile Tyr Arg Ile Leu Glu Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Ser Asp His Val Thr Glu Val
                245                 250                 255

Ala His Glu Phe Tyr Val Arg Lys Gly Gly Ala Ser Lys Arg Pro Ala
            260                 265                 270

Pro Asp Asp Ala Asp Ile Ser Glu Pro Lys Arg Ala Cys Pro Ser Val
        275                 280                 285

Ala Asp Pro Ser Thr Ser Asp Ala Glu Gly Ala Pro Val Asp Phe Ala
    290                 295                 300

Asp Arg Tyr Gln Asn Lys Cys Ser Arg His Ala Gly Met Ile Gln Met
305                 310                 315                 320

Leu Phe Pro Cys Lys Thr Cys Glu Arg Met Asn Gln Asn Phe Asn Ile
                325                 330                 335

Cys Phe Thr His Gly Val Arg Asp Cys Leu Glu Cys Phe Pro Gly Val
            340                 345                 350

Ser Glu Ser Gln Pro Val Val Arg Lys Lys Thr Tyr Arg Lys Leu Cys
            355                 360                 365

Ala Ile His His Leu Leu Gly Arg Ala Pro Glu Ile Ala Cys Ser Ala
            370                 375                 380

Cys Asp Leu Val Asn Val Asp Leu Asp Asp Cys Val Ser Glu Gln
385                 390                 395

<210> SEQ ID NO 102
<211> LENGTH: 399
<212> TYPE: PRT
<213> ORGANISM: Adeno-associated virus 8

<400> SEQUENCE: 102

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Pro Ser
    50                  55                  60

Leu Pro Ala Asp Ile Thr Gln Asn Arg Ile Tyr Arg Ile Leu Ala Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Ser Asp His Val Thr Glu Val
                245                 250                 255

Ala His Glu Phe Tyr Val Arg Lys Gly Gly Ala Ser Lys Arg Pro Ala
            260                 265                 270

Pro Asp Asp Ala Asp Lys Ser Glu Pro Lys Arg Ala Cys Pro Ser Val
            275                 280                 285

Ala Asp Pro Ser Thr Ser Asp Ala Glu Gly Ala Pro Val Asp Phe Ala
        290                 295                 300

Asp Arg Tyr Gln Asn Lys Cys Ser Arg His Ala Gly Met Leu Gln Met

```
                    305                 310                 315                 320
Leu Phe Pro Cys Lys Thr Cys Glu Arg Met Asn Gln Asn Phe Asn Ile
                325                 330                 335

Cys Phe Thr His Gly Val Arg Asp Cys Ser Glu Cys Phe Pro Gly Val
            340                 345                 350

Ser Glu Ser Gln Pro Val Val Arg Lys Arg Thr Tyr Arg Lys Leu Cys
        355                 360                 365

Ala Ile His His Leu Leu Gly Arg Ala Pro Glu Ile Ala Cys Ser Ala
    370                 375                 380

Cys Asp Leu Val Asn Val Asp Leu Asp Asp Cys Val Ser Glu Gln
385                 390                 395

<210> SEQ ID NO 103
<211> LENGTH: 398
<212> TYPE: PRT
<213> ORGANISM: Artificial
<220> FEATURE:
<223> OTHER INFORMATION: AAV Rep52 consensus sequence
<220> FEATURE:
<221> NAME/KEY: MISC_FEATURE
<222> LOCATION: (63)..(63)
<223> OTHER INFORMATION: Xaa can be Gln, Pro or Ser
<220> FEATURE:
<221> NAME/KEY: MISC_FEATURE
<222> LOCATION: (317)..(317)
<223> OTHER INFORMATION: Xaa can be Asn, Asp, Ile or Leu
<220> FEATURE:
<221> NAME/KEY: MISC_FEATURE
<222> LOCATION: (333)..(333)
<223> OTHER INFORMATION: Xaa can be Lys, Phe, Ser or Val
<220> FEATURE:
<221> NAME/KEY: MISC_FEATURE
<222> LOCATION: (341)..(341)
<223> OTHER INFORMATION: Xaa can be Gln, Thr or Val
<220> FEATURE:
<221> NAME/KEY: MISC_FEATURE
<222> LOCATION: (345)..(345)
<223> OTHER INFORMATION: Xaa can be Ala, Gln, Gly, Leu or Ser
<220> FEATURE:
<221> NAME/KEY: MISC_FEATURE
<222> LOCATION: (356)..(356)
<223> OTHER INFORMATION: Xaa can be Pro or Ser
<220> FEATURE:
<221> NAME/KEY: MISC_FEATURE
<222> LOCATION: (364)..(364)
<223> OTHER INFORMATION: Xaa can be Gln or Arg
<220> FEATURE:
<221> NAME/KEY: MISC_FEATURE
<222> LOCATION: (368)..(368)
<223> OTHER INFORMATION: Xaa can be Ala, Pro or Tyr

<400> SEQUENCE: 103

Met Glu Leu Val Gly Trp Leu Val Asp Arg Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ala Leu Thr Lys Ser Ala Pro Asp Tyr Leu Val Gly Xaa Ser
    50                  55                  60

Pro Pro Glu Asp Ile Ser Thr Asn Arg Ile Tyr Arg Ile Leu Ala Leu
65                  70                  75                  80

Asn Gly Tyr Asp Pro Ala Tyr Ala Gly Ser Val Phe Leu Gly Trp Ala
                85                  90                  95

Gln Lys Lys Phe Gly Lys Arg Asn Thr Ile Trp Leu Phe Gly Pro Ala
            100                 105                 110
```

Thr Thr Gly Lys Thr Asn Ile Ala Glu Ala Ile Ala His Ala Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
                180                 185                 190

Ile Val Thr Ser Asn Thr Asn Met Cys Ala Val Ile Asp Gly Asn Ser
                195                 200                 205

Thr Thr Phe Glu His Gln Gln Pro Leu Gln Asp Arg Met Phe Lys Phe
        210                 215                 220

Glu Leu Thr Arg Arg Leu Glu His Asp Phe Gly Lys Val Thr Lys Gln
225                 230                 235                 240

Glu Val Lys Glu Phe Phe Arg Trp Ala Ser Asp His Val Thr Glu Val
                245                 250                 255

Ala His Glu Phe Tyr Val Arg Lys Gly Gly Ala Lys Lys Arg Pro Ala
                260                 265                 270

Pro Asp Asp Ala Asp Lys Ser Glu Pro Lys Arg Ala Cys Pro Ser Val
                275                 280                 285

Ala Asp Pro Ser Thr Ser Asp Ala Glu Ala Pro Val Asp Phe Ala Asp
                290                 295                 300

Arg Tyr Gln Asn Lys Cys Ser Arg His Ala Gly Met Xaa Gln Met Leu
305                 310                 315                 320

Phe Pro Cys Lys Thr Cys Glu Arg Met Asn Gln Asn Xaa Asn Ile Cys
                325                 330                 335

Phe Thr His Gly Xaa Arg Asp Cys Xaa Glu Cys Phe Pro Gly Val Ser
                340                 345                 350

Glu Ser Gln Xaa Val Val Arg Lys Arg Thr Tyr Xaa Lys Leu Cys Xaa
                355                 360                 365

Ile His His Leu Leu Gly Arg Ala Pro Glu Ile Ala Cys Ser Ala Cys
                370                 375                 380

Asp Leu Val Asn Val Asp Leu Asp Asp Cys Val Ser Glu Gln
385                 390                 395

<210> SEQ ID NO 104
<211> LENGTH: 536
<212> TYPE: PRT
<213> ORGANISM: Adeno-associated virus 1

<400> SEQUENCE: 104

Met Pro Gly Phe Tyr Glu Ile Val Ile Lys Val Pro Ser Asp Leu Asp
1               5                   10                  15

Glu His Leu Pro Gly Ile Ser Asp Ser Phe Val Ser Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu

```
            85                  90                  95
Thr Thr Gly Val Lys Ser Met Val Leu Gly Arg Phe Leu Ser Gln Ile
                100                 105                 110
Arg Asp Lys Leu Val Gln Thr Ile Tyr Arg Gly Ile Glu Pro Thr Leu
                115                 120                 125
Pro Asn Trp Phe Ala Val Thr Lys Thr Arg Asn Gly Ala Gly Gly Gly
                130                 135                 140
Asn Lys Val Val Asp Glu Cys Tyr Ile Pro Asn Tyr Leu Leu Pro Lys
145                 150                 155                 160
Thr Gln Pro Glu Leu Gln Trp Ala Trp Thr Asn Met Glu Glu Tyr Ile
                165                 170                 175
Ser Ala Cys Leu Asn Leu Ala Glu Arg Lys Arg Leu Val Ala Gln His
                180                 185                 190
Leu Thr His Val Ser Gln Thr Gln Glu Gln Asn Lys Glu Asn Leu Asn
                195                 200                 205
Pro Asn Ser Asp Ala Pro Val Ile Arg Ser Lys Thr Ser Ala Arg Tyr
                210                 215                 220
Met Glu Leu Val Gly Trp Leu Val Asp Arg Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Gly Lys
                260                 265                 270
Ile Met Ala Leu Thr Lys Ser Ala Pro Asp Tyr Leu Val Gly Pro Ala
                275                 280                 285
Pro Pro Ala Asp Ile Lys Thr Asn Arg Ile Tyr Arg Ile Leu Glu Leu
                290                 295                 300
Asn Gly Tyr Glu Pro Ala Tyr Ala Gly Ser Val Phe Leu Gly Trp Ala
305                 310                 315                 320
Gln Lys Arg Phe Gly Lys Arg Asn Thr Ile Trp Leu Phe Gly Pro Ala
                325                 330                 335
Thr Thr Gly Lys Thr Asn Ile Ala Glu Ala Ile Ala His Ala Val Pro
                340                 345                 350
Phe Tyr Gly Cys Val Asn Trp Thr Asn Glu Asn Phe Pro Phe Asn Asp
                355                 360                 365
Cys Val Asp Lys Met Val Ile Trp Trp Glu Glu Gly Lys Met Thr Ala
                370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
                420                 425                 430
Thr Thr Phe Glu His Gln Gln Pro Leu Gln Asp Arg Met Phe Lys Phe
                435                 440                 445
Glu Leu Thr Arg Arg Leu Glu His Asp Phe Gly Lys Val Thr Lys Gln
                450                 455                 460
Glu Val Lys Glu Phe Phe Arg Trp Ala Gln Asp His Val Thr Glu Val
465                 470                 475                 480
Ala His Glu Phe Tyr Val Arg Lys Gly Gly Ala Asn Lys Arg Pro Ala
                485                 490                 495
Pro Asp Asp Ala Asp Lys Ser Glu Pro Lys Arg Ala Cys Pro Ser Val
                500                 505                 510
```

Ala Asp Pro Ser Thr Ser Asp Ala Glu Gly Ala Pro Val Asp Phe Ala
            515                 520                 525

Asp Leu Ala Arg Gly Gln Pro Leu
        530                 535

<210> SEQ ID NO 105
<211> LENGTH: 536
<212> TYPE: PRT
<213> ORGANISM: Adeno-associated virus 2

<400> SEQUENCE: 105

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
        275                 280                 285

Pro Val Glu Asp Ile Ser Ser Asn Arg Ile Tyr Lys Ile Leu Glu Leu
    290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro

```
            340                 345                 350
Phe Tyr Gly Cys Val Asn Trp Thr Asn Glu Asn Phe Pro Phe Asn Asp
            355                 360                 365

Cys Val Asp Lys Met Val Ile Trp Trp Glu Gly Lys Met Thr Ala
        370                 375             380

Lys Val Val Glu Ser Ala Lys Ala Ile Leu Gly Ser Lys Val Arg
385                 390                 395                 400

Val Asp Gln Lys Cys Lys Ser Ser Ala Gln Ile Asp Pro Thr Pro Val
            405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Gly Gly Ala Lys Lys Arg Pro Ala
            485                 490                 495

Pro Ser Asp Ala Asp Ile Ser Glu Pro Lys Arg Val Arg Glu Ser Val
        500                 505                 510

Ala Gln Pro Ser Thr Ser Asp Ala Glu Ala Ser Ile Asn Tyr Ala Asp
            515                 520                 525

Arg Leu Ala Arg Gly His Ser Leu
        530                 535

<210> SEQ ID NO 106
<211> LENGTH: 535
<212> TYPE: PRT
<213> ORGANISM: Adeno-associated virus 3A

<400> SEQUENCE: 106

Met Pro Gly Phe Tyr Glu Ile Val Leu Lys Val Pro Ser Asp Leu Asp
1               5                   10                  15

Glu Arg Leu Pro Gly Ile Ser Asn Ser Phe Val Asn Trp Val Ala Glu
            20                  25                  30

Lys Glu Trp Asp Val Pro Pro Asp Ser Asp Met Asp Pro Asn Leu Ile
        35                  40                  45

Glu Gln Ala Pro Leu Thr Val Ala Glu Lys Leu Gln Arg Glu Phe Leu
    50                  55                  60

Val Glu Trp Arg Arg Val Ser Lys Ala Pro Glu Ala Leu Phe Phe Val
65                  70                  75                  80

Gln Phe Glu Lys Gly Glu Thr Tyr Phe His Leu His Val Leu Ile Glu
                85                  90                  95

Thr Ile Gly Val Lys Ser Met Val Val Gly Arg Tyr Val Ser Gln Ile
            100                 105                 110

Lys Glu Lys Leu Val Thr Arg Ile Tyr Arg Gly Val Glu Pro Gln Leu
        115                 120                 125

Pro Asn Trp Phe Ala Val Thr Lys Thr Arg Asn Gly Ala Gly Gly Gly
    130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Leu
                165                 170                 175
```

```
Ser Ala Cys Leu Asn Leu Ala Glu Arg Lys Arg Leu Val Ala Gln His
            180                 185                 190
Leu Thr His Val Ser Gln Thr Gln Glu Gln Asn Lys Glu Asn Gln Asn
        195                 200                 205
Pro Asn Ser Asp Ala Pro Val Ile Arg Ser Lys Thr Ser Ala Arg Tyr
    210                 215                 220
Met Glu Leu Val Gly Trp Leu Val Asp Arg Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Ser Lys
            260                 265                 270
Ile Met Ser Leu Thr Lys Thr Ala Pro Asp Tyr Leu Val Gly Ser Asn
        275                 280                 285
Pro Pro Glu Asp Ile Thr Lys Asn Arg Ile Tyr Gln Ile Leu Glu Leu
    290                 295                 300
Asn Gly Tyr Asp Pro Gln Tyr Ala Ala Ser Val Phe Leu Gly Trp Ala
305                 310                 315                 320
Gln Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Ala Val Pro
            340                 345                 350
Phe Tyr Gly Cys Val Asn Trp Thr Asn Glu Asn Phe Pro Phe Asn Asp
        355                 360                 365
Cys Val Asp Lys Met Val Ile Trp Trp Glu Glu Gly Lys Met Thr Ala
    370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Glu Pro Thr Pro Val
                405                 410                 415
Ile Val Thr Ser Asn Thr Asn Met Cys Ala Val Ile Asp Gly Asn Ser
            420                 425                 430
Thr Thr Phe Glu His Gln Gln Pro Leu Gln Asp Arg Met Phe Glu Phe
        435                 440                 445
Glu Leu Thr Arg Arg Leu Asp His Asp Phe Gly Lys Val Thr Lys Gln
    450                 455                 460
Glu Val Lys Asp Phe Phe Arg Trp Ala Ser Asp His Val Thr Asp Val
465                 470                 475                 480
Ala His Glu Phe Tyr Val Arg Lys Gly Gly Ala Lys Lys Arg Pro Ala
                485                 490                 495
Ser Asn Asp Ala Asp Val Ser Glu Pro Lys Arg Glu Cys Thr Ser Leu
            500                 505                 510
Ala Gln Pro Thr Thr Ser Asp Ala Glu Ala Pro Ala Asp Tyr Ala Asp
        515                 520                 525
Leu Ala Arg Gly Gln Pro Phe
    530                 535

<210> SEQ ID NO 107
<211> LENGTH: 535
<212> TYPE: PRT
<213> ORGANISM: Adeno-associated virus 3B

<400> SEQUENCE: 107

Met Pro Gly Phe Tyr Glu Ile Val Leu Lys Val Pro Ser Asp Leu Asp
1               5                   10                  15
```

```
Glu His Leu Pro Gly Ile Ser Asn Ser Phe Val Asn Trp Val Ala Glu
             20                  25                  30

Lys Glu Trp Glu Leu Pro Pro Asp Ser Asp Met Asp Pro Asn Leu Ile
             35                  40                  45

Glu Gln Ala Pro Leu Thr Val Ala Glu Lys Leu Gln Arg Glu Phe Leu
 50                  55                  60

Val Glu Trp Arg Arg Val Ser Lys Ala Pro Glu Ala Leu Phe Phe Val
 65                  70                  75                  80

Gln Phe Glu Lys Gly Glu Thr Tyr Phe His Leu His Val Leu Ile Glu
                 85                  90                  95

Thr Ile Gly Val Lys Ser Met Val Val Gly Arg Tyr Val Ser Gln Ile
             100                 105                 110

Lys Glu Lys Leu Val Thr Arg Ile Tyr Arg Gly Val Glu Pro Gln Leu
             115                 120                 125

Pro Asn Trp Phe Ala Val Thr Lys Thr Arg Asn Gly Ala Gly Gly Gly
 130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Leu
                 165                 170                 175

Ser Ala Cys Leu Asn Leu Ala Glu Arg Lys Arg Leu Val Ala Gln His
             180                 185                 190

Leu Thr His Val Ser Gln Thr Gln Glu Gln Asn Lys Glu Asn Gln Asn
             195                 200                 205

Pro Asn Ser Asp Ala Pro Val Ile Arg Ser Lys Thr Ser Ala Arg Tyr
 210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                 245                 250                 255

Ser Asn Ser Arg Ser Gln Ile Lys Ala Ala Leu Asp Asn Ala Ser Lys
             260                 265                 270

Ile Met Ser Leu Thr Lys Thr Ala Pro Asp Tyr Leu Val Gly Ser Asn
             275                 280                 285

Pro Pro Glu Asp Ile Thr Lys Asn Arg Ile Tyr Gln Ile Leu Glu Leu
 290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                 325                 330                 335

Thr Thr Gly Lys Thr Asn Ile Ala Glu Ala Ile Ala His Ala Val Pro
             340                 345                 350

Phe Tyr Gly Cys Val Asn Trp Thr Asn Glu Asn Phe Pro Phe Asn Asp
             355                 360                 365

Cys Val Asp Lys Met Val Ile Trp Trp Glu Glu Gly Lys Met Thr Ala
 370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Glu Pro Thr Pro Val
                 405                 410                 415

Ile Val Thr Ser Asn Thr Asn Met Cys Ala Val Ile Asp Gly Asn Ser
             420                 425                 430
```

```
Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
450                 455                 460

Glu Val Lys Asp Phe Phe Arg Trp Ala Ser Asp His Val Thr Asp Val
465                 470                 475                 480

Ala His Glu Phe Tyr Val Arg Lys Gly Gly Ala Lys Lys Arg Pro Ala
                485                 490                 495

Ser Asn Asp Ala Asp Val Ser Glu Pro Lys Arg Gln Cys Thr Ser Leu
                500                 505                 510

Ala Gln Pro Thr Thr Ser Asp Ala Glu Ala Pro Ala Asp Tyr Ala Asp
            515                 520                 525

Leu Ala Arg Gly Gln Pro Phe
530                 535

<210> SEQ ID NO 108
<211> LENGTH: 535
<212> TYPE: PRT
<213> ORGANISM: Adeno-associated virus 4

<400> SEQUENCE: 108

Met Pro Gly Phe Tyr Glu Ile Val Leu Lys Val Pro Ser Asp Leu Asp
1               5                   10                  15

Glu His Leu Pro Gly Ile Ser Asp Ser Phe Val Ser Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Glu Phe Leu
50                  55                  60

Val Glu Trp Arg Arg Val Ser Lys Ala Pro Glu Ala Leu Phe Phe Val
65                  70                  75                  80

Gln Phe Glu Lys Gly Asp Ser Tyr Phe His Leu His Ile Leu Val Glu
                85                  90                  95

Thr Val Gly Val Lys Ser Met Val Val Gly Arg Tyr Val Ser Gln Ile
                100                 105                 110

Lys Glu Lys Leu Val Thr Arg Ile Tyr Arg Gly Val Glu Pro Gln Leu
            115                 120                 125

Pro Asn Trp Phe Ala Val Thr Lys Thr Arg Asn Gly Ala Gly Gly Gly
130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Ile
                165                 170                 175

Ser Ala Cys Leu Asn Leu Ala Glu Arg Lys Arg Leu Val Ala Gln His
                180                 185                 190

Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
                260                 265                 270
```

```
Ile Met Ser Leu Thr Lys Thr Ala Pro Asp Tyr Leu Val Gly Gln Asn
            275                 280                 285

Pro Pro Glu Asp Ile Ser Ser Asn Arg Ile Tyr Arg Ile Leu Glu Met
        290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Lys Arg Leu Glu His Asp Phe Gly Lys Val Thr Lys Gln
    450                 455                 460

Glu Val Lys Asp Phe Phe Arg Trp Ala Ser Asp His Val Thr Glu Val
465                 470                 475                 480

Thr His Glu Phe Tyr Val Arg Lys Gly Gly Ala Arg Lys Arg Pro Ala
                485                 490                 495

Pro Asn Asp Ala Asp Ile Ser Glu Pro Lys Arg Ala Cys Pro Ser Val
            500                 505                 510

Ala Gln Pro Ser Thr Ser Asp Ala Glu Ala Pro Val Asp Tyr Ala Asp
        515                 520                 525

Leu Ala Arg Gly Gln Pro Leu
    530                 535

<210> SEQ ID NO 109
<211> LENGTH: 549
<212> TYPE: PRT
<213> ORGANISM: Adeno-associated virus 5

<400> SEQUENCE: 109

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
            20                  25                  30

Gln Ile Trp Glu Leu Pro Pro Gly Ser Asp Leu Asn Leu Thr Leu Val
        35                  40                  45

Glu Gln Pro Gln Leu Thr Val Ala Asp Arg Ile Arg Arg Val Phe Leu
    50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
```

```
            100                 105                 110
Ala Gln Leu Val Lys Val Phe Gln Gly Ile Glu Pro Gln Ile Asn
            115                 120                 125

Asp Trp Val Ala Ile Thr Lys Val Lys Gly Gly Ala Asn Lys Val
            130                 135             140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175

Leu Asn Leu Glu Glu Arg Lys Arg Leu Val Ala Gln Phe Leu Ala Glu
            180                 185                 190

Ser Ser Gln Arg Ser Gln Glu Ala Ala Ser Gln Arg Glu Phe Ser Ala
            195                 200                 205

Asp Pro Val Ile Lys Ser Lys Thr Ser Gln Lys Tyr Met Ala Leu Val
            210                 215                 220

Asn Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
                245                 250                 255

Ser Gln Ile Lys Ala Ala Leu Asp Asn Ala Thr Lys Ile Met Ser Leu
            260                 265                 270

Thr Lys Ser Ala Val Asp Tyr Leu Val Gly Ser Ser Val Pro Glu Asp
            275                 280                 285

Ile Ser Lys Asn Arg Ile Trp Gln Ile Phe Glu Met Asn Gly Tyr Asp
            290                 295                 300

Pro Ala Tyr Ala Gly Ser Ile Leu Tyr Gly Trp Cys Gln Arg Ser Phe
305                 310                 315                 320

Asn Lys Arg Asn Thr Val Trp Leu Tyr Gly Pro Ala Thr Thr Gly Lys
                325                 330                 335

Thr Asn Ile Ala Glu Ala Ile Ala His Thr Val Pro Phe Tyr Gly Cys
            340                 345                 350

Val Asn Trp Thr Asn Glu Asn Phe Pro Phe Asn Asp Cys Val Asp Lys
            355                 360                 365

Met Leu Ile Trp Trp Glu Glu Gly Lys Met Thr Asn Lys Val Val Glu
            370                 375                 380

Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
                405                 410                 415

Asn Thr Asn Met Cys Val Val Asp Gly Asn Ser Thr Thr Phe Glu
            420                 425                 430

His Gln Gln Pro Leu Glu Asp Arg Met Phe Lys Phe Glu Leu Thr Lys
            435                 440                 445

Arg Leu Pro Pro Asp Phe Gly Lys Ile Thr Lys Gln Glu Val Lys Asp
            450                 455                 460

Phe Phe Ala Trp Ala Lys Val Asn Gln Val Pro Val Thr His Glu Phe
465                 470                 475                 480

Lys Val Pro Arg Glu Leu Ala Gly Thr Lys Gly Ala Lys Ser Leu
                485                 490                 495

Lys Arg Pro Leu Gly Asp Val Thr Asn Thr Ser Tyr Lys Ser Leu Glu
            500                 505                 510

Lys Arg Ala Arg Leu Ser Phe Val Pro Glu Thr Pro Arg Ser Ser Asp
            515                 520                 525
```

-continued

Val Thr Val Asp Pro Ala Pro Leu Arg Pro Leu Asn Trp Asn Ser Leu
        530                 535                 540

Val Gly Pro Ser Trp
545

<210> SEQ ID NO 110
<211> LENGTH: 536
<212> TYPE: PRT
<213> ORGANISM: Adeno-associated virus 6

<400> SEQUENCE: 110

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
            100                 105                 110

Arg Asp Lys Leu Val Gln Thr Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala His Asp
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ala
        275                 280                 285

Pro Pro Ala Asp Ile Lys Thr Asn Arg Ile Tyr Arg Ile Leu Glu Leu
    290                 295                 300

Asn Gly Tyr Asp Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro

-continued

```
                340                 345                 350
Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
    435                 440                 445

Glu Leu Thr Arg Arg Leu Glu His Asp Phe Gly Lys Val Thr Lys Gln
450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
                485                 490                 495

Pro Asp Asp Ala Asp Lys Ser Glu Pro Lys Arg Ala Cys Pro Ser Val
            500                 505                 510

Ala Asp Pro Ser Thr Ser Asp Ala Glu Gly Ala Pro Val Asp Phe Ala
    515                 520                 525

Asp Leu Ala Arg Gly Gln Pro Leu
    530                 535

<210> SEQ ID NO 111
<211> LENGTH: 536
<212> TYPE: PRT
<213> ORGANISM: Adeno-associated virus 7

<400> SEQUENCE: 111

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Glu Lys Leu Val Gln Thr Ile Tyr Arg Gly Val Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175
```

```
Ser Ala Cys Leu Asn Leu Ala Glu Arg Lys Arg Leu Val Ala Gln His
                180                 185                 190

Leu Thr His Val Ser Gln Thr Gln Glu Gln Asn Lys Glu Asn Leu Asn
            195                 200                 205

Pro Asn Ser Asp Ala Pro Val Ile Arg Ser Lys Thr Ser Ala Arg Tyr
        210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ser
        275                 280                 285

Leu Pro Ala Asp Ile Lys Thr Asn Arg Ile Tyr Arg Ile Leu Glu Leu
290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
450                 455                 460

Glu Val Lys Glu Phe Phe Arg Trp Ala Ser Asp His Val Thr Glu Val
465                 470                 475                 480

Ala His Glu Phe Tyr Val Arg Lys Gly Gly Ala Ser Lys Arg Pro Ala
                485                 490                 495

Pro Asp Asp Ala Asp Ile Ser Glu Pro Lys Arg Ala Cys Pro Ser Val
            500                 505                 510

Ala Asp Pro Ser Thr Ser Asp Ala Glu Gly Ala Pro Val Asp Phe Ala
        515                 520                 525

Asp Leu Ala Arg Gly Gln Pro Leu
530                 535

<210> SEQ ID NO 112
<211> LENGTH: 538
<212> TYPE: PRT
<213> ORGANISM: Adeno-associated virus 8

<400> SEQUENCE: 112

Met Pro Gly Phe Tyr Glu Ile Val Ile Lys Val Pro Ser Asp Leu Asp
1               5                   10                  15
```

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Arg Asn Leu Ile
            35                  40                  45

Glu Gln Ala Pro Leu Thr Val Ala Glu Lys Leu Gln Arg Asp Phe Leu
 50                  55                  60

Val Gln Trp Arg Arg Val Ser Lys Ala Pro Glu Ala Leu Phe Phe Val
 65                  70                  75                  80

Gln Phe Glu Lys Gly Glu Ser Tyr Phe His Leu His Val Leu Val Glu
                 85                  90                  95

Thr Thr Gly Val Lys Ser Met Val Leu Gly Arg Phe Leu Ser Gln Ile
                100                 105                 110

Arg Glu Lys Leu Gly Pro Asp His Leu Pro Ala Gly Ser Ser Pro Thr
            115                 120                 125

Leu Pro Asn Trp Phe Ala Val Thr Lys Asp Ala Val Met Ala Pro Ala
130                 135                 140

Gly Gly Asn Lys Val Val Asp Glu Cys Tyr Ile Pro Asn Tyr Leu Leu
145                 150                 155                 160

Pro Lys Thr Gln Pro Glu Leu Gln Trp Ala Trp Thr Asn Met Glu Glu
                165                 170                 175

Tyr Ile Ser Ala Cys Leu Asn Leu Ala Glu Arg Lys Arg Leu Val Ala
            180                 185                 190

Gln His Leu Thr His Val Ser Gln Thr Gln Glu Gln Asn Lys Glu Asn
            195                 200                 205

Leu Asn Pro Asn Ser Asp Ala Pro Val Ile Arg Ser Lys Thr Ser Ala
            210                 215                 220

Arg Tyr Met Glu Leu Val Gly Trp Leu Val Asp Arg Gly Ile Thr Ser
225                 230                 235                 240

Glu Lys Gln Trp Ile Gln Glu Asp Gln Ala Ser Tyr Ile Ser Phe Asn
                245                 250                 255

Ala Ala Ser Asn Ser Arg Ser Gln Ile Lys Ala Ala Leu Asp Asn Ala
            260                 265                 270

Gly Lys Ile Met Ala Leu Thr Lys Ser Ala Pro Asp Tyr Leu Val Gly
            275                 280                 285

Pro Ser Leu Pro Ala Asp Ile Thr Gln Asn Arg Ile Tyr Arg Ile Leu
290                 295                 300

Ala Leu Asn Gly Tyr Asp Pro Ala Tyr Ala Gly Ser Val Phe Leu Gly
305                 310                 315                 320

Trp Ala Gln Lys Lys Phe Gly Lys Arg Asn Thr Ile Trp Leu Phe Gly
                325                 330                 335

Pro Ala Thr Thr Gly Lys Thr Asn Ile Ala Glu Ala Ile Ala His Ala
            340                 345                 350

Val Pro Phe Tyr Gly Cys Val Asn Trp Thr Asn Glu Asn Phe Pro Phe
            355                 360                 365

Asn Asp Cys Val Asp Lys Met Val Ile Trp Trp Glu Glu Gly Lys Met
            370                 375                 380

Thr Ala Lys Val Val Glu Ser Ala Lys Ala Ile Leu Gly Gly Ser Lys
385                 390                 395                 400

Val Arg Val Asp Gln Lys Cys Lys Ser Ser Ala Gln Ile Asp Pro Thr
                405                 410                 415

Pro Val Ile Val Thr Ser Asn Thr Asn Met Cys Ala Val Ile Asp Gly
            420                 425                 430

Asn Ser Thr Thr Phe Glu His Gln Gln Pro Leu Gln Asp Arg Met Phe
            435                 440                 445

Lys Phe Glu Leu Thr Arg Arg Leu Glu His Asp Phe Gly Lys Val Thr
    450                 455                 460

Lys Gln Glu Val Lys Glu Phe Phe Arg Trp Ala Ser Asp His Val Thr
465                 470                 475                 480

Glu Val Ala His Glu Phe Tyr Val Arg Lys Gly Gly Ala Ser Lys Arg
                485                 490                 495

Pro Ala Pro Asp Asp Ala Asp Lys Ser Glu Pro Lys Arg Ala Cys Pro
            500                 505                 510

Ser Val Ala Asp Pro Ser Thr Ser Asp Ala Glu Gly Ala Pro Val Asp
            515                 520                 525

Phe Ala Asp Leu Ala Arg Gly Gln Pro Leu
            530                 535

<210> SEQ ID NO 113
<211> LENGTH: 623
<212> TYPE: PRT
<213> ORGANISM: Adeno-associated virus 1

<400> SEQUENCE: 113

Met Pro Gly Phe Tyr Glu Ile Val Ile Lys Val Pro Ser Asp Leu Asp
1               5                   10                  15

Glu His Leu Pro Gly Ile Ser Asp Ser Phe Val Ser Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Ile Leu Val Glu
                85                  90                  95

Thr Thr Gly Val Lys Ser Met Val Leu Gly Arg Phe Leu Ser Gln Ile
            100                 105                 110

Arg Asp Lys Leu Val Gln Thr Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

```
Ile Met Ala Leu Thr Lys Ser Ala Pro Asp Tyr Leu Val Gly Pro Ala
        275                 280                 285

Pro Pro Ala Asp Ile Lys Thr Asn Arg Ile Tyr Arg Ile Leu Glu Leu
        290                 295                 300

Asn Gly Tyr Glu Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
        370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Glu His Asp Phe Gly Lys Val Thr Lys Gln
        450                 455                 460

Glu Val Lys Glu Phe Phe Arg Trp Ala Gln Asp His Val Thr Glu Val
465                 470                 475                 480

Ala His Glu Phe Tyr Val Arg Lys Gly Gly Ala Asn Lys Arg Pro Ala
                485                 490                 495

Pro Asp Asp Ala Asp Lys Ser Glu Pro Lys Arg Ala Cys Pro Ser Val
            500                 505                 510

Ala Asp Pro Ser Thr Ser Asp Ala Glu Gly Ala Pro Val Asp Phe Ala
            515                 520                 525

Asp Arg Tyr Gln Asn Lys Cys Ser Arg His Ala Gly Met Leu Gln Met
        530                 535                 540

Leu Phe Pro Cys Lys Thr Cys Glu Arg Met Asn Gln Asn Phe Asn Ile
545                 550                 555                 560

Cys Phe Thr His Gly Thr Arg Asp Cys Ser Glu Cys Phe Pro Gly Val
                565                 570                 575

Ser Glu Ser Gln Pro Val Val Arg Lys Arg Thr Tyr Arg Lys Leu Cys
            580                 585                 590

Ala Ile His His Leu Leu Gly Arg Ala Pro Glu Ile Ala Cys Ser Ala
            595                 600                 605

Cys Asp Leu Val Asn Val Asp Leu Asp Asp Cys Val Ser Glu Gln
        610                 615                 620

<210> SEQ ID NO 114
<211> LENGTH: 621
<212> TYPE: PRT
<213> ORGANISM: Adeno-associated virus 2

<400> SEQUENCE: 114

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
```

-continued

```
                20                  25                  30
Lys Glu Trp Glu Leu Pro Pro Asp Ser Asp Met Asp Leu Asn Leu Ile
             35                  40                  45
Glu Gln Ala Pro Leu Thr Val Ala Glu Lys Leu Gln Arg Asp Phe Leu
 50                  55                  60
Thr Glu Trp Arg Arg Val Ser Lys Ala Pro Glu Ala Leu Phe Phe Val
 65                  70                  75                  80
Gln Phe Glu Lys Gly Glu Ser Tyr Phe His Met His Val Leu Val Glu
                 85                  90                  95
Thr Thr Gly Val Lys Ser Met Val Leu Gly Arg Phe Leu Ser Gln Ile
                100                 105                 110
Arg Glu Lys Leu Ile Gln Arg Ile Tyr Arg Gly Ile Glu Pro Thr Leu
            115                 120                 125
Pro Asn Trp Phe Ala Val Thr Lys Thr Arg Asn Gly Ala Gly Gly Gly
            130                 135                 140
Asn Lys Val Val Asp Glu Cys Tyr Ile Pro Asn Tyr Leu Leu Pro Lys
145                 150                 155                 160
Thr Gln Pro Glu Leu Gln Trp Ala Trp Thr Asn Met Glu Gln Tyr Leu
                165                 170                 175
Ser Ala Cys Leu Asn Leu Thr Glu Arg Lys Arg Leu Val Ala Gln His
            180                 185                 190
Leu Thr His Val Ser Gln Thr Gln Glu Gln Asn Lys Glu Asn Gln Asn
            195                 200                 205
Pro Asn Ser Asp Ala Pro Val Ile Arg Ser Lys Thr Ser Ala Arg Tyr
    210                 215                 220
Met Glu Leu Val Gly Trp Leu Val Asp Lys Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Gly Lys
            260                 265                 270
Ile Met Ser Leu Thr Lys Thr Ala Pro Asp Tyr Leu Val Gly Gln Gln
            275                 280                 285
Pro Val Glu Asp Ile Ser Ser Asn Arg Ile Tyr Lys Ile Leu Glu Leu
    290                 295                 300
Asn Gly Tyr Asp Pro Gln Tyr Ala Ala Ser Val Phe Leu Gly Trp Ala
305                 310                 315                 320
Thr Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Thr Val Pro
            340                 345                 350
Phe Tyr Gly Cys Val Asn Trp Thr Asn Glu Asn Phe Pro Phe Asn Asp
            355                 360                 365
Cys Val Asp Lys Met Val Ile Trp Trp Glu Glu Gly Lys Met Thr Ala
    370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
            420                 425                 430
Thr Thr Phe Glu His Gln Gln Pro Leu Gln Asp Arg Met Phe Lys Phe
            435                 440                 445
```

```
Glu Leu Thr Arg Arg Leu Asp His Asp Phe Gly Lys Val Thr Lys Gln
    450                 455                 460

Glu Val Lys Asp Phe Phe Arg Trp Ala Lys Asp His Val Val Glu Val
465                 470                 475                 480

Glu His Glu Phe Tyr Val Lys Gly Gly Ala Lys Lys Arg Pro Ala
                485                 490                 495

Pro Ser Asp Ala Asp Ile Ser Glu Pro Lys Arg Val Arg Glu Ser Val
                500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
    530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
                580                 585                 590

Ile His His Ile Met Gly Lys Val Pro Asp Ala Cys Thr Ala Cys Asp
    595                 600                 605

Leu Val Asn Val Asp Leu Asp Asp Cys Ile Phe Glu Gln
    610                 615                 620

<210> SEQ ID NO 115
<211> LENGTH: 624
<212> TYPE: PRT
<213> ORGANISM: Adeno-associated virus 3A

<400> SEQUENCE: 115

Met Pro Gly Phe Tyr Glu Ile Val Leu Lys Val Pro Ser Asp Leu Asp
1               5                   10                  15

Glu Arg Leu Pro Gly Ile Ser Asn Ser Phe Val Asn Trp Val Ala Glu
            20                  25                  30

Lys Glu Trp Asp Val Pro Pro Asp Ser Asp Met Asp Pro Asn Leu Ile
        35                  40                  45

Glu Gln Ala Pro Leu Thr Val Ala Glu Lys Leu Gln Arg Glu Phe Leu
    50                  55                  60

Val Glu Trp Arg Arg Val Ser Lys Ala Pro Glu Ala Leu Phe Phe Val
65                  70                  75                  80

Gln Phe Glu Lys Gly Glu Thr Tyr Phe His Leu His Val Leu Ile Glu
                85                  90                  95

Thr Ile Gly Val Lys Ser Met Val Val Gly Arg Tyr Val Ser Gln Ile
            100                 105                 110

Lys Glu Lys Leu Val Thr Arg Ile Tyr Arg Gly Val Glu Pro Gln Leu
        115                 120                 125

Pro Asn Trp Phe Ala Val Thr Lys Thr Arg Asn Gly Ala Gly Gly Gly
    130                 135                 140

Asn Lys Val Val Asp Asp Cys Tyr Ile Pro Asn Tyr Leu Leu Pro Lys
145                 150                 155                 160

Thr Gln Pro Glu Leu Gln Trp Ala Trp Thr Asn Met Asp Gln Tyr Leu
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Gln Asn
```

-continued

```
            195                 200                 205
Pro Asn Ser Asp Ala Pro Val Ile Arg Ser Lys Thr Ser Ala Arg Tyr
210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Ser Lys
                260                 265                 270

Ile Met Ser Leu Thr Lys Thr Ala Pro Asp Tyr Leu Val Gly Ser Asn
            275                 280                 285

Pro Pro Glu Asp Ile Thr Lys Asn Arg Ile Tyr Gln Ile Leu Glu Leu
290                 295                 300

Asn Gly Tyr Asp Pro Gln Tyr Ala Ala Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
                340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Glu Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Glu Phe
            435                 440                 445

Glu Leu Thr Arg Arg Leu Asp His Asp Phe Gly Lys Val Thr Lys Gln
            450                 455                 460

Glu Val Lys Asp Phe Phe Arg Trp Ala Ser Asp His Val Thr Asp Val
465                 470                 475                 480

Ala His Glu Phe Tyr Val Arg Lys Gly Gly Ala Lys Lys Arg Pro Ala
                485                 490                 495

Ser Asn Asp Ala Asp Val Ser Glu Pro Lys Arg Glu Cys Thr Ser Leu
                500                 505                 510

Ala Gln Pro Thr Thr Ser Asp Ala Glu Ala Pro Ala Asp Tyr Ala Asp
            515                 520                 525

Arg Tyr Gln Asn Lys Cys Ser Arg His Val Gly Met Asn Leu Met Leu
            530                 535                 540

Phe Pro Cys Lys Thr Cys Glu Arg Met Asn Gln Ile Ser Asn Val Cys
545                 550                 555                 560

Phe Thr His Gly Gln Arg Asp Cys Gly Glu Cys Phe Pro Gly Met Ser
                565                 570                 575

Glu Ser Gln Pro Val Ser Val Val Lys Lys Thr Tyr Gln Lys Leu
                580                 585                 590

Cys Pro Ile His His Ile Leu Gly Arg Ala Pro Glu Ile Ala Cys Ser
            595                 600                 605

Ala Cys Asp Leu Ala Asn Val Asp Leu Asp Asp Cys Val Ser Glu Gln
610                 615                 620
```

<210> SEQ ID NO 116
<211> LENGTH: 624
<212> TYPE: PRT
<213> ORGANISM: Adeno-associated virus 3B

<400> SEQUENCE: 116

```
Met Pro Gly Phe Tyr Glu Ile Val Leu Lys Val Pro Ser Asp Leu Asp
1               5                   10                  15
Glu His Leu Pro Gly Ile Ser Asn Ser Phe Val Asn Trp Val Ala Glu
                20                  25                  30
Lys Glu Trp Glu Leu Pro Pro Asp Ser Asp Met Asp Pro Asn Leu Ile
            35                  40                  45
Glu Gln Ala Pro Leu Thr Val Ala Glu Lys Leu Gln Arg Glu Phe Leu
        50                  55                  60
Val Glu Trp Arg Arg Val Ser Lys Ala Pro Glu Ala Leu Phe Phe Val
65                  70                  75                  80
Gln Phe Glu Lys Gly Glu Thr Tyr Phe His Leu His Val Leu Ile Glu
                85                  90                  95
Thr Ile Gly Val Lys Ser Met Val Val Gly Arg Tyr Val Ser Gln Ile
                100                 105                 110
Lys Glu Lys Leu Val Thr Arg Ile Tyr Arg Gly Val Glu Pro Gln Leu
            115                 120                 125
Pro Asn Trp Phe Ala Val Thr Lys Thr Arg Asn Gly Ala Gly Gly Gly
        130                 135                 140
Asn Lys Val Val Asp Asp Cys Tyr Ile Pro Asn Tyr Leu Leu Pro Lys
145                 150                 155                 160
Thr Gln Pro Glu Leu Gln Trp Ala Trp Thr Asn Met Asp Gln Tyr Leu
                165                 170                 175
Ser Ala Cys Leu Asn Leu Ala Glu Arg Lys Arg Leu Val Ala Gln His
                180                 185                 190
Leu Thr His Val Ser Gln Thr Gln Glu Gln Asn Lys Glu Asn Gln Asn
            195                 200                 205
Pro Asn Ser Asp Ala Pro Val Ile Arg Ser Lys Thr Ser Ala Arg Tyr
        210                 215                 220
Met Glu Leu Val Gly Trp Leu Val Asp Arg Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Ser Lys
                260                 265                 270
Ile Met Ser Leu Thr Lys Thr Ala Pro Asp Tyr Leu Val Gly Ser Asn
            275                 280                 285
Pro Pro Glu Asp Ile Thr Lys Asn Arg Ile Tyr Gln Ile Leu Glu Leu
        290                 295                 300
Asn Gly Tyr Asp Pro Gln Tyr Ala Ala Ser Val Phe Leu Gly Trp Ala
305                 310                 315                 320
Gln Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Ala Val Pro
                340                 345                 350
Phe Tyr Gly Cys Val Asn Trp Thr Asn Glu Asn Phe Pro Phe Asn Asp
            355                 360                 365
Cys Val Asp Lys Met Val Ile Trp Trp Glu Glu Gly Lys Met Thr Ala
```

```
            370                 375                 380
Lys Val Glu Ser Ala Lys Ala Ile Leu Gly Gly Ser Lys Val Arg
385                 390                 395                 400

Val Asp Gln Lys Cys Lys Ser Ser Ala Gln Ile Glu Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
        450                 455                 460

Glu Val Lys Asp Phe Phe Arg Trp Ala Ser Asp His Val Thr Asp Val
465                 470                 475                 480

Ala His Glu Phe Tyr Val Arg Lys Gly Gly Ala Lys Lys Arg Pro Ala
                485                 490                 495

Ser Asn Asp Ala Asp Val Ser Glu Pro Lys Arg Gln Cys Thr Ser Leu
            500                 505                 510

Ala Gln Pro Thr Thr Ser Asp Ala Glu Ala Pro Ala Asp Tyr Ala Asp
        515                 520                 525

Arg Tyr Gln Asn Lys Cys Ser Arg His Val Gly Met Asn Leu Met Leu
530                 535                 540

Phe Pro Cys Lys Thr Cys Glu Arg Met Asn Gln Ile Ser Asn Val Cys
545                 550                 555                 560

Phe Thr His Gly Gln Arg Asp Cys Gly Glu Cys Phe Pro Gly Met Ser
                565                 570                 575

Glu Ser Gln Pro Val Ser Val Val Lys Lys Thr Tyr Gln Lys Leu
            580                 585                 590

Cys Pro Ile His His Ile Leu Gly Arg Ala Pro Glu Ile Ala Cys Ser
                595                 600                 605

Ala Cys Asp Leu Ala Asn Val Asp Leu Asp Asp Cys Val Ser Glu Gln
            610                 615                 620

<210> SEQ ID NO 117
<211> LENGTH: 623
<212> TYPE: PRT
<213> ORGANISM: Adeno-associated virus 4

<400> SEQUENCE: 117

Met Pro Gly Phe Tyr Glu Ile Val Leu Lys Val Pro Ser Asp Leu Asp
1               5                   10                  15

Glu His Leu Pro Gly Ile Ser Asp Ser Phe Val Ser Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Glu Phe Leu
        50                  55                  60

Val Glu Trp Arg Arg Val Ser Lys Ala Pro Glu Ala Leu Phe Phe Val
65                  70                  75                  80

Gln Phe Glu Lys Gly Asp Ser Tyr Phe His Leu His Ile Leu Val Glu
                85                  90                  95

Thr Val Gly Val Lys Ser Met Val Val Gly Arg Tyr Val Ser Gln Ile
            100                 105                 110

Lys Glu Lys Leu Val Thr Arg Ile Tyr Arg Gly Val Glu Pro Gln Leu
        115                 120                 125
```

-continued

```
Pro Asn Trp Phe Ala Val Thr Lys Thr Arg Asn Gly Ala Gly Gly
130                 135                 140
Asn Lys Val Val Asp Asp Cys Tyr Ile Pro Asn Tyr Leu Leu Pro Lys
145                 150                 155                 160
Thr Gln Pro Glu Leu Gln Trp Ala Trp Thr Asn Met Asp Gln Tyr Ile
                165                 170                 175
Ser Ala Cys Leu Asn Leu Ala Glu Arg Lys Arg Leu Val Ala Gln His
            180                 185                 190
Leu Thr His Val Ser Gln Thr Gln Glu Asn Lys Glu Asn Gln Asn
        195                 200                 205
Pro Asn Ser Asp Ala Pro Val Ile Arg Ser Lys Thr Ser Ala Arg Tyr
210                 215                 220
Met Glu Leu Val Gly Trp Leu Val Asp Arg Gly Ile Thr Ser Glu Lys
225                 230                 235                 240
Gln Trp Ile Gln Glu Asp Gln Ala Ser Tyr Ile Ser Phe Asn Ala Ala
                245                 250                 255
Ser Asn Ser Arg Ser Gln Ile Lys Ala Ala Leu Asp Asn Ala Ser Lys
            260                 265                 270
Ile Met Ser Leu Thr Lys Thr Ala Pro Asp Tyr Leu Val Gly Gln Asn
        275                 280                 285
Pro Pro Glu Asp Ile Ser Ser Asn Arg Ile Tyr Arg Ile Leu Glu Met
290                 295                 300
Asn Gly Tyr Asp Pro Gln Tyr Ala Ala Ser Val Phe Leu Gly Trp Ala
305                 310                 315                 320
Gln Lys Lys Phe Gly Lys Arg Asn Thr Ile Trp Leu Phe Gly Pro Ala
                325                 330                 335
Thr Thr Gly Lys Thr Asn Ile Ala Glu Ala Ile Ala His Ala Val Pro
            340                 345                 350
Phe Tyr Gly Cys Val Asn Trp Thr Asn Glu Asn Phe Pro Phe Asn Asp
        355                 360                 365
Cys Val Asp Lys Met Val Ile Trp Trp Glu Glu Gly Lys Met Thr Ala
370                 375                 380
Lys Val Val Glu Ser Ala Lys Ala Ile Leu Gly Gly Ser Lys Val Arg
385                 390                 395                 400
Val Asp Gln Lys Cys Lys Ser Ser Ala Gln Ile Asp Pro Thr Pro Val
                405                 410                 415
Ile Val Thr Ser Asn Thr Asn Met Cys Ala Val Ile Asp Gly Asn Ser
            420                 425                 430
Thr Thr Phe Glu His Gln Gln Pro Leu Gln Asp Arg Met Phe Lys Phe
        435                 440                 445
Glu Leu Thr Lys Arg Leu Glu His Asp Phe Gly Lys Val Thr Lys Gln
450                 455                 460
Glu Val Lys Asp Phe Phe Arg Trp Ala Ser Asp His Val Thr Glu Val
465                 470                 475                 480
Thr His Glu Phe Tyr Val Arg Lys Gly Gly Ala Arg Lys Arg Pro Ala
                485                 490                 495
Pro Asn Asp Ala Asp Ile Ser Glu Pro Lys Arg Ala Cys Pro Ser Val
            500                 505                 510
Ala Gln Pro Ser Thr Ser Asp Ala Glu Ala Pro Val Asp Tyr Ala Asp
        515                 520                 525
Arg Tyr Gln Asn Lys Cys Ser Arg His Val Gly Met Asn Leu Met Leu
530                 535                 540
Phe Pro Cys Arg Gln Cys Glu Arg Met Asn Gln Asn Val Asp Ile Cys
```

```
                545                 550                 555                 560
Phe Thr His Gly Val Met Asp Cys Ala Glu Cys Phe Pro Val Ser Glu
                    565                 570                 575

Ser Gln Pro Val Ser Val Val Arg Lys Arg Thr Tyr Gln Lys Leu Cys
            580                 585                 590

Pro Ile His His Ile Met Gly Arg Ala Pro Glu Val Ala Cys Ser Ala
        595                 600                 605

Cys Glu Leu Ala Asn Val Asp Leu Asp Asp Cys Asp Met Glu Gln
    610                 615                 620

<210> SEQ ID NO 118
<211> LENGTH: 610
<212> TYPE: PRT
<213> ORGANISM: Adeno-associated virus 5

<400> SEQUENCE: 118

Met Ala Thr Phe Tyr Glu Val Ile Val Arg Val Pro Phe Asp Val Glu
1               5                   10                  15

Glu His Leu Pro Gly Ile Ser Asp Ser Phe Val Asp Trp Val Thr Gly
                20                  25                  30

Gln Ile Trp Glu Leu Pro Pro Glu Ser Asp Leu Asn Leu Thr Leu Val
            35                  40                  45

Glu Gln Pro Gln Leu Thr Val Ala Asp Arg Ile Arg Arg Val Phe Leu
        50                  55                  60

Tyr Glu Trp Asn Lys Phe Ser Lys Gln Glu Ser Lys Phe Phe Val Gln
65                  70                  75                  80

Phe Glu Lys Gly Ser Glu Tyr Phe His Leu His Thr Leu Val Glu Thr
                85                  90                  95

Ser Gly Ile Ser Ser Met Val Leu Gly Arg Tyr Val Ser Gln Ile Arg
            100                 105                 110

Ala Gln Leu Val Lys Val Val Phe Gln Gly Ile Glu Pro Gln Ile Asn
        115                 120                 125

Asp Trp Val Ala Ile Thr Lys Val Lys Lys Gly Gly Ala Asn Lys Val
    130                 135                 140

Val Asp Ser Gly Tyr Ile Pro Ala Tyr Leu Leu Pro Lys Val Gln Pro
145                 150                 155                 160

Glu Leu Gln Trp Ala Trp Thr Asn Leu Asp Glu Tyr Lys Leu Ala Ala
                165                 170                 175

Leu Asn Leu Glu Glu Arg Lys Arg Leu Val Ala Gln Phe Leu Ala Glu
            180                 185                 190

Ser Ser Gln Arg Ser Gln Glu Ala Ala Ser Gln Arg Glu Phe Ser Ala
        195                 200                 205

Asp Pro Val Ile Lys Ser Lys Thr Ser Gln Lys Tyr Met Ala Leu Val
    210                 215                 220

Asn Trp Leu Val Glu His Gly Ile Thr Ser Glu Lys Gln Trp Ile Gln
225                 230                 235                 240

Glu Asn Gln Glu Ser Tyr Leu Ser Phe Asn Ser Thr Gly Asn Ser Arg
                245                 250                 255

Ser Gln Ile Lys Ala Ala Leu Asp Asn Ala Thr Lys Ile Met Ser Leu
            260                 265                 270

Thr Lys Ser Ala Val Asp Tyr Leu Val Gly Ser Ser Val Pro Glu Asp
        275                 280                 285

Ile Ser Lys Asn Arg Ile Trp Gln Ile Phe Glu Met Asn Gly Tyr Asp
    290                 295                 300
```

Pro Ala Tyr Ala Gly Ser Ile Leu Tyr Gly Trp Cys Gln Arg Ser Phe
305                 310                 315                 320

Asn Lys Arg Asn Thr Val Trp Leu Tyr Gly Pro Ala Thr Thr Gly Lys
            325                 330                 335

Thr Asn Ile Ala Glu Ala Ile Ala His Thr Val Pro Phe Tyr Gly Cys
            340                 345                 350

Val Asn Trp Thr Asn Glu Asn Phe Pro Phe Asn Asp Cys Val Asp Lys
            355                 360                 365

Met Leu Ile Trp Trp Glu Glu Gly Lys Met Thr Asn Lys Val Val Glu
    370                 375                 380

Ser Ala Lys Ala Ile Leu Gly Gly Ser Lys Val Arg Val Asp Gln Lys
385                 390                 395                 400

Cys Lys Ser Ser Val Gln Ile Asp Ser Thr Pro Val Ile Val Thr Ser
                405                 410                 415

Asn Thr Asn Met Cys Val Val Asp Gly Asn Ser Thr Thr Phe Glu
                420                 425                 430

His Gln Gln Pro Leu Glu Asp Arg Met Phe Lys Phe Glu Leu Thr Lys
            435                 440                 445

Arg Leu Pro Pro Asp Phe Gly Lys Ile Thr Lys Gln Glu Val Lys Asp
450                 455                 460

Phe Phe Ala Trp Ala Lys Val Asn Gln Val Pro Val Thr His Glu Phe
465                 470                 475                 480

Lys Val Pro Arg Glu Leu Ala Gly Thr Lys Gly Ala Glu Lys Ser Leu
                485                 490                 495

Lys Arg Pro Leu Gly Asp Val Thr Asn Thr Ser Tyr Lys Ser Leu Glu
            500                 505                 510

Lys Arg Ala Arg Leu Ser Phe Val Pro Glu Thr Pro Arg Ser Ser Asp
            515                 520                 525

Val Thr Val Asp Pro Ala Pro Leu Arg Pro Leu Asn Trp Asn Ser Arg
            530                 535                 540

Tyr Asp Cys Lys Cys Asp Tyr His Ala Gln Phe Asp Asn Ile Ser Asn
545                 550                 555                 560

Lys Cys Asp Glu Cys Glu Tyr Leu Asn Arg Gly Lys Asn Gly Cys Ile
                565                 570                 575

Cys His Asn Val Thr His Cys Gln Ile Cys His Gly Ile Pro Pro Trp
            580                 585                 590

Glu Lys Glu Asn Leu Ser Asp Phe Gly Asp Phe Asp Ala Asn Lys
                595                 600                 605

Glu Gln
610

<210> SEQ ID NO 119
<211> LENGTH: 623
<212> TYPE: PRT
<213> ORGANISM: Adeno-associated virus 6

<400> SEQUENCE: 119

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

```
Val Gln Trp Arg Arg Val Ser Lys Ala Pro Glu Ala Leu Phe Phe Val
 65                  70                  75                  80

Gln Phe Glu Lys Gly Glu Ser Tyr Phe His Leu His Ile Leu Val Glu
                 85                  90                  95

Thr Thr Gly Val Lys Ser Met Val Leu Gly Arg Phe Leu Ser Gln Ile
            100                 105                 110

Arg Asp Lys Leu Val Gln Thr Ile Tyr Arg Gly Ile Glu Pro Thr Leu
            115                 120                 125

Pro Asn Trp Phe Ala Val Thr Lys Thr Arg Asn Gly Ala Gly Gly Gly
130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala His Asp
            180                 185                 190

Leu Thr His Val Ser Gln Thr Gln Glu Gln Asn Lys Glu Asn Leu Asn
            195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ala
            275                 280                 285

Pro Pro Ala Asp Ile Lys Thr Asn Arg Ile Tyr Arg Ile Leu Glu Leu
290                 295                 300

Asn Gly Tyr Asp Pro Ala Tyr Ala Gly Ser Val Phe Leu Gly Trp Ala
305                 310                 315                 320

Gln Lys Arg Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
            370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Glu His Asp Phe Gly Lys Val Thr Lys Gln
            450                 455                 460

Glu Val Lys Glu Phe Phe Arg Trp Ala Gln Asp His Val Thr Glu Val
465                 470                 475                 480
```

```
Ala His Glu Phe Tyr Val Arg Lys Gly Gly Ala Asn Lys Arg Pro Ala
                485                 490                 495

Pro Asp Asp Ala Asp Lys Ser Glu Pro Lys Arg Ala Cys Pro Ser Val
            500                 505                 510

Ala Asp Pro Ser Thr Ser Asp Ala Glu Gly Ala Pro Val Asp Phe Ala
            515                 520                 525

Asp Arg Tyr Gln Asn Lys Cys Ser Arg His Ala Gly Met Leu Gln Met
        530                 535                 540

Leu Phe Pro Cys Lys Thr Cys Glu Arg Met Asn Gln Asn Phe Asn Ile
545                 550                 555                 560

Cys Phe Thr His Gly Thr Arg Asp Cys Ser Glu Cys Phe Pro Gly Val
                565                 570                 575

Ser Glu Ser Gln Pro Val Val Arg Lys Arg Thr Tyr Arg Lys Leu Cys
            580                 585                 590

Ala Ile His His Leu Leu Gly Arg Ala Pro Glu Ile Ala Cys Ser Ala
        595                 600                 605

Cys Asp Leu Val Asn Val Asp Leu Asp Asp Cys Val Ser Glu Gln
610                 615                 620

<210> SEQ ID NO 120
<211> LENGTH: 623
<212> TYPE: PRT
<213> ORGANISM: Adeno-associated virus 7

<400> SEQUENCE: 120

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
                20                  25                  30

Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
        50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
                100                 105                 110

Arg Glu Lys Leu Val Gln Thr Ile Tyr Arg Gly Val Glu Pro Thr Leu
            115                 120                 125

Pro Asn Trp Phe Ala Val Thr Lys Thr Arg Asn Gly Ala Gly Gly Gly
        130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240
```

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Pro Ser
        275                 280                 285

Leu Pro Ala Asp Ile Lys Thr Asn Arg Ile Tyr Arg Ile Leu Glu Leu
    290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

Phe Tyr Gly Cys Val Asn Trp Thr Asn Glu Asn Phe Pro Phe Asn Asp
        355                 360                 365

Cys Val Asp Lys Met Val Ile Trp Trp Glu Glu Gly Lys Met Thr Ala
    370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
        435                 440                 445

Glu Leu Thr Arg Arg Leu Glu His Asp Phe Gly Lys Val Thr Lys Gln
    450                 455                 460

Glu Val Lys Glu Phe Phe Arg Trp Ala Ser Asp His Val Thr Glu Val
465                 470                 475                 480

Ala His Glu Phe Tyr Val Arg Lys Gly Gly Ala Ser Lys Arg Pro Ala
                485                 490                 495

Pro Asp Asp Ala Asp Ile Ser Glu Pro Lys Arg Ala Cys Pro Ser Val
            500                 505                 510

Ala Asp Pro Ser Thr Ser Asp Ala Glu Gly Ala Pro Val Asp Phe Ala
        515                 520                 525

Asp Arg Tyr Gln Asn Lys Cys Ser Arg His Ala Gly Met Ile Gln Met
    530                 535                 540

Leu Phe Pro Cys Lys Thr Cys Glu Arg Met Asn Gln Asn Phe Asn Ile
545                 550                 555                 560

Cys Phe Thr His Gly Val Arg Asp Cys Leu Glu Cys Phe Pro Gly Val
                565                 570                 575

Ser Glu Ser Gln Pro Val Val Arg Lys Lys Thr Tyr Arg Lys Leu Cys
            580                 585                 590

Ala Ile His His Leu Leu Gly Arg Ala Pro Glu Ile Ala Cys Ser Ala
        595                 600                 605

Cys Asp Leu Val Asn Val Asp Leu Asp Asp Cys Val Ser Glu Gln
    610                 615                 620

<210> SEQ ID NO 121
<211> LENGTH: 625
<212> TYPE: PRT
<213> ORGANISM: Adeno-associated virus 8

<400> SEQUENCE: 121

```
Met Pro Gly Phe Tyr Glu Ile Val Ile Lys Val Pro Ser Asp Leu Asp
1               5                   10                  15
Glu His Leu Pro Gly Ile Ser Asp Ser Phe Val Asn Trp Val Ala Glu
            20                  25                  30
Lys Glu Trp Glu Leu Pro Pro Asp Ser Asp Met Asp Arg Asn Leu Ile
        35                  40                  45
Glu Gln Ala Pro Leu Thr Val Ala Glu Lys Leu Gln Arg Asp Phe Leu
    50                  55                  60
Val Gln Trp Arg Arg Val Ser Lys Ala Pro Glu Ala Leu Phe Phe Val
65                  70                  75                  80
Gln Phe Glu Lys Gly Glu Ser Tyr Phe His Leu His Val Leu Val Glu
                85                  90                  95
Thr Thr Gly Val Lys Ser Met Val Leu Gly Arg Phe Leu Ser Gln Ile
            100                 105                 110
Arg Glu Lys Leu Gly Pro Asp His Leu Pro Ala Gly Ser Ser Pro Thr
        115                 120                 125
Leu Pro Asn Trp Phe Ala Val Thr Lys Asp Ala Val Met Ala Pro Ala
    130                 135                 140
Gly Gly Asn Lys Val Val Asp Glu Cys Tyr Ile Pro Asn Tyr Leu Leu
145                 150                 155                 160
Pro Lys Thr Gln Pro Glu Leu Gln Trp Ala Trp Thr Asn Met Glu Glu
                165                 170                 175
Tyr Ile Ser Ala Cys Leu Asn Leu Ala Glu Arg Lys Arg Leu Val Ala
            180                 185                 190
Gln His Leu Thr His Val Ser Gln Thr Gln Glu Gln Asn Lys Glu Asn
        195                 200                 205
Leu Asn Pro Asn Ser Asp Ala Pro Val Ile Arg Ser Lys Thr Ser Ala
    210                 215                 220
Arg Tyr Met Glu Leu Val Gly Trp Leu Val Asp Arg Gly Ile Thr Ser
225                 230                 235                 240
Glu Lys Gln Trp Ile Gln Glu Asp Gln Ala Ser Tyr Ile Ser Phe Asn
                245                 250                 255
Ala Ala Ser Asn Ser Arg Ser Gln Ile Lys Ala Ala Leu Asp Asn Ala
            260                 265                 270
Gly Lys Ile Met Ala Leu Thr Lys Ser Ala Pro Asp Tyr Leu Val Gly
        275                 280                 285
Pro Ser Leu Pro Ala Asp Ile Thr Gln Asn Arg Ile Tyr Arg Ile Leu
    290                 295                 300
Ala Leu Asn Gly Tyr Asp Pro Ala Tyr Ala Gly Ser Val Phe Leu Gly
305                 310                 315                 320
Trp Ala Gln Lys Lys Phe Gly Lys Arg Asn Thr Ile Trp Leu Phe Gly
                325                 330                 335
Pro Ala Thr Thr Gly Lys Thr Asn Ile Ala Glu Ala Ile Ala His Ala
            340                 345                 350
Val Pro Phe Tyr Gly Cys Val Asn Trp Thr Asn Glu Asn Phe Pro Phe
        355                 360                 365
Asn Asp Cys Val Asp Lys Met Val Ile Trp Trp Glu Glu Gly Lys Met
    370                 375                 380
Thr Ala Lys Val Val Glu Ser Ala Lys Ala Ile Leu Gly Gly Ser Lys
385                 390                 395                 400
Val Arg Val Asp Gln Lys Cys Lys Ser Ser Ala Gln Ile Asp Pro Thr
                405                 410                 415
```

```
Pro Val Ile Val Thr Ser Asn Thr Asn Met Cys Ala Val Ile Asp Gly
            420                 425                 430

Asn Ser Thr Thr Phe Glu His Gln Gln Pro Leu Gln Asp Arg Met Phe
        435                 440                 445

Lys Phe Glu Leu Thr Arg Arg Leu Glu His Asp Phe Gly Lys Val Thr
450                 455                 460

Lys Gln Glu Val Lys Glu Phe Phe Arg Trp Ala Ser Asp His Val Thr
465                 470                 475                 480

Glu Val Ala His Glu Phe Tyr Val Arg Lys Gly Gly Ala Ser Lys Arg
                485                 490                 495

Pro Ala Pro Asp Asp Ala Asp Lys Ser Glu Pro Lys Arg Ala Cys Pro
            500                 505                 510

Ser Val Ala Asp Pro Ser Thr Ser Asp Ala Glu Gly Ala Pro Val Asp
        515                 520                 525

Phe Ala Asp Arg Tyr Gln Asn Lys Cys Ser Arg His Ala Gly Met Leu
530                 535                 540

Gln Met Leu Phe Pro Cys Lys Thr Cys Glu Arg Met Asn Gln Asn Phe
545                 550                 555                 560

Asn Ile Cys Phe Thr His Gly Val Arg Asp Cys Ser Glu Cys Phe Pro
                565                 570                 575

Gly Val Ser Glu Ser Gln Pro Val Val Arg Lys Arg Thr Tyr Arg Lys
            580                 585                 590

Leu Cys Ala Ile His His Leu Leu Gly Arg Ala Pro Glu Ile Ala Cys
        595                 600                 605

Ser Ala Cys Asp Leu Val Asn Val Asp Leu Asp Asp Cys Val Ser Glu
    610                 615                 620

Gln
625

<210> SEQ ID NO 122
<211> LENGTH: 622
<212> TYPE: PRT
<213> ORGANISM: Artificial
<220> FEATURE:
<223> OTHER INFORMATION: AAV Rep78 consensus sequence
<220> FEATURE:
<221> NAME/KEY: MISC_FEATURE
<222> LOCATION: (118)..(118)
<223> OTHER INFORMATION: Xaa can be Gln, Lys, Pro or Thr
<220> FEATURE:
<221> NAME/KEY: MISC_FEATURE
<222> LOCATION: (119)..(119)
<223> OTHER INFORMATION: Xaa can be Arg, Asp, Thr or Val
<220> FEATURE:
<221> NAME/KEY: MISC_FEATURE
<222> LOCATION: (287)..(287)
<223> OTHER INFORMATION: Xaa can be Gln, Pro or Ser
<220> FEATURE:
<221> NAME/KEY: MISC_FEATURE
<222> LOCATION: (541)..(541)
<223> OTHER INFORMATION: Xaa can be Asn, Asp, Ile and Leu
<220> FEATURE:
<221> NAME/KEY: MISC_FEATURE
<222> LOCATION: (557)..(557)
<223> OTHER INFORMATION: Xaa can be Lys, Phe, Ser or Val
<220> FEATURE:
<221> NAME/KEY: MISC_FEATURE
<222> LOCATION: (565)..(565)
<223> OTHER INFORMATION: Xaa can be Gln, Thr or Val
<220> FEATURE:
<221> NAME/KEY: MISC_FEATURE
<222> LOCATION: (569)..(569)
<223> OTHER INFORMATION: Xaa can be Ala, Gln, Gly, Leu or Ser
<220> FEATURE:
```

<221> NAME/KEY: MISC_FEATURE
<222> LOCATION: (580)..(580)
<223> OTHER INFORMATION: Xaa can be Pro or Ser
<220> FEATURE:
<221> NAME/KEY: MISC_FEATURE
<222> LOCATION: (588)..(588)
<223> OTHER INFORMATION: Xaa can be Arg or Gln
<220> FEATURE:
<221> NAME/KEY: MISC_FEATURE
<222> LOCATION: (592)..(592)
<223> OTHER INFORMATION: Xaa can be Ala, Pro or Tyr

<400> SEQUENCE: 122

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Arg Asn Leu Ile
        35                  40                  45

Glu Gln Ala Pro Leu Thr Val Ala Glu Lys Leu Gln Arg Asp Phe Leu
    50                  55                  60

Val Gln Trp Arg Arg Val Ser Lys Ala Pro Glu Ala Leu Phe Phe Val
65                  70                  75                  80

Gln Phe Glu Lys Gly Glu Ser Tyr Phe His Leu His Val Leu Val Glu
                85                  90                  95

Thr Thr Gly Val Lys Ser Met Val Leu Gly Arg Phe Leu Ser Gln Ile
            100                 105                 110

Arg Glu Lys Leu Val Xaa Xaa Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Glu Tyr Ile
                165                 170                 175

Ser Ala Cys Leu Asn Leu Ala Glu Arg Lys Arg Leu Val Ala Gln His
            180                 185                 190

Leu Thr His Val Ser Gln Thr Gln Glu Gln Asn Lys Glu Asn Leu Asn
        195                 200                 205

Pro Asn Ser Asp Ala Pro Val Ile Arg Ser Lys Thr Ser Ala Arg Tyr
    210                 215                 220

Met Glu Leu Val Gly Trp Leu Val Asp Arg Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ala Leu Thr Lys Ser Ala Pro Asp Tyr Leu Val Gly Xaa Ser
        275                 280                 285

Pro Pro Glu Asp Ile Ser Thr Asn Arg Ile Tyr Arg Ile Leu Ala Leu
    290                 295                 300

Asn Gly Tyr Asp Pro Ala Tyr Ala Gly Ser Val Phe Leu Gly Trp Ala
305                 310                 315                 320

Gln Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Ala Val Pro
            340                 345                 350

```
Phe Tyr Gly Cys Val Asn Trp Thr Asn Glu Asn Phe Pro Phe Asn Asp
            355                 360                 365

Cys Val Asp Lys Met Val Ile Trp Trp Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
                420                 425                 430

Thr Thr Phe Glu His Gln Gln Pro Leu Gln Asp Arg Met Phe Lys Phe
                435                 440                 445

Glu Leu Thr Arg Arg Leu Glu His Asp Phe Gly Lys Val Thr Lys Gln
            450                 455                 460

Glu Val Lys Glu Phe Phe Arg Trp Ala Ser Asp His Val Thr Glu Val
465                 470                 475                 480

Ala His Glu Phe Tyr Val Arg Lys Gly Ala Lys Lys Arg Pro Ala
                485                 490                 495

Pro Asp Asp Ala Asp Lys Ser Glu Pro Lys Arg Ala Cys Pro Ser Val
                500                 505                 510

Ala Asp Pro Ser Thr Ser Asp Ala Glu Ala Pro Val Asp Phe Ala Asp
                515                 520                 525

Arg Tyr Gln Asn Lys Cys Ser Arg His Ala Gly Met Xaa Gln Met Leu
                530                 535                 540

Phe Pro Cys Lys Thr Cys Glu Arg Met Asn Gln Asn Xaa Asn Ile Cys
545                 550                 555                 560

Phe Thr His Gly Xaa Arg Asp Cys Xaa Glu Cys Phe Pro Gly Val Ser
                565                 570                 575

Glu Ser Gln Xaa Val Val Arg Lys Arg Thr Tyr Xaa Lys Leu Cys Xaa
                580                 585                 590

Ile His His Leu Leu Gly Arg Ala Pro Glu Ile Ala Cys Ser Ala Cys
            595                 600                 605

Asp Leu Val Asn Val Asp Leu Asp Asp Cys Val Ser Glu Gln
            610                 615                 620

<210> SEQ ID NO 123
<211> LENGTH: 122
<212> TYPE: DNA
<213> ORGANISM: Snake parvovirus

<400> SEQUENCE: 123
cgccccaccc ctagtgatcg cgcgcgctct ctcttggggc ctgacggccg aaggccgtca    60
gctgccgagc ttcgctcggc aggccccaag agagagcgcg cgcgatcact aggggtgggg   120
cg                                                                  122

<210> SEQ ID NO 124
<211> LENGTH: 6107
<212> TYPE: DNA
<213> ORGANISM: Artificial
<220> FEATURE:
<223> OTHER INFORMATION: Snake ITR eGFP vector sequence

<400> SEQUENCE: 124
gtggcacttt tcggggaaat gtgcgcggaa cccctatttg tttatttttc taaatacatt    60
caaatatgta tccgctcatg agacaataac cctgataaat gcttcaataa tattgaaaaa   120
```

```
ggaagagtat gagtattcaa catttccgtg tcgcccttat tccctttttt gcggcatttt      180
gccttcctgt ttttgctcac ccagaaacgc tggtgaaagt aaaagatgct gaagatcagt      240
tgggtgcacg agtgggttac atcgaactgg atctcaacag cggtaagatc cttgagagtt      300
ttcgccccga agaacgtttt ccaatgatga gcacttttaa agttctgcta tgtggcgcgg      360
tattatcccg tattgacgcc gggcaagagc aactcggtcg ccgcatacac tattctcaga      420
atgacttggt tgagtactca ccagtcacag aaaagcatct tacgggatggc atgacagtaa     480 gagaattatg cagtgctgcc ataaccatga gtgataacac tgcggccaac ttacttctga      540
caacgatcgg aggaccgaag gagctaaccg cttttttgca caacatgggg gatcatgtaa      600
ctcgccttga tcgttgggaa ccggagctga atgaagccat accaaacgac gagcgtgaca      660
ccacgatgcc tgtagcaatg gcaacaacgt tgcgcaaact attaactggc gaactactta      720
ctctagcttc ccggcaacaa ttaatagact ggatggaggc ggataaagtt gcaggaccac      780
ttctgcgctc ggcccttccg gctggctggt ttattgctga taaatctgga gccggtgagc      840
gtgggtctcg cggtatcatt gcagcactgg ggccagatgg taagccctcc cgtatcgtag      900
ttatctacac gacggggagt caggcaacta tggatgaacg aaatagacag atcgctgaga      960
taggtgcctc actgattaag cattggtaac tgtcagacca agtttactca tatatacttt     1020
agattgattt aaaacttcat ttttaattta aaaggatcta ggtgaagatc ctttttgata     1080
atctcatgac caaaatccct taacgtgagt tttcgttcca ctgagcgtca gaccccgtag     1140
aaaagatcaa aggatcttct tgagatcctt ttttttctgcg cgtaatctgc tgcttgcaaa     1200
caaaaaaacc accgctacca gcggtggttt gtttgccgga tcaagagcta ccaactcttt     1260
ttccgaaggt aactggcttc agcagagcgc agataccaaa tactgtcctt ctagtgtagc     1320
cgtagttagg ccaccacttc aagaactctg tagcaccgcc tacatacctc gctctgctaa     1380
tcctgttacc agtggctgct gccagtggcg ataagtcgtg tcttaccggg ttggactcaa     1440
gacgatagtt accggataag cgcagcggt cgggctgaac ggggggttcg tgcacacagc      1500
ccagcttgga gcgaacgacc tacaccgaac tgagatacct acagcgtgag ctatgagaaa     1560
gcgccacgct tcccgaaggg agaaaggcgg acaggtatcc ggtaagcggc agggtcggaa     1620
caggagagcg cacgagggag cttccagggg gaaacgcctg gtatctttat agtcctgtcg     1680
ggtttcgcca cctctgactt gagcgtcgat ttttgtgatg ctcgtcaggg gggcggagcc     1740
tatggaaaaa cgccagcaac gcggcctttt tacggttcct ggccttttgc tggccttttg     1800
ctcacatgtt ctttcctgcg ttatccctg attctgtgga taaccgtatt accgcctttg     1860
agtgagctga taccgctcgc cgcagccgaa cgaccgagcg cagcgagtca gtgagcgagg     1920
aagcggaaga gcgcccaata cgcaaaccgc ctctccccgc gcgttggccg attcattaat     1980
gcagctggca cgacaggttt cccgactgga aagcgggcag tgagcgcaac gcaattaatg     2040
tgagttagct cactcattag gcaccccagg ctttacactt tatgcttccg gctcgtatgt     2100
tgtgtggaat tgtgagcgga taacaatttc acacaggaaa cagctatgac catgattacg     2160
ccaagcgcgc aattaaccct cactaaaggg aacaaaagct gggtaccggg ccccccctcg     2220
aggtcgacgg tatcgataag cttgatcgcc ccaccccttag tgatcgcgcg cgctctctct     2280
tggggcctga cggccgaagg ccgtcagctg ccgagcttcg ctcggcaggc cccaagagag     2340
agcgcgcgcg atcactaggg gtggggcgag tgccctgctc aacgggtttt ttggtgggcg     2400
gagcaatgac gtcagcggac atgtctggac atgtctttga gcaagtccat ataaggagtt     2460
```

```
ccgccggata tgcaaatgag caatcgcgca aagcattttg ggtagtcacc atgaataaaa    2520
aggacagcaa gaaagatgac gccccataat tttaatagga attttaacca tgttctttcc    2580
tgcgttatcc cctgattctg tggataaccg tattaccgcc tttgagtgag ctgataccgc    2640
tcgccgcagc cgaacgaccg agcgcagcga gtcagtgagc gaggaagcgg aagagcgccc    2700
aatacgcaaa ccgcctctcc ccgcgcgttg gccgattcat taatgcagct ggcacgacag    2760
gtttcccgac tggaaagcgg gcagtgagcg caacgcaatt aatgtgagtt agctcactca    2820
ttaggcaccc caggctttac actttatgct tccggctcgt atgttgtgtg gaattgtgag    2880
cggataacaa tttcacacag gaaacagcta tgaccatgat tacgaattgt tgttgttaac    2940
ttgtttattg cagcttataa tggttacaaa taaagcaata gcatcacaaa tttcacaaat    3000
aaagcatttt tttcactgca ttctagttgt ggtttgtcca aactcatcaa tgtatcttat    3060
catgtctgga tccccgcggc cgctttactt gtacagctcg tccatgccga gagtgatccc    3120
ggcggcggtc acgaactcca gcaggaccat gtgatcgcgc ttctcgttgg ggtctttgct    3180
cagggcggac tgggtgctca ggtagtggtt gtcgggcagc agcacgggc cgtcgccgat    3240 gggggtgttc tgctggtagt ggtcggcgag ctgcacgctg ccgtcctcga tgttgtggcg    3300
gatcttgaag ttcaccttga tgccgttctt ctgcttgtcg gccatgatat agacgttgtg    3360
gctgttgtag ttgtactcca gcttgtgccc caggatgttg ccgtcctcct tgaagtcgat    3420
gcccttcagc tcgatgcggt tcaccagggt gtcgccctcg aacttcacct cggcgcgggt    3480
cttgtagttg ccgtcgtcct tgaagaagat ggtgcgctcc tggacgtagc cttcgggcat    3540
ggcggacttg aagaagtcgt gctgcttcat gtggtcgggg tagcggctga agcactgcac    3600
gccgtaggtc agggtggtca cgagggtggg ccagggcacg gcagcttgc cggtggtgca    3660 gatgaacttc agggtcagct tgccgtaggt ggcatcgccc tcgccctcgc cggacacgct    3720
gaacttgtgg ccgtttacgt cgccgtccag ctcgaccagg atgggcacca ccccggtgaa    3780
cagctcctcg cccttgctca ccatggtggc gaccggtgga tcccgggccg cgggtacaat    3840
tccgcagctt ttagagcaga agtaacactt ccgtacaggc ctagaagtaa aggcaacatc    3900
cactgaggag cagttctttg atttgcacca ccaccggatc cgggacctga aataaaagac    3960
aaaaagacta aacttaccag ttaactttct ggttttttcag ttcctcgagt accggatcct    4020
ctagagtccg gaggctggat cggtcccggt gtcttctatg gaggtcaaaa cagcgtggat    4080
ggcgtctcca ggcgatctga cggttcacta acgagctct gcttatatag acctcccacc    4140
gtacacgcct accgcccatt tgcgtcaatg gggcggagtt gttacgacat tttggaaagt    4200
cccgttgatt ttggtgccaa acaaactcc cattgacgtc aatggggtgg agacttggaa    4260
atccccgtga gtcaaaccgc tatccacgcc cattgatgta ctgccaaaac cgcatcacca    4320
tggtaatagc gatgactaat acgtagatgt actgccaagt aggaaagtcc cataaggtca    4380
tgtactgggc ataatgccag gcgggccatt taccgtcatt gacgtcaata ggggggcgtac    4440 ttggcatatg atacacttga tgtactgcca agtgggcagt ttaccgtaaa tactccaccc    4500
attgacgtca atggaaagtc cctattggcg ttactattga cgtcaatggg cggggtcgt    4560 tgggcggtca gccaggcggg ccatttaccg taagttatgt aacgggtacc ggggatcct    4620 ctagagtcga cctgcagtaa acagaacaat tgaagacgaa atacagggta ccaataattt    4680
tggtaatgct agaaataaca ttgttgctat caatcaacaa acgaaaggaa caaatccaac    4740
aacaggtagt acatctcaat ttgagacaat gccaggtatg gtgtggtcta atagagacat    4800
ttacttacag gggcctattt gggctaaaat tccaaataca gatggacatt ttcatccttc    4860
```

```
tcccagaatg ggtggttttg gattaaaaca tcctccgcct atgattctga tcaaaaatac      4920
accagttcct gctgatcctc caactacctt caatccaatg ccacagacta gtttcattac      4980
tgaatacagt acaggacaag taactgttga atgttgtgg gaggtacaga agaatcctc        5040 caaaagatgg aatccagaag tacagtttac ttccaatttt ggaacttcag atccagctgt     5100
tgatggaata ccgtttggaa ttaataattt gggtacttat gttgaatcta gacctattgg     5160
aactcgttat atttctaaac acttgtaaat aataaaaatt gtcaaatttg cactaagaat     5220
tgttgtcacg tggttgttta catgcttgct aaaacacgcc caccaaaaaa cccgttgagc     5280
agggcactcg ccccaccct agtgatcgcg cgcgctctct cttggggcct gccgagcgaa      5340
gctcggcagc tgacggcctt cggccgtcag gcccaagag agagcgcgcg cgatcactag      5400
gggtggggcg gggggatcca ctagttctag agcggccgcc accgcggtgg agctccaatt    5460
cgccctatag tgagtcgtat tacgcgcgct cactggccgt cgttttacaa cgtcgtgact    5520
gggaaaaccc tggcgttacc caacttaatc gccttgcagc acatccccct ttcgccagct    5580
ggcgtaatag cgaagaggcc cgcaccgatc gcccttccca acagttgcgc agcctgaatg    5640
gcgaatggga cgcgccctgt agcggcgcat taagcgcggc gggtgtggtg gttacgcgca    5700
gcgtgaccgc tacacttgcc agcgccctag cgcccgctcc tttcgctttc ttcccttcct    5760
ttctcgccac gttcgccggc tttccccgtc aagctctaaa tcggggggctc cctttagggt   5820 tccgatttag tgctttacgg cacctcgacc ccaaaaaact tgattagggt gatggttcac    5880
gtagtgggcc atcgccctga tagacggttt ttcgcccttt gacgttggag tccacgttct    5940
ttaatagtgg actcttgttc caaactggaa caacactcaa ccctatctcg gtctattctt    6000
ttgatttata agggattttg ccgatttcgg cctattggtt aaaaaatgag ctgatttaac    6060
aaaaatttaa cgcgaatttt aacaaaatat taacgcttac aatttag                   6107
```

<210> SEQ ID NO 125
<211> LENGTH: 7302
<212> TYPE: DNA
<213> ORGANISM: Artificial
<220> FEATURE:
<223> OTHER INFORMATION: pSnRepCap2 plasmid sequence

<400> SEQUENCE: 125

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg   120
ttggcgggtg tcgggctgg cttaactatg cggcatcaga gcagattgta ctgagagtgc    180
accatatgcg gtgtgaaata ccgcacagat gcgtaaggag aaaataccgc atcaggaaat   240
tgtaaacgtt aatattttgt taaaattcgc gttaaatttt tgttaaatca gctcattttt   300
taaccaatag gccgaaatcg gcaaaatccc ttataaatca aagaataga ccgagatagg    360 gttgagtgtt gttccagttt ggaacaagag tccactatta agaacgtgg actccaacgt    420 caaagggcga aaaaccgtct atcagggcga tggcccacta cgtgaaccat cccctaatc    480 aagttttttg gggtcgaggt gccgtaaagc actaaatcgg aaccctaaag ggagcccccg    540
atttagagct tgacggggaa agccggcgaa cgtggcgagg aaggaaggga agaaagcgaa    600
aggagcgggc gctagggcgc tggcaagtgt agcggtcacg ctgcgcgtaa ccaccacacc    660
cgccgcgctt aatgcgccgc tacagggcgc gtcgcgccat cgccattca ggctgcgcaa    720 ctgttgggaa gggcgatcgg tgcgggcctc ttcgctatta cgccagctgg cgaaaggggg    780
```

```
atgtgctgca aggcgattaa gttgggtaac gccagggttt tcccagtcac gacgttgtaa    840
aacgacggcc agtgaattgt aatacgactc actatagggc gaattcgagc tcgcagcgga    900
catgtctgga catgtctttg agcaagtcca tataaggagt tccgccggat atgcaaatga    960
gcaatcgcgc aaagcatttt gggtagtcac catgaataaa aaggacagca agaaagatga   1020
cgccccataa ttttaatagg aattttaacc atggcgtttt acgaggttgt gtttcgtttg   1080
ccaagagaca ataacaactt gttggatgaa gatagatatc agccagagtt gaaagaagaa   1140
gatgactggc ctgaggaata tttaaccagt gaagatgcca gctttatcgg actagcgtat   1200
gctgtgctaa gtgaaattcg gagattcttt ggaaaggaac tacaatggtt tgcccaggtt   1260
gaatggtgtc ctactgctgg ttaccacatg catgttttgt tgaaccatcc taagctgagt   1320
aaccagactt atggaagaaa ggtcaatgaa ctggcttgcc gtatagtcga taccttggc    1380 ctaattaatc cagaagaagt catcagtacc cattatgtta aaagcaacta tggacataaa   1440
aaggtgagag tcattcacct agagtcttat ttgaagaact acttttttcag aaagacttta   1500 gctcctccca attataccga ggaaggagac tataaaagag aggaagaagt cgtgctgtgg   1560
gcatttacga atatcgtcgc ttggaagcca ttcgtgcgga atctcatcaa gagatcggag   1620
ctagcgactg ttcctaagca accagagaat ccggcggaga acggaccggc acctcgagtg   1680
actgcaggaa cccgccattt tatggaaacc atcgactggt tggtgaaaca tggaattact   1740
acagaacgag aattctgcca cgccaaccgc cctttgtacc tgtctatgct ggcttctact   1800
tcgggtgctg gcagattaa aagagcgctg gaccaggcga acacatgat gaccagcacc     1860 atgtcagcag aggattacct gacaacagaa gaggatgtga tcgaaccacc tactgaaaat   1920
agaatctaca agattatgaa actgaatcgc tatgatccag aactagcagc tgctctcttc   1980
tacggctgga cctgcaagaa ctttggcaag agaaacacca tctggctgta tggtccagct   2040
actaccggca aaaccatcat cgctcaagct attgcacatg ctgttaaact gtttgctggt   2100
gttaattgga ctaatgaaaa cttttccctt c tgtaactgtc cagggaaact gcttatctgg   2160
tgggaggagg gcaagatgac aaacaaaatg gtggagacgg ctaaatgtat actgggggga   2220
tctgctgtac ctgtagacat caaaggcaaa cccgctgaaa tgtgtcctca aacaccctgt   2280
attattacta gcaatactaa catgtgtcaa gtatatgatg gtaatagttc tagctttgag   2340
caccaagaac ccctagagga acgcatgttt atgttcagac ttaatactaa actgccatcg   2400 accttttggca agatcacaga agaggaagtc aaacagttta ttacctgggg gaggagctta   2460
aaggttcaag ttccacatca gttcagagtg cctaccacag gagagtataa aaggccagcc   2520
cccgaggcga aagctcattc ttcggatgag ccgccaaaag agaaggtcgc gcgtattgat   2580
gactctctaa ccaggtatgt taacaatatt gatgagtcag ctaccagtag agaaatgttt   2640
ctagagattg ctaatactaa tcaatgtatg ttgcatcatt gcttttcttg taccgaatgt   2700
tatcctgaat tgcttgatga catggacaag gaacaataaa cttactgata acagatatgg   2760
ctgccgatgg ttatcttcca gattggctcg aggacactct ctctgaagga ataagacagt   2820
ggtggaagct caaacctggc ccaccaccac caaagcccgc agagcggcat aaggacgaca   2880
gcaggggtct tgtgcttcct gggtacaagt acctcggacc cttcaacgga ctcgacaagg   2940
gagagccggt caacgaggca gacgccgcgg ccctcgagca cgacaaagcc tacgaccggc   3000
agctcgacag cggagacaac ccgtacctca agtacaacca cgccgacgcg gagtttcagg   3060
agcgccttaa agaagatacg tcttttgggg gcaacctcgg acgagcagtc ttccaggcga   3120
aaaagagggt tcttgaacct ctgggcctgg ttgaggaacc tgttaagacg ctccgggaa    3180
```

-continued

```
aaaagaggcc ggtagagcac tctcctgtgg agccagactc ctcctcggga accggaaagg    3240
cgggccagca gcctgcaaga aaaagattga attttggtca gactggagac gcagactcag    3300
tacctgaccc ccagcctctc ggacagccac cagcagcccc ctctggtctg ggaactaata    3360
cgatggctac aggcagtggc gcaccaatgg cagacaataa cgagggcgcc gacggagtgg    3420
gtaattcctc gggaaattgg cattgcgatt ccacatggat gggcgacaga gtcatcacca    3480
ccagcacccg aacctgggcc ctgcccacct acaacaacca cctctacaaa caaatttcca    3540
gccaatcagg agcctcgaac gacaatcact actttggcta cagcacccct tgggggtatt    3600
ttgacttcaa cagattccac tgccactttt caccacgtga ctggcaaaga ctcatcaaca    3660
acaactgggg attccgaccc aagagactca acttcaagct ctttaacatt caagtcaaag    3720
aggtcacgca gaatgacggt acgacgacga ttgccaataa ccttaccagc acggttcagg    3780
tgtttactga ctcggagtac cagctcccgt acgtcctcgg ctcggcgcat caaggatgcc    3840
tcccgccgtt cccagcagac gtcttcatgg tgccacagta tggataccte accctgaaca    3900 acgggagtca ggcagtagga cgctcttcat tttactgcct ggagtacttt ccttctcaga    3960
tgctgcgtac cggaaacaac tttaccttca gctacacttt tgaggacgtt cctttccaca    4020
gcagctacgc tcacagccag agtctggacc gtctcatgaa tcctctcatc gaccagtacc    4080
tgtattactt gagcagaaca aacactccaa gtggaaccac cacgcagtca aggcttcagt    4140
tttctcaggc cggagcgagt gacattcggg accagtctag gaactggctt cctggaccct    4200
gttaccgcca gcagcgagta tcaaagacat ctgcggataa caacaacagt gaatactcgt    4260
ggactggagc taccaagtac cacctcaatg gcagagactc tctggtgaat ccgggcccgg    4320
ccatggcaag ccacaaggac gatgaagaaa agttttttcc tcagagcggg gttctcatct    4380
ttgggaagca aggctcagag aaaacaaatg tggacattga aaaggtcatg attacagacg    4440
aagaggaaat caggacaacc aatcccgtgg ctacggagca gtatggttct gtatctacca    4500
acctccagag aggcaacaga caagcagcta ccgcagatgt caacacacaa ggcgttcttc    4560
caggcatggt ctggcaggac agagatgtgt accttcaggg gcccatctgg gcaaagattc    4620
cacacacgga cggacatttt cacccctctc ccctcatggg tggattcgga cttaaacacc    4680
ctcctccaca gattctcatc aagaacaccc cggtacctgc gaatcctccg accaccttca    4740
gtgcggcaaa gtttgcttcc ttcatcacac agtactccac gggacaggtc agcgtggaga    4800
tcgagtggga gctgcagaag gaaaacagca acgctggaa tcccgaaatt cagtacactt    4860
ccaactacaa caagtctgtt aatgtggact ttactgtgga cactaatggc gtgtattcag    4920
agcctcgccc cattggcacc agatacctga ctcgtaatct gtaattgctt gttaatcaat    4980
aaaccgttta attcgtttca gttgaacttt ggtgtcgcgg ccgctcgata gcttttgtt    5040 ccctttagtg agggttaatt ccgagcttgg cgtaatcatg gtcatagctg tttcctgtgt    5100
gaaattgtta tccgctcaca attccacaca acatacgagc cggaagcata agtgtaaag    5160 cctggggtgc ctaatgagtg agctaactca cattaattgc gttgcgctca ctgcccgctt    5220
tccagtcggg aaacctgtcg tgccagctgc attaatgaat cggccaacgc gcgggagag    5280 gcggtttgcg tattgggcgc tcttccgctt cctcgctcac tgactcgctg cgctcggtcg    5340
ttcggctgcg gcgagcggta tcagctcact caaaggcggt aatacggtta ccacagaat    5400 cagggggataa cgcaggaaag aacatgtgag caaaaggcca gcaaaggcc aggaaccgta    5460 aaaaggccgc gttgctggcg ttttccata ggctccgccc cctgacgag catcacaaaa    5520
```

| | |
|---|---|
| atcgacgctc aagtcagagg tggcgaaacc cgacaggact ataaagatac caggcgtttc | 5580 |
| cccctggaag ctccctcgtg cgctctcctg ttccgaccct gccgcttacc ggatacctgt | 5640 |
| ccgcctttct cccttcggga agcgtggcgc tttctcatag ctcacgctgt aggtatctca | 5700 |
| gttcggtgta ggtcgttcgc tccaagctgg gctgtgtgca cgaaccccc gttcagcccg | 5760 |
| accgctgcgc cttatccggt aactatcgtc ttgagtccaa cccggtaaga cacgacttat | 5820 |
| cgccactggc agcagccact ggtaacagga ttagcagagc gaggtatgta ggcggtgcta | 5880 |
| cagagttctt gaagtggtgg cctaactacg gctacactag aaggacagta tttggtatct | 5940 |
| gcgctctgct gaagccagtt accttcggaa aaagagttgg tagctcttga tccggcaaac | 6000 |
| aaaccaccgc tggtagcggt ggtttttttg tttgcaagca gcagattacg cgcagaaaaa | 6060 |
| aaggatctca agaagatcct ttgatctttt ctacggggtc tgacgctcag tggaacgaaa | 6120 |
| actcacgtta agggattttg gtcatgagat tatcaaaaag gatcttcacc tagatccttt | 6180 |
| taaattaaaa atgaagtttt aaatcaatct aaagtatata tgagtaaact tggtctgaca | 6240 |
| gttaccaatg cttaatcagt gaggcaccta tctcagcgat ctgtctattt cgttcatcca | 6300 |
| tagttgcctg actccccgtc gtgtagataa ctacgatacg ggagggctta ccatctggcc | 6360 |
| ccagtgctgc aatgataccg cgagacccac gctcaccggc tccagattta tcagcaataa | 6420 |
| accagccagc cggaagggcc gagcgcagaa gtggtcctgc aactttatcc gcctccatcc | 6480 |
| agtctattaa ttgttgccgg gaagctagag taagtagttc gccagttaat agtttgcgca | 6540 |
| acgttgttgc cattgctaca ggcatcgtgg tgtcacgctc gtcgtttggt atggcttcat | 6600 |
| tcagctccgg ttcccaacga tcaaggcgag ttacatgatc ccccatgttg tgcaaaaaag | 6660 |
| cggttagctc cttcggtcct ccgatcgttg tcagaagtaa gttggccgca gtgttatcac | 6720 |
| tcatggttat ggcagcactg cataattctc ttactgtcat gccatccgta agatgctttt | 6780 |
| ctgtgactgg tgagtactca accaagtcat tctgagaata gtgtatgcgg cgaccgagtt | 6840 |
| gctcttgccc ggcgtcaata cgggataata ccgcgccaca tagcagaact ttaaaagtgc | 6900 |
| tcatcattgg aaaacgttct cggggcgaaa actctcaag gatcttaccg ctgttgagat | 6960 |
| ccagttcgat gtaacccact cgtgcaccca actgatcttc agcatctttt actttcacca | 7020 |
| gcgtttctgg gtgagcaaaa acaggaaggc aaaatgccgc aaaaaaggga taagggcga | 7080 |
| cacggaaatg ttgaatactc atactcttcc ttttcaata ttattgaagc atttatcagg | 7140 |
| gttattgtct catgagcgga tacatatttg aatgtattta gaaaaataaa caaatagggg | 7200 |
| ttccgcgcac atttccccga aaagtgccac ctgacgtcta agaaaccatt attatcatga | 7260 |
| cattaaccta taaaaatagg cgtatcacga ggccctttcg tc | 7302 |

<210> SEQ ID NO 126
<211> LENGTH: 30
<212> TYPE: DNA
<213> ORGANISM: Artificial
<220> FEATURE:
<223> OTHER INFORMATION: PCR primer

<400> SEQUENCE: 126
cgaaaagtgc cacctgacgt ctaagaaacc         30

<210> SEQ ID NO 127
<211> LENGTH: 35
<212> TYPE: DNA
<213> ORGANISM: Artificial
<220> FEATURE:
<223> OTHER INFORMATION: PCR primer

```
<400> SEQUENCE: 127
tcgaattcga cggccagtga attgtaatac gactc                              35

<210> SEQ ID NO 128
<211> LENGTH: 37
<212> TYPE: DNA
<213> ORGANISM: Artificial
<220> FEATURE:
<223> OTHER INFORMATION: PCR primer

<400> SEQUENCE: 128
ccatgattac gccaagctcg gaattaaccg catgcga                            37

<210> SEQ ID NO 129
<211> LENGTH: 23
<212> TYPE: DNA
<213> ORGANISM: Artificial
<220> FEATURE:
<223> OTHER INFORMATION: PCR primer

<400> SEQUENCE: 129
ccatggccgg gcccggattc acc                                           23

<210> SEQ ID NO 130
<211> LENGTH: 69
<212> TYPE: DNA
<213> ORGANISM: Artificial
<220> FEATURE:
<223> OTHER INFORMATION: PCR primer

<400> SEQUENCE: 130
ttcaccccgg tggtttccac gagcacgtgc atgtggaagt agctctctcc cttttcaaac   60
tgcacaaag                                                           69

<210> SEQ ID NO 131
<211> LENGTH: 45
<212> TYPE: DNA
<213> ORGANISM: Artificial
<220> FEATURE:
<223> OTHER INFORMATION: PCR primer

<400> SEQUENCE: 131
cctcggccgc tacgtgagtc agattcgcga aaaactgatt cagag                   45

<210> SEQ ID NO 132
<211> LENGTH: 48
<212> TYPE: DNA
<213> ORGANISM: Artificial
<220> FEATURE:
<223> OTHER INFORMATION: PCR primer

<400> SEQUENCE: 132
gtggtcttcc agggaattga acccactttg ccaaactggt tcgcggtc                48

<210> SEQ ID NO 133
<211> LENGTH: 55
<212> TYPE: DNA
<213> ORGANISM: Artificial
<220> FEATURE:
<223> OTHER INFORMATION: PCR primer

<400> SEQUENCE: 133
ctgggtcgcc atcaccaagg taaagaaggg aggcgggaac aaggtggtgg atgag        55
```

<210> SEQ ID NO 134
<211> LENGTH: 50
<212> TYPE: DNA
<213> ORGANISM: Artificial
<220> FEATURE:
<223> OTHER INFORMATION: PCR primer

<400> SEQUENCE: 134
gcggagccaa taaggtggtg gatgagtgct acatccccaa ttacttgctc                50

<210> SEQ ID NO 135
<211> LENGTH: 35
<212> TYPE: DNA
<213> ORGANISM: Artificial
<220> FEATURE:
<223> OTHER INFORMATION: PCR primer

<400> SEQUENCE: 135
actggagctc aggttggacc ttcggcagca ggtag                                35

<210> SEQ ID NO 136
<211> LENGTH: 57
<212> TYPE: DNA
<213> ORGANISM: Artificial
<220> FEATURE:
<223> OTHER INFORMATION: PCR primer

<400> SEQUENCE: 136
cgtggacaaa cctggacgag tataaattgg cctgtttgaa tctcacggag cgtaaac       57

<210> SEQ ID NO 137
<211> LENGTH: 48
<212> TYPE: DNA
<213> ORGANISM: Artificial
<220> FEATURE:
<223> OTHER INFORMATION: PCR primer

<400> SEQUENCE: 137
ctgaatctgg aggagcgcaa acggttggtg gcgcagcatc tgacgcac                 48

<210> SEQ ID NO 138
<211> LENGTH: 36
<212> TYPE: DNA
<213> ORGANISM: Artificial
<220> FEATURE:
<223> OTHER INFORMATION: PCR primer

<400> SEQUENCE: 138
gatcaccggc gcatccgaga actcacgctg cgaagc                              36

<210> SEQ ID NO 139
<211> LENGTH: 47
<212> TYPE: DNA
<213> ORGANISM: Artificial
<220> FEATURE:
<223> OTHER INFORMATION: PCR primer

<400> SEQUENCE: 139
taaggccccg gaggcccttt tctttgtgca gtttgaaaag ggatctg                  47

<210> SEQ ID NO 140
<211> LENGTH: 50
<212> TYPE: DNA
<213> ORGANISM: Artificial
<220> FEATURE:
<223> OTHER INFORMATION: PCR primer

```
<400> SEQUENCE: 140
ccacatgcac gtgctcgtgg aaacctccgg catctcttcc atggtcctcg           50

<210> SEQ ID NO 141
<211> LENGTH: 38
<212> TYPE: DNA
<213> ORGANISM: Artificial
<220> FEATURE:
<223> OTHER INFORMATION: PCR primer

<400> SEQUENCE: 141
tcagattcgc gaaaaactgg tgaaagtggt cttccagg                        38

<210> SEQ ID NO 142
<211> LENGTH: 47
<212> TYPE: DNA
<213> ORGANISM: Artificial
<220> FEATURE:
<223> OTHER INFORMATION: PCR primer

<400> SEQUENCE: 142
gaatttaccg cgggatcgag ccgcagatca acgactgggt cgccatc              47

<210> SEQ ID NO 143
<211> LENGTH: 54
<212> TYPE: DNA
<213> ORGANISM: Artificial
<220> FEATURE:
<223> OTHER INFORMATION: PCR primer

<400> SEQUENCE: 143
ggtcacaaag accagaaatg gcgccggcgg agccaataag gtggtggatt ctgg      54

<210> SEQ ID NO 144
<211> LENGTH: 48
<212> TYPE: DNA
<213> ORGANISM: Artificial
<220> FEATURE:
<223> OTHER INFORMATION: PCR primer

<400> SEQUENCE: 144
gaggcgggaa caaggtggtg gattctgggt atattcccgc ctacctgc             48

<210> SEQ ID NO 145
<211> LENGTH: 34
<212> TYPE: DNA
<213> ORGANISM: Artificial
<220> FEATURE:
<223> OTHER INFORMATION: PCR primer

<400> SEQUENCE: 145
ccagcctgag ctccagtggg cgtggacaaa cctg                            34

<210> SEQ ID NO 146
<211> LENGTH: 48
<212> TYPE: DNA
<213> ORGANISM: Artificial
<220> FEATURE:
<223> OTHER INFORMATION: PCR primer

<400> SEQUENCE: 146
gtttgaatct cacggagcgt aaacggctcg tcgcgcagtt tctggcag             48

<210> SEQ ID NO 147
```

```
<211> LENGTH: 42
<212> TYPE: DNA
<213> ORGANISM: Artificial
<220> FEATURE:
<223> OTHER INFORMATION: PCR primer

<400> SEQUENCE: 147
atgcgccggt gatcaaaagc aagacttccc agaaatacat gg                              42

<210> SEQ ID NO 148
<211> LENGTH: 29
<212> TYPE: DNA
<213> ORGANISM: Artificial
<220> FEATURE:
<223> OTHER INFORMATION: PCR primer

<400> SEQUENCE: 148
attataggta ccaggaaccc ctagtgatg                                             29

<210> SEQ ID NO 149
<211> LENGTH: 22
<212> TYPE: DNA
<213> ORGANISM: Artificial
<220> FEATURE:
<223> OTHER INFORMATION: PCR primer

<400> SEQUENCE: 149
taatagggcc caaagggccg gg                                                    22

<210> SEQ ID NO 150
<211> LENGTH: 22
<212> TYPE: DNA
<213> ORGANISM: Artificial
<220> FEATURE:
<223> OTHER INFORMATION: PCR primer

<400> SEQUENCE: 150
ttaataggcc ctttgggccg gg                                                    22

<210> SEQ ID NO 151
<211> LENGTH: 32
<212> TYPE: DNA
<213> ORGANISM: Artificial
<220> FEATURE:
<223> OTHER INFORMATION: PCR primer

<400> SEQUENCE: 151
tataataagc ttaggaaccc ctagtgatgg ag                                         32

<210> SEQ ID NO 152
<211> LENGTH: 33
<212> TYPE: DNA
<213> ORGANISM: Artificial
<220> FEATURE:
<223> OTHER INFORMATION: PCR primer

<400> SEQUENCE: 152
attataggta cctacaaaac ctccttgctt gag                                        33

<210> SEQ ID NO 153
<211> LENGTH: 24
<212> TYPE: DNA
<213> ORGANISM: Artificial
<220> FEATURE:
<223> OTHER INFORMATION: PCR primer

<400> SEQUENCE: 153
```

```
ttaataggcc ctttgggccg tcgc                                     24

<210> SEQ ID NO 154
<211> LENGTH: 25
<212> TYPE: DNA
<213> ORGANISM: Artificial
<220> FEATURE:
<223> OTHER INFORMATION: PCR primer

<400> SEQUENCE: 154
ttaataggcc caaagggccg tcgtc                                    25

<210> SEQ ID NO 155
<211> LENGTH: 35
<212> TYPE: DNA
<213> ORGANISM: Artificial
<220> FEATURE:
<223> OTHER INFORMATION: PCR primer

<400> SEQUENCE: 155
tataataagc tttacaaaac ctccttgctt gagag                         35
```

That which is claimed is:

1. A polynucleotide encoding a synthetic large Rep protein comprising a first portion from a first adeno-associated virus (AAV) and a second portion from a second AAV;
   wherein one of the first AAV and the second AAV is AAV5 and the other is an AAV other than AAV5;
   wherein the synthetic large Rep protein functionally interacts with a synthetic inverted terminal repeat (ITR) comprising a first structural element from the first AAV and a second structural element from the second AAV; and
   wherein the synthetic large Rep protein does not functionally interact with a wild-type ITR from the first AAV or with a wild-type ITR from the second AAV; and
   wherein said first and second structural element is a nicking stem, a spacer or an RBE.

2. The polynucleotide of claim 1, wherein said synthetic large Rep protein further comprises a third portion and wherein the synthetic large Rep protein functionally interacts with a synthetic ITR comprising the first structural element, the second structural element, and a third structural element.

3. The polynucleotide of claim 1, wherein said first portion comprises an amino acid sequence from about residue 97 to about residues 146-151 of a wild-type AAV5 Rep sequence.

4. The polynucleotide of claim 1, wherein said second portion comprises an amino acid sequence from about residue 149 to about residue 187 of a wild-type AAV2 Rep sequence.

5. The polynucleotide of claim 1, wherein said first portion comprises an amino acid sequence from about residue 97 to about residues 146-151 of a wild-type AAV5 Rep sequence and said second portion comprises an amino acid sequence from about residue 149 to about residue 187 of a wild-type AAV2 Rep sequence.

6. The polynucleotide of claim 1, wherein said first portion comprises an amino acid sequence from about residue 1 to about residues 146-151 of a wild-type AAV5 Rep sequence and said second portion comprises an amino acid sequence from about residue 149 to about residue 621 of a wild-type AAV2 Rep sequence.

7. The polynucleotide of claim 1, further encoding a parvovirus Cap protein.

8. The polynucleotide of claim 1, wherein said polynucleotide is a DNA sequence.

9. A vector comprising the polynucleotide of claim 1.

10. The vector of claim 9, wherein said vector is a plasmid vector.

11. The vector of claim 9, wherein said vector is a viral vector.

12. The vector of claim 11, wherein said vector is selected from the group consisting of an adenovirus vector, a baculovirus vector, an AAV vector, a herpesvirus vector, and an Epstein-Barr virus vector.

13. The vector of claim 12, wherein the AAV vector is selected from the group consisting of AAV1, AAV2, AAV3, AAV4, AAV5, AAV6, AAV7, AAV8, AAV9, AAV10, AAV11, AAV12, and AAV13.

14. An isolated cell comprising the polynucleotide of claim 1.

15. The cell of claim 14, wherein said polynucleotide is stably integrated into the genome of said cell.

16. An isolated cell comprising the vector of claim 9.

17. The cell of claim 16, wherein the vector is an AAV vector.

18. The cell of claim 17, wherein the AAV vector is selected from the group consisting of AAV1, AAV2, AAV3, AAV4, AAV5, AAV6, AAV7, AAV8, AAV9, AAV10, AAV11, AAV12, and AAV13.

19. The polynucleotide of claim 1, wherein the AAV other than AAV5 is selected from the group consisting of AAV1, AAV2, AAV3a, AAV3b, AAV4, AAV6, AAV7, AAV8, AAV9, AAV10, AAV11, AAV12, and AAV13.

20. The polynucleotide of claim 1, wherein the first AAV is AAV5.

21. The polynucleotide of claim 20, wherein the second AAV is AAV2.

22. The polynucleotide of claim 1, wherein the first AAV is AAV2.

23. The polynucleotide of claim 22, wherein the second AAV is AAV5.

\* \* \* \* \*